(12) United States Patent
Igawa et al.

(10) Patent No.: US 11,168,139 B2
(45) Date of Patent: Nov. 9, 2021

(54) ANTIGEN-BINDING DOMAIN, AND POLYPEPTIDE INCLUDING CONVEYING SECTION

(71) Applicant: CHUGAI SEIYAKU KABUSHIKI KAISHA, Tokyo (JP)

(72) Inventors: Tomoyuki Igawa, Shizuoka (JP); Hiroyuki Ishikawa, Shizuoka (JP); Naoka Hironiwa, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 36 days.

(21) Appl. No.: 16/463,222

(22) PCT Filed: Nov. 28, 2017

(86) PCT No.: PCT/JP2017/042542
§ 371 (c)(1),
(2) Date: May 22, 2019

(87) PCT Pub. No.: WO2018/097307
PCT Pub. Date: May 31, 2018

(65) Prior Publication Data
US 2019/0359721 A1    Nov. 28, 2019

(30) Foreign Application Priority Data

Nov. 28, 2016 (JP) .............................. JP2016-229794

(51) Int. Cl.
*C40B 40/10* (2006.01)
*C07K 16/28* (2006.01)
(Continued)

(52) U.S. Cl.
CPC ...... *C07K 16/2866* (2013.01); *C07K 16/2809* (2013.01); *C07K 16/303* (2013.01);
(Continued)

(58) Field of Classification Search
None
See application file for complete search history.

(56) References Cited

U.S. PATENT DOCUMENTS

| | | |
|---|---|---|
| 8,809,504 B2 | 8/2014 | Lauermann |
| 2004/0259768 A1 | 12/2004 | Lauermann |
| 2011/0064666 A1 | 3/2011 | Ogawa et al. |

FOREIGN PATENT DOCUMENTS

| | | |
|---|---|---|
| CA | 3041279 A1 | 5/2018 |
| EP | 2957633 A1 | 12/2015 |

(Continued)

OTHER PUBLICATIONS

Alley, S. C., et al., "Antibody-drug conjugates: targeted drug delivery for cancer," Curr Opin Chem Biol., 14:529-537 (2010).
(Continued)

*Primary Examiner* — Christian C Boesen
(74) *Attorney, Agent, or Firm* — Nixon & Vanderhye P.C.

(57) ABSTRACT

The present invention relates to a polypeptide comprising an antigen binding domain and a carrying moiety having an inhibiting domain that inhibits the antigen binding activity of the antigen binding domain, and having a longer half-life than that of the antigen binding domain existing alone, methods for producing and screening for the polypeptide, a pharmaceutical composition comprising the polypeptide, methods for producing and screening for a single-domain antibody whose antigen binding activity is inhibited by associating with particular VL, VH or VHH, and a fusion polypeptide library including a single-domain antibody whose antigen binding activity is inhibited by associating with particular VL, VH or VHH.

8 Claims, 35 Drawing Sheets

Specification includes a Sequence Listing.

(51) Int. Cl.
    C07K 16/30    (2006.01)
    G01N 33/68    (2006.01)
(52) U.S. Cl.
    CPC ......... *C40B 40/10* (2013.01); *G01N 33/6854*
        (2013.01); *C07K 2317/22* (2013.01); *C07K
        2317/31* (2013.01); *C07K 2317/569* (2013.01);
        *C07K 2319/50* (2013.01)

(56) References Cited

FOREIGN PATENT DOCUMENTS

| | | |
|---|---|---|
| JP | 2010536370 A | 12/2010 |
| JP | 201126298 A | 2/2011 |
| JP | 2012514982 A | 7/2012 |
| JP | 2013538204 A | 10/2013 |
| JP | 2014509605 A | 4/2014 |
| JP | 2015509952 A | 4/2015 |
| JP | 2015517320 A | 6/2015 |
| JP | 5753903 B2 | 7/2015 |
| JP | 5765894 B2 | 8/2015 |
| JP | 5851842 B2 | 2/2016 |
| JP | 6035009 B2 | 11/2016 |
| JP | 6130307 B2 | 5/2017 |
| JP | 6178846 B2 | 8/2017 |
| JP | 2017529853 A | 10/2017 |
| JP | 6273215 B2 | 1/2018 |
| RU | 2012110127 A | 9/2013 |
| RU | 2583876 C2 | 5/2016 |
| WO | WO-2004021861 A2 | 3/2004 |
| WO | WO 2007063308 A2 | 6/2007 |
| WO | WO 2008149149 A2 | 12/2008 |
| WO | WO 2009021754 A2 | 2/2009 |
| WO | WO-2009025846 A2 | 2/2009 |
| WO | WO-2010081173 A2 | 7/2010 |
| WO | WO-2010115998 A2 | 10/2010 |
| WO | WO 2011020783 A3 | 4/2011 |
| WO | WO-2012025525 A1 | 3/2012 |
| WO | WO 2012123755 A1 | 9/2012 |
| WO | WO-2013128194 A1 | 9/2013 |
| WO | WO 2013176730 A1 | 11/2013 |
| WO | WO-2014052462 A2 | 4/2014 |
| WO | WO2014125955 A1 | 8/2014 |
| WO | WO-2015116933 A2 | 8/2015 |
| WO | WO 2016016269 A1 | 2/2016 |
| WO | WO 2016046778 A2 | 3/2016 |
| WO | WO-2016118629 A1 | 7/2016 |
| WO | WO 2016179003 A1 | 11/2016 |
| WO | WO 2016182064 A1 | 11/2016 |
| WO | WO 2017025698 A1 | 2/2017 |
| WO | WO 2018097307 A1 | 5/2018 |
| WO | WO-2018097308 A1 | 5/2018 |
| WO | WO 2018220225 A1 | 12/2018 |
| WO | WO 2018220236 A1 | 12/2018 |
| WO | WO-2019107380 A1 | 6/2019 |
| WO | WO-2019107384 A1 | 6/2019 |
| WO | WO 2019230866 A1 | 12/2019 |
| WO | WO 2019230867 A1 | 12/2019 |
| WO | WO 2019230868 A1 | 12/2019 |

OTHER PUBLICATIONS

Asano, R. and Kumagai, I., "Functionalization of Bispecific Therapeutic Antibodies Based on Protein Engineering," Yakugaku Zasshi, 135(7):851-856 (2015), with partial English translation.
Baeuerle, P. A., et al., "BiTE: Teaching antibodies to engage T-cells for cancer therapy," Curr Opin Mol Therapeut., 11(1):22-30 (2009).
De Bono, J. S., et al., "ING-1, a Monoclonal Antibody Targeting Ep-CAM in Patients with Advanced Adenocarcinomas," Clin Cancer Res., 10:7555-7565 (2004).
Desjarlais, J. R., et al., "Optimizing engagement of the immune system by anti-tumor antibodies: an engineer's perspective," Drug Discov Today, 12(21/22):898-910 (2007).
Desnoyers, L. R., et al., "Tumor-Specific Activation of an EGFR-Targeting Probody Enhances Therapeutic Index," Sci Transl Med., 5(207):207ra144 (2013), 10 pages.
Erster, O., et al., "Site-specific targeting of antibody activity in vivo mediated by disease-associated proteases," J Control Release, 161:804-812 (2012).
Gerspach, J., et al., "Target-selective activation on a TNF prodrug by urokinase-type plasminogen activator (uPA) mediated proteolytic processing at the cell surface," Cancer Immunol Immunother., 55:1590-1600 (2006).
Gladkov, O., et al., "Cyclophosphamide and tucotuzumab (huKS-IL2) following first-line chemotherapy in responding patients with extensive-disease small-cell lung cancer," Anti-Cancer Drugs, 26:1061-1068 (2015).
International Search Report in International Application No. PCT/JP2017/042542 dated Feb. 27, 2018, 3 pages.
Juszczak, A., et al., "Ipilimumab: a novel immunomodulating therapy causing autoimmune hypophysitis: a case report and review," Eur J Endocrinol., 167:1-5 (2012).
Kim, S. J., et al., "Antibody Engineering for the Development of Therapeutic Antibodies," Mol Cells, 20(1):17-29 (2005).
Lewis, G. D., et al., "Differential responses of human tumor cell lines to anti-p185$^{HER2}$ monoclonal antibodies," Cancer Immunol Immunother., 37:255-263 (1993).
Lutterbuese, R., et al., "T cell-engaging BiTE antibodies specific for EGFR potently eliminate KRAS- and BRAF-mutated colorectal cancer cells," PNAS, 107(28):12605-12610 (2010).
Nam, J. L., et al., "Current evidence for the management of rheumatoid arthritis with biological disease-modifying antirheumatic drugs: a systematic literature review informing the EULAR recommendations for the management of RA," Ann Rheum Dis., 69:976-986 (2010).
Neri, D. and Sondel, P. M., "Immunocytokines for cancer treatment: past, present and future," Curr Opin Immunol., 40:96-102 (2016).
Paoloni, M., et al., "Defining the Pharmacodynamic Profiled and Therapeutic Index of NHS-IL12 Immunocytokine in Dogs with Malignant Melanoma," PLoS One, 10(6):e0129954 (2015).
Papadia, F., et al., "Isolated Limb Perfusion with the Tumor-Targeting Human Monoclonal Antibody-Cytokine Fusion Protein L19-TNF Plus Melphalan and Mild Hyperthermia in Patients with Locally Advanced Extremity Melanoma," J Surg Oncol., 107:173-179 (2013).
Pavlou, A. K. and Belsey, M. J., "The therapeutic antibodies market to 2008," Eur J Pharm Biopharmaceut., 59:389-396 (2005).
Polu, K. R. and Lowman, H. B., "Probody therapeutics for targeting antibodies to diseased tissue," Expert Opin Biol Ther., 14(8):1049-1053 (2014).
Puskas, J., et al., "Development of an attenuated interleukin-2 fusion protein that can be activated by tumour-expressed proteases," Immunol., 133:206-220 (2011).
Reichert, J. M., et al., "Monoclonal antibody successes in the clinic," Nat Biotechnol., 23(9):1073-1078 (2005).
Riechelmann, H., et al., "Phase I trial with the CD44v6-targeting immunoconjugate bivatuzumab mertansine in head and neck squamous cell carcinoma," Oral Oncology, 44:823-829 (2008).
Satoh, M., et al., "Non-fucosylated therapeutic antibodies as next-generation therapeutic antibodies," Expert Opin Biol Ther., 6(11):1161-1173 (2006).
Takeuchi, T. and Kameda, H., "The Japanese experience with biologic therapies for rheumatoid arthritis," Nat Rev Rheumatol., 6:644-652 (2010).
Trinh, V. A. and Hwu, W.-J., "Ipilimumab in the treatment of melanoma," Expert Opin Biol Ther., 12(6):773-782 (2012).
Turk, B. E., et al., "Determination of protease cleavage site motifs using mixture-based oriented peptide libraries," Nat Biotechnoi. 19(7).661-667 (2001).
Tzeng, A., et al., "Antigen specificity can be irrelevant to immunocytokine efficacy and biodistribution," PNAS, 112(11):3320-3325 (2015).
Van Roy, M., et al., "The preclinical pharmacology of the high affinity anti-IL-6R Nanobody® ALX-0061 supports its clinical development in rheumatoid arthritis," Arthitis Res Ther., 17:135, 16 pages (2015).

(56) References Cited

OTHER PUBLICATIONS

Weiner, L. M., et al., "Monoclonal antibodies: versatile platforms for cancer immunotherapy," Nat Rev Immunol., 10:317-327 (2010).
Yamane, B. H., et al., "The development of antibody-IL-2 based immunotherapy with hu14.18-IL2 (EMD-273063) in melanoma and neuroblastoma," Expert Opin Investig Drugs, 18(7):991- 1000 (2009).
U.S. Appl. No. 16/767,085, 371(c) dated May 26, 2020, Igawa, T., et al., related application.
U.S. Appl. No. 16/766,600, 371(c) dated May 22, 2020, Igawa, T., et al., related application.
U.S. Appl. No. 16/463,218, 371(c) dated May 22, 2019, Igawa, T., et al., related application.
Abstract of ACR/ARHP Annual Meeting https://plan.core-apps.com/tristar_acr17/abstract/7f9a3c05b0ca255af11c655b034e5eaa. Apr. 23, 2018.
Anonymous, "Human Aggrecan G1-IGD-G2 Domains Antibody, Monoclonal Mouse IgG$_{2B}$ Clone # 179509, Catalog No. MAB1220," R&D Systems (2018).
Cohen, S. B., et al., "A randomized, double-blind study of AMG 108 (a fully human monoclonal antibody to IL-1R1) in patients with osteoarthritis of the knee," Arthritis Res Ther., 13:R125 (2011).
Harmsen, M. M., et al., "Selection and optimization of proteolytically stable llama single-domain antibody fragments for oral immunotherapy," Appl Microbiol Biotechnol., 72:544-551 (2006).
Hussack, G., et al., "Engineered Single-Domain Antibodies with High Protease Resistance and Thermal Stability," PLoS ONE, 6(11):e28218 (2011).
Kiani, C., et al., "Structure and function of aggrecan," Cell Res., 12(1)1 9-32 (2002).
Kromann-Hansen, T., et al., "A Camelid-derived Antibody Fragment Targeting the Active Site of a Serine Protease Balances between Inhibitor and Substrate Behavior," J Biol Chem., 291(29):15156-15168 (2016).
Martel-Pelletier, J., et al., "Osteoarthritis," Nat Rev Dis Primers, 2:16072 (2016).
Severin, Y. S., editor, "Biochemistry, Textbook for Higher Education," Moscow, GEOTAR-MED, 39-45 (2004).
Wüest, T., et al., "TNF-Selectokine: a novel prodrug generated for tumor targeting and site-specific activation of tumor necrosis factor," Oncogene, 21:4257-4266 (2002).
Xia, B., et al., "Osteoarthritis Pathogenesis: A Review of Molecular Mechanisms," Calcif Tissue Int., 95:495-505 (2014).
U.S. Appl. No. 10/651,584, filed Aug. 30, 2003, Lauermann.
U.S. Appl. No. 12/821,711, filed Jun. 23, 2010, Ogawa et al.
U.S. Appl. No. 17/058,889, 371(c) dated Nov. 25, 2020, Hoshino et al., related application.
U.S. Appl. No. 17/058,896, 371(c) dated Nov. 25, 2020, Ishikawa et al., related application.
U.S. Appl. No. 17/058,961, 371(c) dated Nov. 25, 2020, Kitamura et al., related application.
U.S. Appl. No. 17/058,889, 371(c) dated Nov. 25, 2020, Hoshino et al.
U.S. Appl. No. 17/058,896, 371(c) dated Nov. 25, 2020, Ishikawa et al.
U.S. Appl. No. 17/058,961, 371(c) dated Nov. 25, 2020, Kitamura et al.
Acchione, M., et al., "Impact of linker and conjugation chemistry on antigen binding, Fc receptor binding and thermal stability of model antibody-drug conjugates," mAbs, 4(3):362-372 (2012).
Halin, C., et al., "Synergistic Therapeutic Effects of a Tumor Targeting Antibody Fragment, Fused to Interleukin 12 and to Tumor Necrosis Factor α," Cancer Res., 63:3202-3210 (2003).
Muller, S., et al., "Spliceosomal Peptide P140 for Immunotherapy of Systemic Lupus Erythematosus," Arthritis Rheum., 58(12):3873-3883 (2008).
Roitt, I., et al., Immunology, Moscow, Mir, pp. 109-111 (2000), with corresponding English translation, Roitt, I., et al, Immunology, 5$^{th}$ Edition, 78-81 (2000).
Torres, M. and Casadevall, A., "The immunoglobin constant region contributes to affinity and specificity," Trends Immunol., 29(2):91-97 (2008).

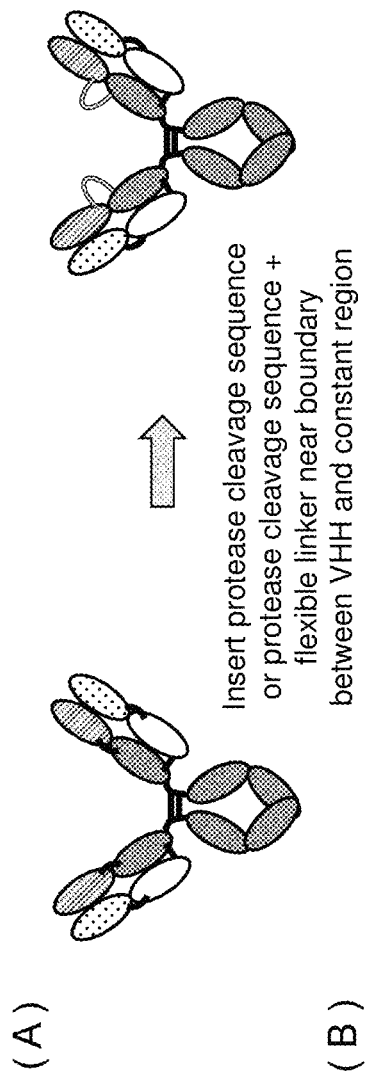

| Name of heavy chain | Insertion site | Inserted amino acid sequence |
|---|---|---|
| 6R90H1001 | TVSSAS [insert] TKGP | LSGRSDNH (SEQ ID NO: 12) |
| 6R90H1002 | TVSSAS [insert] TKGP | SGGSGLSGRSDNHGSSGG (SEQ ID NO: 44) |
| 6R90H1003 | TV [insert] SSASTKGP | LSGRSDNHG (SEQ ID NO: 45) |
| 6R90H1004 | TV [insert] SSASTKGP | SGGSGLSGRSDNHGSSGG (SEQ ID NO: 44) |
| 6R90H1005 | TVSSASTK [insert] GP | LSGRSDNHG (SEQ ID NO: 45) |
| 6R90H1006 | TVSSASTK [insert] GP | SGGSGLSGRSDNHGSSGG (SEQ ID NO: 44) |

Insert protease cleavage sequence or protease cleavage sequence + flexible linker near boundary between VHH and constant region

| | | | |
|---|---|---|---|
| 6R90EIVHEG4SMP9G4S-<br>6R90EICHEG4SMP9G4SG1m | Tris | MMP-9 | 500 nM |
| | | | 0 nM |
| 6R90EIVHEG4SMP2MP9G4S-<br>6R90EICHEG4SMP2MP9G4SG1m | Tris | MMP-9 | 500 nM |
| | | | 0 nM |
| 6R90EIVHEG4SMP2.2G4S-<br>6R90EICHEG4SMP2.2G4SG1m | Tris | MMP-2 | 500 nM |
| | | | 0 nM |
| IgG antibody-like molecule | Buffer | Protease | |
| | | | |
|---|---|---|---|
| IgG antibody-like molecule | Buffer | Protease | |
| 6R90EIVHEG4SMP2MP9G4S-<br>6R90EICHEG4SMP2MP9G4SG1m | Tris | MMP-2 | 500 nM |
| | | | 0 nM |
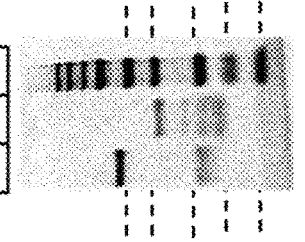
FIG. 30A

SEQUENCE LISTING

```
<160> NUMBER OF SEQ ID NOS: 207

<210> SEQ ID NO 1
<211> LENGTH: 127
<212> TYPE: PRT
<213> ORGANISM: Artificial Sequence
<220> FEATURE:
<223> OTHER INFORMATION: an artificially synthesized sequence

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Ala Leu Glu Trp Val
        35                  40                  45

Ser Ala Ile Ser Trp Asn Gly Asn Asn Thr Tyr Tyr Thr Glu Ser Met
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Val Lys Gly Ser Thr Ala Ile Val Gly Val Pro Pro Thr Tyr Pro Asp
            100                 105                 110

Glu Tyr Asp Tyr Trp Gly Gln Gly Thr Leu Val Thr Val Ser Ser
        115                 120                 125

<210> SEQ ID NO 2
<211> LENGTH: 455
<212> TYPE: PRT
<213> ORGANISM: Artificial Sequence
<220> FEATURE:
```

<223> OTHER INFORMATION: an artificially synthesized sequence

<400> SEQUENCE: 2

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Ala Leu Glu Trp Val
        35                  40                  45

Ser Ala Ile Ser Trp Asn Gly Asn Asn Thr Tyr Tyr Thr Glu Ser Met
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Val Lys Gly Ser Thr Ala Ile Val Gly Val Pro Pro Thr Tyr Pro Asp
            100                 105                 110

Glu Tyr Asp Tyr Trp Gly Gln Gly Thr Leu Val Thr Val Ser Ser Ala
            115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400
```

Tyr Lys Thr Thr Pro Pro Val Leu Asp Ser Asp Gly Ser Phe Phe Leu
            405                 410                 415

Tyr Ser Lys Leu Thr Val Asp Lys Ser Arg Trp Gln Gln Gly Asn Val
        420                 425                 430

Phe Ser Cys Ser Val Met His Glu Ala Leu His Asn His Tyr Thr Gln
        435                 440                 445

Lys Ser Leu Ser Leu Ser Pro
    450                 455

<210> SEQ ID NO 3
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Phe Asp Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 4
<211> LENGTH: 219
<212> TYPE: PRT
<213> ORGANISM: Artificial Sequence
<220> FEATURE:
<223> OTHER INFORMATION: an artificially synthesized sequence

<400> SEQUENCE: 4

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

```
Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Arg
                 85                  90                  95

Leu His Trp Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 5
<211> LENGTH: 215
<212> TYPE: PRT
<213> ORGANISM: Artificial Sequence
<220> FEATURE:
<223> OTHER INFORMATION: an artificially synthesized sequence

<400> SEQUENCE: 5

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Arg Ser Pro
                 85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175
```

```
Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
    210                 215

<210> SEQ ID NO 6
<211> LENGTH: 217
<212> TYPE: PRT
<213> ORGANISM: Artificial Sequence
<220> FEATURE:
<223> OTHER INFORMATION: an artificially synthesized sequence

<400> SEQUENCE: 6

Gln Ser Val Leu Thr Gln Pro Pro Ser Val Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Asn Ser
                85                  90                  95

Leu Asn Ala Val Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
            195                 200                 205

Lys Thr Val Ala Pro Thr Glu Cys Ser
    210                 215

<210> SEQ ID NO 7
<211> LENGTH: 216
<212> TYPE: PRT
<213> ORGANISM: Artificial Sequence
<220> FEATURE:
<223> OTHER INFORMATION: an artificially synthesized sequence

<400> SEQUENCE: 7

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
```

```
                    35                  40                  45
Ile Tyr Ser Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Gly Thr Trp Asp Gly Gly Val
                 85                  90                  95

Thr Gly Val Val Phe Gly Gly Thr Lys Leu Thr Val Leu Gly Gln
                100                 105                 110

Pro Lys Ala Ala Pro Ser Val Thr Leu Phe Pro Pro Ser Ser Glu Glu
                115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
                180                 185                 190

Arg Ser Tyr Ser Cys Gln Val Thr His Glu Gly Ser Thr Val Glu Lys
                195                 200                 205

Thr Val Ala Pro Thr Glu Cys Ser
                210                 215

<210> SEQ ID NO 8
<211> LENGTH: 217
<212> TYPE: PRT
<213> ORGANISM: Artificial Sequence
<220> FEATURE:
<223> OTHER INFORMATION: an artificially synthesized sequence

<400> SEQUENCE: 8

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
             35                  40                  45

Met Ile Tyr Glu Val Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Arg Ser Gly
                 85                  90                  95

Tyr Thr Leu Val Val Phe Gly Gly Thr Lys Leu Thr Val Leu Gly
                100                 105                 110

Gln Pro Lys Ala Ala Pro Ser Val Thr Leu Phe Pro Pro Ser Ser Glu
                115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
```

His Arg Ser Tyr Ser Cys Gln Val Thr His Glu Gly Ser Thr Val Glu
            195                 200                 205

Lys Thr Val Ala Pro Thr Glu Cys Ser
        210                 215

<210> SEQ ID NO 9
<211> LENGTH: 213
<212> TYPE: PRT
<213> ORGANISM: Artificial Sequence
<220> FEATURE:
<223> OTHER INFORMATION: an artificially synthesized sequence

<400> SEQUENCE: 9

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Ala Trp Asp Ser Ser Thr Asp Val
                85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210

<210> SEQ ID NO 10
<211> LENGTH: 107
<212> TYPE: PRT
<213> ORGANISM: Homo sapiens

<400> SEQUENCE: 10

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
50                  55                  60

```
Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 11
<211> LENGTH: 106
<212> TYPE: PRT
<213> ORGANISM: Homo sapiens

<400> SEQUENCE: 11

Gly Gln Pro Lys Ala Ala Pro Ser Val Thr Leu Phe Pro Pro Ser Ser
 1               5                  10                  15

Glu Glu Leu Gln Ala Asn Lys Ala Thr Leu Val Cys Leu Ile Ser Asp
             20                  25                  30

Phe Tyr Pro Gly Ala Val Thr Val Ala Trp Lys Ala Asp Ser Ser Pro
         35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105

<210> SEQ ID NO 12
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 12

Leu Ser Gly Arg Ser Asp Asn His
 1               5

<210> SEQ ID NO 13
<211> LENGTH: 463
<212> TYPE: PRT
<213> ORGANISM: Artificial Sequence
<220> FEATURE:
<223> OTHER INFORMATION: an artificially synthesized sequence

<400> SEQUENCE: 13

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asp Asp Tyr
             20                  25                  30

Gly Met Ser Trp Val Arg Gln Ala Pro Gly Lys Ala Leu Glu Trp Val
         35                  40                  45

Ser Ala Ile Ser Trp Asn Gly Asn Asn Thr Tyr Tyr Thr Glu Ser Met
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Pro Glu Asp Thr Ala Val Tyr Tyr Cys
                 85                  90                  95
```

Val Lys Gly Ser Thr Ala Ile Val Gly Val Pro Thr Tyr Pro Asp
            100                 105                 110

Glu Tyr Asp Tyr Trp Gly Gln Gly Thr Leu Val Thr Val Ser Ser Ala
        115                 120                 125

Ser Leu Ser Gly Arg Ser Asp Asn His Thr Lys Gly Pro Ser Val Phe
        130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro
    450                 455                 460

<210> SEQ ID NO 14
<211> LENGTH: 473
<212> TYPE: PRT
<213> ORGANISM: Artificial Sequence
<220> FEATURE:
<223> OTHER INFORMATION: an artificially synthesized sequence

<400> SEQUENCE: 14

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Ala Leu Glu Trp Val
        35                  40                  45

Ser Ala Ile Ser Trp Asn Gly Asn Asn Thr Tyr Tyr Thr Glu Ser Met
50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
            85                  90                  95

Val Lys Gly Ser Thr Ala Ile Val Gly Val Pro Pro Thr Tyr Pro Asp
        100                 105                 110

Glu Tyr Asp Tyr Trp Gly Gln Gly Thr Leu Val Thr Val Ser Ser Ala
    115                 120                 125

Ser Ser Gly Gly Ser Gly Leu Ser Gly Arg Ser Asp Asn His Gly Ser
    130                 135                 140

Ser Gly Gly Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
            165                 170                 175

Tyr Phe Pro Glu Pro Val Thr Val Ser Trp Asn Ser Gly Ala Leu Thr
        180                 185                 190

Ser Gly Val His Thr Phe Pro Ala Val Leu Gln Ser Ser Gly Leu Tyr
    195                 200                 205

Ser Leu Ser Ser Val Val Thr Val Pro Ser Ser Ser Leu Gly Thr Gln
    210                 215                 220

Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Thr Cys Pro Pro
            245                 250                 255

Cys Pro Ala Pro Glu Leu Leu Gly Gly Pro Ser Val Phe Leu Phe Pro
        260                 265                 270

Pro Lys Pro Lys Asp Thr Leu Met Ile Ser Arg Thr Pro Glu Val Thr
    275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
            325                 330                 335

Leu His Gln Asp Trp Leu Asn Gly Lys Glu Tyr Lys Cys Lys Val Ser
        340                 345                 350

Asn Lys Ala Leu Pro Ala Pro Ile Glu Lys Thr Ile Ser Lys Ala Lys
    355                 360                 365

Gly Gln Pro Arg Glu Pro Gln Val Tyr Thr Leu Pro Pro Ser Arg Glu
    370                 375                 380

Glu Met Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
            405                 410                 415
```

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro
465                 470

<210> SEQ ID NO 15
<211> LENGTH: 464
<212> TYPE: PRT
<213> ORGANISM: Artificial Sequence
<220> FEATURE:
<223> OTHER INFORMATION: an artificially synthesized sequence

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Ala Leu Glu Trp Val
        35                  40                  45

Ser Ala Ile Ser Trp Asn Gly Asn Asn Thr Tyr Tyr Thr Glu Ser Met
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
            85                  90                  95

Val Lys Gly Ser Thr Ala Ile Val Gly Val Pro Pro Tyr Pro Asp
        100                 105                 110

Glu Tyr Asp Tyr Trp Gly Gln Gly Thr Leu Val Thr Val Leu Ser Gly
            115                 120                 125

Arg Ser Asp Asn His Gly Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
            165                 170                 175

Trp Asn Ser Gly Ala Leu Thr Ser Gly Val His Thr Phe Pro Ala Val
        180                 185                 190

Leu Gln Ser Ser Gly Leu Tyr Ser Leu Ser Ser Val Val Thr Val Pro
            195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
            245                 250                 255

Pro Ser Val Phe Leu Phe Pro Pro Lys Pro Lys Asp Thr Leu Met Ile
        260                 265                 270

Ser Arg Thr Pro Glu Val Thr Cys Val Val Val Asp Val Ser His Glu
            275                 280                 285

Asp Pro Glu Val Lys Phe Asn Trp Tyr Val Asp Gly Val Glu Val His
    290                 295                 300

```
Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
            325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
            355                 360                 365

Thr Leu Pro Pro Ser Arg Glu Glu Met Thr Lys Asn Gln Val Ser Leu
        370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
            405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
            435                 440                 445

Glu Ala Leu His Asn His Tyr Thr Gln Lys Ser Leu Ser Leu Ser Pro
450                 455                 460
```

<210> SEQ ID NO 16
<211> LENGTH: 473
<212> TYPE: PRT
<213> ORGANISM: Artificial Sequence
<220> FEATURE:
<223> OTHER INFORMATION: an artificially synthesized sequence

<400> SEQUENCE: 16

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Ala Leu Glu Trp Val
        35                  40                  45

Ser Ala Ile Ser Trp Asn Gly Asn Asn Thr Tyr Tyr Thr Glu Ser Met
50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Val Lys Gly Ser Thr Ala Ile Val Gly Val Pro Pro Thr Tyr Pro Asp
            100                 105                 110

Glu Tyr Asp Tyr Trp Gly Gln Gly Thr Leu Val Thr Val Ser Gly Gly
            115                 120                 125

Ser Gly Leu Ser Gly Arg Ser Asp Asn His Gly Ser Ser Gly Gly Ser
        130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205
```

Ser Leu Ser Ser Val Val Thr Val Pro Ser Ser Ser Leu Gly Thr Gln
210                 215                 220

Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Thr Cys Pro Pro
            245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
            275                 280                 285

Cys Val Val Val Asp Val Ser His Glu Asp Pro Glu Val Lys Phe Asn
290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
                340                 345                 350

Asn Lys Ala Leu Pro Ala Pro Ile Glu Lys Thr Ile Ser Lys Ala Lys
                355                 360                 365

Gly Gln Pro Arg Glu Pro Gln Val Tyr Thr Leu Pro Pro Ser Arg Glu
370                 375                 380

Glu Met Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
                420                 425                 430

Phe Leu Tyr Ser Lys Leu Thr Val Asp Lys Ser Arg Trp Gln Gln Gly
                435                 440                 445

Asn Val Phe Ser Cys Ser Val Met His Glu Ala Leu His Asn His Tyr
                450                 455                 460

Thr Gln Lys Ser Leu Ser Leu Ser Pro
465                 470

<210> SEQ ID NO 17
<211> LENGTH: 464
<212> TYPE: PRT
<213> ORGANISM: Artificial Sequence
<220> FEATURE:
<223> OTHER INFORMATION: an artificially synthesized sequence

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Ala Leu Glu Trp Val
        35                  40                  45

Ser Ala Ile Ser Trp Asn Gly Asn Thr Tyr Tyr Thr Glu Ser Met
50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Val Lys Gly Ser Thr Ala Ile Val Gly Val Pro Pro Thr Tyr Pro Asp
            100                 105                 110

Glu Tyr Asp Tyr Trp Gly Gln Gly Thr Leu Val Thr Val Ser Ser Ala
        115                 120                 125

Ser Thr Lys Leu Ser Gly Arg Ser Asp Asn His Gly Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

<210> SEQ ID NO 18
<211> LENGTH: 473
<212> TYPE: PRT
<213> ORGANISM: Artificial Sequence
<220> FEATURE:
<223> OTHER INFORMATION: an artificially synthesized sequence

<400> SEQUENCE: 18

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Ala Leu Glu Trp Val
            35                  40                  45

Ser Ala Ile Ser Trp Asn Gly Asn Asn Thr Tyr Tyr Thr Glu Ser Met
50                      55                  60

Lys Gly Arg Phe Thr Ile Ser Arg Asp Asn Ala Lys Asn Thr Leu Tyr
65                      70                  75                  80

Leu Gln Met Asn Ser Leu Arg Pro Glu Asp Thr Ala Val Tyr Tyr Cys
                85                  90                  95

Val Lys Gly Ser Thr Ala Ile Val Gly Val Pro Pro Thr Tyr Pro Asp
            100                 105                 110

Glu Tyr Asp Tyr Trp Gly Gln Gly Thr Leu Val Thr Val Ser Ser Ala
            115                 120                 125

Ser Thr Lys Ser Gly Gly Ser Gly Leu Ser Gly Arg Ser Asp Asn His
            130                 135                 140

Gly Ser Ser Gly Gly Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
            195                 200                 205

Ser Leu Ser Ser Val Val Thr Val Pro Ser Ser Ser Leu Gly Thr Gln
210                 215                 220

Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Thr Cys Pro Pro
            245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
            275                 280                 285

Cys Val Val Val Asp Val Ser His Glu Asp Pro Glu Val Lys Phe Asn
            290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
            325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
            355                 360                 365

Gly Gln Pro Arg Glu Pro Gln Val Tyr Thr Leu Pro Pro Ser Arg Glu
            370                 375                 380

Glu Met Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
            405                 410                 415

Asn Asn Tyr Lys Thr Thr Pro Pro Val Leu Asp Ser Asp Gly Ser Phe
```

```
                        420             425                 430
Phe Leu Tyr Ser Lys Leu Thr Val Asp Lys Ser Arg Trp Gln Gln Gly
            435                 440                 445

Asn Val Phe Ser Cys Ser Val Met His Glu Ala Leu His Asn His Tyr
        450                 455                 460

Thr Gln Lys Ser Leu Ser Leu Ser Pro
465                 470

<210> SEQ ID NO 19
<211> LENGTH: 121
<212> TYPE: PRT
<213> ORGANISM: Artificial Sequence
<220> FEATURE:
<223> OTHER INFORMATION: an artificially synthesized sequence

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val Phe Lys Ile Asn
            20                  25                  30

Val Met Ala Trp Tyr Arg Gln Ala Pro Gly Lys Gly Arg Glu Leu Val
        35                  40                  45

Ala Gly Ile Ile Ser Gly Gly Ser Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Ile Thr Thr Glu Ser Asp Tyr Asp Leu Gly Arg Arg Tyr Trp Gly
            100                 105                 110

Gln Gly Thr Leu Val Thr Val Ser Ser
        115                 120

<210> SEQ ID NO 20
<211> LENGTH: 121
<212> TYPE: PRT
<213> ORGANISM: Artificial Sequence
<220> FEATURE:
<223> OTHER INFORMATION: an artificially synthesized sequence

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val Phe Lys Ile Asn
            20                  25                  30

Val Met Ala Trp Val Arg Gln Ala Pro Gly Lys Gly Leu Glu Trp Val
        35                  40                  45

Ala Gly Ile Ile Ser Gly Gly Ser Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Ile Thr Thr Glu Ser Asp Tyr Asp Leu Gly Arg Arg Tyr Trp Gly
            100                 105                 110

Gln Gly Thr Leu Val Thr Val Ser Ser
        115                 120
```

<210> SEQ ID NO 21
<211> LENGTH: 330
<212> TYPE: PRT
<213> ORGANISM: Homo sapiens

<400> SEQUENCE: 21

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 22
<211> LENGTH: 326
<212> TYPE: PRT
<213> ORGANISM: Homo sapiens

<400> SEQUENCE: 22

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 23
<211> LENGTH: 377
<212> TYPE: PRT
<213> ORGANISM: Homo sapiens

<400> SEQUENCE: 23

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45
```

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Gln Thr
 65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
                100                 105                 110

Arg Cys Pro Glu Pro Lys Ser Cys Asp Thr Pro Pro Cys Pro Arg
            115                 120                 125

Cys Pro Glu Pro Lys Ser Cys Asp Thr Pro Pro Cys Pro Arg Cys
 130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
                180                 185                 190

Val Val Asp Val Ser His Glu Asp Pro Glu Val Gln Phe Lys Trp Tyr
                195                 200                 205

Val Asp Gly Val Glu Val His Asn Ala Lys Thr Lys Pro Arg Glu Glu
210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
                260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
                340                 345                 350

Phe Ser Cys Ser Val Met His Glu Ala Leu His Asn Arg Phe Thr Gln
            355                 360                 365

Lys Ser Leu Ser Leu Ser Pro Gly Lys
            370                 375

<210> SEQ ID NO 24
<211> LENGTH: 327
<212> TYPE: PRT
<213> ORGANISM: Homo sapiens

<400> SEQUENCE: 24

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser

```
                35                  40                  45
Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Ser Cys Pro Ala Pro
                100                 105                 110

Glu Phe Leu Gly Gly Pro Ser Val Phe Leu Phe Pro Pro Lys Pro Lys
                115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
                195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 25
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 25

Pro Leu Gly Leu Ala Gly
1               5

<210> SEQ ID NO 26
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 26
```

```
Val Pro Leu Ser Leu Thr Met Gly
1               5

<210> SEQ ID NO 27
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 27

Gly Ser Gly Gly Ser
1               5

<210> SEQ ID NO 28
<211> LENGTH: 4
<212> TYPE: PRT
<213> ORGANISM: Artificial Sequence
<220> FEATURE:
<223> OTHER INFORMATION: an artificially synthesized sequence

<400> SEQUENCE: 28

Gly Gly Gly Ser
1

<210> SEQ ID NO 29
<211> LENGTH: 4
<212> TYPE: PRT
<213> ORGANISM: Artificial Sequence
<220> FEATURE:
<223> OTHER INFORMATION: an artificially synthesized sequence

<400> SEQUENCE: 29

Gly Gly Ser Gly
1

<210> SEQ ID NO 30
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 30

Gly Gly Ser Gly Gly
1               5

<210> SEQ ID NO 31
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 31

Gly Ser Gly Ser Gly
1               5

<210> SEQ ID NO 32
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 32

Gly Ser Gly Gly Gly
```

```
<210> SEQ ID NO 33
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 33

Gly Gly Gly Ser Gly
1               5

<210> SEQ ID NO 34
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 34

Gly Ser Ser Ser Gly
1               5

<210> SEQ ID NO 35
<211> LENGTH: 338
<212> TYPE: PRT
<213> ORGANISM: Homo sapiens

<400> SEQUENCE: 35

Leu Ala Pro Arg Cys Pro Ala Gln Glu Val Ala Arg Gly Val Leu
1               5                   10                  15

Thr Ser Leu Pro Gly Asp Ser Val Thr Leu Thr Cys Pro Gly Val Glu
                20                  25                  30

Pro Glu Asp Asn Ala Thr Val His Trp Val Leu Arg Lys Pro Ala Ala
            35                  40                  45

Gly Ser His Pro Ser Arg Trp Ala Gly Met Gly Arg Arg Leu Leu Leu
        50                  55                  60

Arg Ser Val Gln Leu His Asp Ser Gly Asn Tyr Ser Cys Tyr Arg Ala
65                  70                  75                  80

Gly Arg Pro Ala Gly Thr Val His Leu Leu Val Asp Val Pro Pro Glu
                85                  90                  95

Glu Pro Gln Leu Ser Cys Phe Arg Lys Ser Pro Leu Ser Asn Val Val
            100                 105                 110

Cys Glu Trp Gly Pro Arg Ser Thr Pro Ser Leu Thr Thr Lys Ala Val
        115                 120                 125

Leu Leu Val Arg Lys Phe Gln Asn Ser Pro Ala Glu Asp Phe Gln Glu
130                 135                 140

Pro Cys Gln Tyr Ser Gln Glu Ser Gln Lys Phe Ser Cys Gln Leu Ala
145                 150                 155                 160

Val Pro Glu Gly Asp Ser Ser Phe Tyr Ile Val Ser Met Cys Val Ala
                165                 170                 175

Ser Ser Val Gly Ser Lys Phe Ser Lys Thr Gln Thr Phe Gln Gly Cys
            180                 185                 190

Gly Ile Leu Gln Pro Asp Pro Ala Asn Ile Thr Val Thr Ala Val
        195                 200                 205

Ala Arg Asn Pro Arg Trp Leu Ser Val Thr Trp Gln Asp Pro His Ser
        210                 215                 220

Trp Asn Ser Ser Phe Tyr Arg Leu Arg Phe Glu Leu Arg Tyr Arg Ala
```

```
                225                 230                 235                 240

Glu Arg Ser Lys Thr Phe Thr Thr Trp Met Val Lys Asp Leu Gln His
                245                 250                 255

His Cys Val Ile His Asp Ala Trp Ser Gly Leu Arg His Val Val Gln
                260                 265                 270

Leu Arg Ala Gln Glu Glu Phe Gly Gln Gly Glu Trp Ser Glu Trp Ser
                275                 280                 285

Pro Glu Ala Met Gly Thr Pro Trp Thr Glu Ser Arg Ser Pro Pro Ala
                290                 295                 300

Glu Asn Glu Val Ser Thr Pro Met Gln Ala Leu Thr Thr Asn Lys Asp
305                 310                 315                 320

Asp Asp Asn Ile Leu Phe Arg Asp Ser Ala Asn Ala Thr Ser Leu Pro
                325                 330                 335

Val Gln

<210> SEQ ID NO 36
<211> LENGTH: 15
<212> TYPE: PRT
<213> ORGANISM: Artificial Sequence
<220> FEATURE:
<223> OTHER INFORMATION: an artificially synthesized sequence

<400> SEQUENCE: 36

Gly Leu Asn Asp Ile Phe Glu Ala Gln Lys Ile Glu Trp His Glu
1               5                   10                  15

<210> SEQ ID NO 37
<211> LENGTH: 358
<212> TYPE: PRT
<213> ORGANISM: Artificial Sequence
<220> FEATURE:
<223> OTHER INFORMATION: an artificially synthesized sequence

<400> SEQUENCE: 37

Leu Ala Pro Arg Arg Cys Pro Ala Gln Glu Val Ala Arg Gly Val Leu
1               5                   10                  15

Thr Ser Leu Pro Gly Asp Ser Val Thr Leu Thr Cys Pro Gly Val Glu
                20                  25                  30

Pro Glu Asp Asn Ala Thr Val His Trp Val Leu Arg Lys Pro Ala Ala
                35                  40                  45

Gly Ser His Pro Ser Arg Trp Ala Gly Met Gly Arg Arg Leu Leu Leu
            50                  55                  60

Arg Ser Val Gln Leu His Asp Ser Gly Asn Tyr Ser Cys Tyr Arg Ala
65                  70                  75                  80

Gly Arg Pro Ala Gly Thr Val His Leu Leu Val Asp Val Pro Pro Glu
                85                  90                  95

Glu Pro Gln Leu Ser Cys Phe Arg Lys Ser Pro Leu Ser Asn Val Val
                100                 105                 110

Cys Glu Trp Gly Pro Arg Ser Thr Pro Ser Leu Thr Thr Lys Ala Val
                115                 120                 125

Leu Leu Val Arg Lys Phe Gln Asn Ser Pro Ala Glu Asp Phe Gln Glu
                130                 135                 140

Pro Cys Gln Tyr Ser Gln Glu Ser Gln Lys Phe Ser Cys Gln Leu Ala
145                 150                 155                 160

Val Pro Glu Gly Asp Ser Ser Phe Tyr Ile Val Ser Met Cys Val Ala
                165                 170                 175

Ser Ser Val Gly Ser Lys Phe Ser Lys Thr Gln Thr Phe Gln Gly Cys
```

```
            180                 185                 190
Gly Ile Leu Gln Pro Asp Pro Ala Asn Ile Thr Val Thr Ala Val
            195                 200                 205

Ala Arg Asn Pro Arg Trp Leu Ser Val Thr Trp Gln Asp Pro His Ser
    210                 215                 220

Trp Asn Ser Ser Phe Tyr Arg Leu Arg Phe Glu Leu Arg Tyr Arg Ala
225                 230                 235                 240

Glu Arg Ser Lys Thr Phe Thr Thr Trp Met Val Lys Asp Leu Gln His
                245                 250                 255

His Cys Val Ile His Asp Ala Trp Ser Gly Leu Arg His Val Val Gln
                260                 265                 270

Leu Arg Ala Gln Glu Glu Phe Gly Gln Gly Glu Trp Ser Glu Trp Ser
            275                 280                 285

Pro Glu Ala Met Gly Thr Pro Trp Thr Glu Ser Arg Ser Pro Pro Ala
            290                 295                 300

Glu Asn Glu Val Ser Thr Pro Met Gln Ala Leu Thr Thr Asn Lys Asp
305                 310                 315                 320

Asp Asp Asn Ile Leu Phe Arg Asp Ser Ala Asn Ala Thr Ser Leu Pro
                325                 330                 335

Val Gln Gly Gly Gly Ser Gly Leu Asn Asp Ile Phe Glu Ala Gln
            340                 345                 350

Lys Ile Glu Trp His Glu
            355

<210> SEQ ID NO 38
<211> LENGTH: 449
<212> TYPE: PRT
<213> ORGANISM: Artificial Sequence
<220> FEATURE:
<223> OTHER INFORMATION: an artificially synthesized sequence

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val Phe Lys Ile Asn
            20                  25                  30

Val Met Ala Trp Tyr Arg Gln Ala Pro Gly Lys Gly Arg Glu Leu Val
        35                  40                  45

Ala Gly Ile Ile Ser Gly Gly Ser Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Ile Thr Thr Glu Ser Asp Tyr Asp Leu Gly Arg Arg Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
```

```
            180                 185                 190
Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Arg Glu Glu Met Thr Lys Asn Gln Val Ser
    355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
    435                 440                 445

Pro

<210> SEQ ID NO 39
<211> LENGTH: 449
<212> TYPE: PRT
<213> ORGANISM: Artificial Sequence
<220> FEATURE:
<223> OTHER INFORMATION: an artificially synthesized sequence

<400> SEQUENCE: 39

Glu Val Gln Leu Val Glu Ser Gly Gly Gly Leu Val Gln Pro Gly Gly
1               5                  10                  15

Ser Leu Arg Leu Ser Cys Ala Ala Ser Gly Ser Val Phe Lys Ile Asn
            20                  25                  30

Val Met Ala Trp Val Arg Gln Ala Pro Gly Lys Gly Leu Glu Trp Val
        35                  40                  45

Ala Gly Ile Ile Ser Gly Gly Ser Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
            85                  90                  95
```

```
Phe Ile Thr Thr Glu Ser Asp Tyr Asp Leu Gly Arg Arg Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro
```

<210> SEQ ID NO 40
<211> LENGTH: 457
<212> TYPE: PRT
<213> ORGANISM: Artificial Sequence
<220> FEATURE:
<223> OTHER INFORMATION: an artificially synthesized sequence

<400> SEQUENCE: 40

-continued

```
Glu Val Gln Leu Val Glu Ser Gly Gly Leu Val Gln Pro Gly Gly
1               5                   10                  15

Ser Leu Arg Leu Ser Cys Ala Ala Ser Gly Ser Val Phe Lys Ile Asn
            20                  25                  30

Val Met Ala Trp Tyr Arg Gln Ala Pro Gly Lys Gly Arg Glu Leu Val
        35                  40                  45

Ala Gly Ile Ile Ser Gly Gly Ser Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
            85                  90                  95

Phe Ile Thr Thr Glu Ser Asp Tyr Asp Leu Gly Arg Arg Tyr Trp Gly
        100                 105                 110

Gln Gly Thr Leu Val Thr Val Ser Ser Ala Ser Leu Ser Gly Arg Ser
            115                 120                 125

Asp Asn His Thr Lys Gly Pro Ser Val Phe Pro Leu Ala Pro Ser Ser
        130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
            195                 200                 205

Thr Tyr Ile Cys Asn Val Asn His Lys Pro Ser Asn Thr Lys Val Asp
        210                 215                 220

Lys Lys Val Glu Pro Lys Ser Cys Asp Lys Thr His Thr Cys Pro Pro
225                 230                 235                 240

Cys Pro Ala Pro Glu Leu Leu Gly Gly Pro Ser Val Phe Leu Phe Pro
                245                 250                 255

Pro Lys Pro Lys Asp Thr Leu Met Ile Ser Arg Thr Pro Glu Val Thr
                260                 265                 270

Cys Val Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
        290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350

Gly Gln Pro Arg Glu Pro Gln Val Tyr Thr Leu Pro Pro Ser Arg Glu
        355                 360                 365

Glu Met Thr Lys Asn Gln Val Ser Leu Thr Cys Leu Val Lys Gly Phe
        370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
            405                 410                 415

Phe Leu Tyr Ser Lys Leu Thr Val Asp Lys Ser Arg Trp Gln Gln Gly
```

```
                420              425              430
Asn Val Phe Ser Cys Ser Val Met His Glu Ala Leu His Asn His Tyr
            435              440              445

Thr Gln Lys Ser Leu Ser Leu Ser Pro
    450              455

<210> SEQ ID NO 41
<211> LENGTH: 467
<212> TYPE: PRT
<213> ORGANISM: Artificial Sequence
<220> FEATURE:
<223> OTHER INFORMATION: an artificially synthesized sequence

<400> SEQUENCE: 41

Glu Val Gln Leu Val Glu Ser Gly Gly Gly Leu Val Gln Pro Gly Gly
1               5                  10                  15

Ser Leu Arg Leu Ser Cys Ala Ala Ser Gly Ser Val Phe Lys Ile Asn
            20                  25                  30

Val Met Ala Trp Tyr Arg Gln Ala Pro Gly Lys Gly Arg Glu Leu Val
        35                  40                  45

Ala Gly Ile Ile Ser Gly Gly Ser Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Ile Thr Thr Glu Ser Asp Tyr Asp Leu Gly Arg Arg Tyr Trp Gly
            100                 105                 110

Gln Gly Thr Leu Val Thr Val Ser Ser Ala Ser Ser Gly Gly Ser Gly
        115                 120                 125

Leu Ser Gly Arg Ser Asp Asn His Gly Ser Ser Gly Gly Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
```

```
                      325                 330                 335
Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Glu Glu Met Thr Lys Asn Gln
            370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
450                 455                 460

Leu Ser Pro
465

<210> SEQ ID NO 42
<211> LENGTH: 467
<212> TYPE: PRT
<213> ORGANISM: Artificial Sequence
<220> FEATURE:
<223> OTHER INFORMATION: an artificially synthesized sequence

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val Phe Lys Ile Asn
            20                  25                  30

Val Met Ala Trp Tyr Arg Gln Ala Pro Gly Lys Gly Arg Glu Leu Val
        35                  40                  45

Ala Gly Ile Ile Ser Gly Gly Ser Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Ile Thr Thr Glu Ser Asp Tyr Asp Leu Gly Arg Arg Tyr Trp Gly
            100                 105                 110

Gln Gly Thr Leu Val Thr Val Ser Gly Gly Ser Gly Leu Ser Gly Arg
        115                 120                 125

Ser Asp Asn His Gly Ser Ser Gly Gly Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
```

```
            210                 215                 220
Asn His Lys Pro Ser Asn Thr Lys Val Asp Lys Val Glu Pro Lys
225                 230                 235                 240

Ser Cys Asp Lys Thr His Thr Cys Pro Pro Cys Pro Ala Pro Glu Leu
            245                 250                 255

Leu Gly Gly Pro Ser Val Phe Leu Phe Pro Pro Lys Pro Lys Asp Thr
                260                 265                 270

Leu Met Ile Ser Arg Thr Pro Glu Val Thr Cys Val Val Val Asp Val
            275                 280                 285

Ser His Glu Asp Pro Glu Val Lys Phe Asn Trp Tyr Val Asp Gly Val
290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
                340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Glu Glu Met Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
                420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
450                 455                 460

Leu Ser Pro
465

<210> SEQ ID NO 43
<211> LENGTH: 467
<212> TYPE: PRT
<213> ORGANISM: Artificial Sequence
<220> FEATURE:
<223> OTHER INFORMATION: an artificially synthesized sequence

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val Phe Lys Ile Asn
            20                  25                  30

Val Met Ala Trp Tyr Arg Gln Ala Pro Gly Lys Gly Arg Glu Leu Val
        35                  40                  45

Ala Gly Ile Ile Ser Gly Gly Ser Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Ile Thr Thr Glu Ser Asp Tyr Asp Leu Gly Arg Arg Tyr Trp Gly
```

```
            100                 105                 110
Gln Gly Thr Leu Val Thr Val Ser Ala Ser Thr Lys Ser Gly Gly
            115                 120                 125

Ser Gly Leu Ser Gly Arg Ser Asp Asn His Gly Ser Gly Gly Gly
            130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
                180                 185                 190

Pro Ala Val Leu Gln Ser Ser Gly Leu Tyr Ser Leu Ser Ser Val Val
                195                 200                 205

Thr Val Pro Ser Ser Ser Leu Gly Thr Gln Thr Tyr Ile Cys Asn Val
                210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
                260                 265                 270

Leu Met Ile Ser Arg Thr Pro Glu Val Thr Cys Val Val Val Asp Val
                275                 280                 285

Ser His Glu Asp Pro Glu Val Lys Phe Asn Trp Tyr Val Asp Gly Val
                290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
                340                 345                 350

Pro Ile Glu Lys Thr Ile Ser Lys Ala Lys Gly Gln Pro Arg Glu Pro
                355                 360                 365

Gln Val Tyr Thr Leu Pro Pro Ser Arg Glu Glu Met Thr Lys Asn Gln
                370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
                420                 425                 430

Thr Val Asp Lys Ser Arg Trp Gln Gln Gly Asn Val Phe Ser Cys Ser
                435                 440                 445

Val Met His Glu Ala Leu His Asn His Tyr Thr Gln Lys Ser Leu Ser
                450                 455                 460

Leu Ser Pro
465

<210> SEQ ID NO 44
<211> LENGTH: 18
<212> TYPE: PRT
<213> ORGANISM: Artificial Sequence
<220> FEATURE:
<223> OTHER INFORMATION: an artificially synthesized sequence
```

```
<400> SEQUENCE: 44

Ser Gly Gly Ser Gly Leu Ser Gly Arg Ser Asp Asn His Gly Ser Ser
1               5                   10                  15

Gly Gly

<210> SEQ ID NO 45
<211> LENGTH: 9
<212> TYPE: PRT
<213> ORGANISM: Artificial Sequence
<220> FEATURE:
<223> OTHER INFORMATION: an artificially synthesized sequence

<400> SEQUENCE: 45

Leu Ser Gly Arg Ser Asp Asn His Gly
1               5

<210> SEQ ID NO 46
<211> LENGTH: 4
<212> TYPE: PRT
<213> ORGANISM: Artificial Sequence
<220> FEATURE:
<223> OTHER INFORMATION: an artificially synthesized sequence

<400> SEQUENCE: 46

Gly Ser Gly Gly
1

<210> SEQ ID NO 47
<211> LENGTH: 4
<212> TYPE: PRT
<213> ORGANISM: Artificial Sequence
<220> FEATURE:
<223> OTHER INFORMATION: an artificially synthesized sequence

<400> SEQUENCE: 47

Ser Gly Gly Gly
1

<210> SEQ ID NO 48
<211> LENGTH: 4
<212> TYPE: PRT
<213> ORGANISM: Artificial Sequence
<220> FEATURE:
<223> OTHER INFORMATION: an artificially synthesized sequence

<400> SEQUENCE: 48

Gly Ser Ser Gly
1

<210> SEQ ID NO 49
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 49

Gly Gly Gly Gly Ser
1               5

<210> SEQ ID NO 50
<211> LENGTH: 6
<212> TYPE: PRT
<213> ORGANISM: Artificial Sequence
<220> FEATURE:
<223> OTHER INFORMATION: an artificially synthesized sequence
```

```
<400> SEQUENCE: 50

Gly Gly Gly Gly Gly Ser
1               5

<210> SEQ ID NO 51
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 51

Ser Gly Gly Gly Gly
1               5

<210> SEQ ID NO 52
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 52

Gly Ser Ser Gly Gly
1               5

<210> SEQ ID NO 53
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 53

Ser Gly Gly Ser Gly
1               5

<210> SEQ ID NO 54
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 54

Ser Gly Gly Gly Gly Gly
1               5

<210> SEQ ID NO 55
<211> LENGTH: 7
<212> TYPE: PRT
<213> ORGANISM: Artificial Sequence
<220> FEATURE:
<223> OTHER INFORMATION: an artificially synthesized sequence

<400> SEQUENCE: 55

Gly Gly Gly Gly Gly Gly Ser
1               5

<210> SEQ ID NO 56
<211> LENGTH: 7
<212> TYPE: PRT
<213> ORGANISM: Artificial Sequence
<220> FEATURE:
<223> OTHER INFORMATION: an artificially synthesized sequence
```

```
<400> SEQUENCE: 56

Ser Gly Gly Gly Gly Gly
1               5

<210> SEQ ID NO 57
<211> LENGTH: 641
<212> TYPE: PRT
<213> ORGANISM: Human herpesvirus 4

<400> SEQUENCE: 57

Met Ser Asp Glu Gly Pro Gly Thr Gly Pro Gly Asn Gly Leu Gly Glu
1               5                   10                  15

Lys Gly Asp Thr Ser Gly Pro Glu Gly Ser Gly Ser Gly Pro Gln
            20                  25                  30

Arg Arg Gly Gly Asp Asn His Gly Arg Gly Arg Gly Arg Gly Arg Gly
                35                  40                  45

Arg Gly Gly Gly Arg Pro Gly Ala Pro Gly Gly Ser Gly Ser Gly Pro
            50                  55                  60

Arg His Arg Asp Gly Val Arg Arg Pro Gln Lys Arg Pro Ser Cys Ile
65                  70                  75                  80

Gly Cys Lys Gly Thr His Gly Gly Thr Gly Ala Gly Ala Gly Ala Gly
                85                  90                  95

Gly Ala Gly Ala Gly Gly Ala Gly Ala Gly Gly Ala Gly Ala Gly Gly
            100                 105                 110

Gly Gly Ala Gly Gly Ala Gly Gly Ala Gly Gly Ala Gly Ala Gly Gly
            115                 120                 125

Gly Ala Gly Ala Gly Gly Ala Gly Ala Gly Gly Ala Gly Ala Gly Ala
            130                 135                 140

Gly Gly Gly Ala Gly Ala Gly Gly Ala Gly Gly Ala Gly Ala Gly Gly
145                 150                 155                 160

Gly Gly Ala Gly Gly Ala Gly Ala Gly Ala Gly Gly Gly Ala Gly Gly
                165                 170                 175

Ala Gly Gly Gly Ala Gly Gly Ala Gly Ala Gly Gly Ala Gly Gly Gly
            180                 185                 190

Ala Gly Gly Ala Gly Ala Gly Gly Gly Ala Gly Gly Ala Gly Ala Gly
            195                 200                 205

Gly Ala Gly Gly Ala Gly Ala Gly Gly Ala Gly Ala Gly Gly Gly Ala
            210                 215                 220

Gly Gly Ala Gly Gly Ala Gly Ala Gly Gly Ala Gly Ala Gly Gly Ala
225                 230                 235                 240

Gly Ala Gly Gly Ala Gly Ala Gly Gly Ala Gly Ala Gly Gly Ala Gly
                245                 250                 255

Gly Ala Gly Gly Ala Gly Ala Gly Gly Ala Gly Ala Gly Gly Ala Gly
            260                 265                 270

Gly Gly Ala Gly Gly Ala Gly Ala Gly Gly Ala Gly Gly Ala Gly Gly
            275                 280                 285

Ala Gly Gly Ala Gly Gly Ala Gly Gly Gly Ala Gly Gly Ala Gly Gly
            290                 295                 300

Ala Gly Gly Ala Gly Gly Ala Gly Ala Gly Gly Ala Gly Ala Gly Gly
305                 310                 315                 320

Gly Ala Gly Ala Gly Gly Gly Gly Arg Gly Arg Gly Gly Ser Gly Gly
                325                 330                 335

Arg Gly Arg Gly Gly Ser Gly Gly Arg Gly Arg Gly Gly Ser Gly Gly
            340                 345                 350
```

Arg Arg Gly Arg Gly Arg Glu Arg Ala Arg Gly Ser Arg Glu Arg
            355                 360                 365

Ala Arg Gly Arg Gly Arg Gly Arg Gly Glu Lys Arg Pro Arg Ser Pro
    370                 375                 380

Ser Ser Gln Ser Ser Ser Gly Ser Pro Pro Arg Pro Pro Pro
385                 390                 395                 400

Gly Arg Arg Pro Phe Phe His Pro Val Gly Ala Asp Tyr Phe Glu
                405                 410                 415

Tyr His Gln Glu Gly Gly Pro Asp Gly Glu Pro Asp Val Pro Pro Gly
            420                 425                 430

Ala Ile Glu Gln Gly Pro Ala Asp Asp Pro Gly Glu Gly Pro Ser Thr
        435                 440                 445

Gly Pro Arg Gly Gln Gly Asp Gly Gly Arg Arg Lys Lys Gly Gly Trp
    450                 455                 460

Phe Gly Lys His Arg Gly Gln Gly Gly Ser Asn Pro Lys Phe Glu Asn
465                 470                 475                 480

Ile Ala Glu Gly Leu Arg Ala Leu Leu Ala Arg Ser His Val Glu Arg
                485                 490                 495

Thr Thr Asp Glu Gly Thr Trp Val Ala Gly Val Phe Val Tyr Gly Gly
            500                 505                 510

Ser Lys Thr Ser Leu Tyr Asn Leu Arg Arg Gly Thr Ala Leu Ala Ile
        515                 520                 525

Pro Gln Cys Arg Leu Thr Pro Leu Ser Arg Leu Pro Phe Gly Met Ala
    530                 535                 540

Pro Gly Pro Gly Pro Gln Pro Gly Pro Leu Arg Glu Ser Ile Val Cys
545                 550                 555                 560

Tyr Phe Met Val Phe Leu Gln Thr His Ile Phe Ala Glu Val Leu Lys
                565                 570                 575

Asp Ala Ile Lys Asp Leu Val Met Thr Lys Pro Ala Pro Thr Cys Asn
            580                 585                 590

Ile Arg Val Thr Val Cys Ser Phe Asp Asp Gly Val Asp Leu Pro Pro
        595                 600                 605

Trp Phe Pro Pro Met Val Glu Gly Ala Ala Glu Gly Asp Asp Gly
    610                 615                 620

Asp Asp Gly Asp Glu Gly Gly Asp Gly Asp Glu Gly Glu Glu Gly Gln
625                 630                 635                 640

Glu

<210> SEQ ID NO 58
<211> LENGTH: 321
<212> TYPE: PRT
<213> ORGANISM: Escherichia coli

<400> SEQUENCE: 58

Met Lys Asp Asn Thr Val Pro Leu Lys Leu Ile Ala Leu Leu Ala Asn
1               5                   10                  15

Gly Glu Phe His Ser Gly Glu Gln Leu Gly Glu Thr Leu Gly Met Ser
                20                  25                  30

Arg Ala Ala Ile Asn Lys His Ile Gln Thr Leu Arg Asp Trp Gly Val
            35                  40                  45

Asp Val Phe Thr Val Pro Gly Lys Gly Tyr Ser Leu Pro Glu Pro Ile
        50                  55                  60

Gln Leu Leu Asn Ala Lys Gln Ile Leu Gly Gln Leu Asp Gly Gly Ser
65                  70                  75                  80

-continued

```
Val Ala Val Leu Pro Val Ile Asp Ser Thr Asn Gln Tyr Leu Leu Asp
                85                  90                  95

Arg Ile Gly Glu Leu Lys Ser Gly Asp Ala Cys Ile Ala Glu Tyr Gln
            100                 105                 110

Gln Ala Gly Arg Gly Arg Gly Arg Lys Trp Phe Ser Pro Phe Gly
        115                 120                 125

Ala Asn Leu Tyr Leu Ser Met Phe Trp Arg Leu Glu Gln Gly Pro Ala
    130                 135                 140

Ala Ala Ile Gly Leu Ser Leu Val Ile Gly Ile Val Met Ala Glu Val
145                 150                 155                 160

Leu Arg Lys Leu Gly Ala Asp Lys Val Arg Val Lys Trp Pro Asn Asp
                165                 170                 175

Leu Tyr Leu Gln Asp Arg Lys Leu Ala Gly Ile Leu Val Glu Leu Thr
            180                 185                 190

Gly Lys Thr Gly Asp Ala Ala Gln Ile Val Ile Gly Ala Gly Ile Asn
        195                 200                 205

Met Ala Met Arg Arg Val Glu Glu Ser Val Val Asn Gln Gly Trp Ile
    210                 215                 220

Thr Leu Gln Glu Ala Gly Ile Asn Leu Asp Arg Asn Thr Leu Ala Ala
225                 230                 235                 240

Met Leu Ile Arg Glu Leu Arg Ala Ala Leu Glu Leu Phe Glu Gln Glu
                245                 250                 255

Gly Leu Ala Pro Tyr Leu Ser Arg Trp Glu Lys Leu Asp Asn Phe Ile
            260                 265                 270

Asn Arg Pro Val Lys Leu Ile Ile Gly Asp Lys Glu Ile Phe Gly Ile
        275                 280                 285

Ser Arg Gly Ile Asp Lys Gln Gly Ala Leu Leu Leu Glu Gln Asp Gly
    290                 295                 300

Ile Ile Lys Pro Trp Met Gly Gly Glu Ile Ser Leu Arg Ser Ala Glu
305                 310                 315                 320

Lys
```

<210> SEQ ID NO 59
<211> LENGTH: 373
<212> TYPE: PRT
<213> ORGANISM: Artificial Sequence
<220> FEATURE:
<223> OTHER INFORMATION: an artificially synthesized sequence

<400> SEQUENCE: 59

```
Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Cys Pro Gln Tyr Pro
                20                  25                  30

Gly Ser Glu Ile Leu Trp Gln His Asn Asp Lys Asn Ile Gly Gly Asp
            35                  40                  45

Glu Asp Asp Lys Asn Ile Gly Ser Asp Glu Asp His Leu Ser Leu Lys
        50                  55                  60

Glu Phe Ser Glu Leu Glu Gln Ser Gly Tyr Tyr Val Cys Tyr Pro Arg
65                  70                  75                  80

Gly Ser Lys Pro Glu Asp Ala Asn Phe Tyr Leu Tyr Leu Arg Ala Arg
                85                  90                  95

Val Cys Glu Asn Cys Met Glu Met Asp Asp Ile Glu Gly Arg Met Asp
            100                 105                 110

Pro Lys Ser Cys Asp Lys Thr His Thr Cys Pro Pro Cys Pro Ala Pro
```

```
            115                 120                 125
Glu Leu Leu Gly Gly Pro Ser Val Phe Leu Pro Pro Lys Pro Lys
    130                 135                 140

Asp Thr Leu Met Ile Ser Arg Thr Pro Glu Val Thr Cys Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
                180                 185                 190

Asn Ser Thr Tyr Arg Val Val Ser Val Leu Thr Val Leu His Gln Asp
                195                 200                 205

Trp Leu Asn Gly Lys Glu Tyr Lys Cys Lys Val Ser Asn Lys Ala Leu
    210                 215                 220

Pro Ala Pro Ile Glu Lys Thr Ile Ser Lys Ala Lys Gly Gln Pro Arg
225                 230                 235                 240

Glu Pro Gln Val Cys Thr Leu Pro Pro Ser Arg Asp Glu Leu Thr Lys
                245                 250                 255

Asn Gln Val Ser Leu Trp Cys Leu Val Lys Gly Phe Tyr Pro Ser Asp
                260                 265                 270

Ile Ala Val Glu Trp Glu Ser Asn Gly Gln Pro Glu Asn Asn Tyr Lys
                275                 280                 285

Thr Thr Pro Pro Val Leu Asp Ser Asp Gly Ser Phe Phe Leu Tyr Ser
    290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Gly Ser Gly Gly Ser Gly Gly Asn Leu Tyr
                340                 345                 350

Phe Gln Gly Ser Gly Gly Gly Leu Asn Asp Ile Phe Glu Ala Gln Lys
                355                 360                 365

Ile Glu Trp His Glu
    370

<210> SEQ ID NO 60
<211> LENGTH: 323
<212> TYPE: PRT
<213> ORGANISM: Artificial Sequence
<220> FEATURE:
<223> OTHER INFORMATION: an artificially synthesized sequence

<400> SEQUENCE: 60

Phe Lys Ile Pro Ile Glu Glu Leu Glu Asp Arg Val Phe Val Asn Cys
1               5                   10                  15

Asn Thr Ser Ile Thr Trp Val Glu Gly Thr Val Gly Thr Leu Leu Ser
                20                  25                  30

Asp Ile Thr Arg Leu Asp Leu Gly Lys Arg Ile Leu Asp Pro Arg Gly
                35                  40                  45

Ile Tyr Arg Cys Asn Gly Thr Asp Ile Tyr Lys Asp Lys Glu Ser Thr
    50                  55                  60

Val Gln Val His Tyr Arg Met Cys Gln Ser Cys Val Glu Leu Asp Asp
65                  70                  75                  80

Ile Glu Gly Arg Met Asp Pro Lys Ser Cys Asp Lys Thr His Thr Cys
                85                  90                  95

Pro Pro Cys Pro Ala Pro Glu Leu Leu Gly Gly Pro Ser Val Phe Leu
```

```
            100                 105                 110
Phe Pro Pro Lys Pro Lys Asp Thr Leu Met Ile Ser Arg Thr Pro Glu
            115                 120                 125
Val Thr Cys Val Val Val Asp Val Ser His Glu Asp Pro Glu Val Lys
            130                 135                 140
Phe Asn Trp Tyr Val Asp Gly Val Glu Val His Asn Ala Lys Thr Lys
145                 150                 155                 160
Pro Arg Glu Glu Gln Tyr Asn Ser Thr Tyr Arg Val Val Ser Val Leu
            165                 170                 175
Thr Val Leu His Gln Asp Trp Leu Asn Gly Lys Glu Tyr Lys Cys Lys
            180                 185                 190
Val Ser Asn Lys Ala Leu Pro Ala Pro Ile Glu Lys Thr Ile Ser Lys
            195                 200                 205
Ala Lys Gly Gln Pro Arg Glu Pro Gln Val Tyr Thr Leu Pro Pro Ser
            210                 215                 220
Arg Cys Glu Leu Thr Lys Asn Gln Val Ser Leu Ser Cys Ala Val Lys
225                 230                 235                 240
Gly Phe Tyr Pro Ser Asp Ile Ala Val Glu Trp Glu Ser Asn Gly Gln
            245                 250                 255
Pro Glu Asn Asn Tyr Lys Thr Thr Pro Pro Val Leu Asp Ser Asp Gly
            260                 265                 270
Ser Phe Phe Leu Val Ser Lys Leu Thr Val Asp Lys Ser Arg Trp Gln
            275                 280                 285
Gln Gly Asn Val Phe Ser Cys Ser Val Met His Glu Ala Leu His Asn
            290                 295                 300
His Tyr Thr Gln Lys Ser Leu Ser Leu Ser Pro Asp Tyr Lys Asp Asp
305                 310                 315                 320
Asp Asp Lys

<210> SEQ ID NO 61
<211> LENGTH: 123
<212> TYPE: PRT
<213> ORGANISM: Vicugna pacos

<400> SEQUENCE: 61

Gln Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Asn His Cys
            20                  25                  30
Trp Met Tyr Trp Val Arg Gln Ala Pro Gly Lys Gly Leu Glu Trp Val
            35                  40                  45
Ser Val Ile Asn Thr Asp Gly Gly Ser Ala Tyr Tyr Ala Asp Ser Val
            50                  55                  60
Lys Gly Arg Phe Thr Ile Ser Arg Asp Asn Ala Lys Asn Thr Leu Tyr
65                  70                  75                  80
Leu Gln Met Asn Ser Leu Lys Ser Glu Asp Thr Ala Val Tyr Tyr Cys
            85                  90                  95
Ala Arg Asp Trp Ala Pro Leu Val Asp Tyr Tyr Tyr Gly Met Asp Tyr
            100                 105                 110
Trp Gly Lys Gly Thr Leu Val Thr Val Ser Gly
            115                 120

<210> SEQ ID NO 62
<211> LENGTH: 121
<212> TYPE: PRT
```

<213> ORGANISM: Vicugna pacos

<400> SEQUENCE: 62

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Phe Asp Asn Tyr
            20                  25                  30

Val Met Ser Trp Val Arg Gln Ala Pro Gly Lys Gly Leu Glu Trp Ile
        35                  40                  45

Ser Ala Ile Ser Trp Asn Gly Gly Ser Thr Tyr Tyr Ala Glu Ser Met
    50                  55                  60

Lys Gly Arg Phe Thr Ile Ser Arg Asp Asn Ala Lys Ser Thr Leu Tyr
65                  70                  75                  80

Leu Gln Met Asn Ser Leu Lys Ser Glu Asp Thr Ala Val Tyr Tyr Cys
                85                  90                  95

Ala Lys Glu Pro Arg Val Tyr Tyr Ser Gly Ser Pro Asp Tyr Trp Gly
            100                 105                 110

Gln Gly Thr Gln Val Thr Val Ser Gly
        115                 120

<210> SEQ ID NO 63
<211> LENGTH: 118
<212> TYPE: PRT
<213> ORGANISM: Vicugna pacos

<400> SEQUENCE: 63

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Val Tyr
            20                  25                  30

Gly Met Ser Trp Val Arg His Ser Pro Gly Lys Gly Leu Glu Trp Val
        35                  40                  45

Ser Thr Ile Asn Trp Asn Gly Ser Thr Tyr Tyr Ala Glu Ser Met
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Lys Phe Ala Pro Trp Asp Gly Asp Met Glu Trp Gly Gln Gly Thr
            100                 105                 110

Gln Val Thr Val Ser Gly
        115

<210> SEQ ID NO 64
<211> LENGTH: 469
<212> TYPE: PRT
<213> ORGANISM: Artificial Sequence
<220> FEATURE:
<223> OTHER INFORMATION: an artificially synthesized sequence

<400> SEQUENCE: 64

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn His Cys
            20                  25                  30

Trp Met Tyr Trp Val Arg Gln Ala Pro Gly Lys Gly Leu Glu Trp Val
        35                  40                  45

```
Ser Val Ile Asn Thr Asp Gly Gly Ser Ala Tyr Tyr Ala Asp Ser Val
 50                  55                  60
Lys Gly Arg Phe Thr Ile Ser Arg Asp Asn Ala Lys Asn Thr Leu Tyr
 65                  70                  75                  80
Leu Gln Met Asn Ser Leu Lys Ser Glu Asp Thr Ala Val Tyr Tyr Cys
                 85                  90                  95
Ala Arg Asp Trp Ala Pro Leu Val Asp Tyr Tyr Gly Met Asp Tyr
                100                 105                 110
Trp Gly Lys Gly Thr Leu Val Thr Val Ser Gly Gly Ser Gly Leu Ser
                115                 120                 125
Gly Arg Ser Asp Asn His Gly Ser Ser Gly Ser Ser Ala Ser Thr
130                 135                 140
Lys Gly Pro Ser Val Phe Pro Leu Ala Pro Ser Ser Lys Ser Thr Ser
145                 150                 155                 160
Gly Gly Thr Ala Ala Leu Gly Cys Leu Val Lys Asp Tyr Phe Pro Glu
                165                 170                 175
Pro Val Thr Val Ser Trp Asn Ser Gly Ala Leu Thr Ser Gly Val His
                180                 185                 190
Thr Phe Pro Ala Val Leu Gln Ser Ser Gly Leu Tyr Ser Leu Ser Ser
                195                 200                 205
Val Val Thr Val Pro Ser Ser Ser Leu Gly Thr Gln Thr Tyr Ile Cys
                210                 215                 220
Asn Val Asn His Lys Pro Ser Asn Thr Lys Val Asp Lys Lys Val Glu
225                 230                 235                 240
Pro Lys Ser Cys Asp Lys Thr His Thr Cys Pro Pro Cys Pro Ala Pro
                245                 250                 255
Glu Leu Leu Gly Gly Pro Ser Val Phe Leu Phe Pro Pro Lys Pro Lys
                260                 265                 270
Asp Thr Leu Met Ile Ser Arg Thr Pro Glu Val Thr Cys Val Val Val
                275                 280                 285
Asp Val Ser His Glu Asp Pro Glu Val Lys Phe Asn Trp Tyr Val Asp
                290                 295                 300
Gly Val Glu Val His Asn Ala Lys Thr Lys Pro Arg Glu Glu Gln Tyr
305                 310                 315                 320
Asn Ser Thr Tyr Arg Val Val Ser Val Leu Thr Val Leu His Gln Asp
                325                 330                 335
Trp Leu Asn Gly Lys Glu Tyr Lys Cys Lys Val Ser Asn Lys Ala Leu
                340                 345                 350
Pro Ala Pro Ile Glu Lys Thr Ile Ser Lys Ala Lys Gly Gln Pro Arg
                355                 360                 365
Glu Pro Gln Val Tyr Thr Leu Pro Pro Ser Arg Glu Glu Met Thr Lys
                370                 375                 380
Asn Gln Val Ser Leu Thr Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Val Leu Asp Ser Asp Gly Ser Phe Phe Leu Tyr Ser
                420                 425                 430
Lys Leu Thr Val Asp Lys Ser Arg Trp Gln Gln Gly Asn Val Phe Ser
                435                 440                 445
Cys Ser Val Met His Glu Ala Leu His Asn His Tyr Thr Gln Lys Ser
450                 455                 460

Leu Ser Leu Ser Pro
```

<210> SEQ ID NO 65
<211> LENGTH: 467
<212> TYPE: PRT
<213> ORGANISM: Artificial Sequence
<220> FEATURE:
<223> OTHER INFORMATION: an artificially synthesized sequence

<400> SEQUENCE: 65

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Phe Asp Asn Tyr
            20                  25                  30

Val Met Ser Trp Val Arg Gln Ala Pro Gly Lys Gly Leu Glu Trp Ile
        35                  40                  45

Ser Ala Ile Ser Trp Asn Gly Gly Ser Thr Tyr Tyr Ala Glu Ser Met
    50                  55                  60

Lys Gly Arg Phe Thr Ile Ser Arg Asp Asn Ala Lys Ser Thr Leu Tyr
65                  70                  75                  80

Leu Gln Met Asn Ser Leu Lys Ser Glu Asp Thr Ala Val Tyr Tyr Cys
                85                  90                  95

Ala Lys Glu Pro Arg Val Tyr Tyr Ser Gly Ser Pro Asp Tyr Trp Gly
            100                 105                 110

Gln Gly Thr Gln Val Thr Val Ser Gly Gly Ser Gly Leu Ser Gly Arg
        115                 120                 125

Ser Asp Asn His Gly Ser Ser Gly Gly Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
```

```
                355                 360                 365
Gln Val Tyr Thr Leu Pro Pro Ser Arg Glu Glu Met Thr Lys Asn Gln
            370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
            450                 455                 460

Leu Ser Pro
465

<210> SEQ ID NO 66
<211> LENGTH: 464
<212> TYPE: PRT
<213> ORGANISM: Artificial Sequence
<220> FEATURE:
<223> OTHER INFORMATION: an artificially synthesized sequence

<400> SEQUENCE: 66

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Val Tyr
            20                  25                  30

Gly Met Ser Trp Val Arg His Ser Pro Gly Lys Gly Leu Glu Trp Val
        35                  40                  45

Ser Thr Ile Asn Trp Asn Gly Gly Ser Thr Tyr Tyr Ala Glu Ser Met
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Lys Phe Ala Pro Trp Asp Gly Asp Met Glu Trp Gly Gln Gly Thr
            100                 105                 110

Gln Val Thr Val Ser Gly Gly Ser Gly Leu Ser Gly Arg Ser Asp Asn
        115                 120                 125

His Gly Ser Ser Gly Gly Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
```

-continued

```
                245                 250                 255
Pro Ser Val Phe Leu Phe Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

<210> SEQ ID NO 67
<211> LENGTH: 222
<212> TYPE: PRT
<213> ORGANISM: Artificial Sequence
<220> FEATURE:
<223> OTHER INFORMATION: an artificially synthesized sequence

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Phe Asp Ser Tyr Pro Leu
                85                  90                  95

Thr Phe Gly Gly Gly Thr Lys Val Glu Leu Ser Gly Arg Ser Asp Asn
            100                 105                 110

His Ile Lys Arg Thr Val Ala Ala Pro Ser Val Phe Ile Phe Pro Pro
        115                 120                 125

Ser Asp Glu Gln Leu Lys Ser Gly Thr Ala Ser Val Val Cys Leu Leu
    130                 135                 140

Asn Asn Phe Tyr Pro Arg Glu Ala Lys Val Gln Trp Lys Val Asp Asn
```

```
145                 150                 155                 160
Ala Leu Gln Ser Gly Asn Ser Gln Glu Ser Val Thr Glu Gln Asp Ser
                165                 170                 175

Lys Asp Ser Thr Tyr Ser Leu Ser Thr Leu Thr Leu Ser Lys Ala
            180                 185                 190

Asp Tyr Glu Lys His Lys Val Tyr Ala Cys Glu Val Thr His Gln Gly
            195                 200                 205

Leu Ser Ser Pro Val Thr Lys Ser Phe Asn Arg Gly Glu Cys
        210                 215                 220

<210> SEQ ID NO 68
<211> LENGTH: 222
<212> TYPE: PRT
<213> ORGANISM: Artificial Sequence
<220> FEATURE:
<223> OTHER INFORMATION: an artificially synthesized sequence

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Phe Asp Ser Tyr Pro Leu
                85                  90                  95

Thr Phe Gly Gly Gly Thr Lys Val Glu Ile Leu Ser Gly Arg Ser Asp
            100                 105                 110

Asn His Lys Arg Thr Val Ala Ala Pro Ser Val Phe Ile Phe Pro Pro
        115                 120                 125

Ser Asp Glu Gln Leu Lys Ser Gly Thr Ala Ser Val Val Cys Leu Leu
    130                 135                 140

Asn Asn Phe Tyr Pro Arg Glu Ala Lys Val Gln Trp Lys Val Asp Asn
145                 150                 155                 160

Ala Leu Gln Ser Gly Asn Ser Gln Glu Ser Val Thr Glu Gln Asp Ser
                165                 170                 175

Lys Asp Ser Thr Tyr Ser Leu Ser Thr Leu Thr Leu Ser Lys Ala
            180                 185                 190

Asp Tyr Glu Lys His Lys Val Tyr Ala Cys Glu Val Thr His Gln Gly
            195                 200                 205

Leu Ser Ser Pro Val Thr Lys Ser Phe Asn Arg Gly Glu Cys
        210                 215                 220

<210> SEQ ID NO 69
<211> LENGTH: 222
<212> TYPE: PRT
<213> ORGANISM: Artificial Sequence
<220> FEATURE:
<223> OTHER INFORMATION: an artificially synthesized sequence

<400> SEQUENCE: 69

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Phe Asp Ser Tyr Pro Leu
                 85                  90                  95

Thr Phe Gly Gly Gly Thr Lys Val Glu Ile Lys Leu Ser Gly Arg Ser
             100                 105                 110

Asp Asn His Arg Thr Val Ala Ala Pro Ser Val Phe Ile Phe Pro Pro
         115                 120                 125

Ser Asp Glu Gln Leu Lys Ser Gly Thr Ala Ser Val Val Cys Leu Leu
     130                 135                 140

Asn Asn Phe Tyr Pro Arg Glu Ala Lys Val Gln Trp Lys Val Asp Asn
145                 150                 155                 160

Ala Leu Gln Ser Gly Asn Ser Gln Glu Ser Val Thr Glu Gln Asp Ser
                 165                 170                 175

Lys Asp Ser Thr Tyr Ser Leu Ser Ser Thr Leu Thr Leu Ser Lys Ala
             180                 185                 190

Asp Tyr Glu Lys His Lys Val Tyr Ala Cys Glu Val Thr His Gln Gly
         195                 200                 205

Leu Ser Ser Pro Val Thr Lys Ser Phe Asn Arg Gly Glu Cys
     210                 215                 220

<210> SEQ ID NO 70
<211> LENGTH: 222
<212> TYPE: PRT
<213> ORGANISM: Artificial Sequence
<220> FEATURE:
<223> OTHER INFORMATION: an artificially synthesized sequence

<400> SEQUENCE: 70

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Phe Asp Ser Tyr Pro Leu
                 85                  90                  95

Thr Phe Gly Gly Gly Thr Lys Val Glu Ile Lys Arg Thr Leu Ser Gly
             100                 105                 110

Arg Ser Asp Asn His Val Ala Ala Pro Ser Val Phe Ile Phe Pro Pro
         115                 120                 125

Ser Asp Glu Gln Leu Lys Ser Gly Thr Ala Ser Val Val Cys Leu Leu
     130                 135                 140

Asn Asn Phe Tyr Pro Arg Glu Ala Lys Val Gln Trp Lys Val Asp Asn
145                 150                 155                 160
```

```
Ala Leu Gln Ser Gly Asn Ser Gln Glu Ser Val Thr Glu Gln Asp Ser
                165                 170                 175

Lys Asp Ser Thr Tyr Ser Leu Ser Thr Leu Thr Leu Ser Lys Ala
            180                 185                 190

Asp Tyr Glu Lys His Lys Val Tyr Ala Cys Glu Val Thr His Gln Gly
        195                 200                 205

Leu Ser Ser Pro Val Thr Lys Ser Phe Asn Arg Gly Glu Cys
    210                 215                 220

<210> SEQ ID NO 71
<211> LENGTH: 222
<212> TYPE: PRT
<213> ORGANISM: Artificial Sequence
<220> FEATURE:
<223> OTHER INFORMATION: an artificially synthesized sequence

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Phe Asp Ser Tyr Pro Leu
                85                  90                  95

Thr Phe Gly Gly Gly Thr Lys Val Glu Ile Lys Arg Thr Val Leu Ser
            100                 105                 110

Gly Arg Ser Asp Asn His Ala Ala Pro Ser Val Phe Ile Phe Pro Pro
        115                 120                 125

Ser Asp Glu Gln Leu Lys Ser Gly Thr Ala Ser Val Val Cys Leu Leu
    130                 135                 140

Asn Asn Phe Tyr Pro Arg Glu Ala Lys Val Gln Trp Lys Val Asp Asn
145                 150                 155                 160

Ala Leu Gln Ser Gly Asn Ser Gln Glu Ser Val Thr Glu Gln Asp Ser
                165                 170                 175

Lys Asp Ser Thr Tyr Ser Leu Ser Thr Leu Thr Leu Ser Lys Ala
            180                 185                 190

Asp Tyr Glu Lys His Lys Val Tyr Ala Cys Glu Val Thr His Gln Gly
        195                 200                 205

Leu Ser Ser Pro Val Thr Lys Ser Phe Asn Arg Gly Glu Cys
    210                 215                 220

<210> SEQ ID NO 72
<211> LENGTH: 222
<212> TYPE: PRT
<213> ORGANISM: Artificial Sequence
<220> FEATURE:
<223> OTHER INFORMATION: an artificially synthesized sequence

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30
```

```
Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Phe Asp Ser Tyr Pro Leu
                 85                  90                  95

Thr Phe Gly Gly Gly Thr Lys Val Glu Ile Lys Arg Thr Val Ala Leu
             100                 105                 110

Ser Gly Arg Ser Asp Asn His Ala Pro Ser Val Phe Ile Phe Pro Pro
         115                 120                 125

Ser Asp Glu Gln Leu Lys Ser Gly Thr Ala Ser Val Val Cys Leu Leu
130                 135                 140

Asn Asn Phe Tyr Pro Arg Glu Ala Lys Val Gln Trp Lys Val Asp Asn
145                 150                 155                 160

Ala Leu Gln Ser Gly Asn Ser Gln Glu Ser Val Thr Glu Gln Asp Ser
                 165                 170                 175

Lys Asp Ser Thr Tyr Ser Leu Ser Ser Thr Leu Thr Leu Ser Lys Ala
             180                 185                 190

Asp Tyr Glu Lys His Lys Val Tyr Ala Cys Glu Val Thr His Gln Gly
         195                 200                 205

Leu Ser Ser Pro Val Thr Lys Ser Phe Asn Arg Gly Glu Cys
210                 215                 220

<210> SEQ ID NO 73
<211> LENGTH: 222
<212> TYPE: PRT
<213> ORGANISM: Artificial Sequence
<220> FEATURE:
<223> OTHER INFORMATION: an artificially synthesized sequence

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Phe Asp Ser Tyr Pro Leu
                 85                  90                  95

Thr Phe Gly Gly Gly Thr Lys Val Glu Ile Lys Arg Thr Val Ala Ala
             100                 105                 110

Leu Ser Gly Arg Ser Asp Asn His Pro Ser Val Phe Ile Phe Pro Pro
         115                 120                 125

Ser Asp Glu Gln Leu Lys Ser Gly Thr Ala Ser Val Val Cys Leu Leu
130                 135                 140

Asn Asn Phe Tyr Pro Arg Glu Ala Lys Val Gln Trp Lys Val Asp Asn
145                 150                 155                 160

Ala Leu Gln Ser Gly Asn Ser Gln Glu Ser Val Thr Glu Gln Asp Ser
                 165                 170                 175
```

```
Lys Asp Ser Thr Tyr Ser Leu Ser Ser Thr Leu Thr Leu Ser Lys Ala
            180                 185                 190

Asp Tyr Glu Lys His Lys Val Tyr Ala Cys Glu Val Thr His Gln Gly
        195                 200                 205

Leu Ser Ser Pro Val Thr Lys Ser Phe Asn Arg Gly Glu Cys
    210                 215                 220

<210> SEQ ID NO 74
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 74

Thr Ser Thr Ser Gly Arg Ser Ala Asn Pro Arg Gly
1               5                   10

<210> SEQ ID NO 75
<211> LENGTH: 13
<212> TYPE: PRT
<213> ORGANISM: Artificial Sequence
<220> FEATURE:
<223> OTHER INFORMATION: an artificially synthesized sequence

<400> SEQUENCE: 75

Ile Ser Ser Gly Leu Leu Ser Gly Arg Ser Asp Asn His
1               5                   10

<210> SEQ ID NO 76
<211> LENGTH: 18
<212> TYPE: PRT
<213> ORGANISM: Artificial Sequence
<220> FEATURE:
<223> OTHER INFORMATION: an artificially synthesized sequence

<400> SEQUENCE: 76

Ala Val Gly Leu Leu Ala Pro Pro Gly Gly Leu Ser Gly Arg Ser Asp
1               5                   10                  15

Asn His

<210> SEQ ID NO 77
<211> LENGTH: 13
<212> TYPE: PRT
<213> ORGANISM: Artificial Sequence
<220> FEATURE:
<223> OTHER INFORMATION: an artificially synthesized sequence

<400> SEQUENCE: 77

Gly Ala Gly Val Pro Met Ser Met Arg Gly Gly Ala Gly
1               5                   10

<210> SEQ ID NO 78
<211> LENGTH: 13
<212> TYPE: PRT
<213> ORGANISM: Artificial Sequence
<220> FEATURE:
<223> OTHER INFORMATION: an artificially synthesized sequence

<400> SEQUENCE: 78

Gly Ala Gly Ile Pro Val Ser Leu Arg Ser Gly Ala Gly
1               5                   10

<210> SEQ ID NO 79
```

```
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 79

Gly Pro Leu Gly Ile Ala Gly Gln
1               5

<210> SEQ ID NO 80
<211> LENGTH: 10
<212> TYPE: PRT
<213> ORGANISM: Artificial Sequence
<220> FEATURE:
<223> OTHER INFORMATION: an artificially synthesized sequence

<400> SEQUENCE: 80

Gly Gly Pro Leu Gly Met Leu Ser Gln Ser
1               5                   10

<210> SEQ ID NO 81
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 81

Pro Leu Gly Leu Trp Ala
1               5

<210> SEQ ID NO 82
<211> LENGTH: 13
<212> TYPE: PRT
<213> ORGANISM: Artificial Sequence
<220> FEATURE:
<223> OTHER INFORMATION: an artificially synthesized sequence

<400> SEQUENCE: 82

Gly Ala Gly Arg Pro Phe Ser Met Ile Met Gly Ala Gly
1               5                   10

<210> SEQ ID NO 83
<211> LENGTH: 13
<212> TYPE: PRT
<213> ORGANISM: Artificial Sequence
<220> FEATURE:
<223> OTHER INFORMATION: an artificially synthesized sequence

<400> SEQUENCE: 83

Gly Ala Gly Val Pro Leu Ser Leu Thr Met Gly Ala Gly
1               5                   10

<210> SEQ ID NO 84
<211> LENGTH: 13
<212> TYPE: PRT
<213> ORGANISM: Artificial Sequence
<220> FEATURE:
<223> OTHER INFORMATION: an artificially synthesized sequence

<400> SEQUENCE: 84

Gly Ala Gly Val Pro Leu Ser Leu Tyr Ser Gly Ala Gly
1               5                   10

<210> SEQ ID NO 85
<211> LENGTH: 6
```

```
<212> TYPE: PRT
<213> ORGANISM: Artificial Sequence
<220> FEATURE:
<223> OTHER INFORMATION: an artificially synthesized sequence

<400> SEQUENCE: 85

Ala Ala Asn Leu Arg Asn
1               5

<210> SEQ ID NO 86
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 86

Ala Gln Ala Tyr Val Lys
1               5

<210> SEQ ID NO 87
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 87

Ala Ala Asn Tyr Met Arg
1               5

<210> SEQ ID NO 88
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 88

Ala Ala Ala Leu Thr Arg
1               5

<210> SEQ ID NO 89
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 89

Ala Gln Asn Leu Met Arg
1               5

<210> SEQ ID NO 90
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 90

Ala Ala Asn Tyr Thr Lys
1               5

<210> SEQ ID NO 91
<211> LENGTH: 16
<212> TYPE: PRT
```

<213> ORGANISM: Artificial Sequence
<220> FEATURE:
<223> OTHER INFORMATION: an artificially synthesized sequence

<400> SEQUENCE: 91

```
Gly Ala Gly Pro Gln Gly Leu Ala Gly Gln Arg Gly Ile Val Ala Gly
1               5                   10                  15
```

<210> SEQ ID NO 92
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 92

```
Pro Arg Phe Lys Ile Ile Gly Gly
1               5
```

<210> SEQ ID NO 93
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 93

```
Pro Arg Phe Arg Ile Ile Gly Gly
1               5
```

<210> SEQ ID NO 94
<211> LENGTH: 9
<212> TYPE: PRT
<213> ORGANISM: Artificial Sequence
<220> FEATURE:
<223> OTHER INFORMATION: an artificially synthesized sequence

<400> SEQUENCE: 94

```
Gly Ala Gly Ser Gly Arg Ser Ala Gly
1               5
```

<210> SEQ ID NO 95
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 95

```
Ser Gly Arg Ser Ala
1               5
```

<210> SEQ ID NO 96
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 96

```
Gly Ser Gly Arg Ser Ala
1               5
```

<210> SEQ ID NO 97
<211> LENGTH: 5
<212> TYPE: PRT
<213> ORGANISM: Artificial Sequence

```
<220> FEATURE:
<223> OTHER INFORMATION: an artificially synthesized sequence

<400> SEQUENCE: 97

Ser Gly Lys Ser Ala
1               5

<210> SEQ ID NO 98
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 98

Ser Gly Arg Ser Ser
1               5

<210> SEQ ID NO 99
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 99

Ser Gly Arg Arg Ala
1               5

<210> SEQ ID NO 100
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 100

Ser Gly Arg Asn Ala
1               5

<210> SEQ ID NO 101
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 101

Ser Gly Arg Lys Ala
1               5

<210> SEQ ID NO 102
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 102

Gln Arg Gly Arg Ser Ala
1               5

<210> SEQ ID NO 103
<211> LENGTH: 17
<212> TYPE: PRT
<213> ORGANISM: Artificial Sequence
<220> FEATURE:
```

<223> OTHER INFORMATION: an artificially synthesized sequence

<400> SEQUENCE: 103

Gly Ala Gly Ser Leu Leu Lys Ser Arg Met Val Pro Asn Phe Asn Ala
1               5                   10                  15
Gly

<210> SEQ ID NO 104
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 104

Thr Gln Gly Ala Ala Ala
1               5

<210> SEQ ID NO 105
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 105

Gly Ala Ala Ala Ala Ala
1               5

<210> SEQ ID NO 106
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 106

Gly Ala Gly Ala Ala Gly
1               5

<210> SEQ ID NO 107
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 107

Ala Ala Ala Ala Ala Gly
1               5

<210> SEQ ID NO 108
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 108

Leu Cys Gly Ala Ala Ile
1               5

<210> SEQ ID NO 109
<211> LENGTH: 6
<212> TYPE: PRT
<213> ORGANISM: Artificial Sequence

```
<220> FEATURE:
<223> OTHER INFORMATION: an artificially synthesized sequence

<400> SEQUENCE: 109

Phe Ala Gln Ala Leu Gly
1               5

<210> SEQ ID NO 110
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 110

Leu Leu Gln Ala Asn Pro
1               5

<210> SEQ ID NO 111
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 111

Leu Ala Ala Ala Asn Pro
1               5

<210> SEQ ID NO 112
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 112

Leu Tyr Gly Ala Gln Phe
1               5

<210> SEQ ID NO 113
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 113

Leu Ser Gln Ala Gln Gly
1               5

<210> SEQ ID NO 114
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 114

Ala Ser Ala Ala Ser Gly
1               5

<210> SEQ ID NO 115
<211> LENGTH: 6
<212> TYPE: PRT
<213> ORGANISM: Artificial Sequence
<220> FEATURE:
```

```
<223> OTHER INFORMATION: an artificially synthesized sequence

<400> SEQUENCE: 115

Phe Leu Gly Ala Ser Leu
1               5

<210> SEQ ID NO 116
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 116

Ala Tyr Gly Ala Thr Gly
1               5

<210> SEQ ID NO 117
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 117

Leu Ala Gln Ala Thr Gly
1               5

<210> SEQ ID NO 118
<211> LENGTH: 17
<212> TYPE: PRT
<213> ORGANISM: Artificial Sequence
<220> FEATURE:
<223> OTHER INFORMATION: an artificially synthesized sequence

<400> SEQUENCE: 118

Gly Ala Gly Ser Gly Val Val Ile Ala Thr Val Ile Val Ile Thr Ala
1               5                   10                  15

Gly

<210> SEQ ID NO 119
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 119

Ala Pro Met Ala Glu Gly Gly Gly
1               5

<210> SEQ ID NO 120
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 120

Glu Ala Gln Gly Asp Lys Ile Ile
1               5

<210> SEQ ID NO 121
<211> LENGTH: 8
<212> TYPE: PRT
<213> ORGANISM: Artificial Sequence
```

```
<220> FEATURE:
<223> OTHER INFORMATION: an artificially synthesized sequence

<400> SEQUENCE: 121

Leu Ala Phe Ser Asp Ala Gly Pro
1               5

<210> SEQ ID NO 122
<211> LENGTH: 7
<212> TYPE: PRT
<213> ORGANISM: Artificial Sequence
<220> FEATURE:
<223> OTHER INFORMATION: an artificially synthesized sequence

<400> SEQUENCE: 122

Tyr Val Ala Asp Ala Pro Lys
1               5

<210> SEQ ID NO 123
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 123

Arg Arg Arg Arg Arg
1               5

<210> SEQ ID NO 124
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 124

Arg Arg Arg Arg Arg Arg
1               5

<210> SEQ ID NO 125
<211> LENGTH: 10
<212> TYPE: PRT
<213> ORGANISM: Artificial Sequence
<220> FEATURE:
<223> OTHER INFORMATION: an artificially synthesized sequence

<400> SEQUENCE: 125

Gly Gln Ser Ser Arg His Arg Arg Ala Leu
1               5                   10

<210> SEQ ID NO 126
<211> LENGTH: 9
<212> TYPE: PRT
<213> ORGANISM: Artificial Sequence
<220> FEATURE:
<223> OTHER INFORMATION: an artificially synthesized sequence

<400> SEQUENCE: 126

Ser Ser Arg His Arg Arg Ala Leu Asp
1               5

<210> SEQ ID NO 127
<211> LENGTH: 14
<212> TYPE: PRT
<213> ORGANISM: Artificial Sequence
<220> FEATURE:
```

```
<223> OTHER INFORMATION: an artificially synthesized sequence

<400> SEQUENCE: 127

Arg Lys Ser Ser Ile Ile Ile Arg Met Arg Asp Val Val Leu
1               5                   10

<210> SEQ ID NO 128
<211> LENGTH: 15
<212> TYPE: PRT
<213> ORGANISM: Artificial Sequence
<220> FEATURE:
<223> OTHER INFORMATION: an artificially synthesized sequence

<400> SEQUENCE: 128

Ser Ser Ser Phe Asp Lys Gly Lys Tyr Lys Lys Gly Asp Asp Ala
1               5                   10                  15

<210> SEQ ID NO 129
<211> LENGTH: 15
<212> TYPE: PRT
<213> ORGANISM: Artificial Sequence
<220> FEATURE:
<223> OTHER INFORMATION: an artificially synthesized sequence

<400> SEQUENCE: 129

Ser Ser Ser Phe Asp Lys Gly Lys Tyr Lys Arg Gly Asp Asp Ala
1               5                   10                  15

<210> SEQ ID NO 130
<211> LENGTH: 4
<212> TYPE: PRT
<213> ORGANISM: Artificial Sequence
<220> FEATURE:
<223> OTHER INFORMATION: an artificially synthesized sequence

<400> SEQUENCE: 130

Ile Glu Gly Arg
1

<210> SEQ ID NO 131
<211> LENGTH: 4
<212> TYPE: PRT
<213> ORGANISM: Artificial Sequence
<220> FEATURE:
<223> OTHER INFORMATION: an artificially synthesized sequence

<400> SEQUENCE: 131

Ile Asp Gly Arg
1

<210> SEQ ID NO 132
<211> LENGTH: 7
<212> TYPE: PRT
<213> ORGANISM: Artificial Sequence
<220> FEATURE:
<223> OTHER INFORMATION: an artificially synthesized sequence

<400> SEQUENCE: 132

Gly Gly Ser Ile Asp Gly Arg
1               5

<210> SEQ ID NO 133
<211> LENGTH: 8
<212> TYPE: PRT
<213> ORGANISM: Artificial Sequence
<220> FEATURE:
<223> OTHER INFORMATION: an artificially synthesized sequence
```

```
<400> SEQUENCE: 133

Gly Pro Gln Gly Ile Ala Gly Gln
1               5

<210> SEQ ID NO 134
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 134

Gly Pro Gln Gly Leu Leu Gly Ala
1               5

<210> SEQ ID NO 135
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 135

Gly Ile Ala Gly Gln
1               5

<210> SEQ ID NO 136
<211> LENGTH: 7
<212> TYPE: PRT
<213> ORGANISM: Artificial Sequence
<220> FEATURE:
<223> OTHER INFORMATION: an artificially synthesized sequence

<400> SEQUENCE: 136

Gly Pro Leu Gly Ile Ala Gly
1               5

<210> SEQ ID NO 137
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 137

Gly Pro Glu Gly Leu Arg Val Gly
1               5

<210> SEQ ID NO 138
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 138

Tyr Gly Ala Gly Leu Gly Val Val
1               5

<210> SEQ ID NO 139
<211> LENGTH: 8
<212> TYPE: PRT
<213> ORGANISM: Artificial Sequence
<220> FEATURE:
<223> OTHER INFORMATION: an artificially synthesized sequence
```

```
<400> SEQUENCE: 139

Ala Gly Leu Gly Val Val Glu Arg
1               5

<210> SEQ ID NO 140
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 140

Ala Gly Leu Gly Ile Ser Ser Thr
1               5

<210> SEQ ID NO 141
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 141

Glu Pro Gln Ala Leu Ala Met Ser
1               5

<210> SEQ ID NO 142
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 142

Gln Ala Leu Ala Met Ser Ala Ile
1               5

<210> SEQ ID NO 143
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 143

Ala Ala Tyr His Leu Val Ser Gln
1               5

<210> SEQ ID NO 144
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 144

Met Asp Ala Phe Leu Glu Ser Ser
1               5

<210> SEQ ID NO 145
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 145
```

Glu Ser Leu Pro Val Val Ala Val
1               5

<210> SEQ ID NO 146
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 146

Ser Ala Pro Ala Val Glu Ser Glu
1               5

<210> SEQ ID NO 147
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 147

Asp Val Ala Gln Phe Val Leu Thr
1               5

<210> SEQ ID NO 148
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 148

Val Ala Gln Phe Val Leu Thr Glu
1               5

<210> SEQ ID NO 149
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 149

Ala Gln Phe Val Leu Thr Glu Gly
1               5

<210> SEQ ID NO 150
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 150

Pro Val Gln Pro Ile Gly Pro Gln
1               5

<210> SEQ ID NO 151
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 151

```
Leu Val Pro Arg Gly Ser
1               5
```

<210> SEQ ID NO 152
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 152

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Phe Asp Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ala
    210
```

<210> SEQ ID NO 153
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 153

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80
```

Lys His Lys Val Tyr Ala Cys Glu Val Thr His Gln Gly Leu Ser Ser
                85                  90                  95

Pro Val Thr Lys Ser Phe Asn Arg Gly Glu Ala
            100                 105

<210> SEQ ID NO 154
<211> LENGTH: 464
<212> TYPE: PRT
<213> ORGANISM: Artificial Sequence
<220> FEATURE:
<223> OTHER INFORMATION: an artificially synthesized sequence

<400> SEQUENCE: 154

Gln Leu Gln Leu Val Glu Ser Gly Gly Gly Leu Val Gln Pro Gly Gly
1               5                   10                  15

Ser Leu Arg Leu Ser Cys Thr Ala Ser Gly Ile Ser Phe Ser Ile Ser
            20                  25                  30

Thr Met Gly Trp Tyr Arg Gln Ala Pro Gly Lys Gln Arg Glu Leu Val
        35                  40                  45

Ala Thr Ile Thr Ser Gly Gly Glu Ala Tyr Tyr Ala Asn Ser Met Lys
    50                  55                  60

Asp Arg Phe Thr Ile Ser Arg Asp Asn Ala Glu Asn Thr Val Tyr Leu
65                  70                  75                  80

Gln Met Asn Arg Leu Lys Pro Glu Asp Ser Ala Val Tyr Tyr Cys Asn
                85                  90                  95

Thr Lys Phe Pro Trp Ser Thr Asp Trp Asp Ser Arg Gly Gln Gly Thr
            100                 105                 110

Gln Val Thr Val Ser Gly Gly Ser Gly Leu Ser Gly Arg Ser Asp Asn
        115                 120                 125

His Gly Ser Ser Gly Gly Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

```
Glu Tyr Lys Cys Lys Val Ser Asn Lys Ala Leu Pro Ala Pro Ile Glu
                340                 345                 350

Lys Thr Ile Ser Lys Ala Lys Gly Gln Pro Arg Glu Pro Gln Val Tyr
            355                 360                 365

Thr Leu Pro Pro Ser Arg Glu Glu Met Thr Lys Asn Gln Val Ser Leu
        370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

<210> SEQ ID NO 155
<211> LENGTH: 464
<212> TYPE: PRT
<213> ORGANISM: Artificial Sequence
<220> FEATURE:
<223> OTHER INFORMATION: an artificially synthesized sequence

<400> SEQUENCE: 155

Gln Val Gln Leu Val Glu Ser Gly Gly Gly Leu Val Gln Pro Gly Gly
1               5                   10                  15

Ser Leu Arg Leu Ser Cys Thr Ala Ser Gly Ile Ser Phe Ser Ile Ser
            20                  25                  30

Thr Met Gly Trp Tyr Arg Gln Ala Pro Gly Lys Gln Arg Glu Leu Val
        35                  40                  45

Ala Thr Ile Thr Ser Gly Gly Glu Ala Tyr Tyr Ala Asn Ser Met Lys
    50                  55                  60

Asp Arg Phe Thr Ile Ser Arg Asp Asn Ala Glu Asn Thr Val Tyr Leu
65                  70                  75                  80

Gln Met Asn Arg Leu Lys Pro Glu Asp Ser Ala Val Tyr Tyr Cys Asn
                85                  90                  95

Thr Lys Phe Pro Trp Ser Thr Asp Trp Asp Ser Arg Gly Gln Gly Thr
            100                 105                 110

Gln Val Thr Val Ser Gly Gly Ser Gly Leu Ser Gly Arg Ser Asp Asn
        115                 120                 125

His Gly Ser Ser Gly Gly Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240
```

Lys Thr His Thr Cys Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

<210> SEQ ID NO 156
<211> LENGTH: 464
<212> TYPE: PRT
<213> ORGANISM: Artificial Sequence
<220> FEATURE:
<223> OTHER INFORMATION: an artificially synthesized sequence

<400> SEQUENCE: 156

Gln Val Gln Leu Val Glu Ser Gly Gly Gly Leu Val Gln Pro Gly Gly
1               5                   10                  15

Ser Leu Arg Leu Ser Cys Thr Ala Ser Gly Ile Ser Phe Ser Ile Ser
            20                  25                  30

Thr Met Gly Trp Tyr Arg Gln Ala Pro Gly Lys Gln Arg Glu Leu Val
        35                  40                  45

Ala Thr Ile Thr Ser Gly Gly Glu Ala Tyr Tyr Ala Asn Ser Met Lys
    50                  55                  60

Asp Arg Phe Thr Ile Ser Arg Asp Asn Ala Glu Asn Thr Val Tyr Leu
65                  70                  75                  80

Gln Met Asn Arg Leu Lys Pro Glu Asp Ser Ala Val Tyr Tyr Cys Asn
                85                  90                  95

Thr Lys Phe Pro Trp Ser Thr Asp Trp Asn Ala Arg Gly Gln Gly Thr
            100                 105                 110

Gln Val Thr Val Ser Gly Gly Ser Gly Leu Ser Gly Arg Ser Asp Asn
        115                 120                 125

His Gly Ser Ser Gly Gly Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
            165                 170                 175

Trp Asn Ser Gly Ala Leu Thr Ser Gly Val His Thr Phe Pro Ala Val
        180                 185                 190

Leu Gln Ser Ser Gly Leu Tyr Ser Leu Ser Ser Val Val Thr Val Pro
    195                 200                 205

Ser Ser Ser Leu Gly Thr Gln Thr Tyr Ile Cys Asn Val Asn His Lys
210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
            245                 250                 255

Pro Ser Val Phe Leu Phe Pro Pro Lys Pro Lys Asp Thr Leu Met Ile
        260                 265                 270

Ser Arg Thr Pro Glu Val Thr Cys Val Val Val Asp Val Ser His Glu
    275                 280                 285

Asp Pro Glu Val Lys Phe Asn Trp Tyr Val Asp Gly Val Glu Val His
290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
            325                 330                 335

Glu Tyr Lys Cys Lys Val Ser Asn Lys Ala Leu Pro Ala Pro Ile Glu
        340                 345                 350

Lys Thr Ile Ser Lys Ala Lys Gly Gln Pro Arg Glu Pro Gln Val Tyr
    355                 360                 365

Thr Leu Pro Pro Ser Arg Glu Glu Met Thr Lys Asn Gln Val Ser Leu
370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
            405                 410                 415

Leu Asp Ser Asp Gly Ser Phe Phe Leu Tyr Ser Lys Leu Thr Val Asp
        420                 425                 430

Lys Ser Arg Trp Gln Gln Gly Asn Val Phe Ser Cys Ser Val Met His
    435                 440                 445

Glu Ala Leu His Asn His Tyr Thr Gln Lys Ser Leu Ser Leu Ser Pro
450                 455                 460

<210> SEQ ID NO 157
<211> LENGTH: 464
<212> TYPE: PRT
<213> ORGANISM: Artificial Sequence
<220> FEATURE:
<223> OTHER INFORMATION: an artificially synthesized sequence

<400> SEQUENCE: 157

Gln Leu Gln Leu Val Glu Ser Gly Gly Gly Leu Val Gln Pro Gly Gly
1               5                   10                  15

Ser Leu Arg Leu Ser Cys Thr Ala Ser Gly Ile Ser Phe Ser Ile Ser
            20                  25                  30

Thr Met Gly Trp Tyr Arg Gln Ala Pro Gly Lys Gln Arg Glu Leu Val
        35                  40                  45

```
Ala Thr Ile Ala Ser Gly Gly Glu Ala Tyr Tyr Ala Asn Ser Val Lys
         50                  55                  60

Gly Arg Phe Thr Ile Ser Arg Asp Asn Ala Glu Asn Thr Val Tyr Leu
 65                  70                  75                  80

Gln Met Asn Arg Leu Lys Pro Glu Asp Ser Ala Val Tyr Tyr Cys Asn
                 85                  90                  95

Thr Lys Phe Pro Trp Ser Thr Asp Trp Asn Ala Arg Gly Gln Gly Thr
                100                 105                 110

Gln Val Thr Val Ser Gly Gly Ser Gly Leu Ser Gly Arg Ser Asp Asn
             115                 120                 125

His Gly Ser Ser Gly Gly Ser Ser Ala Ser Thr Lys Gly Pro Ser Val
         130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
                180                 185                 190

Leu Gln Ser Ser Gly Leu Tyr Ser Leu Ser Ser Val Val Thr Val Pro
             195                 200                 205

Ser Ser Ser Leu Gly Thr Gln Thr Tyr Ile Cys Asn Val Asn His Lys
210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
                260                 265                 270

Ser Arg Thr Pro Glu Val Thr Cys Val Val Val Asp Val Ser His Glu
             275                 280                 285

Asp Pro Glu Val Lys Phe Asn Trp Tyr Val Asp Gly Val Glu Val His
         290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
                340                 345                 350

Lys Thr Ile Ser Lys Ala Lys Gly Gln Pro Arg Glu Pro Gln Val Tyr
             355                 360                 365

Thr Leu Pro Pro Ser Arg Glu Glu Met Thr Lys Asn Gln Val Ser Leu
         370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
                420                 425                 430

Lys Ser Arg Trp Gln Gln Gly Asn Val Phe Ser Cys Ser Val Met His
             435                 440                 445

Glu Ala Leu His Asn His Tyr Thr Gln Lys Ser Leu Ser Leu Ser Pro
         450                 455                 460
```

<210> SEQ ID NO 158
<211> LENGTH: 464
<212> TYPE: PRT
<213> ORGANISM: Artificial Sequence
<220> FEATURE:
<223> OTHER INFORMATION: an artificially synthesized sequence

<400> SEQUENCE: 158

```
Gln Leu Gln Leu Val Glu Ser Gly Gly Gly Leu Val Gln Pro Gly Gly
1               5                   10                  15

Ser Leu Arg Leu Ser Cys Thr Ala Ser Gly Ile Ser Phe Ser Ile Ser
            20                  25                  30

Thr Met Gly Trp Tyr Arg Gln Ala Pro Gly Lys Gln Arg Glu Leu Val
        35                  40                  45

Ala Thr Ile Ala Ser Gly Gly Glu Ala Tyr Tyr Ala Asn Ser Val Lys
    50                  55                  60

Gly Arg Phe Thr Ile Ser Arg Glu Tyr Ala Glu Asn Thr Val Phe Leu
65                  70                  75                  80

Gln Met Asn Arg Leu Lys Pro Glu Asp Ser Ala Val Tyr Tyr Cys Asn
                85                  90                  95

Thr Lys Phe Pro Trp Ser Thr Asp Trp Asn Ala Arg Gly Gln Gly Thr
            100                 105                 110

Gln Val Thr Val Ser Gly Gly Ser Gly Leu Ser Gly Arg Ser Asp Asn
        115                 120                 125

His Gly Ser Ser Gly Gly Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365
```

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
450                 455                 460

<210> SEQ ID NO 159
<211> LENGTH: 116
<212> TYPE: PRT
<213> ORGANISM: Artificial Sequence
<220> FEATURE:
<223> OTHER INFORMATION: an artificially synthesized sequence

<400> SEQUENCE: 159

Gln Val Gln Leu Val Gln Ser Gly Gly Gly Leu Val Gln Pro Gly Gly
1               5                   10                  15

Ser Leu Arg Leu Ser Cys Ala Ala Ser Tyr Phe Asp Phe Asp Ser Tyr
            20                  25                  30

Glu Met Ser Trp Val Arg Gln Ala Pro Gly Lys Gly Leu Glu Trp Ile
        35                  40                  45

Gly Ser Ile Tyr His Ser Gly Ser Thr Tyr Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Thr Tyr Tyr Cys Ala
                85                  90                  95

Arg Val Asn Met Asp Arg Phe Asp Tyr Trp Gly Gln Gly Thr Leu Val
            100                 105                 110

Thr Val Ser Ser
        115

<210> SEQ ID NO 160
<211> LENGTH: 124
<212> TYPE: PRT
<213> ORGANISM: Artificial Sequence
<220> FEATURE:
<223> OTHER INFORMATION: an artificially synthesized sequence

<400> SEQUENCE: 160

Glu Val Gln Leu Val Glu Ser Gly Gly Gly Pro Val Gln Ala Gly Gly
1               5                   10                  15

Ser Leu Arg Leu Ser Cys Ala Ala Ser Gly Arg Thr Tyr Arg Gly Tyr
            20                  25                  30

Ser Met Gly Trp Phe Arg Gln Ala Pro Gly Lys Glu Arg Glu Phe Val
        35                  40                  45

Ala Ala Ile Val Trp Ser Gly Asn Thr Tyr Tyr Glu Asp Ser Val
    50                  55                  60

Lys Gly Arg Phe Thr Ile Ser Arg Asp Asn Ala Lys Asn Thr Met Tyr
65                  70                  75                  80

Leu Gln Met Thr Ser Leu Lys Pro Glu Asp Ser Ala Thr Tyr Tyr Cys
                85                  90                  95

Ala Ala Lys Ile Arg Pro Tyr Ile Phe Lys Ile Ala Gly Gln Tyr Asp
            100                 105                 110

Tyr Trp Gly Gln Gly Thr Leu Val Thr Val Ser Ser
            115                 120

<210> SEQ ID NO 161
<211> LENGTH: 354
<212> TYPE: PRT
<213> ORGANISM: Artificial Sequence
<220> FEATURE:
<223> OTHER INFORMATION: an artificially synthesized sequence

<400> SEQUENCE: 161

Gly Ser Gly Leu Ser Gly Arg Ser Asp Asn His Gly Ser Ser Gly Gly
1               5                   10                  15

Ser Ser Ala Ser Thr Lys Gly Pro Ser Val Phe Pro Leu Ala Pro Ser
            20                  25                  30

Ser Lys Ser Thr Ser Gly Gly Thr Ala Ala Leu Gly Cys Leu Val Lys
        35                  40                  45

Asp Tyr Phe Pro Glu Pro Val Thr Val Ser Trp Asn Ser Gly Ala Leu
    50                  55                  60

Thr Ser Gly Val His Thr Phe Pro Ala Val Leu Gln Ser Ser Gly Leu
65                  70                  75                  80

Tyr Ser Leu Ser Ser Val Val Thr Val Pro Ser Ser Ser Leu Gly Thr
                85                  90                  95

Gln Thr Tyr Ile Cys Asn Val Asn His Lys Pro Ser Asn Thr Lys Val
            100                 105                 110

Asp Lys Lys Val Glu Pro Lys Ser Cys Asp Lys Thr His Thr Cys Pro
        115                 120                 125

Pro Cys Pro Ala Pro Glu Leu Arg Gly Gly Pro Lys Val Phe Leu Phe
    130                 135                 140

Pro Pro Lys Pro Lys Asp Thr Leu Met Ile Ser Arg Thr Pro Glu Val
145                 150                 155                 160

Thr Cys Val Val Val Asp Val Ser His Glu Asp Pro Glu Val Lys Phe
                165                 170                 175

Asn Trp Tyr Val Asp Gly Val Glu Val His Asn Ala Lys Thr Lys Pro
            180                 185                 190

Arg Glu Glu Gln Tyr Ala Ser Thr Tyr Arg Val Val Ser Val Leu Thr
        195                 200                 205

Val Leu His Gln Asp Trp Leu Asn Gly Lys Glu Tyr Lys Cys Lys Val
    210                 215                 220

Ser Asn Lys Ala Leu Pro Ala Pro Ile Glu Lys Thr Ile Ser Lys Ala
225                 230                 235                 240

Lys Gly Gln Pro Arg Glu Pro Gln Val Tyr Thr Leu Pro Pro Ser Arg
                245                 250                 255

Cys Glu Met Thr Lys Asn Gln Val Ser Leu Ser Cys Ala Val Lys Gly
            260                 265                 270

Phe Tyr Pro Ser Asp Ile Ala Val Glu Trp Glu Ser Asn Gly Gln Pro
        275                 280                 285

Glu Asn Asn Tyr Lys Thr Thr Pro Pro Val Leu Asp Ser Asp Gly Ser
    290                 295                 300

Phe Phe Leu Val Ser Lys Leu Thr Val Asp Lys Ser Arg Trp Gln Gln
305                 310                 315                 320

Gly Asn Val Phe Ser Cys Ser Val Met His Glu Ala Leu His Asn His
                325                 330                 335

Tyr Thr Gln Lys Ser Leu Ser Leu Ser Pro Asp Tyr Lys Asp Asp
                340                 345                 350
Asp Lys

<210> SEQ ID NO 162
<211> LENGTH: 629
<212> TYPE: PRT
<213> ORGANISM: Artificial Sequence
<220> FEATURE:
<223> OTHER INFORMATION: an artificially synthesized sequence

<400> SEQUENCE: 162

Gln Val Gln Leu Val Gln Ser Gly Gly Gly Leu Val Gln Pro Gly Gly
1               5                   10                  15

Ser Leu Arg Leu Ser Cys Ala Ala Ser Tyr Phe Asp Phe Asp Ser Tyr
            20                  25                  30

Glu Met Ser Trp Val Arg Gln Ala Pro Gly Lys Gly Leu Glu Trp Ile
        35                  40                  45

Gly Ser Ile Tyr His Ser Gly Ser Thr Tyr Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Thr Tyr Tyr Cys Ala
                85                  90                  95

Arg Val Asn Met Asp Arg Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gly Gly Gly Gly Ser Gly Gly Gly Gly Ser Gly Gly Gly
    130                 135                 140

Gly Ser Gly Gly Gly Gly Ser Glu Val Gln Leu Val Glu Ser Gly Gly
145                 150                 155                 160

Gly Pro Val Gln Ala Gly Gly Ser Leu Arg Leu Ser Cys Ala Ala Ser
                165                 170                 175

Gly Arg Thr Tyr Arg Gly Tyr Ser Met Gly Trp Phe Arg Gln Ala Pro
            180                 185                 190

Gly Lys Glu Arg Glu Phe Val Ala Ala Ile Val Trp Ser Gly Gly Asn
        195                 200                 205

Thr Tyr Tyr Glu Asp Ser Val Lys Gly Arg Phe Thr Ile Ser Arg Asp
    210                 215                 220

Asn Ala Lys Asn Thr Met Tyr Leu Gln Met Thr Ser Leu Lys Pro Glu
225                 230                 235                 240

Asp Ser Ala Thr Tyr Tyr Cys Ala Ala Lys Ile Arg Pro Tyr Ile Phe
                245                 250                 255

Lys Ile Ala Gly Gln Tyr Asp Tyr Trp Gly Gln Gly Thr Leu Val Thr
            260                 265                 270

Val Ser Ser Gly Ser Gly Leu Ser Gly Arg Ser Asp Asn His Gly Ser
        275                 280                 285

Ser Gly Gly Ser Ser Ala Ser Thr Lys Gly Pro Ser Val Phe Pro Leu
    290                 295                 300

Ala Pro Ser Ser Lys Ser Thr Ser Gly Gly Thr Ala Ala Leu Gly Cys
305                 310                 315                 320

Leu Val Lys Asp Tyr Phe Pro Glu Pro Val Thr Val Ser Trp Asn Ser
                325                 330                 335

Gly Ala Leu Thr Ser Gly Val His Thr Phe Pro Ala Val Leu Gln Ser
            340                 345                 350

Ser Gly Leu Tyr Ser Leu Ser Ser Val Val Thr Val Pro Ser Ser
            355                 360                 365

Leu Gly Thr Gln Thr Tyr Ile Cys Asn Val Asn His Lys Pro Ser Asn
            370                 375                 380

Thr Lys Val Asp Lys Lys Val Glu Pro Lys Ser Cys Asp Lys Thr His
385                 390                 395                 400

Thr Cys Pro Pro Cys Pro Ala Pro Glu Leu Arg Gly Gly Pro Lys Val
            405                 410                 415

Phe Leu Phe Pro Pro Lys Pro Lys Asp Thr Leu Met Ile Ser Arg Thr
            420                 425                 430

Pro Glu Val Thr Cys Val Val Val Asp Val Ser His Glu Asp Pro Glu
            435                 440                 445

Val Lys Phe Asn Trp Tyr Val Asp Gly Val Glu Val His Asn Ala Lys
            450                 455                 460

Thr Lys Pro Arg Glu Glu Gln Tyr Ala Ser Thr Tyr Arg Val Val Ser
465                 470                 475                 480

Val Leu Thr Val Leu His Gln Asp Trp Leu Asn Gly Lys Glu Tyr Lys
            485                 490                 495

Cys Lys Val Ser Asn Lys Ala Leu Pro Ala Pro Ile Glu Lys Thr Ile
            500                 505                 510

Ser Lys Ala Lys Gly Gln Pro Arg Glu Pro Gln Val Tyr Thr Leu Pro
            515                 520                 525

Pro Ser Arg Cys Glu Met Thr Lys Asn Gln Val Ser Leu Ser Cys Ala
            530                 535                 540

Val Lys Gly Phe Tyr Pro Ser Asp Ile Ala Val Glu Trp Glu Ser Asn
545                 550                 555                 560

Gly Gln Pro Glu Asn Asn Tyr Lys Thr Thr Pro Pro Val Leu Asp Ser
            565                 570                 575

Asp Gly Ser Phe Phe Leu Val Ser Lys Leu Thr Val Asp Lys Ser Arg
            580                 585                 590

Trp Gln Gln Gly Asn Val Phe Ser Cys Ser Val Met His Glu Ala Leu
            595                 600                 605

His Asn His Tyr Thr Gln Lys Ser Leu Ser Leu Ser Pro Asp Tyr Lys
            610                 615                 620

Asp Asp Asp Asp Lys
625

<210> SEQ ID NO 163
<211> LENGTH: 118
<212> TYPE: PRT
<213> ORGANISM: Artificial Sequence
<220> FEATURE:
<223> OTHER INFORMATION: an artificially synthesized sequence

<400> SEQUENCE: 163

Glu Val Gln Leu Val Glu Ser Gly Gly Gly Leu Val Gln Ala Gly Gly
1               5                   10                  15

Ser Leu Arg Leu Ser Cys Ala Ala Ser Gly Ile Thr Phe Ser Ile Asn
            20                  25                  30

Thr Met Gly Trp Tyr Arg Gln Ala Pro Gly Lys Gln Arg Glu Leu Val
            35                  40                  45

Ala Leu Ile Ser Ser Ile Gly Asp Thr Tyr Tyr Ala Asp Ser Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Lys
            85                  90                  95

Arg Phe Arg Thr Ala Ala Gln Gly Thr Asp Tyr Trp Gly Gln Gly Thr
        100                 105                 110

Leu Val Thr Val Ser Ser
        115

<210> SEQ ID NO 164
<211> LENGTH: 631
<212> TYPE: PRT
<213> ORGANISM: Artificial Sequence
<220> FEATURE:
<223> OTHER INFORMATION: an artificially synthesized sequence

<400> SEQUENCE: 164

Glu Val Gln Leu Val Glu Ser Gly Gly Gly Leu Val Gln Ala Gly Gly
1               5                   10                  15

Ser Leu Arg Leu Ser Cys Ala Ala Ser Gly Ile Thr Phe Ser Ile Asn
            20                  25                  30

Thr Met Gly Trp Tyr Arg Gln Ala Pro Gly Lys Gln Arg Glu Leu Val
        35                  40                  45

Ala Leu Ile Ser Ser Ile Gly Asp Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Lys
            85                  90                  95

Arg Phe Arg Thr Ala Ala Gln Gly Thr Asp Tyr Trp Gly Gln Gly Thr
        100                 105                 110

Leu Val Thr Val Ser Ser Gly Gly Gly Gly Ser Gly Gly Gly Gly Ser
        115                 120                 125

Gly Gly Gly Gly Ser Gly Gly Gly Ser Gly Gly Gly Gly Ser Gly
130                 135                 140

Gly Gly Gly Ser Gly Gly Gly Ser Glu Val Gln Leu Val Glu Ser
145                 150                 155                 160

Gly Gly Gly Pro Val Gln Ala Gly Gly Ser Leu Arg Leu Ser Cys Ala
                165                 170                 175

Ala Ser Gly Arg Thr Tyr Arg Gly Tyr Ser Met Gly Trp Phe Arg Gln
            180                 185                 190

Ala Pro Gly Lys Glu Arg Glu Phe Val Ala Ala Ile Val Trp Ser Gly
        195                 200                 205

Gly Asn Thr Tyr Tyr Glu Asp Ser Val Lys Gly Arg Phe Thr Ile Ser
    210                 215                 220

Arg Asp Asn Ala Lys Asn Thr Met Tyr Leu Gln Met Thr Ser Leu Lys
225                 230                 235                 240

Pro Glu Asp Ser Ala Thr Tyr Tyr Cys Ala Ala Lys Ile Arg Pro Tyr
            245                 250                 255

Ile Phe Lys Ile Ala Gly Gln Tyr Asp Tyr Trp Gly Gln Gly Thr Leu
        260                 265                 270

Val Thr Val Ser Ser Gly Ser Gly Leu Ser Gly Arg Ser Asp Asn His
    275                 280                 285

Gly Ser Ser Gly Gly Ser Ser Ala Ser Thr Lys Gly Pro Ser Val Phe
290                 295                 300

```
Pro Leu Ala Pro Ser Ser Lys Ser Thr Ser Gly Gly Thr Ala Ala Leu
305                 310                 315                 320

Gly Cys Leu Val Lys Asp Tyr Phe Pro Glu Pro Val Thr Val Ser Trp
                325                 330                 335

Asn Ser Gly Ala Leu Thr Ser Gly Val His Thr Phe Pro Ala Val Leu
            340                 345                 350

Gln Ser Ser Gly Leu Tyr Ser Leu Ser Ser Val Val Thr Val Pro Ser
        355                 360                 365

Ser Ser Leu Gly Thr Gln Thr Tyr Ile Cys Asn Val Asn His Lys Pro
    370                 375                 380

Ser Asn Thr Lys Val Asp Lys Lys Val Glu Pro Lys Ser Cys Asp Lys
385                 390                 395                 400

Thr His Thr Cys Pro Pro Cys Pro Ala Pro Glu Leu Arg Gly Gly Pro
                405                 410                 415

Lys Val Phe Leu Phe Pro Pro Lys Pro Lys Asp Thr Leu Met Ile Ser
                420                 425                 430

Arg Thr Pro Glu Val Thr Cys Val Val Val Asp Val Ser His Glu Asp
                435                 440                 445

Pro Glu Val Lys Phe Asn Trp Tyr Val Asp Gly Val Glu Val His Asn
450                 455                 460

Ala Lys Thr Lys Pro Arg Glu Glu Gln Tyr Ala Ser Thr Tyr Arg Val
465                 470                 475                 480

Val Ser Val Leu Thr Val Leu His Gln Asp Trp Leu Asn Gly Lys Glu
                485                 490                 495

Tyr Lys Cys Lys Val Ser Asn Lys Ala Leu Pro Ala Pro Ile Glu Lys
                500                 505                 510

Thr Ile Ser Lys Ala Lys Gly Gln Pro Arg Glu Pro Gln Val Tyr Thr
            515                 520                 525

Leu Pro Pro Ser Arg Cys Glu Met Thr Lys Asn Gln Val Ser Leu Ser
        530                 535                 540

Cys Ala Val Lys Gly Phe Tyr Pro Ser Asp Ile Ala Val Glu Trp Glu
545                 550                 555                 560

Ser Asn Gly Gln Pro Glu Asn Asn Tyr Lys Thr Thr Pro Pro Val Leu
                565                 570                 575

Asp Ser Asp Gly Ser Phe Phe Leu Val Ser Lys Leu Thr Val Asp Lys
                580                 585                 590

Ser Arg Trp Gln Gln Gly Asn Val Phe Ser Cys Ser Val Met His Glu
            595                 600                 605

Ala Leu His Asn His Tyr Thr Gln Lys Ser Leu Ser Leu Ser Pro Asp
610                 615                 620

Tyr Lys Asp Asp Asp Asp Lys
625                 630

<210> SEQ ID NO 165
<211> LENGTH: 468
<212> TYPE: PRT
<213> ORGANISM: Artificial Sequence
<220> FEATURE:
<223> OTHER INFORMATION: an artificially synthesized sequence

<400> SEQUENCE: 165

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30
```

-continued

```
Gly Met Ser Trp Val Arg Gln Ala Pro Gly Lys Ala Leu Glu Trp Val
         35                  40                  45
Ser Ala Ile Ser Trp Asn Gly Asn Asn Thr Tyr Tyr Thr Glu Ser Met
 50                  55                  60
Lys Gly Arg Phe Thr Ile Ser Arg Asp Asn Ala Lys Asn Thr Leu Tyr
 65                  70                  75                  80
Leu Gln Met Asn Ser Leu Arg Pro Glu Asp Thr Ala Val Tyr Tyr Cys
                 85                  90                  95
Val Lys Gly Ser Thr Ala Ile Val Gly Val Pro Pro Tyr Pro Asp
             100                 105                 110
Glu Tyr Asp Tyr Trp Gly Gln Gly Thr Leu Val Thr Val Ser Ser Ala
             115                 120                 125
Gly Ala Gly Ile Pro Val Ser Leu Arg Ser Gly Ala Gly Ser Thr Lys
         130                 135                 140
Gly Pro Ser Val Phe Pro Leu Ala Pro Ser Ser Lys Ser Thr Ser Gly
145                 150                 155                 160
Gly Thr Ala Ala Leu Gly Cys Leu Val Lys Asp Tyr Phe Pro Glu Pro
                 165                 170                 175
Val Thr Val Ser Trp Asn Ser Gly Ala Leu Thr Ser Gly Val His Thr
             180                 185                 190
Phe Pro Ala Val Leu Gln Ser Ser Gly Leu Tyr Ser Leu Ser Ser Val
         195                 200                 205
Val Thr Val Pro Ser Ser Ser Leu Gly Thr Gln Thr Tyr Ile Cys Asn
     210                 215                 220
Val Asn His Lys Pro Ser Asn Thr Lys Val Asp Lys Lys Val Glu Pro
225                 230                 235                 240
Lys Ser Cys Asp Lys Thr His Thr Cys Pro Pro Cys Pro Ala Pro Glu
                 245                 250                 255
Leu Leu Gly Gly Pro Ser Val Phe Leu Phe Pro Pro Lys Pro Lys Asp
             260                 265                 270
Thr Leu Met Ile Ser Arg Thr Pro Glu Val Thr Cys Val Val Val Asp
         275                 280                 285
Val Ser His Glu Asp Pro Glu Val Lys Phe Asn Trp Tyr Val Asp Gly
     290                 295                 300
Val Glu Val His Asn Ala Lys Thr Lys Pro Arg Glu Glu Gln Tyr Asn
305                 310                 315                 320
Ser Thr Tyr Arg Val Val Ser Val Leu Thr Val Leu His Gln Asp Trp
                 325                 330                 335
Leu Asn Gly Lys Glu Tyr Lys Cys Lys Val Ser Asn Lys Ala Leu Pro
             340                 345                 350
Ala Pro Ile Glu Lys Thr Ile Ser Lys Ala Lys Gly Gln Pro Arg Glu
         355                 360                 365
Pro Gln Val Tyr Thr Leu Pro Pro Ser Arg Glu Glu Met Thr Lys Asn
370                 375                 380
Gln Val Ser Leu Thr Cys Leu Val Lys Gly Phe Tyr Pro Ser Asp Ile
385                 390                 395                 400
Ala Val Glu Trp Glu Ser Asn Gly Gln Pro Glu Asn Asn Tyr Lys Thr
                 405                 410                 415
Thr Pro Pro Val Leu Asp Ser Asp Gly Ser Phe Phe Leu Tyr Ser Lys
             420                 425                 430
Leu Thr Val Asp Lys Ser Arg Trp Gln Gln Gly Asn Val Phe Ser Cys
         435                 440                 445
Ser Val Met His Glu Ala Leu His Asn His Tyr Thr Gln Lys Ser Leu
```

<210> SEQ ID NO 166
<211> LENGTH: 230
<212> TYPE: PRT
<213> ORGANISM: Artificial Sequence
<220> FEATURE:
<223> OTHER INFORMATION: an artificially synthesized sequence

<400> SEQUENCE: 166

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Cys Thr Leu Pro Pro Ser Arg Asp Glu Leu Thr
    130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro
225                 230

<210> SEQ ID NO 167
<211> LENGTH: 455
<212> TYPE: PRT
<213> ORGANISM: Artificial Sequence
<220> FEATURE:
<223> OTHER INFORMATION: an artificially synthesized sequence

<400> SEQUENCE: 167

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Ala Leu Glu Trp Val
        35                  40                  45

```
Ser Ala Ile Ser Trp Asn Gly Asn Asn Thr Tyr Tyr Thr Glu Ser Met
    50                  55                  60
Lys Gly Arg Phe Thr Ile Ser Arg Asp Asn Ala Lys Asn Thr Leu Tyr
65                  70                  75                  80
Leu Gln Met Asn Ser Leu Arg Pro Glu Asp Thr Ala Val Tyr Tyr Cys
                85                  90                  95
Val Lys Gly Ser Thr Ala Ile Val Gly Val Pro Pro Thr Tyr Pro Asp
                100                 105                 110
Glu Tyr Asp Tyr Trp Gly Gln Gly Thr Leu Val Thr Val Ser Ser Ala
            115                 120                 125
Ser Thr Lys Gly Pro Ser Val Phe Pro Leu Ala Pro Ser Ser Lys Ser
    130                 135                 140
Thr Ser Gly Gly Thr Ala Ala Leu Gly Cys Leu Val Lys Asp Tyr Phe
145                 150                 155                 160
Pro Glu Pro Val Thr Val Ser Trp Asn Ser Gly Ala Leu Thr Ser Gly
                165                 170                 175
Val His Thr Phe Pro Ala Val Leu Gln Ser Ser Gly Leu Tyr Ser Leu
                180                 185                 190
Ser Ser Val Val Thr Val Pro Ser Ser Ser Leu Gly Thr Gln Thr Tyr
    195                 200                 205
Ile Cys Asn Val Asn His Lys Pro Ser Asn Thr Lys Val Asp Lys Arg
210                 215                 220
Val Glu Pro Lys Ser Cys Asp Lys Thr His Thr Cys Pro Pro Cys Pro
225                 230                 235                 240
Ala Pro Glu Leu Arg Arg Gly Pro Ser Val Phe Leu Phe Pro Pro Lys
                245                 250                 255
Pro Lys Asp Thr Leu Met Ile Ser Arg Thr Pro Glu Val Thr Cys Val
                260                 265                 270
Val Val Asp Val Ser His Glu Asp Pro Glu Val Lys Phe Asn Trp Tyr
            275                 280                 285
Val Asp Gly Val Glu Val His Asn Ala Lys Thr Lys Pro Arg Glu Glu
    290                 295                 300
Gln Tyr Asn Ser Thr Tyr Arg Val Val Ser Val Leu Thr Val Leu His
305                 310                 315                 320
Gln Asp Trp Leu Asn Gly Lys Glu Tyr Lys Cys Lys Val Ser Asn Lys
                325                 330                 335
Gly Leu Pro Ser Ser Ile Glu Lys Thr Ile Ser Lys Ala Lys Gly Gln
                340                 345                 350
Pro Arg Glu Pro Gln Val Tyr Thr Leu Pro Pro Ser Arg Glu Glu Met
            355                 360                 365
Thr Lys Asn Gln Val Ser Leu Thr Cys Leu Val Lys Gly Phe Tyr Pro
    370                 375                 380
Ser Asp Ile Ala Val Glu Trp Glu Ser Asn Gly Gln Pro Glu Asn Asn
385                 390                 395                 400
Tyr Lys Thr Thr Pro Pro Val Leu Asp Ser Asp Gly Ser Phe Phe Leu
                405                 410                 415
Tyr Ser Lys Leu Thr Val Asp Lys Ser Arg Trp Gln Glu Gly Asn Val
                420                 425                 430
Phe Ser Cys Ser Val Met His Glu Ala Leu His Asn His Tyr Thr Gln
            435                 440                 445
Lys Ser Leu Ser Leu Ser Pro
    450                 455
```

<210> SEQ ID NO 168

<400> SEQUENCE: 168

000

<210> SEQ ID NO 169

<400> SEQUENCE: 169

000

<210> SEQ ID NO 170

<400> SEQUENCE: 170

000

<210> SEQ ID NO 171

<400> SEQUENCE: 171

000

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 178

Thr Ser Thr Ser Gly Arg Ser Ala Asn Pro Arg Gly
1               5                   10

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189
<211> LENGTH: 467
<212> TYPE: PRT
<213> ORGANISM: Artificial Sequence
<220> FEATURE:

<223> OTHER INFORMATION: an artificially synthesized sequence

<400> SEQUENCE: 189

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Ala Leu Glu Trp Val
        35                  40                  45

Ser Ala Ile Ser Trp Asn Gly Asn Asn Thr Tyr Tyr Thr Glu Ser Met
50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Val Lys Gly Ser Thr Ala Ile Val Gly Val Pro Pro Thr Tyr Pro Asp
            100                 105                 110

Glu Tyr Asp Tyr Trp Gly Gln Gly Thr Leu Val Thr Val Ser Ser Thr
        115                 120                 125

Ser Thr Ser Gly Arg Ser Ala Asn Pro Arg Gly Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
210                 215                 220

Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Leu
                245                 250                 255

Arg Arg Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Gly Leu Pro Ser
            340                 345                 350

Ser Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
370                 375                 380

Val Ser Leu Thr Cys Leu Val Lys Gly Phe Tyr Pro Ser Asp Ile Ala
385                 390                 395                 400
```

```
Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Glu Gly Asn Val Phe Ser Cys Ser
        435                 440                 445

Val Met His Glu Ala Leu His Asn His Tyr Thr Gln Lys Ser Leu Ser
450                 455                 460

Leu Ser Pro
465

<210> SEQ ID NO 190
<211> LENGTH: 127
<212> TYPE: PRT
<213> ORGANISM: Artificial Sequence
<220> FEATURE:
<223> OTHER INFORMATION: an artificially synthesized sequence

<400> SEQUENCE: 190

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Ile Gly Trp Phe Arg Gln Ala Pro Gly Lys Gly Arg Glu Gly Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
        115                 120                 125

<210> SEQ ID NO 191
<211> LENGTH: 455
<212> TYPE: PRT
<213> ORGANISM: Artificial Sequence
<220> FEATURE:
<223> OTHER INFORMATION: an artificially synthesized sequence

<400> SEQUENCE: 191

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Ile Gly Trp Phe Arg Gln Ala Pro Gly Lys Gly Arg Glu Gly Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110
```

```
Phe Phe Lys Tyr Trp Gly Gln Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro
    450                 455

<210> SEQ ID NO 192
<211> LENGTH: 455
<212> TYPE: PRT
<213> ORGANISM: Artificial Sequence
<220> FEATURE:
<223> OTHER INFORMATION: an artificially synthesized sequence

<400> SEQUENCE: 192

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Asp Tyr
            20                  25                  30

Asp Ile Gly Trp Val Arg Gln Ala Pro Gly Lys Gly Leu Glu Trp Val
            35                  40                  45

Ser Gly Ile Ser Ser Ser Asp Gly Asn Thr Tyr Tyr Ala Asp Ser Val
 50                  55                  60

Lys Gly Arg Phe Thr Ile Ser Arg Asp Asn Ala Lys Asn Thr Leu Tyr
65                   70                  75                  80

Leu Gln Met Asn Ser Leu Arg Pro Glu Asp Thr Ala Val Tyr Tyr Cys
                85                  90                  95

Ala Ala Glu Pro Pro Asp Ser Ser Trp Tyr Leu Asp Gly Ser Pro Glu
                100                 105                 110

Phe Phe Lys Tyr Trp Gly Gln Gly Thr Leu Val Thr Val Ser Ser Ala
                115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
                180                 185                 190

Ser Ser Val Val Thr Val Pro Ser Ser Ser Leu Gly Thr Gln Thr Tyr
            195                 200                 205

Ile Cys Asn Val Asn His Lys Pro Ser Asn Thr Lys Val Asp Lys Lys
210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
            275                 280                 285

Val Asp Gly Val Glu Val His Asn Ala Lys Thr Lys Pro Arg Glu Glu
290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
                340                 345                 350

Pro Arg Glu Pro Gln Val Tyr Thr Leu Pro Pro Ser Arg Glu Glu Met
            355                 360                 365

Thr Lys Asn Gln Val Ser Leu Thr Cys Leu Val Lys Gly Phe Tyr Pro
            370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
                420                 425                 430
```

```
Phe Ser Cys Ser Val Met His Glu Ala Leu His Asn His Tyr Thr Gln
            435                 440                 445

Lys Ser Leu Ser Leu Ser Pro
    450                 455

<210> SEQ ID NO 193
<211> LENGTH: 16
<212> TYPE: PRT
<213> ORGANISM: Artificial Sequence
<220> FEATURE:
<223> OTHER INFORMATION: an artificially synthesized sequence

<400> SEQUENCE: 193

Gly Gly Gly Gly Ser Pro Leu Gly Leu Ala Gly Gly Gly Gly Gly Ser
1               5                   10                  15

<210> SEQ ID NO 194
<211> LENGTH: 18
<212> TYPE: PRT
<213> ORGANISM: Artificial Sequence
<220> FEATURE:
<223> OTHER INFORMATION: an artificially synthesized sequence

<400> SEQUENCE: 194

Gly Gly Gly Gly Ser Gly Pro Leu Gly Ile Ala Gly Gln Gly Gly Gly
1               5                   10                  15

Gly Ser

<210> SEQ ID NO 195
<211> LENGTH: 23
<212> TYPE: PRT
<213> ORGANISM: Artificial Sequence
<220> FEATURE:
<223> OTHER INFORMATION: an artificially synthesized sequence

<400> SEQUENCE: 195

Gly Gly Gly Gly Ser Gly Ala Gly Val Pro Leu Ser Leu Tyr Ser Gly
1               5                   10                  15

Ala Gly Gly Gly Gly Gly Ser
            20

<210> SEQ ID NO 196
<211> LENGTH: 471
<212> TYPE: PRT
<213> ORGANISM: Artificial Sequence
<220> FEATURE:
<223> OTHER INFORMATION: an artificially synthesized sequence

<400> SEQUENCE: 196

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Ala Leu Glu Trp Val
        35                  40                  45

Ser Ala Ile Ser Trp Asn Gly Asn Asn Thr Tyr Tyr Thr Glu Ser Met
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Val Lys Gly Ser Thr Ala Ile Val Gly Val Pro Pro Thr Tyr Pro Asp
```

```
            100                 105                 110
Glu Tyr Asp Tyr Trp Gly Gln Gly Thr Leu Val Thr Val Ser Ser Ala
            115                 120                 125

Gly Gly Gly Gly Ser Pro Leu Gly Leu Ala Gly Gly Gly Gly Ser
        130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Glu Glu Met
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
450                 455                 460

Lys Ser Leu Ser Leu Ser Pro
465                 470

<210> SEQ ID NO 197
<211> LENGTH: 473
<212> TYPE: PRT
<213> ORGANISM: Artificial Sequence
<220> FEATURE:
<223> OTHER INFORMATION: an artificially synthesized sequence
```

```
<400> SEQUENCE: 197

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Ala Leu Glu Trp Val
        35                  40                  45

Ser Ala Ile Ser Trp Asn Gly Asn Asn Thr Tyr Tyr Thr Glu Ser Met
50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Val Lys Gly Ser Thr Ala Ile Val Gly Val Pro Pro Thr Tyr Pro Asp
            100                 105                 110

Glu Tyr Asp Tyr Trp Gly Gln Gly Thr Leu Val Thr Val Ser Ser Ala
        115                 120                 125

Gly Gly Gly Gly Ser Gly Pro Leu Gly Ile Ala Gly Gln Gly Gly Gly
130                 135                 140

Gly Ser Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Leu Gly Thr Gln
210                 215                 220

Thr Tyr Ile Cys Asn Val Asn His Lys Pro Ser Asn Thr Lys Val Asp
225                 230                 235                 240

Lys Arg Val Glu Pro Lys Ser Cys Asp Lys Thr His Thr Cys Pro Pro
                245                 250                 255

Cys Pro Ala Pro Glu Leu Arg Arg Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Gly Leu Pro Ser Ser Ile Glu Lys Thr Ile Ser Lys Ala Lys
        355                 360                 365

Gly Gln Pro Arg Glu Pro Gln Val Tyr Thr Leu Pro Pro Ser Arg Glu
370                 375                 380

Glu Met Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415
```

```
Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Glu Gly
            435                 440                 445

Asn Val Phe Ser Cys Ser Val Met His Glu Ala Leu His Asn His Tyr
450                 455                 460

Thr Gln Lys Ser Leu Ser Leu Ser Pro
465                 470

<210> SEQ ID NO 198
<211> LENGTH: 478
<212> TYPE: PRT
<213> ORGANISM: Artificial Sequence
<220> FEATURE:
<223> OTHER INFORMATION: an artificially synthesized sequence

<400> SEQUENCE: 198

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Ala Leu Glu Trp Val
        35                  40                  45

Ser Ala Ile Ser Trp Asn Gly Asn Asn Thr Tyr Tyr Thr Glu Ser Met
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Val Lys Gly Ser Thr Ala Ile Val Gly Val Pro Pro Tyr Tyr Pro Asp
            100                 105                 110

Glu Tyr Asp Tyr Trp Gly Gln Gly Thr Leu Val Thr Val Ser Ser Ala
        115                 120                 125

Gly Gly Gly Gly Ser Gly Ala Gly Val Pro Leu Ser Leu Tyr Ser Gly
    130                 135                 140

Ala Gly Gly Gly Gly Ser Ser Thr Lys Gly Pro Ser Val Phe Pro
145                 150                 155                 160

Leu Ala Pro Ser Ser Lys Ser Thr Ser Gly Gly Thr Ala Ala Leu Gly
                165                 170                 175

Cys Leu Val Lys Asp Tyr Phe Pro Glu Pro Val Thr Val Ser Trp Asn
            180                 185                 190

Ser Gly Ala Leu Thr Ser Gly Val His Thr Phe Pro Ala Val Leu Gln
        195                 200                 205

Ser Ser Gly Leu Tyr Ser Leu Ser Ser Val Val Thr Val Pro Ser Ser
    210                 215                 220

Ser Leu Gly Thr Gln Thr Tyr Ile Cys Asn Val Asn His Lys Pro Ser
225                 230                 235                 240

Asn Thr Lys Val Asp Lys Lys Val Glu Pro Lys Ser Cys Asp Lys Thr
                245                 250                 255

His Thr Cys Pro Pro Cys Pro Ala Pro Glu Leu Leu Gly Gly Pro Ser
            260                 265                 270

Val Phe Leu Phe Pro Pro Lys Pro Lys Asp Thr Leu Met Ile Ser Arg
        275                 280                 285

Thr Pro Glu Val Thr Cys Val Val Val Asp Val Ser His Glu Asp Pro
    290                 295                 300
```

Glu Val Lys Phe Asn Trp Tyr Val Asp Gly Val Glu Val His Asn Ala
305                 310                 315                 320

Lys Thr Lys Pro Arg Glu Glu Gln Tyr Asn Ser Thr Tyr Arg Val Val
            325                 330                 335

Ser Val Leu Thr Val Leu His Gln Asp Trp Leu Asn Gly Lys Glu Tyr
            340                 345                 350

Lys Cys Lys Val Ser Asn Lys Ala Leu Pro Ala Pro Ile Glu Lys Thr
            355                 360                 365

Ile Ser Lys Ala Lys Gly Gln Pro Arg Glu Pro Gln Val Tyr Thr Leu
370                 375                 380

Pro Pro Ser Arg Glu Glu Met Thr Lys Asn Gln Val Ser Leu Thr Cys
385                 390                 395                 400

Leu Val Lys Gly Phe Tyr Pro Ser Asp Ile Ala Val Glu Trp Glu Ser
                405                 410                 415

Asn Gly Gln Pro Glu Asn Asn Tyr Lys Thr Thr Pro Pro Val Leu Asp
            420                 425                 430

Ser Asp Gly Ser Phe Phe Leu Tyr Ser Lys Leu Thr Val Asp Lys Ser
            435                 440                 445

Arg Trp Gln Gln Gly Asn Val Phe Ser Cys Ser Val Met His Glu Ala
450                 455                 460

Leu His Asn His Tyr Thr Gln Lys Ser Leu Ser Leu Ser Pro
465                 470                 475

<210> SEQ ID NO 199
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 199

Asp Tyr Lys Asp Asp Asp Asp Lys
1               5

<210> SEQ ID NO 200
<211> LENGTH: 1267
<212> TYPE: PRT
<213> ORGANISM: Artificial Sequence
<220> FEATURE:
<223> OTHER INFORMATION: an artificially synthesized sequence

<400> SEQUENCE: 200

Met Trp Trp Arg Leu Trp Leu Leu Leu Leu Leu Leu Leu Leu Leu Trp
1               5                   10                  15

Pro Met Val Trp Ala Glu Ala Gly Leu Pro Arg Ala Gly Gly Gly Ser
            20                  25                  30

Gln Pro Pro Phe Arg Thr Phe Ser Ala Ser Asp Trp Gly Leu Thr His
        35                  40                  45

Leu Val Val His Glu Gln Thr Gly Glu Val Tyr Val Gly Ala Val Asn
    50                  55                  60

Arg Ile Tyr Lys Leu Ser Gly Asn Leu Thr Leu Leu Arg Ala His Val
65                  70                  75                  80

Thr Gly Pro Val Glu Asp Asn Glu Lys Cys Tyr Pro Pro Pro Ser Val
                85                  90                  95

Gln Ser Cys Pro His Gly Leu Gly Ser Thr Asp Asn Val Asn Lys Leu
            100                 105                 110

Leu Leu Leu Asp Tyr Ala Ala Asn Arg Leu Leu Ala Cys Gly Ser Ala

```
            115                 120                 125
Ser Gln Gly Ile Cys Gln Phe Leu Arg Leu Asp Asp Leu Phe Lys Leu
            130                 135                 140

Gly Glu Pro His His Arg Lys Glu His Tyr Leu Ser Ser Val Gln Glu
145                 150                 155                 160

Ala Gly Ser Met Ala Gly Val Leu Ile Ala Gly Pro Pro Gly Gln Gly
                165                 170                 175

Gln Ala Lys Leu Phe Val Gly Thr Pro Ile Asp Gly Lys Ser Glu Tyr
            180                 185                 190

Phe Pro Thr Leu Ser Ser Arg Arg Leu Met Ala Asn Glu Glu Asp Ala
                195                 200                 205

Asp Met Phe Gly Phe Val Tyr Gln Asp Glu Phe Val Ser Ser Gln Leu
    210                 215                 220

Lys Ile Pro Ser Asp Thr Leu Ser Lys Phe Pro Ala Phe Asp Ile Tyr
225                 230                 235                 240

Tyr Val Tyr Ser Phe Arg Ser Glu Gln Phe Val Tyr Tyr Leu Thr Leu
                245                 250                 255

Gln Leu Asp Thr Gln Leu Thr Ser Pro Asp Ala Ala Gly Glu His Phe
            260                 265                 270

Phe Thr Ser Lys Ile Val Arg Leu Cys Val Asp Asp Pro Lys Phe Tyr
                275                 280                 285

Ser Tyr Val Glu Phe Pro Ile Gly Cys Glu Gln Ala Gly Val Glu Tyr
    290                 295                 300

Arg Leu Val Gln Asp Ala Tyr Leu Ser Arg Pro Gly Arg Ala Leu Ala
305                 310                 315                 320

His Gln Leu Gly Leu Ala Glu Asp Glu Asp Val Leu Phe Thr Val Phe
                325                 330                 335

Ala Gln Gly Gln Lys Asn Arg Val Lys Pro Pro Lys Glu Ser Ala Leu
                340                 345                 350

Cys Leu Phe Thr Leu Arg Ala Ile Lys Glu Lys Ile Lys Glu Arg Ile
            355                 360                 365

Gln Ser Cys Tyr Arg Gly Glu Gly Lys Leu Ser Leu Pro Trp Leu Leu
    370                 375                 380

Asn Lys Glu Leu Gly Cys Ile Asn Ser Pro Leu Gln Ile Asp Asp Asp
385                 390                 395                 400

Phe Cys Gly Gln Asp Phe Asn Gln Pro Leu Gly Gly Thr Val Thr Ile
                405                 410                 415

Glu Gly Thr Pro Leu Phe Val Asp Lys Asp Asp Gly Leu Thr Ala Val
            420                 425                 430

Ala Ala Tyr Asp Tyr Arg Gly Arg Thr Val Val Phe Ala Gly Thr Arg
                435                 440                 445

Ser Gly Arg Ile Arg Lys Ile Leu Val Asp Leu Ser Asn Pro Gly Gly
    450                 455                 460

Arg Pro Ala Leu Ala Tyr Glu Ser Val Val Ala Gln Glu Gly Ser Pro
465                 470                 475                 480

Ile Leu Arg Asp Leu Val Leu Ser Pro Asn His Gln Tyr Leu Tyr Ala
                485                 490                 495

Met Thr Glu Lys Gln Val Thr Arg Val Pro Val Glu Ser Cys Val Gln
            500                 505                 510

Tyr Thr Ser Cys Glu Leu Cys Leu Gly Ser Arg Asp Pro His Cys Gly
    515                 520                 525

Trp Cys Val Leu His Ser Ile Cys Ser Arg Arg Asp Ala Cys Glu Arg
            530                 535                 540
```

-continued

```
Ala Asp Glu Pro Gln Arg Phe Ala Asp Leu Leu Gln Cys Val Gln
545                 550                 555                 560

Leu Thr Val Gln Pro Arg Asn Val Ser Val Thr Met Ser Gln Val Pro
                565                 570                 575

Leu Val Leu Gln Ala Trp Asn Val Pro Asp Leu Ser Ala Gly Val Asn
            580                 585                 590

Cys Ser Phe Glu Asp Phe Thr Glu Ser Glu Ser Val Leu Glu Asp Gly
        595                 600                 605

Arg Ile His Cys Arg Ser Pro Ser Ala Arg Glu Val Ala Pro Ile Thr
    610                 615                 620

Arg Gly Gln Gly Asp Gln Arg Val Val Lys Leu Tyr Leu Lys Ser Lys
625                 630                 635                 640

Glu Thr Gly Lys Lys Phe Ala Ser Val Asp Phe Val Phe Tyr Asn Cys
                645                 650                 655

Ser Val His Gln Ser Cys Leu Ser Cys Val Asn Gly Ser Phe Pro Cys
            660                 665                 670

His Trp Cys Lys Tyr Arg His Val Cys Thr His Asn Val Ala Asp Cys
        675                 680                 685

Ala Phe Leu Glu Gly Arg Val Asn Val Ser Glu Asp Cys Pro Gln Ile
    690                 695                 700

Leu Pro Ser Thr Gln Ile Tyr Val Pro Val Gly Val Val Lys Pro Ile
705                 710                 715                 720

Thr Leu Ala Ala Arg Asn Leu Pro Gln Pro Gln Ser Gly Gln Arg Gly
                725                 730                 735

Tyr Glu Cys Leu Phe His Ile Pro Gly Ser Pro Ala Arg Val Thr Ala
            740                 745                 750

Leu Arg Phe Asn Ser Ser Ser Leu Gln Cys Gln Asn Ser Ser Tyr Ser
        755                 760                 765

Tyr Glu Gly Asn Asp Val Ser Asp Leu Pro Val Asn Leu Ser Val Val
    770                 775                 780

Trp Asn Gly Asn Phe Val Ile Asp Asn Pro Gln Asn Ile Gln Ala His
785                 790                 795                 800

Leu Tyr Lys Cys Pro Ala Leu Arg Glu Ser Cys Gly Leu Cys Leu Lys
                805                 810                 815

Ala Asp Pro Arg Phe Glu Cys Gly Trp Cys Val Ala Glu Arg Arg Cys
            820                 825                 830

Ser Leu Arg His His Cys Ala Ala Asp Thr Pro Ala Ser Trp Met His
        835                 840                 845

Ala Arg His Gly Ser Ser Arg Cys Thr Asp Pro Lys Ile Leu Lys Leu
    850                 855                 860

Ser Pro Glu Thr Gly Pro Arg Gln Gly Gly Thr Arg Leu Thr Ile Thr
865                 870                 875                 880

Gly Glu Asn Leu Gly Leu Arg Phe Glu Asp Val Arg Leu Gly Val Arg
                885                 890                 895

Val Gly Lys Val Leu Cys Ser Pro Val Glu Ser Glu Tyr Ile Ser Ala
            900                 905                 910

Glu Gln Ile Val Cys Glu Ile Gly Asp Ala Ser Ser Val Arg Ala His
        915                 920                 925

Asp Ala Leu Val Glu Val Cys Val Arg Asp Cys Ser Pro His Tyr Arg
    930                 935                 940

Ala Leu Ser Pro Lys Arg Phe Thr Phe Val Thr Pro Thr Phe Tyr Arg
945                 950                 955                 960
```

Val Ser Pro Ser Arg Gly Pro Leu Ser Gly Gly Thr Trp Ile Gly Ile
                965                 970                 975

Glu Gly Ser His Leu Asn Ala Gly Ser Asp Val Ala Val Ser Val Gly
            980                 985                 990

Gly Arg Pro Cys Ser Phe Ser Trp Arg Asn Ser Arg Glu Ile Arg Cys
        995                 1000                1005

Leu Thr Pro Pro Gly Gln Ser Pro Gly Ser Ala Pro Ile Ile Ile
    1010                1015                1020

Asn Ile Asn Arg Ala Gln Leu Thr Asn Pro Glu Val Lys Tyr Asn
    1025                1030                1035

Tyr Thr Glu Asp Pro Thr Ile Leu Arg Ile Asp Pro Glu Trp Ser
    1040                1045                1050

Ile Asn Ser Gly Gly Thr Leu Leu Thr Val Thr Gly Thr Asn Leu
    1055                1060                1065

Ala Thr Val Arg Glu Pro Arg Ile Arg Ala Lys Tyr Gly Gly Ile
    1070                1075                1080

Glu Arg Glu Asn Gly Cys Leu Val Tyr Asn Asp Thr Thr Met Val
    1085                1090                1095

Cys Arg Ala Pro Ser Val Ala Asn Pro Val Arg Ser Pro Pro Glu
    1100                1105                1110

Leu Gly Glu Arg Pro Asp Glu Leu Gly Phe Val Met Asp Asn Val
    1115                1120                1125

Arg Ser Leu Leu Val Leu Asn Ser Thr Ser Phe Leu Tyr Tyr Pro
    1130                1135                1140

Asp Pro Val Leu Glu Pro Leu Ser Pro Thr Gly Leu Leu Glu Leu
    1145                1150                1155

Lys Pro Ser Ser Pro Leu Ile Leu Lys Gly Arg Asn Leu Leu Pro
    1160                1165                1170

Pro Ala Pro Gly Asn Ser Arg Leu Asn Tyr Thr Val Leu Ile Gly
    1175                1180                1185

Ser Thr Pro Cys Thr Leu Thr Val Ser Glu Thr Gln Leu Leu Cys
    1190                1195                1200

Glu Ala Pro Asn Leu Thr Gly Gln His Lys Val Thr Val Arg Ala
    1205                1210                1215

Gly Gly Phe Glu Phe Ser Pro Gly Thr Leu Gln Val Tyr Ser Asp
    1220                1225                1230

Ser Leu Leu Thr Leu Pro Asp Tyr Lys Asp Asp Asp Lys Gly
    1235                1240                1245

Gly Gly Gly Ser Gly Leu Asn Asp Ile Phe Glu Ala Gln Lys Ile
    1250                1255                1260

Glu Trp His Glu
    1265

<210> SEQ ID NO 201
<211> LENGTH: 347
<212> TYPE: PRT
<213> ORGANISM: Artificial Sequence
<220> FEATURE:
<223> OTHER INFORMATION: an artificially synthesized sequence

<400> SEQUENCE: 201

Met Val Leu Ala Ser Ser Thr Thr Ser Ile His Thr Met Leu Leu Leu
1               5                   10                  15

Leu Leu Met Leu Ala Gln Pro Ala Met Ala Met Lys Asp Asn Thr Val
            20                  25                  30

```
Pro Leu Lys Leu Ile Ala Leu Leu Ala Asn Gly Glu Phe His Ser Gly
             35                  40                  45

Glu Gln Leu Gly Glu Thr Leu Gly Met Ser Arg Ala Ala Ile Asn Lys
 50                  55                  60

His Ile Gln Thr Leu Arg Asp Trp Gly Val Asp Val Phe Thr Val Pro
 65                  70                  75                  80

Gly Lys Gly Tyr Ser Leu Pro Glu Pro Ile Gln Leu Leu Asn Ala Lys
                 85                  90                  95

Gln Ile Leu Gly Gln Leu Asp Gly Gly Ser Val Ala Val Leu Pro Val
                100                 105                 110

Ile Asp Ser Thr Asn Gln Tyr Leu Leu Asp Arg Ile Gly Glu Leu Lys
                115                 120                 125

Ser Gly Asp Ala Cys Ile Ala Glu Tyr Gln Gln Ala Gly Arg Gly Arg
130                 135                 140

Arg Gly Arg Lys Trp Phe Ser Pro Phe Gly Ala Asn Leu Tyr Leu Ser
145                 150                 155                 160

Met Phe Trp Arg Leu Glu Gln Gly Pro Ala Ala Ile Gly Leu Ser
                165                 170                 175

Leu Val Ile Gly Ile Val Met Ala Glu Val Leu Arg Lys Leu Gly Ala
                180                 185                 190

Asp Lys Val Arg Val Lys Trp Pro Asn Asp Leu Tyr Leu Gln Asp Arg
                195                 200                 205

Lys Leu Ala Gly Ile Leu Val Glu Leu Thr Gly Lys Thr Gly Asp Ala
                210                 215                 220

Ala Gln Ile Val Ile Gly Ala Gly Ile Asn Met Ala Met Arg Arg Val
225                 230                 235                 240

Glu Glu Ser Val Val Asn Gln Gly Trp Ile Thr Leu Gln Glu Ala Gly
                245                 250                 255

Ile Asn Leu Asp Arg Asn Thr Leu Ala Ala Met Leu Ile Arg Glu Leu
                260                 265                 270

Arg Ala Ala Leu Glu Leu Phe Glu Gln Glu Gly Leu Ala Pro Tyr Leu
                275                 280                 285

Ser Arg Trp Glu Lys Leu Asp Asn Phe Ile Asn Arg Pro Val Lys Leu
                290                 295                 300

Ile Ile Gly Asp Lys Glu Ile Phe Gly Ile Ser Arg Gly Ile Asp Lys
305                 310                 315                 320

Gln Gly Ala Leu Leu Leu Glu Gln Asp Gly Ile Ile Lys Pro Trp Met
                325                 330                 335

Gly Gly Glu Ile Ser Leu Arg Ser Ala Glu Lys
                340                 345

<210> SEQ ID NO 202
<211> LENGTH: 463
<212> TYPE: PRT
<213> ORGANISM: Artificial Sequence
<220> FEATURE:
<223> OTHER INFORMATION: an artificially synthesized sequence

<400> SEQUENCE: 202

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asp Asp Tyr
                20                  25                  30

Gly Met Ser Trp Val Arg Gln Ala Pro Gly Lys Ala Leu Glu Trp Val
             35                  40                  45
```

```
Ser Ala Ile Ser Trp Asn Gly Asn Asn Thr Tyr Tyr Thr Glu Ser Met
    50              55                  60
Lys Gly Arg Phe Thr Ile Ser Arg Asp Asn Ala Lys Asn Thr Leu Tyr
 65              70              75                  80
Leu Gln Met Asn Ser Leu Arg Pro Glu Asp Thr Ala Val Tyr Tyr Cys
                85              90                  95
Val Lys Gly Ser Thr Ala Ile Val Gly Val Pro Pro Thr Tyr Pro Asp
            100             105             110
Glu Tyr Asp Tyr Trp Gly Gln Gly Thr Leu Val Thr Val Ser Ser Ala
            115             120             125
Gly Pro Leu Gly Ile Ala Gly Gln Ser Thr Lys Gly Pro Ser Val Phe
    130             135             140
Pro Leu Ala Pro Ser Ser Lys Ser Thr Ser Gly Gly Thr Ala Ala Leu
145             150             155             160
Gly Cys Leu Val Lys Asp Tyr Phe Pro Glu Pro Val Thr Val Ser Trp
                165             170             175
Asn Ser Gly Ala Leu Thr Ser Gly Val His Thr Phe Pro Ala Val Leu
            180             185             190
Gln Ser Ser Gly Leu Tyr Ser Leu Ser Ser Val Val Thr Val Pro Ser
            195             200             205
Ser Ser Leu Gly Thr Gln Thr Tyr Ile Cys Asn Val Asn His Lys Pro
    210             215             220
Ser Asn Thr Lys Val Asp Lys Lys Val Glu Pro Lys Ser Cys Asp Lys
225             230             235             240
Thr His Thr Cys Pro Pro Cys Pro Ala Pro Glu Leu Leu Gly Gly Pro
                245             250             255
Ser Val Phe Leu Phe Pro Pro Lys Pro Lys Asp Thr Leu Met Ile Ser
            260             265             270
Arg Thr Pro Glu Val Thr Cys Val Val Val Asp Val Ser His Glu Asp
            275             280             285
Pro Glu Val Lys Phe Asn Trp Tyr Val Asp Gly Val Glu Val His Asn
    290             295             300
Ala Lys Thr Lys Pro Arg Glu Glu Gln Tyr Asn Ser Thr Tyr Arg Val
305             310             315             320
Val Ser Val Leu Thr Val Leu His Gln Asp Trp Leu Asn Gly Lys Glu
                325             330             335
Tyr Lys Cys Lys Val Ser Asn Lys Ala Leu Pro Ala Pro Ile Glu Lys
            340             345             350
Thr Ile Ser Lys Ala Lys Gly Gln Pro Arg Glu Pro Gln Val Tyr Thr
            355             360             365
Leu Pro Pro Ser Arg Glu Glu Met Thr Lys Asn Gln Val Ser Leu Thr
    370             375             380
Cys Leu Val Lys Gly Phe Tyr Pro Ser Asp Ile Ala Val Glu Trp Glu
385             390             395             400
Ser Asn Gly Gln Pro Glu Asn Asn Tyr Lys Thr Thr Pro Pro Val Leu
                405             410             415
Asp Ser Asp Gly Ser Phe Phe Leu Tyr Ser Lys Leu Thr Val Asp Lys
            420             425             430
Ser Arg Trp Gln Gln Gly Asn Val Phe Ser Cys Ser Val Met His Glu
            435             440             445
Ala Leu His Asn His Tyr Thr Gln Lys Ser Leu Ser Leu Ser Pro
    450             455             460
```

-continued

```
<210> SEQ ID NO 203
<211> LENGTH: 465
<212> TYPE: PRT
<213> ORGANISM: Artificial Sequence
<220> FEATURE:
<223> OTHER INFORMATION: an artificially synthesized sequence

<400> SEQUENCE: 203
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Ala Leu Glu Trp Val
        35                  40                  45

Ser Ala Ile Ser Trp Asn Gly Asn Asn Thr Tyr Tyr Thr Glu Ser Met
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Val Lys Gly Ser Thr Ala Ile Val Gly Val Pro Pro Thr Tyr Pro Asp
            100                 105                 110

Glu Tyr Asp Tyr Trp Gly Gln Gly Thr Leu Val Thr Val Ser Ser Ala
        115                 120                 125

Gly Gly Pro Leu Gly Met Leu Ser Gln Ser Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser

```
                370                375                380
Leu Thr Cys Leu Val Lys Gly Phe Tyr Pro Ser Asp Ile Ala Val Glu
385                390                395                400

Trp Glu Ser Asn Gly Gln Pro Glu Asn Asn Tyr Lys Thr Thr Pro Pro
                405                410                415

Val Leu Asp Ser Asp Gly Ser Phe Phe Leu Tyr Ser Lys Leu Thr Val
                420                425                430

Asp Lys Ser Arg Trp Gln Gln Gly Asn Val Phe Ser Cys Ser Val Met
                435                440                445

His Glu Ala Leu His Asn His Tyr Thr Gln Lys Ser Leu Ser Leu Ser
                450                455                460

Pro
465

<210> SEQ ID NO 204
<211> LENGTH: 461
<212> TYPE: PRT
<213> ORGANISM: Artificial Sequence
<220> FEATURE:
<223> OTHER INFORMATION: an artificially synthesized sequence

<400> SEQUENCE: 204

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Asp Asp Tyr
                20                  25                  30

Gly Met Ser Trp Val Arg Gln Ala Pro Gly Lys Ala Leu Glu Trp Val
            35                  40                  45

Ser Ala Ile Ser Trp Asn Gly Asn Asn Thr Tyr Tyr Thr Glu Ser Met
        50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Val Lys Gly Ser Thr Ala Ile Val Gly Val Pro Pro Thr Tyr Pro Asp
                100                 105                 110

Glu Tyr Asp Tyr Trp Gly Gln Gly Thr Leu Val Thr Val Ser Ser Ala
            115                 120                 125

Pro Leu Gly Leu Trp Ala Ser Thr Lys Gly Pro Ser Val Phe Pro Leu
        130                 135                 140

Ala Pro Ser Ser Lys Ser Thr Ser Gly Gly Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
                180                 185                 190

Ser Gly Leu Tyr Ser Leu Ser Ser Val Val Thr Val Pro Ser Ser Ser
            195                 200                 205

Leu Gly Thr Gln Thr Tyr Ile Cys Asn Val Asn His Lys Pro Ser Asn
        210                 215                 220

Thr Lys Val Asp Lys Lys Val Glu Pro Lys Ser Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
```

```
                260                 265                 270
Pro Glu Val Thr Cys Val Val Asp Val Ser His Glu Asp Pro Glu
            275                 280                 285
Val Lys Phe Asn Trp Tyr Val Asp Gly Val Glu Val His Asn Ala Lys
        290                 295                 300
Thr Lys Pro Arg Glu Glu Gln Tyr Asn Ser Thr Tyr Arg Val Val Ser
305                 310                 315                 320
Val Leu Thr Val Leu His Gln Asp Trp Leu Asn Gly Lys Glu Tyr Lys
                325                 330                 335
Cys Lys Val Ser Asn Lys Ala Leu Pro Ala Pro Ile Glu Lys Thr Ile
            340                 345                 350
Ser Lys Ala Lys Gly Gln Pro Arg Glu Pro Gln Val Tyr Thr Leu Pro
        355                 360                 365
Pro Ser Arg Glu Glu Met Thr Lys Asn Gln Val Ser Leu Thr Cys Leu
    370                 375                 380
Val Lys Gly Phe Tyr Pro Ser Asp Ile Ala Val Glu Trp Glu Ser Asn
385                 390                 395                 400
Gly Gln Pro Glu Asn Asn Tyr Lys Thr Thr Pro Pro Val Leu Asp Ser
                405                 410                 415
Asp Gly Ser Phe Phe Leu Tyr Ser Lys Leu Thr Val Asp Lys Ser Arg
            420                 425                 430
Trp Gln Gln Gly Asn Val Phe Ser Cys Ser Val Met His Glu Ala Leu
        435                 440                 445
His Asn His Tyr Thr Gln Lys Ser Leu Ser Leu Ser Pro
    450                 455                 460

<210> SEQ ID NO 205
<211> LENGTH: 463
<212> TYPE: PRT
<213> ORGANISM: Artificial Sequence
<220> FEATURE:
<223> OTHER INFORMATION: an artificially synthesized sequence

<400> SEQUENCE: 205

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Asp Asp Tyr
            20                  25                  30
Gly Met Ser Trp Val Arg Gln Ala Pro Gly Lys Ala Leu Glu Trp Val
        35                  40                  45
Ser Ala Ile Ser Trp Asn Gly Asn Asn Thr Tyr Tyr Thr Glu Ser Met
    50                  55                  60
Lys Gly Arg Phe Thr Ile Ser Arg Asp Asn Ala Lys Asn Thr Leu Tyr
65                  70                  75                  80
Leu Gln Met Asn Ser Leu Arg Pro Glu Asp Thr Ala Val Tyr Tyr Cys
                85                  90                  95
Val Lys Gly Ser Thr Ala Ile Val Gly Val Pro Pro Tyr Pro Asp
            100                 105                 110
Glu Tyr Asp Tyr Trp Gly Gln Gly Thr Leu Val Thr Val Ser Ser Ala
        115                 120                 125
Val Pro Leu Ser Leu Thr Met Gly Ser Thr Lys Gly Pro Ser Val Phe
    130                 135                 140
Pro Leu Ala Pro Ser Ser Lys Ser Thr Ser Gly Gly Thr Ala Ala Leu
145                 150                 155                 160
Gly Cys Leu Val Lys Asp Tyr Phe Pro Glu Pro Val Thr Val Ser Trp
```

```
                    165                 170                 175
Asn Ser Gly Ala Leu Thr Ser Gly Val His Thr Phe Pro Ala Val Leu
                180                 185                 190

Gln Ser Ser Gly Leu Tyr Ser Leu Ser Ser Val Val Thr Val Pro Ser
                195                 200                 205

Ser Ser Leu Gly Thr Gln Thr Tyr Ile Cys Asn Val Asn His Lys Pro
            210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
                260                 265                 270

Arg Thr Pro Glu Val Thr Cys Val Val Val Asp Val Ser His Glu Asp
            275                 280                 285

Pro Glu Val Lys Phe Asn Trp Tyr Val Asp Gly Val Glu Val His Asn
            290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
                340                 345                 350

Thr Ile Ser Lys Ala Lys Gly Gln Pro Arg Glu Pro Gln Val Tyr Thr
            355                 360                 365

Leu Pro Pro Ser Arg Glu Glu Met Thr Lys Asn Gln Val Ser Leu Thr
370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro
    450                 455                 460

<210> SEQ ID NO 206
<211> LENGTH: 468
<212> TYPE: PRT
<213> ORGANISM: Artificial Sequence
<220> FEATURE:
<223> OTHER INFORMATION: an artificially synthesized sequence

<400> SEQUENCE: 206

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Ala Leu Glu Trp Val
        35                  40                  45

Ser Ala Ile Ser Trp Asn Gly Asn Asn Thr Tyr Tyr Thr Glu Ser Met
    50                  55                  60

Lys Gly Arg Phe Thr Ile Ser Arg Asp Asn Ala Lys Asn Thr Leu Tyr
```

```
                65                  70                  75                  80
Leu Gln Met Asn Ser Leu Arg Pro Glu Asp Thr Ala Val Tyr Tyr Cys
                    85                  90                  95

Val Lys Gly Ser Thr Ala Ile Val Gly Val Pro Pro Thr Tyr Pro Asp
                100                 105                 110

Glu Tyr Asp Tyr Trp Gly Gln Gly Thr Leu Val Thr Val Ser Ser Ala
                115                 120                 125

Gly Ala Gly Val Pro Leu Ser Leu Thr Met Gly Ala Gly Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
                195                 200                 205

Val Thr Val Pro Ser Ser Leu Gly Thr Gln Thr Tyr Ile Cys Asn
210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Val Asp
                275                 280                 285

Val Ser His Glu Asp Pro Glu Val Lys Phe Asn Trp Tyr Val Asp Gly
                290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
                355                 360                 365

Pro Gln Val Tyr Thr Leu Pro Pro Ser Arg Glu Glu Met Thr Lys Asn
                370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
                435                 440                 445

Ser Val Met His Glu Ala Leu His Asn His Tyr Thr Gln Lys Ser Leu
                450                 455                 460

Ser Leu Ser Pro
465

<210> SEQ ID NO 207
```

<211> LENGTH: 471
<212> TYPE: PRT
<213> ORGANISM: Artificial Sequence
<220> FEATURE:
<223> OTHER INFORMATION: an artificially synthesized sequence

<400> SEQUENCE: 207

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Ala Leu Glu Trp Val
        35                  40                  45

Ser Ala Ile Ser Trp Asn Gly Asn Asn Thr Tyr Tyr Thr Glu Ser Met
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Val Lys Gly Ser Thr Ala Ile Val Gly Val Pro Pro Thr Tyr Pro Asp
            100                 105                 110

Glu Tyr Asp Tyr Trp Gly Gln Gly Thr Leu Val Thr Val Ser Ser Ala
        115                 120                 125

Gly Ala Gly Pro Gln Gly Leu Ala Gly Gln Arg Gly Ile Val Ala Gly
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Glu Glu Met
    370                 375                 380
```

-continued

```
Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro
465             470
```

ANTIGEN-BINDING DOMAIN, AND POLYPEPTIDE INCLUDING CONVEYING SECTION

CROSS-REFERENCE TO RELATED APPLICATIONS

This application is a U.S. National Phase of PCT Application No. PCT/JP2017/042,542, filed Nov. 28, 2017, which claims priority to Japanese Patent Application No. 2016-0229794, filed Nov. 28, 2016, each of which is incorporated herein by reference.

REFERENCE TO SEQUENCE LISTING SUBMITTED ELECTRONICALLY

The content of the electronically submitted sequence listing (Name: 6663_0112_sequence_listing.txt; Size: 266 kilobytes; and Date of Creation: May 22, 2019) filed with the application is incorporated herein by reference in its entirety.

TECHNICAL FIELD

The present invention relates to a polypeptide comprising an antigen binding domain and a carrying moiety having an inhibiting domain that inhibits the antigen binding activity of the antigen binding domain, and having a longer half-life than the half-life of the antigen binding domain which exists alone, methods for producing and screening for the polypeptide, a pharmaceutical composition comprising the polypeptide, methods for producing and screening for a single-domain antibody whose antigen binding activity can be inhibited by associating with particular VL, VH or VHH, and a library of fusion polypeptides in which a single-domain antibody whose antigen binding activity can be inhibited by associating with particular VL, VH or VHH is included.

BACKGROUND

Antibodies have received attention as drugs because of being highly stable in plasma and causing few adverse reactions. Among them, many IgG-type antibody drugs have been launched, and a large number of antibody drugs are currently under development (Non Patent Literatures 1 and 2).

Rituxan against CD20, cetuximab against EGFR, Herceptin against HER2, and the like have been approved so far as therapeutic drugs for cancer using antibody drugs (Non Patent Literature 3). These antibody molecules bind to their antigens expressed on cancer cells and thereby exert cytotoxic activity against the cancer cells through ADCC activity, etc. Such cytotoxic activity based on ADCC activity, etc. is known to depend on the number of antigens expressed on target cells of therapeutic antibodies (Non Patent Literature 4). Therefore, high expression levels of targeted antigens are preferred from the viewpoint of the effects of therapeutic antibodies. However, if an antigen, albeit having a high expression level, is expressed in normal tissues, the cytotoxic activity based on ADCC activity, etc. is exerted against the normal cells. Hence, adverse reactions become a serious problem. Therefore, it is preferred that antigens targeted by therapeutic antibodies as therapeutic drugs for cancer should be expressed specifically on cancer cells. For example, an antibody molecule against EpCAM known as a cancer antigen had been considered promising as a therapeutic drug for cancer. However, the EpCAM is known to be also expressed in the pancreas. In actuality, it has been reported in clinical trials that the administration of an anti-EpCAM antibody causes pancreatitis as an adverse reaction due to cytotoxic activity against the pancreas (Non Patent Literature 5).

In the wake of the success of antibody drugs exerting cytotoxic activity based on ADCC activity, second-generation improved antibody molecules exerting strong cytotoxic activity have been reported as a result of, for example, enhancing ADCC activity by the removal of fucose from the N-linked oligosaccharide of a natural human IgG1 Fc region (Non Patent Literature 6) or enhancing ADCC activity by enhancing binding to FcγRIIIa through the amino acid substitution of a natural human IgG1 Fc region (Non Patent Literature 7). Improved antibody molecules exerting stronger cytotoxic activity, such as an antibody drug conjugate (ADC) containing an antibody conjugated with a drug having strong cytotoxic activity (Non Patent Literature 8), and a low-molecular antibody exerting cytotoxic activity against cancer cells by recruiting T cells to the cancer cells (Non Patent Literature 9) have also been reported as antibody drugs exerting cytotoxic activity against cancer cells under a mechanism other than NK cell-mediated ADCC activity as mentioned above.

Such antibody molecules exerting stronger cytotoxic activity can exert cytotoxic activity even against cancer cells expressing an antigen at a level that is not high, but also exert cytotoxic activity against normal tissues expressing the antigen at a low level, similarly to cancer cells. In actuality, EGFR-BiTE, a bispecific antibody against CD3 and EGFR, can exert strong cytotoxic activity against cancer cells and exert an antitumor effect, by recruiting T cells to the cancer cells, as compared with cetuximab, natural human IgG1 against the EGFR. On the other hand, it has also been found that serious adverse reactions appear by the administration of EGFR-BiTE to cynomolgus monkeys, because EGFR is also expressed in normal tissues (Non Patent Literature 10). Also, ADC bivatuzumab mertansine containing mertansine conjugated with an antibody against CD44v6 highly expressed on cancer cells has been clinically found to cause severe dermal toxicity and hepatotoxicity, because CD44v6 is also expressed in normal tissues (Non Patent Literature 11).

As mentioned above, use of an antibody that can exert strong cytotoxic activity even against cancer cells expressing an antigen at low levels requires the target antigen to be expressed in an exceedingly cancer-specific manner. However, considering that a target antigen HER2 of Herceptin or a target antigen EGFR of cetuximab is also expressed in normal tissues, only a limited number of cancer antigens may be expressed in an exceedingly cancer-specific manner. Therefore, adverse reactions ascribable to a cytotoxic effect on normal tissues may become a problem, though cytotoxic activity against cancer can be enhanced.

Recently, ipilimumab, which enhances tumor immunity by inhibiting CTLA4 contributing to immunosuppression in cancer, has been shown to extend overall survival in metastatic melanoma (Non Patent Literature 12). However, ipilimumab systemically inhibits CTLA4 and therefore causes autoimmune disease-like severe adverse reactions due to the systemic activation of immunity, though enhancing the tumor immunity (Non Patent Literature 13).

Meanwhile, antibody drugs exerting a therapeutic effect by inhibiting inflammatory cytokines in inflammatory or autoimmune diseases are known as antibody drugs against diseases other than cancer (Non Patent Literature 14). It is known that, for example, Remicade or Humira targeting TNF, and Actemra targeting IL-6R exert a high therapeutic effect on rheumatoid arthritis, whereas infectious disease is seen as an adverse reaction due to the systemic neutralization of these cytokines (Non Patent Literature 15).

Various techniques have been developed as techniques applicable to second-generation antibody drugs. For example, techniques of improving effector functions, antigen binding capacity, pharmacokinetics, or stability or reducing a risk of immunogenicity have been reported (Non Patent Literature 16). However, there are still a few reports on techniques that allow antibody drugs to act specifically on a target tissue in order to solve adverse reactions as described above. The reported techniques include a method which involves: connecting an antibody to a masking peptide via a linker that is cleaved by protease expressed at a lesion site such as a cancer tissue or an inflammatory tissue, thereby masking the antigen binding site of the antibody with the masking peptide and inhibiting the antigen binding activity of the antibody; and dissociating the masking peptide therefrom by the protease cleavage of this linker so that the antibody restores its antigen binding activity and becomes capable of binding to the antigen in a target pathological tissue (Non Patent Literatures 17 and 18 and Patent Literature 1).

CITATION LIST

Patent Literature

[Patent Literature 1] International Publication No. WO2010/081173

Non Patent Literature

[Non Patent Literature 1] Monoclonal antibody successes in the clinic. Janice M Reichert, Clark J Rosensweig, Laura B Faden & Matthew C Dewitz, Nat. Biotechnol. (2005) 23, 1073-1078

[Non Patent Literature 2] The therapeutic antibodies market to 2008. Pavlou A K, Belsey M J., Eur. J. Pharm. Biopharm. (2005) 59 (3), 389-396

[Non Patent Literature 3] Monoclonal antibodies: versatile platforms for cancer immunotherapy. Weiner L M, Surana R, Wang S., Nat. Rev. Immunol. (2010) 10 (5), 317-327

[Non Patent Literature 4] Differential responses of human tumor cell lines to anti-p185HER2 monoclonal antibodies. Lewis G D, Figari I, Fendly B, Wong W L, Carter P, Gorman C, Shepard H M, Cancer Immunol Immunotherapy (1993) 37, 255-263

[Non Patent Literature 5] ING-1, a monoclonal antibody targeting Ep-CAM in patients with advanced adenocarcinomas. de Bono J S, Tolcher A W, Forero A, Vanhove G F, Takimoto C, Bauer R J, Hammond L A, Patnaik A, White M L, Shen S, Khazaeli M B, Rowinsky E K, LoBuglio A F, Clin. Cancer Res. (2004) 10 (22), 7555-7565

[Non Patent Literature 6] Non-fucosylated therapeutic antibodies as next-generation therapeutic antibodies. Satoh M, Lida S, shitara K., Expert Opin. Biol. Ther. (2006) 6 (11), 1161-1173

[Non Patent Literature 7] Optimizing engagement of the immune system by anti-tumor antibodies: an engineer's perspective. Desjarlais J R, Lazar G A, Zhukovsky E A, Chu S Y., Drug Discov. Today (2007) 12 (21-22), 898-910

[Non Patent Literature 8] Antibody-drug conjugates: targeted drug delivery for cancer. Alley S C, Okeley N M, Senter P D., Curr. Opin. Chem. Biol. (2010) 14 (4), 529-537

[Non Patent Literature 9] BiTE: Teaching antibodies to engage T-cells for cancer therapy. Baeuerle P A, Kufer P, Bargou R., Curr. Opin. Mol. Ther. (2009) 11 (1), 22-30

[Non Patent Literature 10] T cell-engaging BiTE antibodies specific for EGFR potently eliminate KRAS- and BRAF-mutated colorectal cancer cells. Lutterbuese R, Raum T, Kischel R, Hoffmann P, Mangold S, Rattel B, Friedrich M, Thomas O, Lorenczewski G, Rau D, Schaller E, Herrmann I, Wolf A, Urbig T, Baeuerle P A, Kufer P., Proc. Natl. Acad. Sci. U.S.A. (2010) 107 (28), 12605-12610

[Non Patent Literature 11] Phase I trial with the CD44v6-targeting immunoconjugate bivatuzumab mertansine in head and neck squamous cell carcinoma. Riechelmann H, Sauter A, Golze W, Hanft G, Schroen C, Hoermann K, Erhardt T, Gronau S., Oral Oncol. (2008) 44 (9), 823-829

[Non Patent Literature 12] Ipilimumab in the treatment of melanoma. Trinh V A, Hwu W J., Expert Opin. Biol. Ther., (2012) April 14 (doi: 10.1517/14712598.2012.675325)

[Non Patent Literature 13] IPILIMUMAB—A NOVEL IMMUNOMODULATING THERAPY CAUSING AUTOIMMUNE HYPOPHYSITIS: A CASE REPORT AND REVIEW. Juszczak A, Gupta A, Karavitaki N, Middleton M R, Grossman A, Eur. J. Endocrinol. (2012) April 10 (doi: 10.1530/EJE-12-0167)

[Non Patent Literature 14] The Japanese experience with biologic therapies for rheumatoid arthritis. Takeuchi T, Kameda H., Nat. Rev. Rheumatol. (2010) 6 (11), 644-652

[Non Patent Literature 15] Current evidence for the management of rheumatoid arthritis with biological disease-modifying antirheumatic drugs: a systematic literature review informing the EULAR recommendations for the management of R A. Nam J L, Winthrop K L, van Vollenhoven R F, Pavelka K, Valesini G, Hensor E M, Worthy G, Landewe R, Smolen J S, Emery P, Buch M H., Ann. Rheum. Dis. (2010) 69 (6), 976-986

[Non Patent Literature 16] Antibody engineering for the development of therapeutic antibodies. Kim S J, Park Y, Hong H J., Mol. Cells. (2005) 20 (1), 17-29

[Non Patent Literature 17] Tumor-specific activation of an EGFR-targeting probody enhances therapeutic index. Desnoyers L R, Vasiljeva O, Richardson J H, Yang A, Menendez E E, Liang T W, Wong C, Bessette P H, Kamath K, Moore S J, Sagert J G, Hostetter D R, Han F, Gee J, Flandez J, Markham K, Nguyen M, Krimm M, Wong K R, Liu S, Daugherty P S, West J W, Lowman H B. Sci Transl Med. 2013 Oct. 16; 5(207): 207ra144.

[Non Patent Literature 18] Probody therapeutics for targeting antibodies to diseased tissue. Polu K R, Lowman H B. Expert Opin Biol Ther. 2014 August; 14(8): 1049-53.

SUMMARY

Technical Problem to be Solved

The present inventors have thought that the techniques of dissociating, by protease cleavage, a masking peptide inhibiting the antigen binding activity of an antibody so that the antibody restores its antigen binding activity, as described above might cause adverse reactions, because the antibody cleaved at a lesion site may distribute to normal tissues through blood flow, as the cleavage by protease is irreversible.

The present invention has been made on the basis of such an idea. An object of the present invention is to provide a pharmaceutical composition useful in disease treatment with a reduced adverse reaction, and an active ingredient thereof. Another object of the present invention is to provide methods for screening for and producing the pharmaceutical composition and the active ingredient.

Solution to Problem

The present inventors have conducted diligent studies and consequently developed a polypeptide comprising an antigen binding domain and a carrying moiety having an inhibiting domain that inhibits the binding activity of the antigen binding domain, and having a longer half-life than the half-life of the antigen binding domain which exists alone. It is considered that use of the polypeptide can allow the antigen binding domain to restore its antigen binding activity in a disease tissue and exert the antigen binding activity in the disease tissue. Furthermore, the systemic distribution of an activated form of the antigen binding domain can be suppressed owing to the difference in half-life between the polypeptide comprising the antigen binding domain whose antigen binding activity is inhibited and a polypeptide comprising the antigen binding domain whose antigen binding activity is restored. Moreover, the present inventors have found that the polypeptide or a pharmaceutical composition comprising the polypeptide is useful in disease treatment and also found that: the polypeptide or the pharmaceutical composition is useful in disease treatment which involves administering the polypeptide; and the polypeptide is useful in the production of a drug for disease treatment. The present inventors have further developed methods for screening for and producing the polypeptide, methods for producing and screening for a single-domain antibody whose antigen binding activity can be inhibited by associating with particular VL, VH or VHH, and a library including a single-domain antibody whose antigen binding activity can be inhibited by associating with particular VL, VH or VHH, completing the present invention.

The present invention is based on these findings and specifically encompasses exemplary embodiments described below.

(1) A polypeptide comprising an antigen binding domain and a carrying moiety, the carrying moiety having an inhibiting domain that inhibits the antigen binding activity of the antigen binding domain, and the antigen binding domain having a shorter half-life in blood than that of the carrying moiety.

(2) The polypeptide according to (1), wherein the molecular weight of the antigen binding domain is smaller than that of the carrying moiety.

(3) The polypeptide according to (1) or (2), wherein the molecular weight of the antigen binding domain is 60 kDa or smaller.

(4) The polypeptide according to any of (1) to (3), wherein the carrying moiety has FcRn binding activity, and the antigen binding domain has no FcRn binding activity or has weaker FcRn binding activity than that of the carrying moiety.

(5) The polypeptide according to any of (1) to (4), wherein the antigen binding domain is capable of being released from the polypeptide, and the antigen binding domain released from the polypeptide has higher antigen binding activity than that before the release (6) The polypeptide according to any of (1) to (5), wherein the inhibiting domain of the carrying moiety associates with the antigen binding domain and thereby inhibits the antigen binding activity of the antigen binding domain.

(7) The polypeptide according to (5), wherein the polypeptide comprises a cleavage site, wherein the cleavage site is cleaved so that the antigen binding domain becomes capable of being released from the polypeptide (8) The polypeptide according to (6), wherein the polypeptide comprises a cleavage site, wherein the cleavage site is cleaved so that the association of the inhibiting domain of the carrying moiety with the antigen binding domain is canceled.

(9) The polypeptide according to (7) or (8), wherein the cleavage site comprises a protease cleavage sequence.

(10) The polypeptide according to (9), wherein the protease is a target tissue specific protease.

(11) The polypeptide according to (10), wherein the target tissue is a cancer tissue or an inflammatory tissue.

(12) The polypeptide according to (9), wherein the protease is at least one protease selected from matriptase, urokinase (uPA), and metalloproteinase.

(13) The polypeptide according to (12), wherein the protease is at least one protease selected from MT-SP1, uPA, MMP2, MMP9, ADAMTS5, MMP7, and MMP13.

(14) The polypeptide according to (9), wherein the protease cleavage sequence comprises a sequence selected from SEQ ID NOs: 12, 25, 34, 35, 70 to 73, 75, 76, 91, 178, and 193 to 195.

(15) The polypeptide according to any of (9) to (14), wherein a first flexible linker is further attached to one end of the protease cleavage sequence.

(16) The polypeptide according to (15), wherein a second flexible linker is further attached to the other end of the protease cleavage sequence.

(17) The polypeptide according to (15), wherein the first flexible linker is a flexible linker consisting of a glycine-serine polymer.

(18) The polypeptide according to (16), wherein the second flexible linker is a flexible linker consisting of a glycine-serine polymer.

(19) The polypeptide according to any of (1) to (18), wherein the antigen binding domain comprises a single-domain antibody or is a single-domain antibody, wherein the inhibiting domain of the carrying moiety inhibits the antigen binding activity of the single-domain antibody.

(20) The polypeptide according to (19), wherein the single-domain antibody is VHH, VH having antigen binding activity by itself, or VL having antigen binding activity by itself.

(21) The polypeptide according to any of (1) to (20), wherein the antigen binding domain comprises a single-domain antibody, and the inhibiting domain of the carrying moiety is VHH, antibody VH, or antibody VL, wherein the antigen binding activity of the single-domain antibody is inhibited by the VHH, the antibody VH, or the antibody VL.

(22) The polypeptide according to any of (1) to (21), wherein the antigen binding domain comprises a single-domain antibody, and the inhibiting domain of the carrying moiety is VHH, antibody VH, or antibody VL, wherein the antigen binding activity of the single-domain antibody is inhibited by associating with the VHH, the antibody VH, or the antibody VL.

(23) The polypeptide according to any of (19) to (22), wherein the single-domain antibody is VHH or VH having antigen binding activity by itself, and the inhibiting domain of the carrying moiety is antibody VL, wherein the antigen binding activity of the VHH or the VH having antigen binding activity by itself is inhibited by associating with the antibody VL.

(24) The polypeptide according to any of (19) to (23), wherein the single-domain antibody is VHH, wherein the VHH has an amino acid substitution at at least one position selected from amino acid positions 37, 44, 45, and 47 (all according to the Kabat numbering).

(25) The polypeptide according to any of (19) to (23), wherein the single-domain antibody is VHH, wherein the VHH contains at least one amino acid selected from amino acids 37V, 44G, 45L, and 47W (all according to the Kabat numbering).

(26) The polypeptide according to any of (19) to (23), wherein the single-domain antibody is VHH, wherein the VHH contains at least one amino acid substitution selected from amino acid substitutions F37V, Y37V, E44G, Q44G, R45L, H45L, G47W, F47W, L47W, T47W, and S47W (all according to the Kabat numbering).

(27) The polypeptide according to any of (19) to (23), wherein the single-domain antibody is VHH, wherein the VHH has amino acid substitutions at at least one set of positions selected from positions 37/44, positions 37/45, positions 37/47, positions 44/45, positions 44/47, positions 45/47, positions 37/44/45, positions 37/44/47, positions 37/45/47, positions 44/45/47, and positions 37/44/45/47 (all according to the Kabat numbering).

(28) The polypeptide according to any of (19) to (23), wherein the single-domain antibody is VHH, wherein the VHH contains at least one set of amino acids selected from 37V/44G, 37V/45L, 37V/47W, 44G/45L, 44G/47W, 45L/47W, 37V/44G/45L, 37V/44G/47W, 37V/45L/47W, 44G/45L/47W, and 37V/44G/45L/47W (all according to the Kabat numbering).

(29) The polypeptide according to any of (19) to (23), wherein the single-domain antibody is VHH, wherein the VHH contains at least one set of amino acid substitutions selected from F37V/R45L, F37V/G47W, R45L/G47W, and F37V/R45L/G47W (all according to the Kabat numbering).

(30) The polypeptide according to any of (19) to (22), wherein the single-domain antibody is VL having antigen binding activity by itself, and the inhibiting domain of the carrying moiety is antibody VH, wherein the antigen binding activity of the VL having antigen binding activity by itself is inhibited by associating with the antibody VH.

(31) The polypeptide according to any of (1) to (30), wherein the carrying moiety has an FcRn binding region.

(32) The polypeptide according to any of (1) to (31), wherein the carrying moiety comprises an antibody constant region.

(33) The polypeptide according to (32), wherein the antibody constant region of the carrying moiety and the antigen binding domain are fused via a linker or without a linker.

(34) The polypeptide according to (32), wherein the carrying moiety comprises an antibody heavy chain constant region, wherein the antibody heavy chain constant region and the antigen binding domain are fused via a linker or without a linker.

(35) The polypeptide according to (32), wherein the carrying moiety comprises an antibody light chain constant region, wherein the antibody light chain constant region and the antigen binding domain are fused via a linker or without a linker.

(36) The polypeptide according to (34), wherein in the polypeptide, the N terminus of the antibody heavy chain constant region of the carrying moiety and the C terminus of the antigen binding domain are fused via a linker or without a linker, and the polypeptide further has a protease cleavage sequence, wherein the protease cleavage sequence is located within the sequence of the antigen binding domain, or on the antigen binding domain side compared with amino acid position 122 (EU numbering) of the antibody heavy chain constant region.

(37) The polypeptide according to (35), wherein in the polypeptide, the N terminus of the antibody light chain constant region of the carrying moiety and the C terminus of the antigen binding domain are fused via a linker or without a linker, and the polypeptide further has a protease cleavage sequence, wherein the protease cleavage sequence is located within the sequence of the antigen binding domain, or on the antigen binding domain side compared with amino acid position 113 (EU numbering) (Kabat numbering position 113) of the antibody light chain constant region.

(38) The polypeptide according to any of (33) to (35), wherein in the polypeptide, the N terminus of the antibody constant region of the carrying moiety and the C terminus of the antigen binding domain are fused via a linker or without a linker, the antigen binding domain is a single-domain antibody prepared from VH, or VHH, and the polypeptide further has a protease cleavage sequence, wherein the protease cleavage sequence is located within the sequence of the antibody constant region, or on the antibody constant region side compared with amino acid position 109 (Kabat numbering) of the single-domain antibody of the antigen binding domain.

(39) The polypeptide according to (33), wherein in the polypeptide, the N terminus of the antibody constant region of the carrying moiety and the C terminus of the antigen binding domain are fused via a linker or without a linker, and the polypeptide further has a protease cleavage sequence, wherein the protease cleavage sequence is located near the boundary between the antigen binding domain and the antibody constant region.

(40) The polypeptide according to (34), wherein in the polypeptide, the N terminus of the antibody heavy chain constant region of the carrying moiety and the C terminus of the antigen binding domain are fused via a linker or without a linker, and the polypeptide further has a protease cleavage sequence, wherein the protease cleavage sequence is located near the boundary between the antigen binding domain and the antibody heavy chain constant region.

(41) The polypeptide according to (35), wherein in the polypeptide, the N terminus of the antibody light chain constant region of the carrying moiety and the C terminus of the antigen binding domain are fused via a linker or without a linker, and the polypeptide further has a protease cleavage sequence, wherein the protease cleavage sequence is located near the boundary between the antigen binding domain and the antibody light chain constant region.

(42) The polypeptide according to (40), wherein the antigen binding domain is a single-domain antibody prepared from VH, or VHH, and the protease cleavage sequence is located at any position between amino acid position 109 (Kabat numbering) of the single-domain antibody of the antigen binding domain and amino acid position 122 (EU numbering) of the antibody heavy chain constant region.

(43) The polypeptide according to (41), wherein the antigen binding domain is a single-domain antibody prepared from VH, or VHH, and the protease cleavage sequence is located at any position between amino acid position 109 (Kabat numbering) of the single-domain antibody of the antigen binding domain and amino acid position 113 (EU numbering) (Kabat numbering position 113) of the antibody light chain constant region.

(44) The polypeptide according to (40), wherein the antigen binding domain is a single-domain antibody prepared from VL, and the protease cleavage sequence is located at any position between amino acid position 104 (Kabat numbering) of the single-domain antibody of the antigen binding domain and amino acid position 122 (EU numbering) of the antibody heavy chain constant region.

(45) The polypeptide according to (41), wherein the antigen binding domain is a single-domain antibody prepared from VL, and the protease cleavage sequence is located at any position between amino acid position 109 (Kabat numbering) of the single-domain antibody of the antigen binding domain and amino acid position 113 (EU numbering) (Kabat numbering position 113) of the antibody light chain constant region.

(46) The polypeptide according to any of (32) to (45), wherein the antibody constant region of the polypeptide is an IgG antibody constant region.

(47) The polypeptide according to any of (1) to (46), wherein the polypeptide is an IgG antibody-like molecule.

(48) The polypeptide according to any of (1) to (47), wherein when the antigen binding domain is assayed in an unreleased state by use of BLI (bio-layer interferometry) (Octet), the binding of the antigen binding domain to the antigen is not seen.

(49) The polypeptide according to any of (1) to (48), wherein a second antigen binding domain is further linked to the antigen binding domain.

(50) The polypeptide according to (49), wherein the second antigen binding domain has antigen binding specificity different from that of the antigen binding domain.

(51) The polypeptide according to (49) or (50), wherein the second antigen binding domain comprises a second single-domain antibody.

(52) The polypeptide according to (51), wherein the antigen binding domain is a single-domain antibody, the second antigen binding domain is a second single-domain antibody, and the antigen binding domain and the second antigen binding domain are capable of being released from the polypeptide, wherein the single-domain antibody and the second single-domain antibody form a bispecific antigen binding molecule in released states of the antigen binding domain and the second antigen binding domain.

(53) The polypeptide according to any of (49) to (52), wherein the second antigen binding domain is directed to HER2 or GPC3 as a target antigen.

(54) The polypeptide according to any of (1) to (53), wherein the polypeptide further has an additional antigen binding domain different from the antigen binding domain, wherein the antigen binding activity of the additional antigen binding domain is also inhibited by linking to the carrying moiety of the polypeptide.

(55) The polypeptide according to (54), wherein the additional antigen binding domain and the antigen binding domain differ in antigen binding specificity.

(56) The polypeptide according to any of (1) to (55), wherein the antigen binding domain is an antigen binding domain directed to plexin A1, IL6R or CD3 as a target antigen.

(57) A pharmaceutical composition comprising the polypeptide of any of (1) to (56).

(58) A method for producing the polypeptide of any of (1) to (56).

(59) The production method according to (58), comprising the following steps:
(a) obtaining a single-domain antibody binding to a target antigen;
(b) linking the single-domain antibody obtained in the step (a) to a carrying moiety such that the antigen binding activity of the single-domain antibody is inhibited by an inhibiting domain of the carrying moiety, to form a polypeptide precursor; and
(c) introducing a protease cleavage sequence into the polypeptide precursor.

(60) The production method according to (58), comprising the following steps:
(a) obtaining a single-domain antibody binding to a target antigen;
(b) linking the single-domain antibody obtained in the step (a) to a carrying moiety such that the antigen binding activity of the single-domain antibody is inhibited by an inhibiting domain of the carrying moiety, to form a polypeptide precursor; and
(c) introducing a protease cleavage sequence to near the boundary between the single-domain antibody and the carrying moiety.

(61) The production method according to (58), comprising the following steps:
(a) obtaining a single-domain antibody binding to a target antigen; and
(b) linking the single-domain antibody obtained in the step (a) to a carrying moiety via a protease cleavage sequence such that the antigen binding activity of the single-domain antibody is inhibited by an inhibiting domain of the carrying moiety, to form a polypeptide.

(62) The production method according to any of (59) to (61), further comprising the following step:
(d) confirming that the binding activity of the single-domain antibody incorporated in the polypeptide or the polypeptide precursor against the target antigen is weakened or lost.

(63) The production method according to any of (59) to (62), further comprising the following step:
(e) releasing the single-domain antibody by the protease cleavage of the protease cleavage sequence and confirming that the released single-domain antibody binds to the antigen.

(64) The production method according to (58), wherein the polypeptide is an IgG antibody-like molecule. (65) The production method according to (64), comprising the following steps:
(a) obtaining a single-domain antibody binding to a target antigen;
(b) associating the single-domain antibody obtained in the step (a) as a substitute for VH of an IgG antibody with VL, or associating the single-domain antibody as a substitute for VL of an IgG antibody with VH such that the antigen binding activity of the single-domain antibody is inhibited, to form an IgG antibody-like molecule precursor harboring the single-domain antibody; and
(c) introducing a protease cleavage sequence into the IgG antibody-like molecule precursor harboring the single-domain antibody.

(66) The production method according to (64), comprising the following steps:
(a) obtaining a single-domain antibody binding to a target antigen;
(b) associating the single-domain antibody obtained in the step (a) as a substitute for VH of an IgG antibody with VL, or associating the single-domain antibody as a substitute for VL of an IgG antibody with VH such that the antigen binding activity of the single-domain antibody is inhibited, to form an IgG antibody-like molecule precursor harboring the single-domain antibody; and (c) introducing a protease cleavage sequence to near the boundary between the single-domain antibody and an antibody constant region in the IgG antibody-like molecule precursor.

(67) The production method according to (64), comprising the following steps:
(a) obtaining a single-domain antibody binding to a target antigen; and
(b) linking the single-domain antibody obtained in the step (a) as a substitute for IgG antibody VH or VL to an IgG antibody heavy chain constant region or light chain constant region via a protease cleavage sequence such that the antigen binding activity of the single-domain antibody is inhibited, to form an IgG antibody-like molecule harboring the single-domain antibody.

(68) The production method according to any of (65) to (67), further comprising the following step:
(d) confirming that the binding activity of the single-domain antibody harbored in the IgG antibody-like molecule or the IgG antibody-like molecule precursor against the target antigen is weakened or lost.

(69) The production method according to any of (65) to (68), further comprising the following step:
(e) releasing the single-domain antibody by the protease cleavage of the protease cleavage sequence and confirming that the released single-domain antibody binds to the target antigen. (70) The production method according to (64), comprising the following steps:
(a) substituting an amino acid residue in a single-domain antibody that involves in association of the single-domain antibody with antibody VH, or substituting an amino acid residue in a single-domain antibody that involves in association of the single-domain antibody with antibody VL, to prepare an single-domain antibody variant retaining the binding activity of the single-domain antibody against the target antigen;
(b) associating the single-domain antibody variant prepared in the step (a) with antibody VL, or associating the single-domain antibody variant with antibody VH such that the antigen binding activity of the single-domain antibody variant is inhibited, to form an IgG antibody-like molecule precursor harboring the single-domain antibody variant; and
(c) introducing a protease cleavage sequence into the IgG antibody-like molecule precursor harboring the single-domain antibody variant.

(71) The production method according to (64), comprising the following steps:
(a) substituting an amino acid residue in a single-domain antibody that involves in association with antibody VH, or substituting an amino acid residue in a single-domain antibody that involves in association with antibody VL, to prepare an single-domain antibody variant retaining the binding activity of the single-domain antibody against the target antigen;
(b) associating the single-domain antibody variant prepared in the step (a) with antibody VL, or associating the single-domain antibody variant with antibody VH such that the antigen binding activity of the single-domain antibody variant is inhibited, to form an IgG antibody-like molecule precursor harboring the single-domain antibody variant; and
(c) introducing a protease cleavage sequence to near the boundary between the single-domain antibody variant and a constant region in the IgG antibody-like molecule precursor.

(72) The production method according to (64), comprising the following steps:
(a) substituting an amino acid residue in a single-domain antibody that involves in association with antibody VH, or substituting an amino acid residue in a single-domain antibody that involves in association with antibody VL, to prepare an single-domain antibody variant retaining the binding activity of the single-domain antibody against the target antigen; and
(b) linking the single-domain antibody variant prepared in the step (a) to an IgG antibody heavy chain constant region via a protease cleavage sequence, or linking the single-domain antibody variant to an IgG antibody light chain constant region via a protease cleavage sequence such that the antigen binding activity of the single-domain antibody variant is inhibited, to form an IgG antibody-like molecule harboring the single-domain antibody variant.

(73) The production method according to any of (70) to (72), further comprising the following step:
(d) confirming that the binding activity of the single-domain antibody variant harbored in the IgG antibody-like molecule or the binding activity of the single-domain antibody variant harbored in the IgG antibody-like molecule precursor against the target antigen is weakened or lost.

(74) The production method according to any of (70) to (73), further comprising the following step:
(e) releasing the single-domain antibody variant by cleaving the protease cleavage sequence with a protease and confirming that the released single-domain antibody variant binds to the target antigen.

(75) A polynucleotide encoding the polypeptide according to any of (1) to (56).

(76) A vector comprising the polynucleotide according to (75).

(77) A host cell comprising the polynucleotide according to (75) or the vector according to (76).

(78) A method for producing the polypeptide according to any of (1) to (56), comprising the step of culturing the host cell according to (77).

(79) A method for screening for a single-domain antibody whose antigen binding activity can be inhibited by associating with particular VL, associating with particular VH, or associating with particular VHH.

(80) The screening method according to (79), wherein the method is a method for screening for a single-domain antibody whose antigen binding activity can be inhibited by associating with particular VL.

(81) The screening method according to (80), comprising the following steps:
(a) obtaining a single-domain antibody having target antigen binding activity;
(b) associating the single-domain antibody obtained in the step (a) with a particular VL; and
(c) confirming that the binding activity of the single-domain antibody associated with the particular VL in the step (b) against the antigen is weakened or lost as compared with that before the association.

(82) The screening method according to (80), comprising the following steps:
(a) associating a single-domain antibody with a particular VL;
(b) selecting an association of the VL and the single-domain antibody on the basis that the single-domain antibody associated with the particular VL in the step (a) has no binding activity or binding activity of a predetermined value or lower against the antigen; and
(c) confirming that the single-domain antibody in the associate selected in the step (b) has stronger binding activity against the antigen in a state unassociated with the particular VL than that in a state associated therewith.

(83) The screening method according to (79), wherein the method is a method for screening for a single-domain antibody whose antigen binding activity can be inhibited by associating with particular VH.

(84) The screening method according to (83), comprising the following steps:
(a) obtaining a single-domain antibody having target antigen binding activity;
(b) associating the single-domain antibody obtained in the step (a) with a particular VH; and
(c) confirming that the binding activity of the single-domain antibody associated with the particular VH in the step (b) against the antigen is weakened or lost as compared with that before the association.

(85) The screening method according to (83), comprising the following steps:
(a) associating a single-domain antibody with a particular VH;
(b) selecting an association of the VH and the single-domain antibody on the basis that the single-domain antibody associated with the particular VH in the step (a) has no binding activity or binding activity of a predetermined value or lower against the antigen; and
(c) confirming that the single-domain antibody in the associate selected in the step (b) has stronger binding activity against the antigen in a state unassociated with the particular VH than that in a state associated therewith.

(86) The screening method according to (79), wherein the method is a method for screening for a single-domain antibody whose antigen binding activity can be inhibited by associating with particular VHH.

(87) The screening method according to (86), comprising the following steps:
(a) obtaining a single-domain antibody having target antigen binding activity;
(b) associating the single-domain antibody obtained in the step (a) with a particular VHH; and
(c) confirming that the binding activity of the single-domain antibody associated with the particular VHH in the step (b) against the antigen is weakened or lost as compared with that before the association.

(88) The screening method according to (86), comprising the following steps:
(a) associating a single-domain antibody with a particular VHH;
(b) selecting an association of the VHH and the single-domain antibody on the basis that the single-domain antibody associated with the particular VHH in the step (a) has no binding activity or binding activity of a predetermined value or lower against the antigen; and
(c) confirming that the single-domain antibody in the associate selected in the step (b) has stronger binding activity against the antigen in a state unassociated with the particular VHH than that in a state associated therewith.

(89) A method for producing a single-domain antibody whose antigen binding activity can be inhibited by associating with particular VL, associating with particular VH, or associating with particular VHH.

(90) The production method according to (89), wherein the method is a method for producing a single-domain antibody whose antigen binding activity can be inhibited by associating with particular VL.

(91) The production method according to (90), comprising the following step:
(a) substituting an amino acid residue in a single-domain antibody that involves in association with antibody VL, to prepare an single-domain antibody variant retaining the binding activity of the single-domain antibody against the target antigen.

(92) The production method according to (91), further comprising the following steps:
(b) associating the single-domain antibody variant prepared in the step (a) with the VL; and
(c) confirming that the antigen binding activity of the single-domain antibody variant associated with the VL is weakened or lost as compared with that before the association.

(93) The production method according to (89), wherein the method is a method for producing a single-domain antibody whose antigen binding activity can be inhibited by associating with particular VH.

(94) The production method according to (93), comprising the following step:
(a) substituting an amino acid residue in a single-domain antibody that involves in association with IgG antibody-like molecule VH, to prepare an single-domain antibody variant retaining the binding activity of the single-domain antibody against the target antigen.

(95) The production method according to (94), further comprising the following steps:
(b) associating the single-domain antibody variant prepared in the step (a) with the VH; and
(c) confirming that the antigen binding activity of the single-domain antibody variant associated with the VH is weakened or lost as compared with that before the association.

(96) The production method according to (89), wherein the method is a method for producing a single-domain antibody whose antigen binding activity can be inhibited by associating with particular VHH.

(97) The production method according to (96), comprising the following step:
(a) substituting an amino acid residue in a single-domain antibody that involves in association with VHH, to prepare an single-domain antibody variant retaining the binding activity of the single-domain antibody against the target antigen.

(98) The production method according to (97), further comprising the following steps:
(b) associating the single-domain antibody variant prepared in the step (a) with the VHH; and
(c) confirming that the antigen binding activity of the single-domain antibody variant associated with the VHH is weakened or lost as compared with that before the association. (99)

A library comprising a plurality of fusion polypeptides of single-domain antibodies each linked to a first association sustaining domain, wherein the single-domain antibodies include a single-domain antibody whose antigen binding activity can be inhibited or lost by associating with particular VL, a single-domain antibody whose antigen binding activity can be inhibited or lost by associating with particular VH, or a single-domain antibody whose antigen binding activity can be inhibited or lost by associating with particular VHH.

(100) The library according to (99), wherein the single-domain antibody moieties of the fusion polypeptides in the library include a single-domain antibody obtained from an animal of the family Camelidae or a transgenic animal harboring a gene capable of raising the single-domain antibody, or a humanized antibody thereof, a single-domain antibody obtained by the immunization of an animal of the family Camelidae or a transgenic animal harboring a gene capable of raising the single-domain antibody, or a humanized antibody thereof, or an artificially prepared single-domain antibody originating from human antibody VH or VL.

(101) The library according to (99) or (100) which is a library comprising a plurality of fusion polypeptides of single-domain antibodies each linked to a first association sustaining domain, wherein the single-domain antibodies include a single-domain antibody whose antigen binding activity can be inhibited or lost by associating with particular VL.

(102) The library according to (99) or (100) which is a library comprising a plurality of fusion polypeptides of single-domain antibodies each linked to a first association sustaining domain, wherein the single-domain antibodies include a single-domain antibody whose antigen binding activity can be inhibited or lost by associating with particular VH.

(103) The library according to (99) or (100) which is a library comprising a plurality of fusion polypeptides of single-domain antibodies each linked to a first association sustaining domain, wherein the single-domain antibodies include a single-domain antibody whose antigen binding activity can be inhibited or lost by associating with particular VHH.

(104) A method for screening a library according to (99) or (100) for a fusion polypeptide comprising a single-domain antibody whose antigen binding activity can be inhibited or could lost by associating with particular VL, a single-domain antibody whose antigen binding activity can be inhibited or lost by associating with particular VH, or a single-domain antibody whose antigen binding activity can be inhibited or lost by associating with particular VHH.

(105) A method for screening a library according to (101) for a fusion polypeptide comprising a single-domain antibody whose antigen binding activity can be inhibited or could lost by associating with particular VL.

(106) The screening method according to (105), comprising the following steps:
(a) in vitro displaying the fusion polypeptides of the library;
(b) providing an association partner of a second association sustaining domain fused with a particular VL;
(c) associating the fusion polypeptides displayed in the step (a) with the association partner provided in the step (b) and selecting a fusion polypeptide that does not bind to the antigen or has antigen binding activity of a predetermined value or lower in a state where the single-domain antibody associates with the VL; and
(d) selecting, from the fusion polypeptides thus selected in the step (c), a fusion polypeptide that binds to the antigen or has antigen binding activity of a predetermined value or higher in a state where the single-domain antibody contained therein does not associate with the VL.

(107) The screening method according to (106), wherein the association partner provided in the step (b) further comprises a protease cleavage sequence, and the step (d) comprises cleaving the association partner by protease treatment so that the association of the single-domain antibody with the VL is canceled.

(108) The screening method according to (107), wherein the protease cleavage sequence of the association partner provided in the step (b) is located near the boundary between the particular VL and the second association sustaining domain.

(109) The screening method according to (106), wherein the fusion polypeptides of the library further comprise a protease cleavage sequence, and the step (d) comprises cleaving the fusion polypeptides by protease treatment so that the association of the single-domain antibody with the VL is canceled.

(110) The screening method according to (109), wherein the protease cleavage sequence contained in each fusion polypeptide is located near the boundary between the single-domain antibody and the first association sustaining domain.

(111) The screening method according to (106), wherein the step (d) comprises in vitro displaying again the full lengths of the fusion polypeptides selected in the step (c) or their moieties comprising the single-domain antibodies.

(112) The screening method according to (106), wherein the step (d) comprises in vitro displaying again the full lengths of the fusion polypeptides selected in the step (c) and selecting a fusion polypeptide that binds to the antigen or has antigen binding activity of a predetermined value or higher in a state associated only with the second association sustaining domain.

(113) A method for screening a library according to (102) for a fusion polypeptide comprising a single-domain antibody whose antigen binding activity can be inhibited or could lost by associating with particular VH.

(114) The screening method according to (113), comprising the following steps:
(a) in vitro displaying the fusion polypeptides of the library;
(b) providing an association partner of a second association sustaining domain fused with a particular VH;
(c) associating the fusion polypeptides displayed in the step (a) with the association partner provided in the step (b) and selecting a fusion polypeptide that does not bind to the antigen or has antigen binding activity of a predetermined value or lower in a state where the single-domain antibody associates with the VH; and
(d) selecting, from the fusion polypeptides thus selected in the step (c), a fusion polypeptide that binds to the antigen or has antigen binding activity of a predetermined value or higher in a state where the single-domain antibody contained therein does not associate with the VH.

(115) The screening method according to (114), wherein the association partner provided in the step (b) further comprises a protease cleavage sequence, and the step (d) comprises cleaving the association partner by protease treatment so that the association of the single-domain antibody with the VH is canceled.

(116) The screening method according to (115), wherein the protease cleavage sequence of the association partner provided in the step (b) is located near the boundary between the particular VH and the second association sustaining domain.

(117) The screening method according to (114), wherein the fusion polypeptides of the library further comprise a protease cleavage sequence, and the step (d) comprises cleaving the fusion polypeptides by protease treatment so that the association of the single-domain antibody with the VH is canceled.

(118) The screening method according to (117), wherein the protease cleavage sequence contained in each fusion polypeptide is located near the boundary between the single-domain antibody and the first association sustaining domain.

(119) The screening method according to (114), wherein the step (d) comprises in vitro displaying again the full lengths of the fusion polypeptides selected in the step (c) or their moieties comprising the single-domain antibodies.

(120) The screening method according to (114), wherein the step (d) comprises in vitro displaying again the full lengths of the fusion polypeptides selected in the step (c) and selecting a fusion polypeptide that binds to the antigen or has antigen binding activity of a predetermined value or higher in a state associated only with the second association sustaining domain.

(121) A method for screening a library according to (103) for a fusion polypeptide comprising a single-domain antibody whose antigen binding activity can be inhibited or could lost by associating with particular VHH.

(122) The screening method according to (121), comprising the following steps:

(a) in vitro displaying the fusion polypeptides of the library;

(b) providing an association partner of a second association sustaining domain fused with a particular VHH;

(c) associating the fusion polypeptides displayed in the step (a) with the association partner provided in the step (b) and selecting a fusion polypeptide that does not bind to the antigen or has antigen binding activity of a predetermined value or lower in a state where the single-domain antibody associates with the particular VHH; and (d) selecting, from the fusion polypeptides thus selected in the step (c), a fusion polypeptide that binds to the antigen or has antigen binding activity of a predetermined value or higher in a state where the single-domain antibody contained therein does not associate with the VHH.

(123) The screening method according to (122), wherein the association partner provided in the step (b) further comprises a protease cleavage sequence, and the step (d) comprises cleaving the association partner by protease treatment so that the association of the single-domain antibody with the VHH is canceled.

(124) The screening method according to (123), wherein the protease cleavage sequence of the association partner provided in the step (b) is located near the boundary between the particular VHH and the second association sustaining domain.

(125) The screening method according to (122), wherein the fusion polypeptides of the library further comprise a protease cleavage sequence, and the step (d) comprises cleaving the fusion polypeptides by protease treatment so that the association of the single-domain antibody with the VHH is canceled.

(126) The screening method according to (125), wherein the protease cleavage sequence contained in each fusion polypeptide is located near the boundary between the single-domain antibody and the first association sustaining domain.

(127) The screening method according to (122), wherein the step (d) comprises in vitro displaying again the full lengths of the fusion polypeptides selected in the step (c) or their moieties comprising the single-domain antibodies.

(128) The screening method according to (122), wherein the step (d) comprises in vitro displaying again the full lengths of the fusion polypeptides selected in the step (c) and selecting a fusion polypeptide that binds to the antigen or has antigen binding activity of a predetermined value or higher in a state associated only with the second association sustaining domain.

(129) The screening method according to any of (106) to (112), (114) to (120), and (122) to (128), wherein the step of providing an association partner in the step (b) is the step of displaying the association partner and the fusion polypeptides together.

(130) The library according to any of (99) to (103), wherein the first association sustaining domain comprises an IgG antibody CH1 domain or an antibody light chain constant region.

(131) The screening method according to any of (106) to (112), (114) to (120), and (122) to (128), wherein the first association sustaining domain comprises an IgG antibody CH1 domain, and the second association sustaining domain comprises an antibody light chain constant region.

(132) The screening method according to any of (106) to (112), (114) to (120), and (122) to (128), wherein the first association sustaining domain comprises an antibody light chain constant region, and the second association sustaining domain comprises an IgG antibody CH1 domain.

(133) The screening method according to (105), comprising the following steps:

(a) in vitro displaying the fusion polypeptides of the library;

(b) providing an association partner of a second association sustaining domain fused with a particular VL;

(c) selecting a fusion polypeptide comprising a single-domain antibody that binds to the antigen or has antigen binding activity of a predetermined value or higher; and (d) associating the fusion polypeptides thus selected in the step (c) with the association partner provided in the step (b) and selecting a fusion polypeptide that does not bind to the antigen or has antigen binding activity of a predetermined value or lower in a state where the single-domain antibody associates with the VL.

(134) The screening method according to (129), wherein the step (d) comprises in vitro displaying again the fusion polypeptides selected in the step (c).

(135) The screening method according to (133), wherein the step (c) comprises associating the fusion polypeptide only with the second association sustaining domain or confirming the antigen binding of the single-domain antibody contained in the fusion polypeptide associated only with the second association sustaining domain.

(136) The screening method according to (113), comprising the following steps:

(a) in vitro displaying the fusion polypeptides of the library;

(b) providing an association partner of a second association sustaining domain fused with a particular VH;

(c) selecting a fusion polypeptide comprising a single-domain antibody that binds to the antigen or has antigen binding activity of a predetermined value or higher; and (d) associating the fusion polypeptides thus selected in the step (c) with the association partner provided in the step (b) and selecting a fusion polypeptide that does not bind to the antigen or has antigen binding activity of a predetermined value or lower in a state where the single-domain antibody associates with the VH.

(137) The screening method according to (136), wherein the step (d) comprises in vitro displaying again the fusion polypeptides selected in the step (c).

(138) The screening method according to (136), wherein the step (c) comprises associating the fusion polypeptide only with the second association sustaining domain or confirming the antigen binding of the single-domain antibody contained in the fusion polypeptide associated only with the second association sustaining domain.

(139) The screening method according to (121), comprising the following steps:

(a) in vitro displaying the fusion polypeptides of the library;

(b) providing an association partner of a second association sustaining domain fused with a particular VHH;

(c) selecting a fusion polypeptide comprising a single-domain antibody that binds to the antigen or has antigen binding activity of a predetermined value or higher; and (d) associating the fusion polypeptides thus selected in the step (c) with the association partner provided in the step (b) and selecting a fusion polypeptide that does not bind to the antigen or has antigen binding activity of a predetermined value or lower in a state where the single-domain antibody associates with the VHH.

(140) The screening method according to (139), wherein the step (d) comprises in vitro displaying again the fusion polypeptides selected in the step (c).

(141) The screening method according to (139), wherein the step (c) comprises associating the fusion polypeptide only with the second association sustaining domain or confirming the antigen binding of the single-domain antibody contained in the fusion polypeptide associated only with the second association sustaining domain.

(142) The screening method according to any of (133) to (141), wherein the step of associating the fusion polypeptides with the association partner in the step (d) is the step of displaying the association partner and the fusion polypeptides together.

(143) The screening method according to any of (133) to (142), wherein the first association sustaining domain comprises an IgG antibody CH1 domain, and the second association sustaining domain comprises an antibody light chain constant region.

(144) The screening method according to any of (133) to (142), wherein the first association sustaining domain comprises an antibody light chain constant region, and the second association sustaining domain comprises an IgG antibody CH1 domain.

BRIEF DESCRIPTION OF DRAWINGS

FIG. 8(A) is a diagram showing the polypeptide in an unreleased state. The antigen binding activity of the antigen binding domain is inhibited. FIG. 8(B) is a diagram showing the release of the bispecific antigen binding molecule formed by the antigen binding domain and the second antigen binding domain. FIG. 8(C) is a diagram showing a bispecific antigen binding molecule against, for example, a T cell surface antigen and a cancer cell surface antigen, as an example of the bispecific antigen binding molecule after the release.

FIG. 9A(1) is a diagram showing the library comprising a plurality of fusion polypeptides of single-domain antibodies each linked to a first association sustaining domain. FIG. 9A(2) is a diagram showing that the antigen binding activity of each single-domain antibody is confirmed in a state where the fusion polypeptide associates with an association partner. A fusion polypeptide comprising a single-domain antibody that does not bind to the target antigen or has antigen binding activity of a predetermined value or lower in this state of association is selected. FIG. 9A(3) is a diagram showing that the association of the single-domain antibody in the fusion polypeptide selected in (2) with the inhibiting domain in the association partner is canceled, and the antigen binding activity of the single-domain antibody is confirmed. A fusion polypeptide comprising a single-domain antibody that binds to the target antigen or has antigen binding activity of a predetermined value or higher in this state of non-association is selected. FIG. 9A(2') is a diagram showing that the antigen binding activity of the single-domain antibody in each fusion polypeptide is confirmed. A fusion polypeptide comprising a single-domain antibody that binds to the target antigen or has antigen binding activity of a predetermined value or higher in this state of the fusion polypeptide existing alone is selected. FIG. 9A(3') is a diagram showing that the antigen binding activity of the single-domain antibody is confirmed in a state where the fusion polypeptide selected in (2') associates with an association partner. A fusion polypeptide comprising a single-domain antibody that does not bind to the target antigen or has antigen binding activity of a predetermined value or lower in this state of association is selected.

FIG. 11(A) is a diagram showtibody-like molecule model prepared by inserting a protease cleavage sequence near the boundary between VHH and the constant region in IL6R90-G1m. FIG. 11(B) is a diagram showing the name of each prepared antibody heavy chain, the insertion site of the amino acid sequence, and the inserted amino acid sequence. The insertion site is indicated by [insert].

FIG. 12-1 is a diagram showing results of evaluating the degree of cleavage by reducing SDS-PAGE after protease (MT-SP1) treatment of IL6R90-G1m or antibody-like molecules prepared by inserting a protease cleavage sequence near the boundary between VHH and the constant region in IL6R90-G1m. Of two new bands resulting from the protease treatment, the band appearing at 25 kDa or smaller is a band derived from the VHH, and the band appearing at a position of 25 to 50 kDa is a band derived from the constant region.

FIG. 12-2 is a diagram continued from FIG. 12-1.

FIG. 30A is a diagram showing the evaluation of the protease cleavage of IgG antibody-like molecules harboring a protease cleavage sequence in their heavy chains.

DESCRIPTION OF EMBODIMENTS

Figure 1:
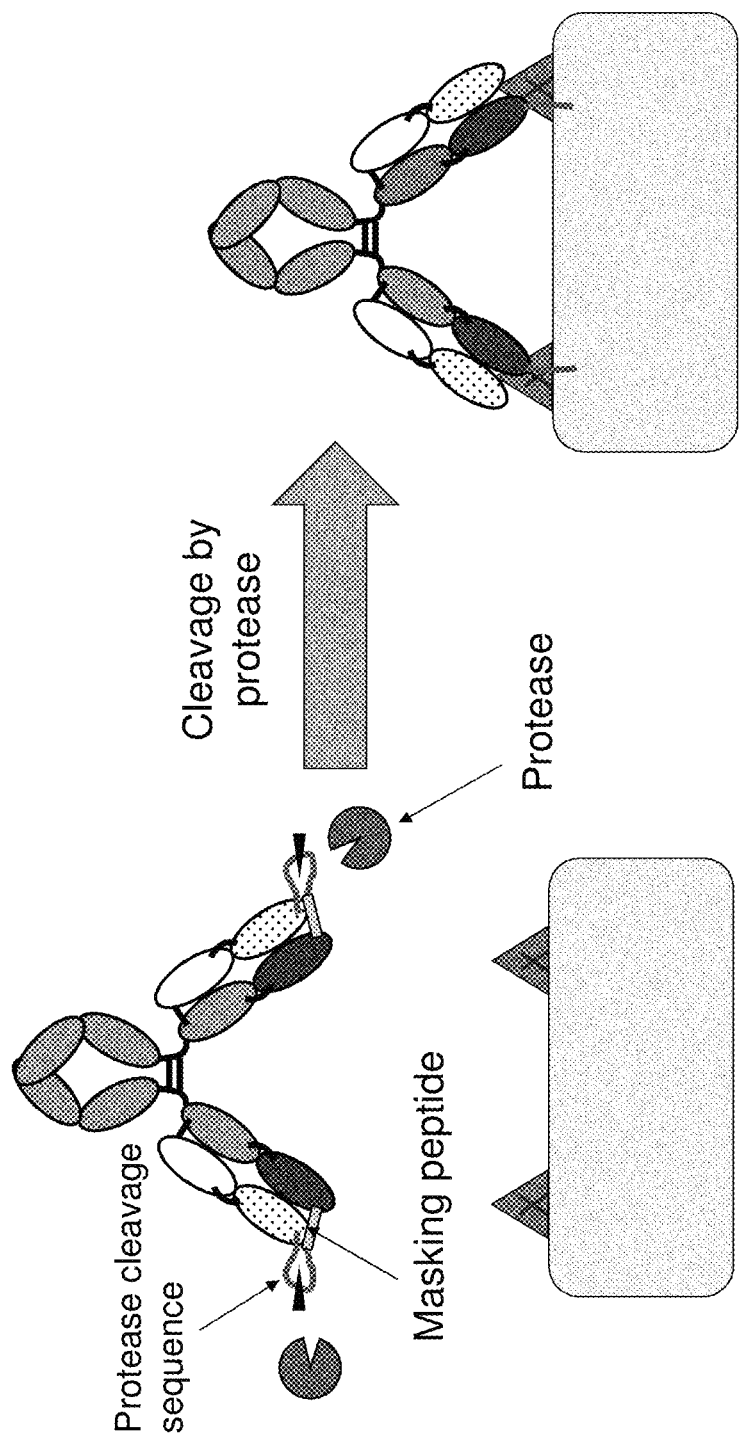
FIG. 1 is a diagram showing the concept of Probody technology. The Probody is an antibody molecule whose antigen binding activity is inhibited by connecting an antibody to a peptide masking the antigen binding site of the antibody via a linker that is cleaved by protease expressed at a lesion site.

The polypeptide according to the present invention usually refers to a peptide having a length on the order of 4 amino acids or longer, and a protein. Also, the polypeptide according to the present invention is usually a polypeptide consisting of an artificially designed sequence, but is not limited thereto. For example, an organism-derived polypeptide may be used. Alternatively, the polypeptide according to the present invention may be any of a natural polypeptide, a synthetic polypeptide, a recombinant polypeptide, and the like. Furthermore, fragments of these polypeptides are also included in the polypeptide of the present invention.

In the present specification, each amino acid is indicated by one-letter code or three-letter code, or both, as represented by, for example, Ala/A, Leu/L, Arg/R, Lys/K, Asn/N, Met/M, Asp/D, Phe/F, Cys/C, Pro/P, Ser/S, Glu/E, Thr/T, Gly/G, Trp/W, His/H, Tyr/Y, Ile/I, or Val/V. For expressing an amino acid located at a particular position, an expression using a number representing the particular position in combination with the one-letter code or the three-letter code of the amino acid can be appropriately used. For example, an amino acid 37V, which is an amino acid contained in a single-domain antibody, represents Val located at position 37 defined by the Kabat numbering.

For the alteration of an amino acid in the amino acid sequence of a polypeptide, a method known in the art such as site-directed mutagenesis (Kunkel et al. (Proc. Natl. Acad. Sci. USA (1985) 82, 488-492)) or overlap extension PCR can be appropriately adopted. A plurality of methods known in the art can also be adopted as alteration methods for substituting an amino acid by an amino acid other than a natural amino acid (Annu. Rev. Biophys. Biomol. Struct. (2006) 35, 225-249; and Proc. Natl. Acad. Sci. U.S.A. (2003) 100 (11), 6353-6357). For example, a tRNA-containing cell-free translation system (Clover Direct (Protein Express)) having a non-natural amino acid bound with amber suppressor tRNA complementary to UAG codon (amber codon), which is a stop codon, is also preferably used. In the present specification, examples of the alteration include, but are not limited to, substitution.

In the present specification, the term "and/or" used to represent amino acid alteration sites is meant to include every combination appropriately represented by "and" and "or". Specifically, for example, the phrase "amino acids at positions 37, 45, and/or 47 are substituted" includes the following variations of amino acid alteration:

(a) position 37, (b) position 45, (c) position 47, (d) positions 37 and 45, (e) positions 37 and 47, (f) positions 45 and 47, and (g) positions 37, 45 and 47.

In the present specification, expression in which the one-letter codes or three-letter-codes of amino acids before and after alteration are used previous and next to a number representing a particular position can be appropriately used for representing amino acid alteration. For example, an alteration F37V or Phe37Val used for substituting an amino acid contained in an antibody variable region or a single-domain antibody represents the substitution of Phe at position 37 defined by the Kabat numbering by Val. Specifically, the number represents an amino acid position defined by the Kabat numbering; the one-letter code or three-letter code of the amino acid previous to the number represents the amino acid before the substitution; and the one-letter code or three-letter code of the amino acid next to the number represents the amino acid after the substitution. Likewise, an alteration P238A or Pro238Ala used for substituting an amino acid in a Fc region contained in an antibody constant region represents the substitution of Pro at position 238 defined by the EU numbering by Ala. Specifically, the number represents an amino acid position defined by the EU numbering; the one-letter code or three-letter code of the amino acid previous to the number represents the amino acid before the substitution; and the one-letter code or three-letter code of the amino acid next to the number represents the amino acid after the substitution.

In the present specification, the term "antibody" is used in the broadest sense and encompasses various antibody structures including, but are not limited to, a monoclonal antibody, a polyclonal antibody, a multispecific antibody (e.g., a bispecific antibody), a single-domain antibody, and an antibody fragment as long as the antibody exhibits the desired antigen binding activity.

The "antibody fragment" refers to a molecule, other than a complete antibody, containing a portion of the complete antibody and binding to an antigen to which the complete antibody binds. Examples of the antibody fragment include, but are not limited to, Fv, Fab, Fab', Fab'-SH, $F(ab')_2$, diabody, linear antibodies, single-chain antibody molecules (e.g., scFv), and multispecific antibodies formed from antibody fragments.

The terms "full-length antibody", "complete antibody", and "whole antibody" are used interchangeably with each other in the present specification and refer to an antibody having a structure substantially similar to a natural antibody structure, or having heavy chains containing a Fc region defined in the present specification.

The term "variable region" or "variable domain" refers to a region or a domain of an antibody heavy chain or light chain involved in the binding of the antibody to its antigen. Usually, antibody heavy chain and light chain variable domains (VH and VL, respectively) are structurally similar and each contain 4 conserved framework regions (FRs) and 3 complementarity determining regions (CDRs) (see e.g., Kindt et al., Kuby Immunology, 6th ed., W.H. Freeman and Co., page 91 (2007)). One VH or VL domain may suffice for conferring antigen binding specificity.

The term "complementarity determining region" or "CDR" used in the present specification is hypervariable in the sequence, and/or forms a structurally determined loop ("hypervariable loop"), and/or refers to antigen contact residues ("antigen contacts") or each region of an antibody variable domain. Usually, an antibody contains 6 CDRs: three in VH (H1, H2, and H3), and three in VL (L1, L2, and L3). In the present specification, exemplary CDRs include the following:

(a) hypervariable loops formed at amino acid residues 26 to 32 (L1), 50 to 52 (L2), 91 to 96 (L3), 26 to 32 (H1), 53 to 55 (H2), and 96 to 101 (H3) (Chothia and Lesk, J. Mol. Biol. 196: 901-917 (1987));

(b) CDRs formed at amino acid residues 24 to 34 (L1), 50 to 56 (L2), 89 to 97 (L3), 31 to 35b (H1), 50 to 65 (H2), and 95 to 102 (H3) (Kabat et al., Sequences of Proteins of Immunological Interest, 5th Ed. Public Health Service, National Institutes of Health, Bethesda, Md. (1991));

(c) antigen contacts formed at amino acid residues 27c to 36 (L1), 46 to 55 (L2), 89 to 96 (L3), 30 to 35b (H1), 47 to 58 (H2), and 93 to 101 (H3) (MacCallum et al., J. Mol. Biol. 262: 732-745 (1996)); and (d) a combination of (a), (b), and/or (c) containing HVR amino acid residues 46 to 56 (L2), 47 to 56 (L2), 48 to 56 (L2), 49 to 56 (L2), 26 to 35 (H1), 26 to 35b (H1), 49 to 65 (H2), 93 to 102 (H3), and 94 to 102 (H3).

In the present specification, CDR residues and other residues (e.g., FR residues) in a variable domain are numbered according to Kabat et al. (supra), unless otherwise specified.

The term "framework" or "FR" refers to variable domain residues other than complementarity determining region (CDR) residues. FRs in a variable domain consist of 4 FR domains: FR1, FR2, FR3, and FR4. Accordingly, the sequences of CDRs and FRs usually appear in VH (or VL) in the following order: FR1-H1 (L1)-FR2-H2 (L2)-FR3-H3 (L3)-FR4.

In the present specification, the term "constant region" or "constant domain" refers to a region or a domain other than variable regions in an antibody. For example, an IgG antibody is a heterotetrameric glycoprotein of approximately 150,000 Da constituted by two identical light chains and two identical heavy chains connected through disulfide bonds. Each heavy chain has a variable region (VH) also called variable heavy chain domain or heavy chain variable domain, followed by a heavy chain constant region (CH) containing a CH1 domain, a hinge region, a CH2 domain, and a CH3 domain, from the N terminus toward the C terminus. Likewise, each light chain has a variable region (VL) also called variable light chain domain or light chain variable domain, followed by a constant light chain (CL) domain, from the N terminus toward the C terminus. The light chains of natural antibodies may be attributed to one of two types called kappa (κ) and lambda (λ) on the basis of the amino acid sequences of their constant domains.

In the present specification, the term "Fc region" is used for defining the C-terminal region of immunoglobulin heavy chains, including at least a portion of constant regions. This term includes a Fc region having a natural sequence and a mutant Fc region. In one embodiment, the heavy chain Fc region of human IgG1 spans from Cys226 or Pro230 to the carboxyl terminus of the heavy chain. However, the C-terminal lysine (Lys447) or glycine-lysine (Gly446-Lys447) of the Fc region may be present or absent. In the present specification, amino acid residues in a Fc region or a constant region are numbered according to the EU numbering system (also called EU index) described in Kabat et al., Sequences of Proteins of Immunological Interest, 5th Ed. Public Health Service, National Institutes of Health, Bethesda, Md. 1991, unless otherwise specified.

The "class" of an antibody refers to the type of a constant domain or a constant region carried by the heavy chain of the antibody. Antibodies have 5 major classes: IgA, IgD, IgE, IgG, and IgM. Some of these classes may be further divided into subclasses (isotypes), for example, IgG1, IgG2, IgG3, IgG4, IgA1, and IgA2. Heavy chain constant domains corresponding to immunoglobulins of different classes are called α, δ, ε, γ, and μ, respectively.

In the present specification, the "antigen binding domain" is limited only by binding to the antigen of interest. The antigen binding domain can be a domain having any structure as long as the domain used binds to the antigen of interest. Examples of such a domain include, but are not limited to, an antibody heavy chain variable region (VH), an antibody light chain variable region (VL), a single-domain antibody (sdAb), a module called A domain of approximately 35 amino acids contained in an in vivo cell membrane protein avimer (International Publication Nos. WO2004/044,011 and WO2005/040,229), adnectin containing a 10Fn3 domain serving as a protein binding domain derived from a glycoprotein fibronectin expressed on cell membranes (International Publication No. WO2002/032, 925), Affibody containing an IgG binding domain scaffold constituting a three-helix bundle composed of 58 amino acids of protein A (International Publication No. WO1995/ 001,937), DARPins (designed ankyrin repeat proteins) which are molecular surface-exposed regions of ankyrin repeats (AR) each having a 33-amino acid residue structure folded into a subunit of a turn, two antiparallel helices, and a loop (International Publication No. WO2002/020,565), anticalin having four loop regions connecting eight antiparallel strands bent toward the central axis in one end of a barrel structure highly conserved in lipocalin molecules such as neutrophil gelatinase-associated lipocalin (NGAL) (International Publication No. WO2003/029,462), and a depressed region in the internal parallel sheet structure of a horseshoe-shaped fold composed of repeated leucine-rich-repeat (LRR) modules of an immunoglobulin structure-free variable lymphocyte receptor (VLR) as seen in the acquired immune systems of jawless vertebrates such as lamprey or hagfish (International Publication No. WO2008/016,854).

Preferred examples of the antigen binding domain of the present invention include an antigen binding domain that can exert an antigen binding function by a molecule constituted only by the antigen binding domain, and an antigen binding domain that can exert an antigen binding function by itself after being released from an additional peptide linked thereto. Examples of such an antigen binding domain include, but are not limited to, a single-domain antibody, scFv, Fv, Fab, Fab', and F(ab')2.

One preferred example of the antigen binding domain of the present invention includes an antigen binding domain having a molecular weight of 60 kDa or smaller. Examples of such an antigen binding domain include, but are not limited to, single-domain antibodies, scFv, Fab, and Fab'. The antigen binding domain having a molecular weight of 60 kDa or smaller is usually likely to cause clearance by the kidney when existing as a monomer in blood (see J Biol Chem. 1988 Oct. 15; 263 (29): 15064-70).

From another viewpoint, one preferred example of the antigen binding domain of the present invention includes an antigen binding domain having a half-life in blood of 12 hours or shorter. Examples of such an antigen binding domain include, but are not limited to, single-domain antibodies, scFv, Fab, and Fab'.

One preferred example of the antigen binding domain of the present invention includes a single-domain antibody (sdAb).

In the present specification, the term "single-domain antibody" is not limited by its structure as long as the domain can exert antigen binding activity by itself. It is known that a general antibody, for example, an IgG antibody, exhibits antigen binding activity in a state where a variable region is formed by the pairing of VH and VL, whereas the own domain structure of the single-domain antibody can exert antigen binding activity by itself without pairing with another domain. Usually, the single-domain antibody has a relatively low molecular weight and exists in the form of a monomer.

Examples of the single-domain antibody include, but are not limited to, antigen binding molecules congenitally lacking a light chain, such as VHH of an animal of the family Camelidae and shark $V_{NAR}$, and antibody fragments containing the whole or a portion of an antibody VH domain or the whole or a portion of an antibody VL domain. Examples of the single-domain antibody which is an antibody fragment containing the whole or a portion of an antibody VH or VL domain include, but are not limited to, artificially prepared single-domain antibodies originating from human antibody VH or human antibody VL as described in U.S. Pat. No. 6,248,516 B1, etc. In some embodiments of the present invention, one single-domain antibody has three CDRs (CDR1, CDR2 and CDR3).

The single-domain antibody can be obtained from an animal capable of producing the single-domain antibody or by the immunization of the animal capable of producing the single-domain antibody. Examples of the animal capable of producing the single-domain antibody include, but are not limited to, animals of the family Camelidae, and transgenic animals harboring a gene capable of raising the single-domain antibody. The animals of the family Camelidae include camels, lamas, alpacas, one-hump camels and guanacos, etc. Examples of the transgenic animals harboring a gene capable of raising the single-domain antibody include, but are not limited to, transgenic animals described in International Publication No. WO2015/143414 and U.S. Patent Publication No. US2011/0123527 A1. The framework sequences of the single-domain antibody obtained from the animal may be converted to human germline sequences or sequences similar thereto to obtain a humanized single-domain antibody. The humanized single-domain antibody (e.g., humanized VHH) is also one embodiment of the single-domain antibody of the present invention.

Alternatively, the single-domain antibody can be obtained by ELISA, panning, or the like from a polypeptide library containing single-domain antibodies. Examples of the polypeptide library containing single-domain antibodies include, but are not limited to, naive antibody libraries obtained from various animals or humans (e.g., Methods in Molecular Biology 2012 911 (65-78); and Biochimica et Biophysica Acta—Proteins and Proteomics 2006 1764: 8 (1307-1319)), antibody libraries obtained by the immunization of various animals (e.g., Journal of Applied Microbiology 2014 117: 2 (528-536)), and synthetic antibody libraries prepared from antibody genes of various animals or humans (e.g., Journal of Biomolecular Screening 2016 21: 1 (35-43); Journal of Biological Chemistry 2016 291:24 (12641-12657); and AIDS 2016 30: 11 (1691-1701)).

In the present specification, the "antigen" is limited only by containing an epitope to which the antigen binding domain binds. Preferred examples of the antigen include, but are not limited to, animal- or human-derived peptides, polypeptides, and proteins. Preferred examples of the antigen for use in the treatment of a disease caused by a target tissue include, but are not limited to, molecules expressed on the surface of target cells (e.g., cancer cells and inflammatory cells), molecules expressed on the surface of other cells in tissues containing target cells, molecules expressed on the surface of cells having an immunological role against target cells and tissues containing target cells, and large molecules present in the stromata of tissues containing target cells.

Examples of the antigen can include the following molecules: 17-IA, 4-1BB, 4Dc, 6-keto-PGF1a, 8-iso-PGF2a, 8-oxo-dG, A1 adenosine receptor, A33, ACE, ACE-2, activin, activin A, activin AB, activin B, activin C, activin RIA, activin RIA ALK-2, activin RIB ALK-4, activin RIIA, activin RIIB, ADAM, ADAM10, ADAM12, ADAM15, ADAM17/TACE, ADAMS, ADAMS, ADAMTS, ADAMTS4, ADAMTS5, addressin, aFGF, ALCAM, ALK, ALK-1, ALK-7, alpha-1-antitrypsin, alpha-V/beta-1 antagonist, ANG, Ang, APAF-1, APE, APJ, APP, APRIL, AR, ARC, ART, artemin, anti-Id, ASPARTIC, atrial natriuretic factor, av/b3 integrin, Axl, b2M, B7-1, B7-2, B7-H, B-lymphocyte stimulator (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMP, b-NGF, BOK, bombesin, bone-derived neurotrophic factor, BPDE, BPDE-DNA, BTC, complement factor 3 (C3), C3a, C4, C5, CSa, C10, CA125, CAD-8, calcitonin, cAMP, carcinoembryonic antigen (CEA), cancer-associated antigens, cathepsin A, cathepsin B, cathepsin C/DPPI, cathepsin D, cathepsin E, cathepsin H, cathepsin L, cathepsin 0, cathepsin S, cathepsin V, cathepsin X/Z/P, CBL, CCI, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCLS, CCL6, CCL7, CCL8, CCL9/10, CCR, CCR1, CCR10, CCR10, CCR2, CCR3, CCR4, CCRS, CCR6, CCR7, CCR8, CCR9, CD1, CD2, CD3, CD3E, CD4, CDS, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD30L, CD32, CD33 (p67 protein), CD34, CD38, CD40, CD40L, CD44, CD45, CD46, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAMS, CFTR, cGMP, CINC, botulinum toxin, *Clostridium perfringens* toxin, CKb8-1, CLC, CMV, CMV UL, CNTF, CNTN-1, COX, C-Ret, CRG-2, CT-1, CTACK, CTGF, CTLA-4, PD1, PDL1, LAGS, TIM3, galectin-9, CX3CL1, CX3CR1, CXCL, CXCL1, CXCL2, CXCL3, CXCL4, CXCLS, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCRS, CXCR6, cytokeratin tumor-associated antigens, DAN, DCC, DcR3, DC-SIGN, decay accelerating factor, des(1-3)-IGF-I (brain IGF-1), Dhh, digoxin, DNAM-1, Dnase, Dpp, DPPIV/CD26, Dtk, ECAD, EDA, EDA-A1, EDA-A2, EDAR, EGF, EGFR (ErbB-1), EMA, EMMPRIN, ENA, endothelin receptor, enkephalinase, eNOS, Eot, eotaxin 1, EpCAM, ephrin B2/EphB4, EPO, ERCC, E-selectin, ET-1, factor IIa, factor VII, factor VIIIc, factor IX, fibroblast-activating protein (FAP), Fas, FcR1, FEN-1, ferritin, FGF, FGF-19, FGF-2, FGF3, FGF-8, FGFR, FGFR-3, fibrin, FL, FLIP, Flt-3, Flt-4, follicle-stimulating hormone, fractalkine, FZD1, FZD2, FZD3, FZD4, FZDS, FZD6, FZD7, FZD8, FZD9, FZD10, G250, Gas6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (myostatin), GDF-9, GDF-15 (MIC-1), GDNF, GDNF, GFAP, GFRa-1, GFR-alpha 1, GFR-alpha 2, GFR-alpha 3, GITR, glucagon, Glut4, glycoprotein IIb/IIIa (GPIIb/IIIa), GM-CSF, gp130, gp72, GRO, growth hormone-releasing factor, hapten (NP-cap or NIP-cap), HB-EGF, HCC, HCMV gB envelope glycoprotein, HCMV gH envelope glycoprotein, HCMV UL, hematopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, high-molecular-weight melanoma-associated antigen (HMW-MAA), HIV gp120, HIV IIIB gp 120 V3 loop, HLA, HLA-DR, HM1.24, HMFG PEM, HRG, Hrk, human heart myosin, human cytomegalovirus (HCMV), human growth hormone (HGH), HVEM, 1-309, IAP, ICAM, ICAM-1, ICAM-3, ICE, ICOS, IFNg, Ig, IgA receptor, IgE, IGF, IGF binding protein, IGF-1R, IGFBP, IGF-I, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-18, IL-18R, IL-21, IL-23, IL-27, interferon (INF)-alpha, INF-beta, INF-gamma, inhibin, iNOS, insulin chain A, insulin chain B, insulin-like growth factor 1, integrin alpha 2, integrin alpha 3, integrin alpha 4, integrin alpha 4/beta 1, integrin alpha 4/beta 7, integrin alpha 5 (alpha V), integrin alpha 5/beta 1, integrin alpha 5/beta 3, integrin alpha 6, integrin beta 1, integrin beta 2, interferon gamma, IP-10, I-TAC, JE, kallikrein 2, kallikrein 5, kallikrein 6, kallikrein 11, kallikrein 12, kallikrein 14, kallikrein 15, kallikrein L1, kallikrein L2, kallikrein L3, kallikrein L4, KC, KDR, keratinocyte growth factor (KGF), laminin 5, LAMP, LAP, LAP (TGF-1), latent TGF-1, latent TGF-1 bpl, LBP, LDGF, LECT2, lefty, Lewis-Y antigen, Lewis-Y-related antigen, LFA-1, LFA-3, Lfo, LIF, LIGHT, lipoprotein, LIX, LKN, Lptn, L-selectin, LT-a, LT-b, LTB4, LTBP-1, lung surface, luteinizing hormone, lymphotoxin beta receptor, Mac-1, MAdCAM, MAG, MAP2, MARC, MCAM, MCAM, MCK-2, MCP, M-CSF, MDC, Mer, metalloproteinases, MGDF receptor, MGMT, MHC (HLA-DR), MIF, MIG, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Mucl), MUC18, mullerian-inhibiting substance, Mug, MuSK, NAIP, NAP, NCAD, N-C adherin, NCA 90, NCAM, NCAM, neprilysin, neurotrophin-3, -4, or -6, neurturin, nerve growth factor (NGF), NGFR, NGF-beta, nNOS, NO, NOS, Npn, NRG-3, NT, NTN, OB, OGG1, OPG, OPN, OSM, OX40L, OX40R, p150, p95, PADPr, parathyroid hormone, PARC, PARP, PBR, PBSF, PCAD, P-cadherin, PCNA, PDGF, PDGF, PDK-1, PECAM, PEM, PF4, PGE, PGF, PGI2, PGJ2, PIN, PLA2, placental alkaline phosphatase (PLAP), P1GF, PLP, PP14, proinsulin, prorelaxin, protein C, PS, PSA, PSCA, prostate-specific membrane antigen (PSMA), PTEN, PTHrp, Ptk, PTN, R51, RANK, RANKL, RANTES, RANTES, relaxin A chain, relaxin B chain, renin, respiratory syncytial virus (RSV) F, RSV Fgp, Ret, rheumatoid factor, RLIP76, RPA2, RSK, 5100, SCF/KL, SDF-1, SERINE, serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T cell receptor (e.g., T cell receptor alpha/beta), TdT, TECK, TEM1, TEMS, TEM7, TEM8, TERT, testicular PLAP-like alkaline phosphatase, TfR, TGF, TGF-alpha, TGF-beta, TGF-beta Pan Specific, TGF-beta RI (ALK-5), TGF-beta RII, TGF-beta RIIb, TGF-beta RIII, TGF-beta 1, TGF-beta 2, TGF-beta 3, TGF-beta 4, TGF-beta 5, thrombin, thymus Ck-1, thyroid stimulating hormone, Tie, TIMP, TIQ, tissue factor, TMEFF2, Tmpo, TMPRSS2, TNF, TNF-alpha, TNF-alpha/beta, TNF-beta 2, TNFc, TNF-RI, TNF-RII, TNFRSF10A (TRAIL R1 Apo-2, DR4), TNFRSF10B (TRAIL R2 DRS, KILLER, TRICK-2A, TRICK-B), TNFRSF10C (TRAIL R3 DcR1, LIT, TRID), TNFRSF10D (TRAIL R4 DcR2, TRUNDD), TNFRSF11A (RANK ODF R, TRANCE R), TNFRSF11B (OPG OCIF, TR1), TNFRSF12 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSF1A (TNF RI CD120a, p55-60), TNFRSF1B (TNF RII CD120b, p75-80), TNFRSF26 (TNFRH3), TNFRSF3 (LTbR TNF RIII, TNFC R), TNFRSF4 (OX40 ACT35, TXGP1 R), TNFRSFS (CD40 p50), TNFRSF6 (Fas Apo-1, APT1, CD95), TNFRSF6B (DcR3 M68, TR6), TNFRSF7 (CD27), TNFRSF8 (CD30), TNFRSF9 (4-1BB CD137, ILA), TNFRSF21 (DR6), TNFRSF22 (DcTRAIL R2 TNFRH2), TNFRST23 (DcTRAIL R1 TNFRH1), TNFRSF25 (DR3 Apo-3, LARD, TR-3, TRAMP, WSL-1), TNFSF10 (TRAIL Apo-2 ligand, TL2), TNFSF11 (TRANCE/RANK ligand ODF, OPG ligand), TNFSF12 (TWEAK Apo-3 ligand, DR3 ligand), TNFSF13 (APRIL TALL2), TNFSF13B (BAFF BLYS, TALL1, THANK, TNFSF20), TNFSF14 (LIGHT HVEM ligand, LTg), TNFSF15 (TL1A/VEGI), TNFSF18 (GITR ligand AITR ligand, TL6), TNFSF1A (TNF-α Conectin, DIF, TNFSF2), TNFSF1B (TNF-b LTa, TNFSF1), TNFSF3 (LTb TNFC, p33), TNFSF4 (OX40 ligand gp34, TXGP1), TNFSF5 (CD40 ligand CD154, gp39, HIGM1, IMD3, TRAP), TNFSF6 (Fas ligand Apo-1 ligand, APT1 ligand), TNFSF7 (CD27 ligand CD70), TNFSF8 (CD30 ligand CD153), TNFSF9 (4-1BB ligand CD137 ligand), TP-1, t-PA, Tpo, TRAIL, TRAIL R, TRAIL-R1, TRAIL-R2, TRANCE, transferrin receptor, TRF, Trk, TROP-2, TLR (toll-like receptor) 1, TLR2, TLR3, TLR4, TLRS, TLR6, TLR7, TLR8, TLR9, TLR10, TSG, TSLP, tumor-associated antigen CA125, tumor-associated antigen-expressing Lewis-Y-related carbohydrate, TWEAK, TXB2, Ung, uPAR, uPAR-1, urokinase, VCAM, VCAM-1, VECAD, VE-cadherin, VE-cadherin-2, VEFGR-1 (flt-1), VEGF, VEGFR, VEGFR-3 (flt-4), VEGI, VIM, viral antigens, VLA, VLA-1, VLA-4, VNR integrin, von Willebrand factor, WIF-1, WNT1, WNT2, WNT2B/13, WNT3, WNT3A, WNT4, WNTSA, WNTSB, WNT6, WNT7A, WNT7B, WNT8A, WNT8B, WNT9A, WNT9A, WNT9B, WNT10A, WNT10B, WNT11, WNT16, XCL1, XCL2, XCR1, XCR1, XEDAR, XIAP, XPD, HMGB1, IgA, A13, CD81, CD97, CD98, DDR1, DKK1, EREG, Hsp90, IL-17/IL-17R, IL-20/IL-20R, oxidized LDL, PCSK9, prekallikrein, RON, TMEM16F, SOD1, chromogranin A, chromogranin B, tau, VAP1, high-molecular-weight kininogen, IL-31, IL-31R, Nav1.1, Nav1.2, Nav1.3, Nav1.4, Nav1.5, Nav1.6, Nav1.7, Nav1.8, Nav1.9, EPCR, C1, C1q, C1r, C1s, C2, C2a, C2b, C3, C3a, C3b, C4, C4a, C4b, C5, C5a, C5b, C6, C7, C8, C9, factor B, factor D, factor H, properdin, sclerostin, fibrinogen, fibrin, prothrombin, thrombin, tissue factor, factor V, factor Va, factor VII, factor VIIa, factor VIII, factor VIIIa, factor IX, factor IXa, factor X, factor Xa, factor XI, factor XIa, factor XII, factor XIIa, factor XIII, factor XIIIa, TFPI, antithrombin III, EPCR, thrombomodulin, TAPI, tPA, plasminogen, plasmin, PAI-1, PAI-2, GPC3, syndecan-1, syndecan-2, syndecan-3, syndecan-4, LPA, S1P, and receptors for hormones or growth factors.

Although the examples of the antigen listed above also include receptors, these receptors even existing in a soluble form in a body fluid can be used as the antigen to which the antigen binding domain of the present invention binds. One non-limiting example of the soluble form of such a receptor can include the protein represented by SEQ ID NO: 35 which is soluble IL-6R as described by Mullberg et al. (J. Immunol. (1994) 152 (10), 4958-4968).

The examples of the antigen listed above include membrane molecules expressed on cell membranes, and soluble molecules secreted from cells to the outside of the cells. When the antigen binding domain of the present invention binds to a soluble molecule secreted from cells, the antigen binding domain preferably has neutralizing activity.

The solution containing the soluble molecule is not limited, and this soluble molecule may exist in a body fluid, i.e., every vascular liquid or every liquid filling between tissues or cells in living bodies. In a non-limiting aspect, the soluble molecule to which the antigen binding domain of the present invention binds can exist in an extracellular fluid. The extracellular fluid refers to a generic name for plasma, intercellular fluid, lymph, tight connective tissues, cerebrospinal fluid, spinal fluid, aspirates, synovial fluid, or such components in the bone and cartilage, alveolar fluid (bronchoalveolar lavage fluid), ascitic fluid, pleural effusion, cardiac effusion, cyst fluid, aqueous humor (hydatoid), or such transcellular fluids (various fluids in glandular cavities resulting from the active transport or secretory activity of cells, and fluids in the lumen of the gut and other body cavities) in vertebrates.

The epitope, which means an antigenic determinant, present in the antigen means a site on the antigen to which the antigen binding domain disclosed in the present specification binds. Accordingly, for example, the epitope can be defined by its structure. Alternatively, the epitope may be defined by the antigen-binding activity of the antigen binding domain recognizing the epitope. When the antigen is a peptide or a polypeptide, the epitope may be identified by amino acid residues constituting the epitope. When the epitope is a sugar chain, the epitope may be identified by a particular sugar chain structure.

A linear epitope refers to an epitope comprising an epitope that is recognized by its primary sequence of amino acids. The linear epitope contains typically at least 3 and most commonly at least 5, for example, approximately 8 to approximately 10 or 6 to 20 amino acids, in its unique sequence.

In contrast to the linear epitope, a conformational epitope refers to an epitope that is contained in a primary sequence of amino acids containing a component other than the single defined component of the epitope to be recognized (e.g., an epitope whose primary sequence of amino acids may not be recognized by an antibody that determines the epitope). The conformational epitope may contain an increased number of amino acids, as compared with the linear epitope. As for the recognition of the conformational epitope, the antigen binding domain recognizes the three-dimensional structure of the peptide or the protein. For example, when a protein molecule is folded to form a three-dimensional structure, certain amino acids and/or polypeptide backbone constituting the conformational epitope are arranged in parallel to allow the antibody to recognize the epitope. Examples of the method for determining the conformation of the epitope include, but are not limited to, X-ray crystallography, two-dimensional nuclear magnetic resonance spectroscopy, and site-specific spin labeling and electron paramagnetic resonance spectroscopy. See, for example, Epitope Mapping Protocols in Methods in Molecular Biology (1996), Vol. 66, Morris ed.

The structure of the antigen binding domain binding to the epitope is called paratope. The paratope stably binds to the epitope through a hydrogen bond, electrostatic force, van der Waals' forces, a hydrophobic bond, or the like acting between the epitope and the paratope. This binding force between the epitope and the paratope is called affinity. The total binding force when a plurality of antigen binding domains bind to a plurality of antigens is called avidity. The affinity works synergistically when, for example, an antibody comprising a plurality of antigen binding domains (i.e., a polyvalent antibody) bind to a plurality of epitopes. Therefore, the avidity is higher than the affinity.

In a particular embodiment, the antigen binding domain provided in the present specification has a dissociation constant (Kd) of ≤1 μM, ≤100 nM, ≤10 nM, ≤1 nM, ≤0.1 nM, ≤0.01 nM or 0.001 nM (e.g., $10^{-8}$ M or less, for example, $10^{-8}$ M to $10^{-13}$ M, for example, $10^{-9}$ M to $10^{-13}$ M).

Hereinafter, an exemplary method for confirming the binding of an antigen binding domain directed to IL-6R, or a polypeptide comprising the antigen binding domain to the epitope will be shown. However, a method for confirming the binding of an antigen binding domain directed to an antigen other than IL-6R, or a polypeptide comprising the antigen binding domain to the epitope can also be appropriately carried out according to the example given below.

For example, whether the antigen binding domain directed to IL-6R recognizes a linear epitope present in the IL-6R molecule can be confirmed, for example, as follows: a linear peptide comprising an amino acid sequence constituting the extracellular domain of IL-6R is synthesized for the purpose described above. The peptide can be chemically synthesized. Alternatively, the peptide is obtained by a genetic engineering approach using a region encoding an amino acid sequence corresponding to the extracellular domain in IL-6R cDNA. Next, the antigen binding domain directed to IL-6R is evaluated for its binding activity against the linear peptide comprising an amino acid sequence constituting the extracellular domain. For example, the binding activity of the antigen binding domain against the peptide can be evaluated by ELISA using an immobilized linear peptide as an antigen. Alternatively, the binding activity against the linear peptide may be determined on the basis of a level at which the linear peptide inhibits the binding of the antigen binding domain to IL-6R-expressing cells. These tests can determine the binding activity of the antigen binding domain against the linear peptide.

Also, whether the antigen binding domain directed to IL-6R recognizes the conformational epitope can be confirmed as follows: IL-6R-expressing cells are prepared for the purpose described above. The recognition of the conformational epitope by the antigen binding domain directed to IL-6R is confirmed, for example, when the antigen binding domain directed to IL-6R strongly binds to the IL-6R-expressing cells upon contact with the cells, whereas the antigen binding domain does not substantially bind to an immobilized linear peptide comprising an amino acid sequence constituting the extracellular domain of IL-6R or a denatured (using a general denaturant such as guanidine) linear peptide comprising an amino acid sequence constituting the extracellular domain of IL-6R. In this context, the term "not substantially bind" means that the binding activity is 80% or less, usually 50% or less, preferably 30% or less, particularly preferably 15% or less of binding activity against cells expressing human IL-6R.

The method for confirming the antigen binding activity of the antigen binding domain also includes a method of measuring a Kd value by, for example, radiolabeled antigen binding assay (RIA). In one embodiment, RIA is carried out using the antigen binding domain of interest and its antigen. For example, the binding affinity in a solution of the antigen binding domain for the antigen is measured by equilibrating the antigen binding domain with the smallest concentration of a (125I)-labeled antigen in the presence of a titration series of an unlabeled antigen, and subsequently capturing the bound antigen by a plate coated with the antigen binding domain (see e.g., Chen et al., J. Mol. Biol. 293: 865-881 (1999)).

According to an alternative embodiment, Kd is measured by a surface plasmon resonance method using BIACORE®. For example, assay using BIACORE®-2000 or BIACORE®-3000 (BIAcore, Inc., Piscataway, N.J.) is carried out at 25° C. using a CM5 chip with approximately 10 response units (RU) of the antigen immobilized thereon. In one embodiment, a carboxymethylated dextran biosensor chip (CM5, BIAcore, Inc.) is activated using N-ethyl-N'-(3-dimethylaminopropyl)-carbodiimide hydrochloride (EDC) and N-hydroxysuccinimide (NHS) according to the supplier's instruction. The antigen is diluted to 5 μg/ml (approximately 0.2 μM) with 10 mM sodium acetate (pH 4.8) and then injected thereto at a flow rate of 5 μl/min so as to attain protein binding at approximately 10 response units (RU). After the antigen injection, 1 M ethanolamine is injected thereto in order to block unreacted groups. For kinetic measurement, 2-fold dilutions (0.78 nM to 500 nM) of the antigen binding domain in PBS containing 0.05% Polysorbate 20 (TWEEN-20™) as a surfactant (PBST) are injected thereto at a flow rate of approximately 25 μl/min at 25° C. An association rate (kon) and a dissociation rate (koff) are calculated by fitting sensorgrams of association and dissociation at the same time using a simple 1:1 Langmuir binding model (BIACORE® evaluation software version 3.2). An equilibrium dissociation constant (Kd) is calculated as a koff/kon ratio. Furthermore, an apparent dissociation constant (Kd) may be determined by use of equilibrium analysis. For these procedures, see the protocol attached to BIACORE®. See, for example, Chen et al., J. Mol. Biol. 293: 865-881 (1999) and Methods Enzymol. 2000; 323: 325-40. In the surface plasmon resonance assay, the amount of the protein immobilized, the amount of the protein used in reaction, temperature, and solution composition can be variously changed by those skilled in the art. When the on-rate in the surface plasmon resonance assay described above exceeds $10^6 \text{ M}^{-1}\text{s}^{-1}$, the on-rate can be determined by use of a fluorescence quenching technique of using a spectrometer (e.g. a stopped-flow spectrophotometer (Aviv Instruments, Inc.) or SLM-AMINCO™ spectrophotometer 8000 series (Thermo Spectronic/Thermo Fisher Scientific Inc.) using a stirring cuvette) to measure increase or decrease in fluorescence intensity (excitation=295 nm; emission=340 nm, band path: 16 nm) at 25° C. for 20 nM antigen binding domain in PBS (pH 7.2) in the presence of gradually increased concentrations of the antigen.

Furthermore, the antigen binding activity of the antigen binding domain can also be measured by a known molecule-molecule interaction measurement method such as electro-generated chemiluminescence.

Examples of the method for measuring the binding activity of the antigen binding domain directed to IL-6R against the IL-6R-expressing cells include methods described in Antibodies: A Laboratory Manual (Ed Harlow, David Lane, Cold Spring Harbor Laboratory (1988) 359-420). Specifically, the binding activity can be evaluated on the basis of the principle of ELISA or FACS (fluorescence activated cell sorting) using the IL-6R-expressing cells as an antigen.

In the ELISA format, the binding activity of the antigen binding domain directed to IL-6R against the IL-6R-expressing cells is quantitatively evaluated by comparing the levels of signals generated through enzymatic reaction. Specifically, a test polypeptide associate is added to an ELISA plate with the IL-6R-expressing cells immobilized thereon. Then, the test antigen binding domain bound with the cells is detected through the use of an enzyme-labeled antibody recognizing the test antigen binding domain. Alternatively, in the FACS, a dilution series of a test antigen binding domain is prepared, and the antibody binding titer for the IL-6R-expressing cells can be determined to compare the binding activity of the test antigen binding domain against the IL-6R-expressing cells.

The binding of the test antigen binding domain to the antigen expressed on the surface of cells suspended in a buffer solution or the like can be detected using a flow cytometer. For example, the following apparatuses are known as the flow cytometer:

FACSCanto™ II
FACSAria™
FACSArray™
FACSVantage™ SE
FACSCalibur™ (all are trade names of BD Biosciences)
EPICS ALTRA HyPerSort
Cytomics FC 500
EPICS XL-MCL ADC EPICS XL ADC
Cell Lab Quanta/Cell Lab Quanta SC (all are trade names of Beckman Coulter, Inc.)

One preferred example of the method for measuring the antigen binding activity of the antigen binding domain directed to IL-6R includes the following method: first, IL-6R-expressing cells reacted with a test antigen binding domain are stained with a FITC-labeled secondary antibody recognizing the test antigen binding domain. The test antigen binding domain is appropriately diluted with a suitable buffer solution to prepare the antigen binding domain at the desired concentration for use. The antigen binding domain can be used, for example, at any concentration from 10 µg/ml to 10 ng/ml. Next, fluorescence intensity and the number of cells are measured using FACSCalibur (Becton, Dickinson and Company). The amount of the antigen binding domain bound to the cells is reflected in the fluorescence intensity obtained by analysis using CELL QUEST Software (Becton, Dickinson and Company), i.e., a geometric mean value. In short, the binding activity of the test antigen binding domain indicated by the amount of the test antigen binding domain bound can be determined by obtaining the geometric mean value.

Whether the antigen binding domain directed to IL-6R shares an epitope with a certain antigen binding domain can be confirmed by the competition between these antigen binding domains for the same epitope. The competition between the antigen binding domains is detected by cross-blocking assay or the like. The cross-blocking assay is preferably, for example, competitive ELISA assay.

Specifically, in the cross-blocking assay, IL-6R protein-coated wells of a microtiter plate are preincubated in the presence or absence of a candidate competitor antigen binding domain. Then, a test antigen binding domain is added thereto. The amount of the test antigen binding domain bound with the IL-6R protein in the wells indirectly correlates with the binding capacity of the candidate competitor antigen binding domain that competes for the binding to the same epitope. In short, larger affinity of the competitor antigen binding domain for the same epitope means lower binding activity of the test antigen binding domain against the IL-6R protein-coated wells.

The amount of the test antigen binding domain bound with the wells via the IL-6R protein can be easily measured by labeling the antigen binding domain in advance. For example, a biotin-labeled antigen binding domain is assayed by using an avidin-peroxidase conjugate and an appropriate substrate. In particular, cross-blocking assay that utilizes enzyme labels such as peroxidase is called competitive ELISA assay. The antigen binding domain can be labeled with an alternative detectable or measurable labeling material. Specifically, radiolabels, fluorescent labels, and the like are known in the art.

Provided that the competitor antigen binding domain can block the binding of the antigen binding domain directed to IL-6R by at least 20%, preferably at least 20 to 50%, more preferably at least 50% as compared with binding activity obtained in a control test carried out in the absence of the candidate competitor antigen binding domain associate, the test antigen binding domain is determined as an antigen binding domain substantially binding to the same epitope as that for the competitor antigen binding domain, or competing for the binding to the same epitope.

When the epitope to which the antigen binding domain directed to IL-6R binds has an identified structure, whether a test antigen binding domain and a control antigen binding domain share an epitope can be evaluated by comparing the binding activity of these antigen binding domains against a peptide or a polypeptide prepared by introducing an amino acid mutation to a peptide constituting the epitope.

In such a method for measuring binding activity, for example, the binding activity of a test antigen binding domain and a control antigen binding domain against a linear peptide containing an introduced mutation can be compared in the ELISA format described above. In a method other than ELISA, the binding activity against the mutated peptide bound with a column may be measured by flowing the test antigen binding domain and the control antigen binding domain in the column, and then quantifying the antigen binding domain eluted in the eluate. A method for adsorbing a mutated peptide, for example, as a fusion peptide with GST, to a column is known in the art.

When the identified epitope is a conformational epitope, whether a test antigen binding domain and a control antigen binding domain share an epitope can be evaluated by the following method: first, IL-6R-expressing cells and cells expressing IL-6R with a mutation introduced to the epitope are prepared. The test antigen binding domain and the control antigen binding domain are added to cell suspensions containing these cells suspended in an appropriate buffer solution such as PBS. Subsequently, the cell suspensions are appropriately washed with a buffer solution, and a FITC-labeled antibody capable of recognizing the test antigen binding domain and the control antigen binding domain is then added thereto. The fluorescence intensity and the number of cells stained with the labeled antibody are measured using FACSCalibur (Becton, Dickinson and Company). The test antigen binding domain and the control antigen binding domain are appropriately diluted with a suitable buffer solution and used at concentrations thereby adjusted to the desired ones. These antigen binding domains are used, for example, at any concentration from 10 μg/ml to 10 ng/ml. The amount of the labeled antibody bound to the cells is reflected in the fluorescence intensity obtained by analysis using CELL QUEST Software (Becton, Dickinson and Company), i.e., a geometric mean value. In short, the binding activity of the test antigen binding domain and the control antigen binding domain indicated by the amount of the labeled antibody bound can be determined by obtaining the geometric mean value.

The competition of the antigen binding domain with another antigen binding domain for the same epitope can also be confirmed by use of radiolabeled antigen binding assay (RIA), BIACORE® surface plasmon resonance assay, electrogenerated chemiluminescence, or the like, in addition to ELISA or FACS described above.

In the present method, whether to "not substantially bind to cells expressing mutated IL-6R" can be determined, for example, by the following method: first, a test antigen binding domain and a control antigen binding domain bound with the cells expressing mutated IL-6R are stained with a labeled antibody. Subsequently, the fluorescence intensity of the cells is detected. In the case of using FACSCalibur in the fluorescence detection by flow cytometry, the obtained fluorescence intensity can be analyzed using the CELL QUEST Software. From geometric mean values obtained in the presence and absence of the polypeptide associate, their comparison value (ΔGeo-Mean) can be calculated according to expression 1 given below to determine the rate of increase in fluorescence intensity caused by the binding of the antigen binding domain.

$$\Delta \textit{Geo}\text{-Mean}=\textit{Geo}\text{-Mean (in the presence of the polypeptide associate)}/\textit{Geo}\text{-Mean (in the absence of the polypeptide associate)} \quad \text{(Expression 1)}$$

The geometric mean comparison value (ΔGeo-Mean value for the mutated IL-6R molecule) thus obtained by analysis, which reflects the amount of the test antigen binding domain bound with the cells expressing mutated IL-6R, is compared with the ΔGeo-Mean comparison value that reflects the amount of the test antigen binding domain bound to the IL-6R-expressing cells. In this case, the concentrations of the test antigen binding domain used for determining the ΔGeo-Mean comparison values for the cells expressing mutated IL-6R and the IL-6R-expressing cells are particularly preferably adjusted to equal or substantially equal concentrations. An antigen binding domain already confirmed to recognize an epitope in IL-6R is used as the control antigen binding domain.

Provided that the ΔGeo-Mean comparison value of the test antigen binding domain for the cells expressing mutated IL-6R is smaller than at least 80%, preferably 50%, more preferably 30%, particularly preferably 15% of the ΔGeo-Mean comparison value of the test antigen binding domain for the IL-6R-expressing cells, the test antigen binding domain "does not substantially bind to cells expressing mutate IL-6R". The calculation expression for determining the Geo-Mean (geometric mean) value is described in the CELL QUEST Software User's Guide (BD biosciences). The epitope for the test antigen binding domain and the control antigen binding domain can be assessed as being the same when their comparison values can be regarded as being substantially equivalent as a result of comparison.

In the present specification, the term "carrying moiety" refers to a moiety other than an antigen binding domain in a polypeptide. The carrying moiety of the present invention is usually a peptide or a polypeptide constituted by amino acids. In a specific embodiment, the carrying moiety in the polypeptide is linked to the antigen binding domain via a cleavage site. The carrying moiety of the present invention may be a series of peptides or polypeptides connected through an amide bond, or may be a complex formed from a plurality of peptides or polypeptides through a covalent bond such as a disulfide bond or a noncovalent bond such as a hydrogen bond or hydrophobic interaction.

The carrying moiety of the present invention has an inhibiting domain that inhibits the antigen binding activity of the antigen binding domain. In the present specification, the term "inhibiting domain" is limited only by the inhibition the antigen binding activity of the antigen binding domain. The inhibiting domain can be a domain having any structure as long as the domain used can inhibit the antigen binding activity of the antigen binding domain. Examples of such an inhibiting domain include, but are not limited to, an antibody heavy chain variable region (VH), an antibody light chain variable region (VL), pre-B cell receptors, and single-domain antibodies. The inhibiting domain may constitute the whole of the carrying moiety or may constitute a portion of the carrying moiety.

In some embodiments of the present invention, the antigen binding domain released from the polypeptide has higher antigen binding activity than that before the release. In other words, the antigen binding activity of the antigen binding domain is inhibited by the inhibiting domain in a state where the antigen binding domain is unreleased from the polypeptide. Whether the antigen binding activity of the antigen binding domain is inhibited by the inhibiting domain is confirmed by a method such as FACS (fluorescence activated cell sorting), ELISA (enzyme-linked immunosorbent assay), ECL (electrogenerated chemiluminescence), a SPR (surface plasmon resonance) method (Biacore), BLI (biolayer interferometry) (Octet). In some embodiments of the present invention, the antigen binding activity of the antigen binding domain released from the polypeptide is a value equal to or larger than 2 times, 3 times, 4 times, 5 times, 6 times, 7 times, 8 times, 9 times, 10 times, 20 times, 30 times, 40 times, 50 times, 60 times, 70 times, 80 times, 90 times, 100 times, 200 times, 300 times, 400 times, 500 times, 600 times, 700 times, 800 times, 900 times, 1,000 times, 2000 times, or 3000 times the binding activity of the antigen binding domain unreleased from the polypeptide. In some more specific embodiments of the present invention, the binding of the antigen binding domain before the release to the antigen is not seen when the antigen binding activity of the antigen binding domain is measured by one method selected from among the methods described above.

In some aspects of the present invention, the cleavage site is cleaved so that the antigen binding domain becomes capable of being released from the polypeptide. In such aspects, therefore, the antigen binding activity can be compared between before and after the cleavage of the polypeptide. Specifically, the antigen binding activity measured using the cleaved polypeptide is a value equal to or larger than 2 times, 3 times, 4 times, 5 times, 6 times, 7 times, 8 times, 9 times, 10 times, 20 times, 30 times, 40 times, 50 times, 60 times, 70 times, 80 times, 90 times, 100 times, 200 times, 300 times, 400 times, 500 times, 600 times, 700 times, 800 times, 900 times, 1,000 times, 2000 times, or 3000 times the antigen binding activity measured using the uncleaved polypeptide. In some more specific embodiments, the binding of the antigen binding domain of the uncleaved polypeptide to the antigen is not seen when the antigen binding activity is measured by one method selected from among the methods described above.

In some aspects of the present invention, the cleavage site is cleaved by protease. In such aspects, therefore, the antigen binding activity can be compared between before and after the protease treatment of the polypeptide. Specifically, the antigen binding activity measured using the polypeptide after the protease treatment is a value equal to or larger than 2 times, 3 times, 4 times, 5 times, 6 times, 7 times, 8 times, 9 times, 10 times, 20 times, 30 times, 40 times, 50 times, 60 times, 70 times, 80 times, 90 times, 100 times, 200 times, 300 times, 400 times, 500 times, 600 times, 700 times, 800 times, 900 times, 1,000 times, 2000 times, or 3000 times the antigen binding activity measured using the polypeptide without the protease treatment. In some more specific embodiments, the binding of the antigen binding domain of the protease-untreated polypeptide to the antigen is not seen when the antigen binding activity is measured by one method selected from among the methods described above.

In the present invention, the polypeptide comprising an antigen binding domain and a carrying moiety has a longer half-life in blood than that of the antigen binding domain existing alone. In some embodiments of the present invention, for the longer half-life of the polypeptide, the carrying moiety is designed so as to have a longer half-life in blood. In such embodiments, examples of the approach of extending the half-life in blood of the carrying moiety include, but are not limited to, a large molecular weight of the carrying moiety, FcRn binding activity possessed by the carrying moiety, albumin binding activity possessed by the carrying moiety, and the PEGylation of the carrying moiety. In some embodiments of the present invention, the carrying moiety has a longer half-life in blood than that of the antigen binding domain (in other words, the antigen binding domain has a shorter half-life in blood than that of the carrying moiety).

In the present invention, the half-lives of the antigen binding domain alone and the polypeptide, or the half-lives in blood of the antigen binding domain and the carrying moiety are preferably compared in terms of their half-lives in blood in humans. If the half-lives in blood are difficult to measure in humans, the half-lives in blood in humans can be predicted on the basis of their half-lives in blood in mice (e.g., normal mice, transgenic mice expressing a human antigen, and transgenic mice expressing human FcRn) or monkeys (e.g., cynomolgus monkeys).

In one embodiment, the approach of extending the half-life in blood of the carrying moiety includes a large molecular weight of the carrying moiety. In one embodiment, the approach of rendering the half-life in blood of the carrying moiety longer than that of the antigen binding domain includes a larger molecular weight of the carrying moiety than that of the antigen binding domain.

In one embodiment, the approach of extending the half-life in blood of the carrying moiety includes FcRn binding activity possessed by the carrying moiety. The carrying moiety can usually possess FcRn binding activity by a method of establishing a FcRn binding region in the carrying moiety. The FcRn binding region refers to a region having binding activity against FcRn and may have any structure as long as the region used has binding activity against FcRn.

The carrying moiety containing a FcRn binding region is capable of being taken up into cells and then brought back into plasma through the salvage pathway of FcRn. For example, an IgG molecule has a relatively long circulation time in plasma (slow disappearance) because FcRn known as a salvage receptor of the IgG molecule functions. An IgG molecule taken up into the endosome through pinocytosis binds to FcRn expressed in the endosome under intraendosomal acidic conditions. An IgG molecule that has failed to bind to FcRn is moved to the lysosome and degraded therein, whereas the IgG molecule bound with FcRn is transferred to cell surface, then dissociated from the FcRn under neutral conditions in plasma, and thereby brought back into plasma.

The FcRn binding region is preferably a region binding directly to FcRn. Preferred examples of the FcRn binding region can include antibody Fc regions. However, a region capable of binding to a polypeptide, such as albumin or IgG, which has FcRn binding capacity is capable of binding indirectly to FcRn via albumin, IgG, or the like. Therefore, the FcRn binding region according to the present invention may be a region binding to such a polypeptide having FcRn binding capacity.

The binding activity of the FcRn binding region according to the present invention against FcRn, particularly, human FcRn may be measured by a method known to those skilled in the art, as mentioned in the above section about binding activity. The conditions therefor may be appropriately determined by those skilled in the art. The binding activity against human FcRn can be evaluated as KD (dissociation constant), apparent KD (apparent dissociation constant), kd (dissociation rate), or apparent kd (apparent dissociation rate), etc. These values can be measured by methods known to those skilled in the art. For example, Biacore (GE Healthcare Japan Corp.), Scatchard plot, a flow cytometer, and the like can be used.

The conditions for measuring the binding activity of the FcRn binding region against FcRn are not particularly limited and may be appropriately selected by those skilled in the art. The binding activity can be measured under conditions involving, for example, a MES buffer and 37° C., as described in WO2009/125,825. Also, the binding activity of the FcRn binding region of the present invention against FcRn may be measured by a method known to those skilled in the art and can be measured using, for example, Biacore (GE Healthcare Japan Corp.). In the measurement of the binding activity of the FcRn binding region against FcRn, FcRn and the FcRn binding region or the carrying moiety containing the FcRn binding region can be injected as analytes to chips on which the FcRn binding region or the carrying moiety containing the FcRn binding region and FcRn, respectively, are immobilized, followed by evaluation.

As for pH for use in the measurement conditions, the binding affinity of the FcRn binding region for FcRn may be evaluated at any pH of 4.0 to 6.5. Preferably, a pH of 5.8 to 6.0, which is close to pH in the early endosome in vivo, is used for determining the binding affinity of the FcRn binding region for human FcRn. As for temperature for use in the measurement conditions, the binding affinity of the FcRn binding region for FcRn may be evaluated at any temperature of 10° C. to 50° C. Preferably, a temperature of 15° C. to 40° C. is used for determining the binding affinity of the FcRn binding region for human FcRn. More preferably, any temperature from 20° C. to 35° C., for example, any one of 20, 21, 22, 23, 24, 25, 26, 27, 28, 29, 30, 31, 32, 33, 34, and 35° C., is also used for determining the binding affinity of the FcRn binding region for FcRn. The temperature of 25° C. is one non-limiting example of the temperature of the present invention.

One example of the FcRn binding region includes, but is not limited to, an IgG antibody Fc region. In the case of using an IgG antibody Fc region, its type is not limited, and for example, IgG1, IgG2, IgG3, or IgG4 Fc region may be used. For example, a Fc region containing one sequence selected from the amino acid sequences represented by SEQ ID NOs: 21, 22, 23, and 24 may be used.

A natural IgG antibody Fc region as well as an Fc region variant having one or more amino acid substitutions may be used as long as the Fc region has FcRn binding activity.

For example, an Fc region variant containing an amino acid sequence derived from an IgG antibody Fc region by the substitution of at least one amino acid selected from EU numbering positions 237, 238, 239, 248, 250, 252, 254, 255, 256, 257, 258, 265, 270, 286, 289, 297, 298, 303, 305, 307, 308, 309, 311, 312, 314, 315, 317, 325, 332, 334, 360, 376, 380, 382, 384, 385, 386, 387, 389, 424, 428, 433, 434 and 436 by another amino acid may be used.

More specifically, an Fc region variant containing at least one amino acid substitution selected from an amino acid substitution to substitute Gly at position 237 by Met,
an amino acid substitution to substitute Pro at position 238 by Ala,
an amino acid substitution to substitute Ser at position 239 by Lys,
an amino acid substitution to substitute Lys at position 248 by Ile,
an amino acid substitution to substitute Thr at position 250 by Ala, Phe, Ile, Met, Gln, Ser, Val, Trp, or Tyr,
an amino acid substitution to substitute Met at position 252 by Phe, Trp, or Tyr,
an amino acid substitution to substitute Ser at position 254 by Thr,
an amino acid substitution to substitute Arg at position 255 by Glu,
an amino acid substitution to substitute Thr at position 256 by Asp, Glu, or Gln,
an amino acid substitution to substitute Pro at position 257 by Ala, Gly, Ile, Leu, Met, Asn, Ser, Thr, or Val,
an amino acid substitution to substitute Glu at position 258 by His,
an amino acid substitution to substitute Asp at position 265 by Ala,
an amino acid substitution to substitute Asp at position 270 by Phe,
an amino acid substitution to substitute Asn at position 286 by Ala or Glu,
an amino acid substitution to substitute Thr at position 289 by His,
an amino acid substitution to substitute Asn at position 297 by Ala,
an amino acid substitution to substitute Ser at position 298 by Gly,
an amino acid substitution to substitute Val at position 303 by Ala,
an amino acid substitution to substitute Val at position 305 by Ala,
an amino acid substitution to substitute Thr at position 307 by Ala, Asp, Phe, Gly, His, Ile, Lys, Leu, Met, Asn, Pro, Gln, Arg, Ser, Val, Trp, or Tyr,
an amino acid substitution to substitute Val at position 308 by Ala, Phe, Ile, Leu, Met, Pro, Gln, or Thr,
an amino acid substitution to substitute Leu or Val at position 309 by Ala, Asp, Glu, Pro, or Arg,
an amino acid substitution to substitute Gln at position 311 by Ala, His, or Ile,
an amino acid substitution to substitute Asp at position 312 by Ala or His,
an amino acid substitution to substitute Leu at position 314 by Lys or Arg,
an amino acid substitution to substitute Asn at position 315 by Ala or His,
an amino acid substitution to substitute Lys at position 317 by Ala,
an amino acid substitution to substitute Asn at position 325 by Gly,
an amino acid substitution to substitute Ile at position 332 by Val,
an amino acid substitution to substitute Lys at position 334 by Leu,
an amino acid substitution to substitute Lys at position 360 by His,
an amino acid substitution to substitute Asp at position 376 by Ala,
an amino acid substitution to substitute Glu at position 380 by Ala,
an amino acid substitution to substitute Glu at position 382 by Ala,
an amino acid substitution to substitute Asn or Ser at position 384 by Ala,
an amino acid substitution to substitute Gly at position 385 by Asp or His,
an amino acid substitution to substitute Gln at position 386 by Pro,
an amino acid substitution to substitute Pro at position 387 by Glu,
an amino acid substitution to substitute Asn at position 389 by Ala or Ser,
an amino acid substitution to substitute Ser at position 424 by Ala,
an amino acid substitution to substitute Met at position 428 by Ala, Asp, Phe, Gly, His, Ile, Lys, Leu, Asn, Pro, Gln, Ser, Thr, Val, Trp, or Tyr,
an amino acid substitution to substitute His at position 433 by Lys,
an amino acid substitution to substitute Asn at position 434 by Ala, Phe, His, Ser, Trp, or Tyr, and
an amino acid substitution to substitute Tyr or Phe at position 436 by His (all according to the EU numbering) in an IgG antibody Fc region may be used.

From another viewpoint, a Fc region containing at least one amino acid selected from
Met as the amino acid at position 237,
Ala as the amino acid at position 238,
Lys as the amino acid at position 239,
Ile as the amino acid at position 248,
Ala, Phe, Ile, Met, Gln, Ser, Val, Trp, or Tyr as the amino acid at position 250,
Phe, Trp, or Tyr as the amino acid at position 252,
Thr as the amino acid at position 254,
Glu as the amino acid at position 255,
Asp, Glu, or Gln as the amino acid at position 256,
Ala, Gly, Ile, Leu, Met, Asn, Ser, Thr, or Val as the amino acid at position 257,
His as the amino acid at position 258,
Ala as the amino acid at position 265,
Phe as the amino acid at position 270,
Ala or Glu as the amino acid at position 286,
His as the amino acid at position 289,
Ala as the amino acid at position 297,
Gly as the amino acid at position 298,
Ala as the amino acid at position 303,
Ala as the amino acid at position 305,
Ala, Asp, Phe, Gly, His, Ile, Lys, Leu, Met, Asn, Pro, Gln, Arg, Ser, Val, Trp, or Tyr as the amino acid at position 307,
Ala, Phe, Ile, Leu, Met, Pro, Gln, or Thr as the amino acid at position 308,
Ala, Asp, Glu, Pro, or Arg as the amino acid at position 309,
Ala, His, or Ile as the amino acid at position 311,
Ala or His as the amino acid at position 312,
Lys or Arg as the amino acid at position 314,
Ala or His as the amino acid at position 315,
Ala as the amino acid at position 317,
Gly as the amino acid at position 325,
Val as the amino acid at position 332,
Leu as the amino acid at position 334,
His as the amino acid at position 360,
Ala as the amino acid at position 376,
Ala as the amino acid at position 380,
Ala as the amino acid at position 382,
Ala as the amino acid at position 384,
Asp or His as the amino acid at position 385,
Pro as the amino acid at position 386,
Glu as the amino acid at position 387,
Ala or Ser as the amino acid at position 389,
Ala as the amino acid at position 424,
Ala, Asp, Phe, Gly, His, Ile, Lys, Leu, Asn, Pro, Gln, Ser, Thr, Val, Trp, or Tyr as the amino acid at position 428,
Lys as the amino acid at position 433,
Ala, Phe, His, Ser, Trp, or Tyr as the amino acid at position 434, and
His as the amino acid at position 436 (all according to the EU numbering)
in an IgG antibody Fc region may be used.

The FcRn binding activity possessed by the carrying moiety does not mean that the antigen binding domain has no FcRn binding activity. In the embodiments in which the carrying moiety has a longer half-life in blood than that of the antigen binding domain, the antigen binding domain may have no FcRn binding activity, as a matter of course, or the antigen binding domain may have FcRn binding activity as long as the FcRn binding activity is weaker than that of the carrying moiety.

In one embodiment, the method for extending the half-life in blood of the carrying moiety involves binding the carrying moiety to albumin Since albumin does not undergo renal excretion and has FcRn binding activity, its half-life in blood is as long as 17 to 19 days (J Clin Invest. 1953 August; 32 (8): 746-768). Hence, it has been reported that a protein bound with albumin becomes bulky and capable of binding indirectly to FcRn and therefore has an increased half-life in blood (Antibodies 2015, 4 (3), 141-156).

In one embodiment, the alternative method for extending the half-life in blood of the carrying moiety involves PEGylating the carrying moiety. The PEGylation of a protein is considered to render the protein bulky and also suppress its degradation by protease in blood, thereby extending the half-life in blood of the protein (J Pharm Sci. 2008 October; 97 (10): 4167-83).

In some embodiments of the present invention, the carrying moiety contains an antibody Fc region. In a specific embodiment, the carrying moiety contains a CH2 domain and a CH3 domain of a human IgG antibody. In a specific embodiment, the carrying moiety contains a moiety spanning from human IgG1 antibody heavy chain Cys226 or Pro230 to the carboxyl terminus of the heavy chain. However, the C-terminal lysine (Lys447) or glycine-lysine (Gly446-Lys447) of the Fc region may be present or absent.

In some embodiments of the present invention, the carrying moiety contains an antibody constant region. In a more preferred embodiment, the carrying moiety contains an IgG antibody constant region. In a further preferred embodiment, the carrying moiety contains a human IgG antibody constant region.

In some embodiments of the present invention, the carrying moiety contains: a region substantially similar in structure to an antibody heavy chain constant region; and a region substantially similar in structure to an antibody light chain, connected to the region via a covalent bond such as a disulfide bond or a noncovalent bond such as a hydrogen bond or hydrophobic interaction.

In the present specification, the "polypeptide comprising an antigen binding domain and a carrying moiety" is usually a series of polypeptides connected through an amide bond, or a protein containing a plurality of polypeptides connected through an amide bond.

In some embodiments of the present invention, the antigen binding domain is capable of being released from the polypeptide, and the antigen binding domain released from the polypeptide has higher antigen binding activity. In the present specification, the term "release" refers to the mutual separation of two moieties of the polypeptide. The release of the antigen binding domain from the polypeptide can be attributed to the cancellation of the interaction between the antigen binding domain and the carrying moiety. The antigen binding activity of the antigen binding domain incorporated in the polypeptide is inhibited. Hence, the antigen binding domain released from the polypeptide can be confirmed by measuring the antigen binding activity of a subject and comparing it with the antigen binding activity of the antigen binding domain incorporated in the polypeptide.

In some embodiments, the polypeptide comprises a cleavage site, and the cleavage site is cleaved so that the antigen binding domain is released from the polypeptide. The cleavage site can be cleaved by, for example, an enzyme, can be reduced with a reducing agent, or can be photodegraded. The cleavage site may be placed at any position in the polypeptide as long as the antigen binding domain can be released and does not lose its antigen binding activity after the release. The polypeptide may further contain an additional cleavage site other than the cleavage site for the release of the antigen binding domain. In one embodiment of the present invention, the cleavage site comprises a protease cleavage sequence and can be cleaved by protease.

In the present specification, the term "cleaved" refers to a state where the antigen binding domain and the carrying moiety are separated from each other after alteration of the cleavage site by protease, reduction of a cysteine-cysteine disulfide bond at the cleavage site, and/or photoactivation. In the present specification, the term "uncleaved" refers to a state where the antigen binding domain is linked to the carrying moiety in the absence of the protease cleavage of the cleavage site, in the absence of the reduction of a cysteine-cysteine disulfide bond at the cleavage site, and/or in the absence of light.

The cleavage of the cleavage site can be detected by subjecting a solution containing the cleavage site-containing polypeptide to SDS-PAGE (polyacrylamide gel electrophoresis) and measuring the molecular weights of the fragments or detecting change in molecular weight between before and after the cleavage.

The cleavage site can be specifically modified (cleaved, reduced or photodegraded) by an agent (i.e., protease, a reducing agent, or light) at a rate of approximately 0.001 to $1,500 \times 10^4$ $M^{-1}S^{-1}$ or at least 0.001, 0.005, 0.01, 0.05, 0.1, 0.5, 1, 2.5, 5, 7.5, 10, 15, 20, 25, 50, 75, 100, 125, 150, 200, 250, 500, 750, 1,000, 1,250, or $1,500 \times 10^4$ $M^{-1}S^{-1}$.

The specific cleavage by protease is performed by the contact between the protease and the cleavage site or a molecule containing the cleavage site. The cleavage site can be cleaved in the presence of sufficient enzyme activity. The sufficient enzyme activity can refer to the ability of the enzyme to bring about cleavage upon contact with the cleavage site.

In the present specification, the term "protease" refers to an enzyme such as endopeptidase or exopeptidase which hydrolyzes a peptide bond, typically, endopeptidase. The protease used in the present invention is limited only by being capable of cleaving the protease cleavage sequence and is not particularly limited by its type. In some embodiments, target tissue specific protease is used. The target tissue specific protease can refer to, for example, any of (1) protease that is expressed at a higher level in the target tissue than in normal tissues, (2) protease that has higher activity in the target tissue than in normal tissues, (3) protease that is expressed at a higher level in the target cells than in normal cells, and (4) protease that has higher activity in the target cells than in normal cells.

In a more specific embodiment, a cancer tissue specific protease or an inflammatory tissue specific protease is used.

In the present specification, the term "target tissue" means a tissue containing at least one target cell. In some embodiments of the present invention, the target tissue is a cancer tissue. In some embodiments of the present invention, the target tissue is an inflammatory tissue.

The term "cancer tissue" means a tissue containing at least one cancer cell. Thus, considering that, for example, the cancer tissue contains cancer cells and vascular vessels, every cell type that contributes to the formation of tumor mass containing cancer cells and endothelial cells is included in the scope of the present invention. In the present specification, the tumor mass refers to a foci of tumor tissue. The term "tumor" is generally used to mean benign neoplasm or malignant neoplasm.

In the present specification, examples of the "inflammatory tissue" include the following:

a joint tissue in rheumatoid arthritis or osteoarthritis, a lung (alveolus) tissue in bronchial asthma or COPD, a digestive organ tissue in inflammatory bowel disease, Crohn disease, or ulcerative colitis, a fibrotic tissue in fibrosis in the liver, the kidney, or the lung, a tissue under rejection of organ transplantation, a vascular vessel or heart (cardiac muscle) tissue in arteriosclerosis or heart failure, a visceral fat tissue in metabolic syndrome, a skin tissue in atopic dermatitis and other dermatitides, and a spinal nerve tissue in disk herniation or chronic lumbago.

Specifically expressed or specifically activated protease, or protease considered to be related to the disease condition of a target tissue (target tissue specific protease) is known for some types of target tissues. For example, International Publication Nos. WO2013/128,194, WO2010/081,173, and WO2009/025,846 disclose protease specifically expressed in a cancer tissue. Also, J Inflamm (Lond). 2010; 7: 45, Nat Rev Immunol. 2006 July; 6 (7): 541-50, Nat Rev Drug Discov. 2014 December; 13 (12): 904-27, Respir Res. 2016 Mar. 4; 17: 23, Dis Model Mech. 2014 February; 7 (2): 193-203, and Biochim Biophys Acta. 2012 January; 1824 (1): 133-45 disclose protease considered to be related to inflammation.

In addition to the protease specifically expressed in a target tissue, there also exists protease specifically activated in a target tissue. For example, protease may be expressed in an inactive form and then converted to an active form. Many tissues contain a substance inhibiting active protease and control the activity by the process of activation and the presence of the inhibitor (Nat Rev Cancer. 2003 July; 3 (7): 489-501). In a target tissue, the active protease may be specifically activated by escaping inhibition.

The active protease can be measured by use of a method using an antibody recognizing the active protease (PNAS 2013 Jan. 2; 110 (1): 93-98) or a method of fluorescently labeling a peptide recognizable by protease so that the fluorescence is quenched before cleavage, but emitted after cleavage (Nat Rev Drug Discov. 2010 September; 9 (9): 690-701. doi: 10.1038/nrd3053). From one viewpoint, the term "target tissue specific protease" can refer to any of (i) protease that is expressed at a higher level in the target tissue than in normal tissues, (ii) protease that has higher activity in the target tissue than in normal tissues, (iii) protease that is expressed at a higher level in the target cells than in normal cells, and (iv) protease that has higher activity in the target cells than in normal cells.

Specific examples of the protease include, but are not limited to, cysteine protease (including cathepsin families B, L, S, etc.), aspartyl protease (cathepsins D, E, K, O, etc.), serine protease (including matriptase (including MT-SP1), cathepsins A and G, thrombin, plasmin, urokinase (uPA), tissue plasminogen activator (tPA), elastase, proteinase 3, thrombin, kallikrein, tryptase, and chymase), metalloproteinase (metalloproteinase (MMP1-28) including both membrane-bound forms (MMP14-17 and MMP24-25) and secreted forms (MMP1-13, MMP18-23 and MMP26-28), A disintegrin and metalloproteinase (ADAM), A disintegrin and metalloproteinase with thrombospondin motifs (ADAMTS), meprin (meprin alpha and meprin beta), CD10

(CALLA), prostate-specific antigen (PSA), legumain, TMPRSS3, TMPRSS4, human neutrophil elastase (HNE), beta secretase (BACE), fibroblast activation protein alpha (FAP), granzyme B, guanidinobenzoatase (GB), hepsin, neprilysin, NS3/4A, HCV-NS3/4, calpain, ADAMDEC1, renin, cathepsin C, cathepsin V/L2, cathepsin X/Z/P, cruzipain, otubain 2, kallikrein-related peptidases (KLKs (KLK3, KLK4, KLKS, KLK6, KLK7, KLK8, KLK10, KLK11, KLK13, and KLK14)), bone morphogenetic protein 1 (BMP-1), activated protein C, blood coagulation-related protease (Factor VIIa, Factor IXa, Factor Xa, Factor XIa, and Factor XIIa), HtrA1, lactoferrin, marapsin, PACE4, DESC1, dipeptidyl peptidase 4 (DPP-4), TMPRSS2, cathepsin F, cathepsin H, cathepsin L2, cathepsin O, cathepsin S, granzyme A, Gepsin calpain 2, glutamate carboxypeptidase 2, AMSH-like proteases, AMSH, gamma secretase, antiplasmin cleaving enzyme (APCE), decysin 1, N-acetylated alpha-linked acidic dipeptidase-like 1 (NAALADL1), and furin.

From another viewpoint, the target tissue specific protease can refer to a cancer tissue specific protease or an inflammatory tissue specific protease.

Examples of cancer tissue specific protease include protease specifically expressed in a cancer tissue disclosed in International Publication Nos. WO2013/128,194, WO2010/081,173, and WO2009/025,846.

As for the type of cancer tissue specific protease, the protease having higher expression specificity in the cancer tissue to be treated is more effective for reducing adverse reactions. Preferable cancer tissue specific protease has a concentration in the cancer tissue at least 5 times, more preferably at least 10 times, further preferably at least 100 times, particularly preferably at least 500 times, most preferably at least 1,000 times higher than its concentration in normal tissues. Also, preferable cancer tissue specific protease has activity in the cancer tissue at least 2 times, more preferably at least 3 times, at least 4 times, at least 5 times, or at least 10 times, further preferably at least 100 times, particularly preferably at least 500 times, most preferably at least 1,000 times higher than its activity in normal tissues.

The cancer tissue specific protease may be in a form bound with a cancer cell membrane or may be in a form secreted extracellularly without being bound with a cell membrane. When the cancer tissue specific protease is not bound with a cancer cell membrane, it is preferred for immunocyte-mediated cytotoxicity specific for cancer cells that the cancer tissue specific protease should exist within or in the vicinity of the cancer tissue. In the present specification, the "vicinity of the cancer tissue" means to fall within the scope of location where the protease cleavage sequence specific for the cancer tissue is cleaved so that the antigen binding domain exerts antigen binding activity. However, it is preferred that damage on normal cells should be minimized in this scope of location.

From an alternative viewpoint, cancer tissue specific protease is any of
(i) protease that is expressed at a higher level in the cancer tissue than in normal tissues,
(ii) protease that has higher activity in the cancer tissue than in normal tissues,
(iii) protease that is expressed at a higher level in the cancer cells than in normal cells, and
(iv) protease that has higher activity in the cancer cells than in normal cells.

One type of cancer tissue specific protease may be used alone, or two or more types of cancer tissue specific proteases may be combined. The number of types of cancer tissue specific protease can be appropriately set by those skilled in the art in consideration of the cancer type to be treated.

From these viewpoints, cancer tissue specific protease is preferably serine protease or metalloproteinase, more preferably matriptase (including MT-SP1), urokinase (uPA), or metalloproteinase, further preferably MT-SP1, uPA, MMP2, or MMP9, among the proteases listed above.

As for the type of inflammatory tissue specific protease, the protease having higher expression specificity in the inflammatory tissue to be treated is more effective for reducing adverse reactions. Preferable inflammatory tissue specific protease has a concentration in the inflammatory tissue at least 5 times, more preferably at least 10 times, further preferably at least 100 times, particularly preferably at least 500 times, most preferably at least 1,000 times higher than its concentration in normal tissues. Also, preferable inflammatory tissue specific protease has activity in the inflammatory tissues at least 2 times, more preferably at least 3 times, at least 4 times, at least 5 times, or at least 10 times, further preferably at least 100 times, particularly preferably at least 500 times, most preferably at least 1,000 times higher than its activity in normal tissues.

The inflammatory tissue specific protease may be in a form bound with an inflammatory cell membrane or may be in a form secreted extracellularly without being bound with a cell membrane. When the inflammatory tissue specific protease is not bound with an inflammatory cell membrane, it is preferred for immunocyte-mediated cytotoxicity specific for inflammatory cells that the inflammatory tissue specific protease should exist within or in the vicinity of the inflammatory tissue. In the present specification, the "vicinity of the inflammatory tissue" means to fall within the scope of location where the protease cleavage sequence specific for the inflammatory tissue is cleaved so that the antigen binding domain exerts antigen binding activity. However, it is preferred that damage on normal cells should be minimized in this scope of location.

From an alternative viewpoint, inflammatory tissue specific protease is any of
(i) protease that is expressed at a higher level in the inflammatory tissue than in normal tissues,
(ii) protease that has higher activity in the inflammatory tissue than in normal tissues,
(iii) protease that is expressed at a higher level in the inflammatory cells than in normal cells,
and (iv) protease that has higher activity in the inflammatory cells than in normal cells.

One type of inflammatory tissue specific protease may be used alone, or two or more types of inflammatory tissue specific proteases may be combined. The number of types of inflammatory tissue specific protease can be appropriately set by those skilled in the art in consideration of the pathological condition to be treated.

From these viewpoints, t inflammatory tissue specific protease is preferably metalloproteinase among the proteases listed above. The metalloproteinase is more preferably ADAMTS5, MMP2, MMP7, MMP9, or MMP13.

The protease cleavage sequence is a particular amino acid sequence that is specifically recognized by target tissue specific protease when the polypeptide is hydrolyzed by the target tissue specific protease in an aqueous solution.

The protease cleavage sequence is preferably an amino acid sequence that is hydrolyzed with high specificity by target tissue specific protease more specifically expressed in the target tissue or cells to be treated or more specifically activated in the target tissue/cells to be treated, from the viewpoint of reduction in adverse reactions.

Specific examples of the protease cleavage sequence include target sequences that are specifically hydrolyzed by the above-listed protease specifically expressed in a cancer tissue disclosed in International Publication Nos. WO2013/128,194, WO2010/081,173, and WO2009/025,846, the protease specific for an inflammatory tissue, and the like. A sequence artificially altered by, for example, introducing an appropriate amino acid mutation to a target sequence that is specifically hydrolyzed by known protease can also be used. Alternatively, a protease cleavage sequence identified by a method known to those skilled in the art as described in Nature Biotechnology 19, 661-667 (2001) may be used.

Furthermore, a naturally occurring protease cleavage sequence may be used. For example, TGFβ is converted to a latent form by protease cleavage. Likewise, a protease cleavage sequence in a protein that changes its molecular form by protease cleavage can also be used.

Examples of the protease cleavage sequence that can be used include, but are not limited to, sequences disclosed in International Publication No. WO2015/116,933, International Publication No. WO2015/048,329, International Publication No. WO2016/118,629, International Publication No. WO2016/179,257, International Publication No. WO2016/179,285, International Publication No. WO2016/179,335, International Publication No. WO2016/179,003, International Publication No. WO2016/046,778, International Publication No. WO2016/014,974, U.S. Patent Publication No. US2016/0289324, U.S. Patent Publication No. US2016/0311903, PNAS (2000) 97: 7754-7759, Biochemical Journal (2010) 426: 219-228, and Beilstein J Nanotechnol. (2016) 7: 364-373.

The protease cleavage sequence is more preferably an amino acid sequence that is specifically hydrolyzed by suitable target tissue specific protease as mentioned above. The amino acid sequence that is specifically hydrolyzed by target tissue specific protease is preferably a sequence comprising any of the following amino acid sequences:

```
(SEQ ID NO: 12, cleavable by MT-SP1 or uPA)
LSGRSDNH, (SEQ ID NO: 25, cleavable by MMP2 or MMP9)
PLALAG,
and (SEQ ID NO: 26, cleavable by MMP7)
VPLSLTMG.
```

Any of the following sequences can also be used as the protease cleavage sequence:

```
(SEQ ID NO: 74, cleavable by MT-SP1 or uPA)
TSTSGRSANPRG, (SEQ ID NO: 75, cleavable by MT-SP1 or uPA)
ISSGLLSGRSDNH, (SEQ ID NO: 76, cleavable by MT-SP1 or uPA)
AVGLLAPPGGLSGRSDNH, (SEQ ID NO: 77, cleavable by MMP1)
GAGVPMSMRGGAG, (SEQ ID NO: 78, cleavable by MMP2)
GAGIPVSLRSGAG, (SEQ ID NO: 79, cleavable by MMP2)
GPLGIAGQ, (SEQ ID NO: 80, cleavable by MMP2)
GGPLGMLSQS, (SEQ ID NO: 81, cleavable by MMP2)
PLGLWA, (SEQ ID NO: 82, cleavable by MMP3)
GAGRPFSMIMGAG, (SEQ ID NO: 83, cleavable by MMP7)
GAGVPLSLTMGAG, (SEQ ID NO: 84, cleavable by MMP9)
GAGVPLSLYSGAG, (SEQ ID NO: 85, cleavable by MMP11)
AANLRN, (SEQ ID NO: 86, cleavable by MMP11)
AQAYVK, (SEQ ID NO: 87, cleavable by MMP11)
AANYMR, (SEQ ID NO: 88, cleavable by MMP11)
AAALTR, (SEQ ID NO: 89, cleavable by MMP11)
AQNLMR, (SEQ ID NO: 90, cleavable by MMP11)
AANYTK, (SEQ ID NO: 91, cleavable by MMP13)
GAGPQGLAGQRGIVAG, (SEQ ID NO: 92, cleavable by pro-urokinase)
PRFKIIGG, (SEQ ID NO: 93, cleavable by pro-urokinase)
PRFRIIGG, (SEQ ID NO: 94, cleavable by uPA)
GAGSGRSAG, (SEQ ID NO: 95, cleavable by uPA)
SGRSA, (SEQ ID NO: 96, cleavable by uPA)
GSGRSA, (SEQ ID NO: 97, cleavable by uPA)
SGKSA, (SEQ ID NO: 98, cleavable by uPA)
SGRSS, (SEQ ID NO: 99, cleavable by uPA)
SGRRA, (SEQ ID NO: 100, cleavable by uPA)
SGRNA, (SEQ ID NO: 101, cleavable by uPA)
SGRKA, (SEQ ID NO: 102, cleavable by tPA)
QRGRSA, (SEQ ID NO: 103, cleavable by cathepsin B)
GAGSLLKSRMVPNFNAG (SEQ ID NO: 104, cleavable by cathepsin B)
TQGAAA, (SEQ ID NO: 105, cleavable by cathepsin B)
GAAAAA, (SEQ ID NO: 106, cleavable by cathepsin B)
GAGAAG,
```

(SEQ ID NO: 107, cleavable by cathepsin B)
AAAAAG, (SEQ ID NO: 108, cleavable by cathepsin B)
LCGAAI, (SEQ ID NO: 109, cleavable by cathepsin B)
FAQALG, (SEQ ID NO: 110, cleavable by cathepsin B)
LLQANP, (SEQ ID NO: 111, cleavable by cathepsin B)
LAAANP, (SEQ ID NO: 112, cleavable by cathepsin B)
LYGAQF, (SEQ ID NO: 113, cleavable by cathepsin B)
LSQAQG, (SEQ ID NO: 114, cleavable by cathepsin B)
ASAASG, (SEQ ID NO: 115, cleavable by cathepsin B)
FLGASL, (SEQ ID NO: 116, cleavable by cathepsin B)
AYGATG, (SEQ ID NO: 117, cleavable by cathepsin B)
LAQATG, (SEQ ID NO: 118, cleavable by cathepsin L)
GAGSGVVIATVIVITAG, (SEQ ID NO: 119, cleavable by meprin alpha or meprin beta)
APMAEGGG, (SEQ ID NO: 120, cleavable by meprin alpha or meprin beta)
EAQGDKII, (SEQ ID NO: 121, cleavable by meprin alpha or meprin beta)
LAFSDAGP, (SEQ ID NO: 122, cleavable by meprin alpha or meprin beta)
YVADAPK, (SEQ ID NO: 123, cleavable by furin)
RRRRR, (SEQ ID NO: 124, cleavable by furin)
RRRRRR, (SEQ ID NO: 125, cleavable by furin)
GQSSRHRRAL, (SEQ ID NO: 126)
SSRHRRALD, (SEQ ID NO: 127, cleavable by plasminogen)
RKSSIIIRMRDVVL, (SEQ ID NO: 128, cleavable by staphylokinase)
SSSFDKGKYKKGDDA, (SEQ ID NO: 129, cleavable by staphylokinase)
SSSFDKGKYKRGDDA, (SEQ ID NO: 130, cleavable by Factor Xa)
IEGR, (SEQ ID NO: 131, cleavable by Factor Xa)
IDGR, (SEQ ID NO: 132, cleavable by Factor Xa)
GGSIDGR, (SEQ ID NO: 133, cleavable by collagenase)
GPQGIAGQ, (SEQ ID NO: 134, cleavable by collagenase)
GPQGLLGA, (SEQ ID NO: 135, cleavable by collagenase)
GIAGQ, (SEQ ID NO: 136, cleavable by collagenase)
GPLGIAG, (SEQ ID NO: 137, cleavable by collagenase)
GPEGLRVG, (SEQ ID NO: 138, cleavable by collagenase)
YGAGLGVV, (SEQ ID NO: 139, cleavable by collagenase)
AGLGVVER, (SEQ ID NO: 140, cleavable by collagenase)
AGLGISST, (SEQ ID NO: 141, cleavable by collagenase)
EPQALAMS, (SEQ ID NO: 142, cleavable by collagenase)
QALAMSAI, (SEQ ID NO: 143, cleavable by collagenase)
AAYHLVSQ, (SEQ ID NO: 144, cleavable by collagenase)
MDAFLESS, (SEQ ID NO: 145, cleavable by collagenase)
ESLPVVAV, (SEQ ID NO: 146, cleavable by collagenase)
SAPAVESE, (SEQ ID NO: 147, cleavable by collagenase)
DVAQFVLT, (SEQ ID NO: 148, cleavable by collagenase)
VAQFVLTE, (SEQ ID NO: 149, cleavable by collagenase)
AQFVLTEG, (SEQ ID NO: 150, cleavable by collagenase)
PVQPIGPQ, (SEQ ID NO: 151, cleavable by thrombin)
LVPRGS,
and (SEQ ID NO: 178, cleavable by uPA or MT-SP1)
TSTSGRSANPRG.

In one embodiment of the present invention, a flexible linker is further attached to either one end or both ends of the protease cleavage sequence. The flexible linker at one end of the protease cleavage sequence can be referred to as a first flexible linker, and the flexible linker at the other end can be referred to as a second flexible linker. In a particular embodiment, the protease cleavage sequence and the flexible linker have any of the following formulas:
(protease cleavage sequence),
(first flexible linker)-(protease cleavage sequence),
(protease cleavage sequence)-(second flexible linker), and
(first flexible linker)-(protease cleavage sequence)-(second flexible linker).

The flexible linker according to the present embodiment is preferably a peptide linker. The first flexible linker and the second flexible linker each independently and arbitrarily exist and are identical or different flexible linkers each containing at least one flexible amino acid (Gly, etc.). The flexible linker contains, for example, a sufficient number of residues (amino acids arbitrarily selected from Arg, Ile, Gln, Glu, Cys, Tyr, Trp, Thr, Val, His, Phe, Pro, Met, Lys, Gly, Ser, Asp, Asn, Ala, etc., particularly Gly, Ser, Asp, Asn, and Ala, in particular, Gly and Ser, especially Gly, etc.) for the protease cleavage sequence to obtain the desired protease accessibility.

The flexible linker usable for use at both ends of the protease cleavage sequence is usually a flexible linker that improves the access of protease to the protease cleavage sequence and elevates the cleavage efficiency of the protease. A suitable flexible linker may be readily selected and can be preferably selected from among different lengths such as 1 amino acid (Gly, etc.) to 20 amino acids, 2 amino acids to 15 amino acids, or 3 amino acids to 12 amino acids including 4 amino acids to 10 amino acids, 5 amino acids to 9 amino acids, 6 amino acids to 8 amino acids, or 7 amino acids to 8 amino acids. In some embodiments of the present invention, the flexible linker is a peptide linker of 1 to 7 amino acids.

Examples of the flexible linker include, but are not limited to, glycine polymers (G)n, glycine-serine polymers (including e.g., (GS)n, (GSGGS: SEQ ID NO: 27)n and (GGGS: SEQ ID NO: 28)n, wherein n is an integer of at least 1), glycine-alanine polymers, alanine-serine polymers, and other flexible linkers well known in conventional techniques.

Among them, glycine and glycine-serine polymers are receiving attention because these amino acids are relatively unstructured and easily function as neutral tethers between components.

Examples of the flexible linker consisting of the glycine-serine polymer include, but are not limited to, Ser Gly·Ser (GS)

Ser·Gly (SG)

Gly·Gly·Ser (GGS)

Gly·Ser·Gly (GSG)

Ser·Gly·Gly (SGG)

Gly·Ser·Ser (GSS)

Ser·Ser·Gly (SSG)

Ser·Gly·Ser (SGS)

Gly·Gly·Gly·Ser (GGGS, SEQ ID NO: 28)

Gly·Gly·Ser·Gly (GGSG, SEQ ID NO: 29)

Gly·Ser·Gly·Gly (GSGG, SEQ ID NO: 46)

Ser·Gly·Gly·Gly (SGGG, SEQ ID NO: 47)

Gly·Ser·Ser·Gly (GSSG, SEQ ID NO: 48)

Gly·Gly·Gly·Gly·Ser (GGGGS, SEQ ID NO: 49)

Gly·Gly·Gly·Ser·Gly (GGGSG, SEQ ID NO: 33)

Gly·Gly·Ser·Gly·Gly (GGSGG, SEQ ID NO: 30)

Gly·Ser·Gly·Gly·Gly (GSGGG, SEQ ID NO: 32)

Gly·Ser·Gly·Gly·Ser (GSGGS, SEQ ID NO: 27)

Ser·Gly·Gly·Gly·Gly (SGGGG, SEQ ID NO: 51)

Gly·Ser·Ser·Gly·Gly (GSSGG, SEQ ID NO: 52)

Gly·Ser·Gly·Ser·Gly (GSGSG, SEQ ID NO: 31)

Ser·Gly·Gly·Ser·Gly (SGGSG, SEQ ID NO: 53)

Gly·Ser·Ser·Ser·Gly (GSSSG, SEQ ID NO: 34)

Gly·Gly·Gly·Gly·Gly·Ser (GGGGGS, SEQ ID NO: 50)

Ser·Gly·Gly·Gly·Gly·Gly (SGGGGG, SEQ ID NO: 54)

Gly·Gly·Gly·Gly·Gly·Gly·Ser (GGGGGGS, SEQ ID NO: 55)

Ser·Gly·Gly·Gly·Gly·Gly·Gly (SGGGGGG, SEQ ID NO: 56)

(Gly·Gly·Gly·Gly·Ser (GGGGS, SEQ ID NO: 49))n (Ser·Gly·Gly·Gly·Gly (SGGGG, SEQ ID NO: 51))n

In the present specification, the "association" can refer to, for example, a state where two or more polypeptide regions interact with each other. In general, a hydrophobic bond, a hydrogen bond, an ionic bond, or the like is formed between the intended polypeptide regions to form an associate. As one example of common association, an antibody typified by a natural antibody is known to retain a paired structure of a heavy chain variable region (VH) and a light chain variable region (VL) through a noncovalent bond or the like therebetween.

In some embodiments of the present invention, the inhibiting domain of the carrying moiety associates with the antigen binding domain. The inhibiting domain may constitute a portion of the carrying moiety or may constitute the whole of the carrying moiety. From another viewpoint, the inhibiting domain can also be defined as a moiety associating with the antigen binding domain, in the carrying moiety.

In a more specific embodiment, the antigen binding domain which is a single-domain antibody and the inhibiting domain which is VL, VH or VHH form association as found between antibody VH and antibody VL. In a further specific embodiment, the antigen binding domain which is a single-domain antibody and the inhibiting domain which is VL, VH or VHH form association as found between antibody VH and antibody VL, and in a state of the association thus formed, the inhibiting domain conformationally inhibits the binding of the antigen binding domain to the antigen or conformationally changes the antigen binding site of the antigen binding domain so that the antigen binding activity of the single-domain antibody is inhibited by the VL, the VH or the VHH. In an embodiment using VHH as the single-domain antibody, it is considered that the binding of the VHH to the antigen is conformationally inhibited by the inhibiting domain when CDR3, a main antigen binding site of the VHH, or its neighboring site exists at the interface of association with the inhibiting domain.

The association of the antigen binding domain with the inhibiting domain may be canceled, for example, by cleaving the cleavage site. The cancellation of the association can be used interchangeably with, for example, the cancellation of the state where two or more polypeptide regions interact with each other. The interaction between the two or more polypeptide regions may be wholly canceled, or the interaction between the two or more polypeptide regions may be partially canceled.

In the present specification, the "interface" usually refers to a face at which two regions associate or interact with each other. Amino acid residues forming the interface are usually one or more amino acid residues contained in each polypeptide region subjected to the association and more preferably refer to amino acid residues that approach each other upon association and participate in interaction. Specifically, the interaction includes a noncovalent bond such as a hydrogen bond, electrostatic interaction, or salt bridge formation between the amino acid residues approaching each other upon association.

In the present specification, the "amino acid residues forming the interface" specifically refers to amino acid residues contained in polypeptide regions constituting the interface. As one example, the polypeptide regions constituting the interface refer to polypeptide regions responsible for intramolecular or intermolecular selective binding in antibodies, ligands, receptors, substrates, etc. Specific examples of such polypeptide regions in antibodies can include a heavy chain variable region and a light chain variable region. In some embodiments of the present invention, examples of such polypeptide regions can include an antigen binding domain and an inhibiting domain.

Examples of the amino acid residues forming the interface include, but are not limited to, amino acid residues approaching each other upon association. The amino acid residues approaching each other upon association can be found, for example, by analyzing the conformations of polypeptides and examining the amino acid sequences of polypeptide regions forming the interface upon association of the polypeptides.

In some embodiments of the present invention, an amino acid residue involved in association in the antigen binding domain, or an amino acid residue involved in association in the inhibiting domain can be altered in order to promote the association of the antigen binding domain with the inhibiting domain. In a further specific embodiment, an amino acid residue forming the interface with the inhibiting domain, in the antigen binding domain, or an amino acid residue forming the interface with the antigen binding domain, in the inhibiting domain can be altered. In a preferred embodiment, the amino acid residue forming the interface can be altered by a method of introducing a mutation to the interface amino acid residue such that two or more amino acid residues forming the interface have different charges. The alteration of the amino acid residue to result in different charges includes the alteration of a positively charged amino acid residue to a negatively charged amino acid residue or an uncharged amino acid residue, the alteration of a negatively charged amino acid residue to a positively charged amino acid residue or an uncharged amino acid residue, and the alteration of an uncharged amino acid residue to a positively or negatively charged amino acid residue. Such an amino acid alteration is performed for the purpose of promoting the association and is not limited by the position of the amino acid alteration or the type of the amino acid as long as the purpose of promoting the association can be achieved. Examples of the alteration include, but are not limited to, substitution.

In some embodiments of the present invention, VHH serving as the antigen binding domain associates with VL serving as the inhibiting domain. The amino acid residue involved in association with VL, in VHH can refer to, for example, an amino acid residue forming the interface between the VHH and the VL. Examples of the amino acid residue involved in association with VL, in VHH include, but are not limited to, amino acid residues at positions 37, 44, 45, and 47 (J. Mol. Biol. (2005) 350, 112-125). The activity of the VHH is inhibited by promoting the association between the VHH and the VL. Likewise, the amino acid residue involved in association with VHH, in VL can refer to, for example, an amino acid residue forming the interface between the VHH and the VL.

An amino acid residue involved in association with VL, in VHH can be altered in order to promote the association between the VHH and the VL. Examples of such an amino acid substitution include, but are not limited to, F37V, Y37V, E44G, Q44G, R45L, H45L, G47W, F47W, L47W, T47W, or/and S47W. Instead of altering each residue in VHH, VHH originally having an amino acid residue 37V, 44G, 45L, or/and 47W may be used.

Instead of the VHH amino acid, an amino acid residue involved in association with VHH, in VL may be altered, and amino acid alterations may also be introduced to both VHH and VL, as long as the purpose of promoting the association between the VHH and the VL can be achieved.

In some alternative embodiments of the present invention, the antigen binding domain and the inhibiting domain can be associated with each other by using VHH as the antigen binding domain and using VH or VHH as the inhibiting domain. An amino acid residue involved in association with VH or VHH serving as the inhibiting domain, in VHH serving as the antigen binding domain can be identified and altered in order to promote the association of the antigen binding domain VHH with the inhibiting domain VH or VHH. Also, an amino acid residue involved in association with VHH serving as the antigen binding domain, in VH or VHH serving as the inhibiting domain, can be identified and altered.

In the case of using a single-domain antibody other than VHH as the antigen binding domain, an amino acid residue involved in association, in the antigen binding domain or the inhibiting domain can also be identified and altered similarly to above.

In some embodiments of the present invention, the carrying moiety and the antigen binding domain are fused via a linker. In a more specific embodiment, the carrying moiety and the antigen binding domain are fused via a linker containing a cleavage site. In an alternative specific embodiment, the carrying moiety and the antigen binding domain are fused via a linker, and the fusion protein thus formed contains a cleavage site.

In another embodiment of the present invention, the carrying moiety and the antigen binding domain are fused without a linker. In a more specific embodiment, an amino bond is formed between the N-terminal amino acid of the carrying moiety and the C-terminal amino acid of the antigen binding domain to form a fusion protein. The formed fusion protein contains a cleavage site. In a particular embodiment, one to several N-terminal amino acids of the carrying moiety or/and one to several C-terminal amino acids of the antigen binding domain are altered, and the N terminus of the carrying moiety and the C terminus of the antigen binding domain are fused to form a cleavage site near the fusion position. More specifically, the cleavage site can be formed, for example, by converting four C-terminal amino acids of the antigen binding domain to a LSGR sequence and converting four N-terminal amino acids of the carrying moiety to a SDNH sequence.

In some embodiments of the present invention, the cleavage site of the polypeptide comprising a carrying moiety and an antigen binding domain comprises a protease cleavage sequence. The protease cleavage sequence may be placed at any position in the polypeptide as long as the antigen binding domain is released by protease cleavage and does not lose its antigen binding activity after the release.

In some embodiments of the present invention, the carrying moiety comprises an antibody constant region, and the N terminus of the antibody constant region and the C terminus of the antigen binding domain are fused via a linker or without a linker.

In a particular embodiment, the protease cleavage sequence is located within the antibody constant region contained in the carrying moiety. In this case, the protease cleavage sequence can be located within the antibody constant region such that the antigen binding domain is released by protease cleavage. In a specific embodiment, the protease cleavage sequence is located within an antibody heavy chain constant region contained in the carrying moiety, and more specifically located on the antigen binding domain side with respect to amino acid position 140 (EU numbering) in the antibody heavy chain constant region, preferably on the antigen binding domain side with respect to amino acid position 122 (EU numbering) in the antibody heavy chain constant region. In an alternative specific embodiment, the protease cleavage sequence is located within an antibody light chain constant region contained in the carrying moiety, and more specifically located on the antigen binding domain side with respect to amino acid position 130 (EU numbering) (Kabat numbering position 130) in the antibody light chain constant region, preferably on the antigen binding domain side with respect to amino acid position 113 (EU numbering) (Kabat numbering position 113) in the antibody light chain constant region.

In some embodiments of the present invention, the antigen binding domain is a single-domain antibody, and the C terminus of the single-domain antibody and the N terminus of the carrying moiety are fused via a linker or without a linker.

In a particular embodiment, the protease cleavage sequence is located within the single-domain antibody. In a more specific embodiment, the single-domain antibody is a single-domain antibody prepared from VH, or VHH, and the protease cleavage sequence is located on the carrying moiety side with respect to amino acid position 35b (Kabat numbering) of the single-domain antibody, preferably on the carrying moiety side with respect to amino acid position 95 (Kabat numbering) of the single-domain antibody, more preferably on the carrying moiety side with respect to amino acid position 109 (Kabat numbering) of the single-domain antibody. In an alternative specific embodiment, the single-domain antibody is a single-domain antibody prepared from VL, and the protease cleavage sequence is located on the carrying moiety side with respect to amino acid position 32 (Kabat numbering) of the single-domain antibody, preferably on the carrying moiety side with respect to amino acid position 91 (Kabat numbering) of the single-domain antibody, more preferably on the carrying moiety side with respect to amino acid position 104 (Kabat numbering) of the single-domain antibody.

In some embodiments of the present invention, the carrying moiety comprises an antibody constant region, the antigen binding domain is a single-domain antibody, and the antibody constant region and the single-domain antibody are fused via a linker or without a linker. In a more specific embodiment, the N terminus of the antibody constant region and the C terminus of the single-domain antibody are fused via a linker or without a linker. In an alternative specific embodiment, the C terminus of the antibody constant region and the N terminus of the single-domain antibody are fused via a linker or without a linker.

In a particular embodiment, the protease cleavage sequence is located within the antibody constant region contained in the carrying moiety. In a more specific embodiment, the protease cleavage sequence is located on the single-domain antibody side with respect to amino acid position 140 (EU numbering) in an antibody heavy chain constant region, preferably on the single-domain antibody side with respect to amino acid position 122 (EU numbering) in an antibody heavy chain constant region. In an alternative specific embodiment, the protease cleavage sequence is located on the antigen binding domain side with respect to amino acid position 130 (EU numbering) (Kabat numbering position 130) in an antibody light chain constant region, preferably on the antigen binding domain side with respect to amino acid position 113 (EU numbering) (Kabat numbering position 113) in an antibody light chain constant region.

In a particular embodiment, the protease cleavage sequence is located within the single-domain antibody. In a more specific embodiment, the single-domain antibody is a single-domain antibody prepared from VH, or VHH, and the protease cleavage sequence is located on the antibody constant region side with respect to amino acid position 35b (Kabat numbering) of the single-domain antibody, preferably on the antibody constant region side with respect to amino acid position 95 (Kabat numbering) of the single-domain antibody, more preferably on the antibody constant region side with respect to amino acid position 109 (Kabat numbering) of the single-domain antibody. In an alternative specific embodiment, the single-domain antibody is a single-domain antibody prepared from VL, and the protease cleavage sequence is located on the antibody constant region side with respect to amino acid position 32 (Kabat numbering) of the single-domain antibody, preferably on the antibody constant region side with respect to amino acid position 91 (Kabat numbering) of the single-domain antibody, more preferably on the antibody constant region side with respect to amino acid position 104 (Kabat numbering) of the single-domain antibody.

In a particular embodiment, the protease cleavage sequence is located near the boundary between the antigen binding domain and the carrying moiety. The phrase "near the boundary between the antigen binding domain and the carrying moiety" refers to a moiety that resides upstream or downstream of the linking site between the antigen binding domain and the carrying moiety and does not largely influence the secondary structure of the antigen binding domain.

In a more specific embodiment, the antigen binding domain is linked to the antibody constant region contained in the carrying moiety, and the protease cleavage sequence is located near the boundary between the antigen binding domain and the antibody constant region. The phrase "near the boundary between the antigen binding domain and the antibody constant region" can refer to near the boundary between the antigen binding domain and an antibody heavy chain constant region, or near the boundary between the antigen binding domain and an antibody light chain constant region. When the antigen binding domain is a single-domain antibody prepared from VH, or VHH and is connected to an antibody heavy chain constant region, the phrase "near the boundary between the antigen binding domain and the antibody constant region" can refer to between amino acid position 101 (Kabat numbering) of the single-domain antibody and amino acid position 140 (EU numbering) of the antibody heavy chain constant region and can preferably refer to between amino acid position 109 (Kabat numbering) of the single-domain antibody and amino acid position 122 (EU numbering) of the antibody heavy chain constant region. When the antigen binding domain is a single-domain antibody prepared from VH, or VHH and is connected to an antibody light chain constant region, the phrase "near the boundary between the antigen binding domain and the antibody light chain constant region" can refer to between amino acid position 101 (Kabat numbering) of the single-domain antibody and amino acid position 130 (EU numbering) (Kabat numbering position 130) of the antibody light chain constant region and can preferably refer to between amino acid position 109 (Kabat numbering) of the single-domain antibody and amino acid position 113 (EU numbering) (Kabat numbering position 113) of the antibody light chain constant region. When the antigen binding domain is a single-domain antibody prepared from VL, the phrase "near the boundary between the antigen binding domain and the antibody constant region" refers to between amino acid position 96 (Kabat numbering) of the single-domain antibody and the prescribed position of the antibody constant region, preferably between amino acid position 104 (Kabat numbering) of the single-domain antibody and the prescribed position of the antibody constant region.

In some embodiments of the present invention, the polypeptide is an IgG antibody-like molecule. Examples of such embodiments include, but are not limited to: an embodiment in which the carrying moiety comprises an IgG antibody constant region, a single-domain antibody serving as the antigen binding domain takes the place of VH of an IgG antibody, and the antigen binding activity is inhibited by VL; an embodiment in which the carrying moiety comprises an IgG antibody constant region, a single-domain antibody serving as the antigen binding domain takes the place of VL of an IgG antibody, and the antigen binding activity is inhibited by VH; and an embodiment in which the carrying moiety comprises an IgG antibody constant region, a single-domain antibody serving as the antigen binding domain takes the place of one of VH and VL of an IgG antibody, and an additional single-domain antibody inhibits the antigen binding activity of the antigen binding domain takes the place of the other domain of the IgG antibody.

The term "IgG antibody-like molecule" used in the present specification is used to define a molecule having moieties substantially similar in structure to constant domains or constant regions as in an IgG antibody, and moieties substantially similar in structure to variable domains or variable regions as in the IgG antibody, and having conformation substantially similar to that of the IgG antibody. However, in the present specification, the "IgG antibody-like molecule" may or may not exert antigen binding activity while retaining the structures similar to those of the IgG antibody.

The polypeptide may comprise one or more antigen binding domains. One or more inhibiting domains may inhibit the antigen binding activity of a plurality of antigen binding domains. A plurality of antigen binding domains may each be associated with the inhibiting domain. A plurality of antigen binding domains may each be fused with the carrying moiety. A plurality of antigen binding domains may each be capable of released from the polypeptide. The cleavage site(s) for release a plurality of antigen binding domains may be a plurality of cleavage sites corresponding to the number of antigen binding domains.

Figure 7:
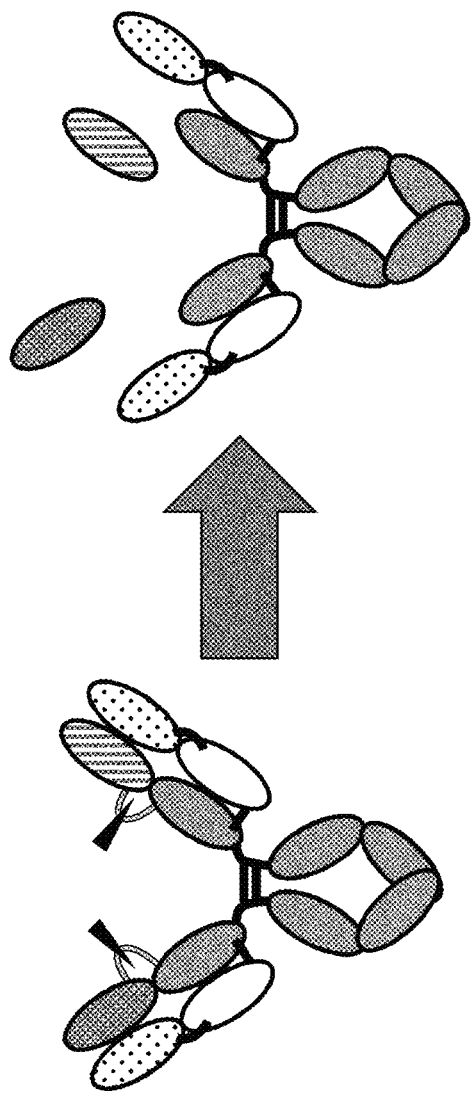
FIG. 7 is a diagram showing one embodiment of the polypeptide of the present invention. In the present embodiment, the polypeptide is an IgG antibody-like molecule, and antigen binding domains are respectively established at moieties corresponding to two variable regions of the IgG antibody. The two antigen binding domains may have the same antigen binding specificity or may differ in antigen binding specificity.

When the polypeptide is an IgG antibody-like molecule, antigen binding domains may be respectively established at moieties corresponding to two variable regions of the IgG antibody, as shown in FIG. 7. Such an embodiment should be understandable by those skilled in the art with reference to the present invention. The antigen binding domains incorporated in both arms may have the same antigen binding specificity or may differ in antigen binding specificity. Such an embodiment should be understandable by those skilled in the art with reference to the present invention. It is obvious that these embodiments are included in the scope of the present invention.

In some embodiments of the present invention, the antigen binding domain is further linked to a second antigen binding domain. Examples of the second antigen binding domain include, but are not limited to, single-domain antibodies, antibody fragments, a module called A domain of approximately 35 amino acids contained in an in vivo cell membrane protein avimer (International Publication Nos. WO2004/044011 and WO2005/040229), adnectin containing a 10Fn3 domain serving as a protein binding domain derived from a glycoprotein fibronectin expressed on cell membranes (International Publication No. WO2002/032925), Affibody containing an IgG binding domain scaffold constituting a three-helix bundle composed of 58 amino acids of protein A (International Publication No. WO1995/001937), DARPins (designed ankyrin repeat proteins) which are molecular surface-exposed regions of ankyrin repeats (AR) each having a 33-amino acid residue structure folded into a subunit of a turn, two antiparallel helices, and a loop (International Publication No. WO2002/020565), anticalin having four loop regions connecting eight antiparallel strands bent toward the central axis in one end of a barrel structure highly conserved in lipocalin molecules such as neutrophil gelatinase-associated lipocalin (NGAL) (International Publication No. WO2003/029462), and a depressed region in the internal parallel sheet structure of a horseshoe-shaped fold composed of repeated leucine-rich-repeat (LRR) modules of an immunoglobulin structure-free variable lymphocyte receptor (VLR) as seen in the acquired immune systems of jawless vertebrates such as lamprey or hagfish (International Publication No. WO2008/016854). In a preferred embodiment, the second antigen binding domain has antigen binding specificity different from that of the antigen binding domain. In a preferred embodiment, the molecular weight of the antigen binding domain and the second antigen binding domain linked is 60 kDa or smaller.

In some more specific embodiments, the antigen binding domain and the second antigen binding domain are single-domain antibodies differing in antigen binding specificity, the antigen binding domain and the second antigen binding domain linked are capable of being released from the polypeptide, and the antigen binding domain and the second antigen binding domain form a bispecific antigen binding molecule after release. Examples of such a bispecific antigen binding molecule include, but are not limited to, a bispecific antigen binding molecule having an antigen binding domain specifically binding to the target cell surface antigen and a second antigen binding domain specifically binding to an immunocyte surface antigen, a bispecific antigen binding molecule having an antigen binding domain and a second antigen binding domain binding to different subunits of the same antigen, and a bispecific antigen binding molecule having an antigen binding domain and a second antigen binding domain binding to different epitopes in the same antigen. Such a bispecific antigen binding molecule can recruit immunocytes to the vicinity of target cells and is thus considered useful in the treatment of a disease caused by the target cells.

The antigen binding activity of the second antigen binding domain may or may not be inhibited by the carrying moiety. The second antigen binding domain may or may not be associated with a partial structure of the carrying moiety. Particularly, when the antigen binding domain and the second antigen binding domain differ in antigen binding specificity, the antigen binding domain in an unreleased state cannot exert antigen binding activity, as shown in, for example, FIG. 8, even if the antigen binding activity of the second antigen binding domain is not inhibited and even if the second antigen binding domain is not associated with a partial structure of the carrying moiety. This bispecific antigen binding molecule comprising the antigen binding domain linked to the second antigen binding domain cannot exert a function of bispecifically binding to two types of antigens.

Figure 8:
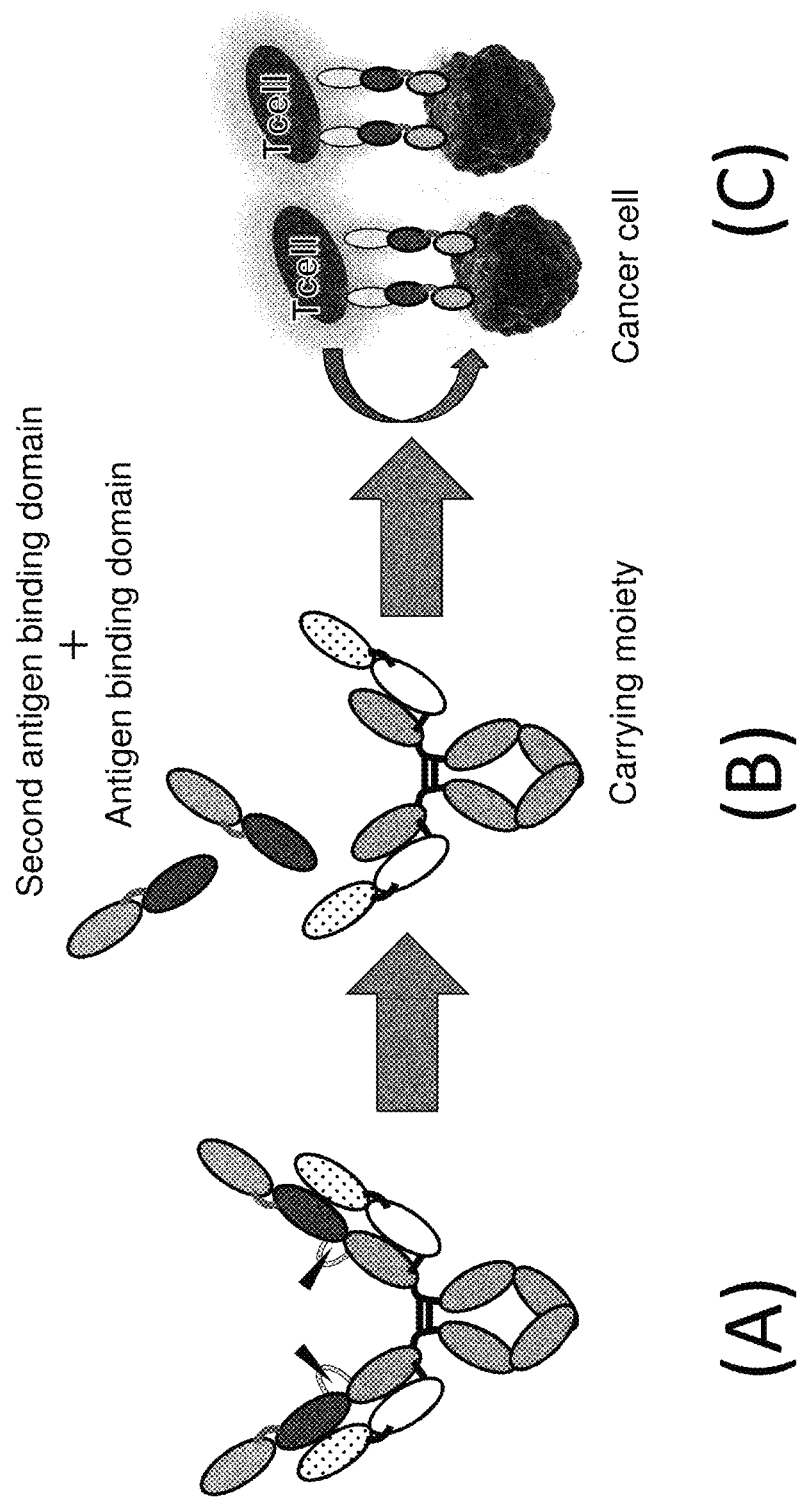
FIG. 8 is a diagram showing an embodiment in which a second antigen binding domain is further linked to the antigen binding domain of the present invention. In this embodiment, the antigen binding domain and the second antigen binding domain form a bispecific antigen binding molecule after release.

FIG. 8 shows one exemplary form in which the antigen binding domain is further linked to the second antigen binding domain.

In the present specification, the term "specificity" refers to a property by which one of specifically binding molecules does not substantially bind to a molecule other than its one or more binding partner molecules. This term is also used when the antigen binding domain has specificity for an epitope contained in a particular antigen. The term is also used when the antigen binding domain has specificity for a particular epitope among a plurality of epitopes contained in an antigen. In this context, the term "not substantially bind" is determined according to the method described in the section about binding activity and means that the binding activity of a specific binding molecule for a molecule other than the binding partner(s) is 80% or less, usually 50% or less, preferably 30% or less, particularly preferably 15% or less, of its binding activity for the binding partner molecule(s).

The present invention also relates to a pharmaceutical composition (drug) comprising the polypeptide of the present invention and a pharmaceutically acceptable carrier.

The "treatment" (and its grammatically derived words, for example, "treat" and "treating") used in the present specification means clinical intervention that intends to alter the natural course of an individual to be treated and can be carried out both for prevention and during the course of a clinical pathological condition. The desirable effect of the treatment includes, but is not limited to, the prevention of the development or recurrence of a disease, the alleviation of symptoms, the attenuation of any direct or indirect pathological influence of the disease, the prevention of metastasis, reduction in the rate of progression of the disease, recovery from or alleviation of a disease condition, and ameliorated or improved prognosis. In some embodiments, the polypeptide of the present invention is used for delaying the onset of a disease or delaying the progression of the disease.

In the present invention, the pharmaceutical composition usually refers to a drug for the treatment or prevention of a disease or for examination or diagnosis. In the present invention, the term "pharmaceutical composition comprising the polypeptide" may be used interchangeably with a "method for treating a disease, comprising administering the polypeptide to a subject to be treated" and may be used interchangeably with "use of the polypeptide for the production of a drug for the treatment of a disease". Also, the term "pharmaceutical composition comprising the polypeptide" may be used interchangeably with "use of the polypeptide for treating a disease".

The pharmaceutical composition of the present invention can be formulated by use of a method known to those skilled in the art. For example, the pharmaceutical composition can be parenterally used in an injection form of a sterile solution or suspension with water or any of other pharmaceutically acceptable liquids. The pharmaceutical composition can be formulated, for example, by appropriately combining the polypeptide with a pharmacologically acceptable carrier or medium, specifically, sterile water or physiological saline, a plant oil, an emulsifier, a suspending agent, a surfactant, a stabilizer, a flavoring agent, an excipient, a vehicle, an antiseptic, a binder, etc. and mixing them into a unit dosage form required for generally accepted pharmaceutical practice. The amount of the active ingredient in these formulations is set so as to give an appropriate volume in a prescribed range.

A sterile composition for injection can be formulated according to usual pharmaceutical practice using a vehicle such as injectable distilled water. Examples of the injectable aqueous solution include isotonic solutions containing physiological saline, glucose, or other adjuvants (e.g., D-sorbitol, D-mannose, D-mannitol, and sodium chloride). The aqueous solution can be used in combination with an appropriate solubilizer, for example, an alcohol (ethanol, etc.), a polyalcohol (propylene glycol, polyethylene glycol, etc.), or a nonionic surfactant (Polysorbate 80™, HCO-50, etc.).

Examples of the oil solution include sesame oil and soybean oil. The oil solution can also be used in combination with benzyl benzoate and/or benzyl alcohol as a solubilizer. The oil solution can be supplemented with a buffer (e.g., a phosphate buffer solution and a sodium acetate buffer solution), a soothing agent (e.g., procaine hydrochloride), a stabilizer (e.g., benzyl alcohol and phenol), and an antioxidant. The prepared injection solution is usually filled into an appropriate ampule.

The pharmaceutical composition of the present invention is preferably administered through a parenteral route. For example, a composition having an injection, transnasal, transpulmonary, or percutaneous dosage form is administered. The pharmaceutical composition can be administered systemically or locally by, for example, intravenous injection, intramuscular injection, intraperitoneal injection, or subcutaneous injection.

The administration method can be appropriately selected according to the age and symptoms of a patient. The dose of the pharmaceutical composition containing the polypeptide can be set to the range of, for example, 0.0001 mg to 1,000 mg per kg body weight per dose. Alternatively, the dose of the pharmaceutical composition containing the polypeptide can be set to a dose of, for example, 0.001 to 100,000 mg per patient. However, the present invention is not necessarily limited by these numerical values. Although the dose and the administration method vary depending on the body weight, age, symptoms, etc. of a patient, those skilled in the art can set an appropriate dose and administration method in consideration of these conditions.

The present invention also relates to a method for producing a polypeptide comprising a carrying moiety having an inhibiting domain, and an antigen binding domain.

One method for producing the polypeptide of the present invention is a method comprising: obtaining an antigen binding domain having antigen binding activity; linking the antigen binding domain to a carrying moiety such that the antigen binding activity of the antigen binding domain is inhibited by an inhibiting domain, to form a polypeptide precursor; and further inserting a cleavage site into the polypeptide precursor or altering a portion of the polypeptide precursor to a cleavage site. The method for introducing the cleavage site can be any of the insertion of the cleavage site and the alteration of a portion of the polypeptide precursor as long as the cleavage site can be introduced into the polypeptide precursor. Alternatively, an alteration site may be introduced into the polypeptide precursor by the combination of both the approaches. Such an embodiment should be obvious to those skilled in the art with reference to the present specification and is included in the scope of the present invention.

Another method for producing the polypeptide of the present invention is a method comprising: obtaining an antigen binding domain having antigen binding activity; and linking the antigen binding domain to a carrying moiety via a cleavage site such that the antigen binding activity of the antigen binding domain is inhibited by an inhibiting domain, to form a polypeptide. When the antigen binding domain is linked to the carrying moiety via a cleavage site, the cleavage site may be sandwiched between the antigen binding domain and the carrying moiety, or a portion of the antigen binding domain or/and a portion of the carrying moiety may be altered and used as a portion of the cleavage site.

In an embodiment using a single-domain antibody as the antigen binding domain and using a protease cleavage sequence as the cleavage site, the method for producing the polypeptide will be described below.

In one embodiment of the present invention, the method for producing a polypeptide comprising a carrying moiety having an inhibiting domain, and an antigen binding domain is a production method comprising the following steps:
(a) obtaining a single-domain antibody binding to a target antigen;
(b) linking the single-domain antibody obtained in the step (a) to a carrying moiety such that the antigen binding activity of the single-domain antibody is inhibited by an inhibiting domain of the carrying moiety, to form a polypeptide precursor; and
(c) introducing a protease cleavage sequence to the polypeptide precursor.

In one embodiment of the present invention, the method for producing a polypeptide comprising a carrying moiety having an inhibiting domain, and an antigen binding domain is a production method comprising the following steps:
(a) obtaining a single-domain antibody binding to a target antigen;
(b) linking the single-domain antibody obtained in the step (a) to a carrying moiety such that the antigen binding activity of the single-domain antibody is inhibited by an inhibiting domain of the carrying moiety, to form a polypeptide precursor; and
(c) introducing a protease cleavage sequence to near the boundary between the single-domain antibody and the carrying moiety.

In one embodiment of the present invention, the method for producing a polypeptide comprising a carrying moiety having an inhibiting domain, and an antigen binding domain is a production method comprising the following steps:
(a) obtaining a single-domain antibody binding to a target antigen; and
(b) linking the single-domain antibody obtained in the step (a) to the carrying moiety via a protease cleavage sequence such that the antigen binding activity of the single-domain antibody is inhibited by an inhibiting domain of the carrying moiety, to form a polypeptide.

In a particular embodiment, the method for producing a polypeptide comprising a carrying moiety having an inhibiting domain, and an antigen binding domain is the production method further comprising the following step:
(d) confirming that the binding activity of the single-domain antibody incorporated in the polypeptide or the polypeptide precursor against the target antigen is weakened or lost.

In the present invention, the phrase "binding activity is weakened" means that the binding activity against the target antigen is decreased as compared with that before the linking, and the degree of this decrease is not limited.

In a particular embodiment, the method for producing a polypeptide comprising a carrying moiety having an inhibiting domain, and an antigen binding domain is the production method further comprising the following step:
(e) releasing the single-domain antibody by the protease cleavage of the protease cleavage sequence and confirming that the released single-domain antibody binds to the antigen.

In one embodiment of the present invention, the method for producing a polypeptide which is an IgG antibody-like molecule comprising a carrying moiety having an inhibiting domain, and an antigen binding domain is a production method comprising the following steps:
(a) obtaining a single-domain antibody binding to a target antigen;
(b) associating the single-domain antibody obtained in the step (a) as a substitute for VH of an IgG antibody with VL, or associating the single-domain antibody as a substitute for VL of an IgG antibody with VH such that the antigen binding activity of the single-domain antibody is inhibited, to form an IgG antibody-like molecule precursor harboring the single-domain antibody; and
(c) introducing a protease cleavage sequence to the IgG antibody-like molecule precursor harboring the single-domain antibody.

In one embodiment of the present invention, the method for producing a polypeptide which is an IgG antibody-like molecule comprising a carrying moiety having an inhibiting domain, and an antigen binding domain is a production method comprising the following steps:
(a) obtaining a single-domain antibody binding to a target antigen;
(b) associating the single-domain antibody obtained in the step (a) as a substitute for VH of an IgG antibody with VL, or associating the single-domain antibody as a substitute for VL of an IgG antibody with VH such that the antigen binding activity of the single-domain antibody is inhibited, to form an IgG antibody-like molecule precursor harboring the single-domain antibody; and
(c) introducing a protease cleavage sequence to near the boundary between the single-domain antibody and an antibody constant region in the IgG antibody-like molecule precursor.

In one embodiment of the present invention, the method for producing a polypeptide which is an IgG antibody-like molecule comprising a carrying moiety having an inhibiting domain, and an antigen binding domain is a production method comprising the following steps:
(a) obtaining a single-domain antibody binding to a target antigen; and
(b) linking the single-domain antibody obtained in the step (a) as a substitute for IgG antibody VH or VL to an IgG antibody heavy chain constant region or light chain constant region via a protease cleavage sequence such that the antigen binding activity of the single-domain antibody is inhibited, to form an IgG antibody-like molecule harboring the single-domain antibody.

In a particular embodiment, the method for producing a polypeptide which is an IgG antibody-like molecule comprising a carrying moiety having an inhibiting domain, and an antigen binding domain is the production method further comprising the following step:

(d) confirming that the binding activity of the single-domain antibody introduced into the IgG antibody-like molecule or the IgG antibody-like molecule precursor against the target antigen is weakened or lost.

In the present invention, the phrase "binding activity is weakened" means that the binding activity against the target antigen is decreased as compared with that before the association or the linking, and the degree of this decrease is not limited.

In a particular embodiment, the method for producing a polypeptide which is an IgG antibody-like molecule comprising a carrying moiety having an inhibiting domain, and an antigen binding domain is the production method further comprising the following step:

(e) releasing the single-domain antibody by the protease cleavage of the protease cleavage sequence and confirming that the released single-domain antibody binds to the target antigen.

In the case of using VH, VL or VHH as the inhibiting domain, the method for inhibiting the antigen binding activity of the single-domain antibody by the inhibiting domain of the carrying moiety includes a method of associating the single-domain antibody with VH, VL or VHH. The VH, the VL or the VHH that inhibits the antigen binding activity of the provided single-domain antibody can be screened for by associating known VH, VL or VHH with the single-domain antibody and comparing the antigen binding activity of the single-domain antibody between before and after the association.

In another method for inhibiting the antigen binding activity of the single-domain antibody by particular VH, VL or VHH, an amino acid residue involved in association with VH, VL or VHH, in the single-domain antibody can be substituted to promote the association, or a single-domain antibody/inhibiting domain pair having the desired level of difference in antigen binding activity between before and after the association can also be provided by using a single-domain antibody originally having, as such an amino acid residue, an amino acid that can promote the association.

In one embodiment of the present invention, the method for producing a polypeptide which is an IgG antibody-like molecule comprising a carrying moiety having an inhibiting domain, and an antigen binding domain is a production method comprising the following steps:

(a) substituting an amino acid residue in a single-domain antibody that involves in association with antibody VH, or substituting an amino acid residue in a single-domain antibody that involves in association with antibody VL to prepare an single-domain antibody variant retaining the binding activity of the single-domain antibody against the target antigen;

(b) associating the single-domain antibody variant prepared in the step (a) with antibody VL, or associating the single-domain antibody variant with antibody VH such that the antigen binding activity of the single-domain antibody variant is inhibited, to form an IgG antibody-like molecule precursor harboring the single-domain antibody variant; and (c) introducing a protease cleavage sequence to the IgG antibody-like molecule precursor harboring the single-domain antibody variant.

In one embodiment of the present invention, the method for producing a polypeptide which is an IgG antibody-like molecule comprising a carrying moiety having an inhibiting domain, and an antigen binding domain is a production method comprising the following steps:

(a) substituting an amino acid residue in a single-domain antibody that involves in association with antibody VH, or substituting an amino acid residue in a single-domain antibody that involves in association with antibody VL, to prepare an single-domain antibody variant retaining the binding activity of the single-domain antibody against the target antigen;

(b) associating the single-domain antibody variant prepared in the step (a) with antibody VL, or associating the single-domain antibody variant with antibody VH such that the antigen binding activity of the single-domain antibody variant is inhibited, to form an IgG antibody-like molecule precursor harboring the single-domain antibody variant; and (c) introducing a protease cleavage sequence to near the boundary between the single-domain antibody variant and a constant region in the IgG antibody-like molecule precursor.

In one embodiment of the present invention, the method for producing a polypeptide which is an IgG antibody-like molecule comprising a carrying moiety having an inhibiting domain, and an antigen binding domain is a production method comprising the following steps:

(a) substituting an amino acid residue in a single-domain antibody that involves in association with antibody VH, or substituting an amino acid residue in a single-domain antibody that involves in association with antibody VL, to prepare an single-domain antibody variant retaining the binding activity of the single-domain antibody against the target antigen; and (b) linking the single-domain antibody variant prepared in the step (a) to an IgG antibody heavy chain constant region via a protease cleavage sequence, or linking the single-domain antibody variant to an IgG antibody light chain constant region via a protease cleavage sequence such that the antigen binding activity of the single-domain antibody variant is inhibited, to form an IgG antibody-like molecule harboring the single-domain antibody variant.

In a particular embodiment, the method for producing a polypeptide which is an IgG antibody-like molecule comprising a carrying moiety having an inhibiting domain, and an antigen binding domain is the production method further comprising the following step:

(d) confirming that the binding activity of the single-domain antibody variant harbored in the IgG antibody-like molecule or the IgG antibody-like molecule precursor against the target antigen is weakened or lost.

In the present invention, the phrase "binding activity is weakened" means that the binding activity against the target antigen is decreased as compared with that before the association or the linking, and the degree of this decrease is not limited.

In a particular embodiment, the method for producing a polypeptide which is an IgG antibody-like molecule comprising a carrying moiety having an inhibiting domain, and an antigen binding domain is the production method further comprising the following step:

(e) releasing the single-domain antibody variant by the protease cleavage of the protease cleavage sequence and confirming that the released single-domain antibody variant binds to the target antigen.

The present invention also relates to a polynucleotide encoding the polypeptide comprising a carrying moiety having an inhibiting domain, and an antigen binding domain.

The polynucleotide according to the present invention is usually carried by (or inserted in) an appropriate vector and transfected into host cells. The vector is not particularly limited as long as the vector can stably retain an inserted nucleic acid. For example, when *E. coli* is used as the host, a pBluescript vector (manufactured by Stratagene Corp.) or the like is preferred as a vector for cloning. Various commercially available vectors can be used. In the case of using the vector for the purpose of producing the polypeptide of the present invention, an expression vector is particularly useful. The expression vector is not particularly limited as long as the vector permits expression of the polypeptide in vitro, in *E. coli*, in cultured cells, or in organism individuals. The expression vector is preferably, for example, a pBEST vector (manufactured by Promega Corp.) for in vitro expression, a pET vector (manufactured by Invitrogen Corp.) for *E. coli*, a pME18S-FL3 vector (GenBank Accession No. AB009864) for cultured cells, and a pME18S vector (Mol Cell Biol. 8: 466-472 (1988)) for organism individuals. The insertion of the DNA of the present invention into the vector can be performed by a routine method, for example, ligase reaction using restriction sites (Current protocols in Molecular Biology edit. Ausubel et al. (1987) Publish. John Wiley & Sons. Section 11.4-11.11).

The host cells are not particularly limited, and various host cells are used according to the purpose. Examples of the cells for expressing the polypeptide can include bacterial cells (e.g., *Streptococcus, Staphylococcus, E. coli, Streptomyces*, and *Bacillus subtilis*), fungal cells (e.g., yeasts and *Aspergillus*), insect cells (e.g., *Drosophila* S2 and *Spodoptera* SF9), animal cells (e.g., CHO, COS, HeLa, C127, 3T3, BHK, HEK293, and Bowes melanoma cells) and plant cells. The transfection of the vector to the host cells may be performed by a method known in the art, for example, a calcium phosphate precipitation method, an electroporation method (Current protocols in Molecular Biology edit. Ausubel et al., (1987) Publish. John Wiley & Sons. Section 9.1-9.9), a Lipofectamine method (manufactured by GIBCO-BRL/Thermo Fisher Scientific Inc.), or a microinjection method.

An appropriate secretory signal can be incorporated into the polypeptide of interest in order to secrete the polypeptide expressed in the host cells to the lumen of the endoplasmic reticulum, periplasmic space, or an extracellular environment. The signal may be endogenous to the polypeptide of interest or may be a foreign signal.

When the polypeptide of the present invention is secreted into a medium, the recovery of the polypeptide in the production method is performed by the recovery of the medium. When the polypeptide of the present invention is produced into cells, the cells are first lysed, followed by the recovery of the polypeptide.

A method known in the art including ammonium sulfate or ethanol precipitation, acid extraction, anion- or cation-exchange chromatography, phosphocellulose chromatography, hydrophobic interaction chromatography, affinity chromatography, hydroxyapatite chromatography, and lectin chromatography can be used for recovering and purifying the polypeptide of the present invention from the recombinant cell cultures.

Examples of the antigen binding domain used in some embodiments of the present invention include a single-domain antibody. In these embodiments, the antigen binding activity of the single-domain antibody can be inhibited by associating with particular VL, associating with particular VH, or associating with particular VHH. The present invention also relates to a method for screening for such a single-domain antibody.

VL, VH or VHH having a known sequence, for example, VL, VH or VHH having a sequence registered in the IMGT or Kabat database, can be used as the VL, the VH or the VHH that inhibits the antigen binding activity of the single-domain antibody. Also, a VL, VH or VHH sequence newly identified from a human antibody library or the like can be used. The VL, the VH or the VHH that inhibits the binding activity of the single-domain antibody can be selected by preparing a protein by the combination of these sequences and measuring the binding activity by use of the method described above.

In some embodiments of the present invention, VL, VH or VHH having a human antibody germline sequence can be used as the VL, the VH or the VHH that inhibits the antigen binding activity of the single-domain antibody. In the case of using, for example, VL as the inhibiting domain, VL having kappa chain framework sequences or VL having lambda chain framework sequences can be used. Also, VL having modified framework sequences such as combined framework sequences of kappa chain and lambda chain framework sequences can be used.

In one embodiment, the present invention provides a method for screening for a single-domain antibody whose antigen binding activity can be inhibited by associating with particular VL, comprising the following steps:

(a) obtaining a single-domain antibody having target antigen binding activity;

(b) associating the single-domain antibody obtained in the step (a) with a particular VL; and (c) confirming that the binding activity of the single-domain antibody associated with the particular VL in the step (b) against the antigen is weakened or lost.

In the present invention, the phrase "binding activity is weakened" means that the binding activity against the target antigen is decreased as compared with that before the association, and the degree of this decrease is not limited.

In one embodiment, the present invention provides a method for screening for a single-domain antibody whose antigen binding activity can be inhibited by associating with particular VH, comprising the following steps:

(a) obtaining a single-domain antibody having target antigen binding activity;

(b) associating the single-domain antibody obtained in the step (a) with a particular VH; and (c) confirming that the binding activity of the single-domain antibody associated with the particular VH in the step (b) against the antigen is weakened or lost.

In the present invention, the phrase "binding activity is weakened" means that the binding activity against the target antigen is decreased as compared with that before the association, and the degree of this decrease is not limited.

In one embodiment, the present invention provides a method for screening for a single-domain antibody whose antigen binding activity can be inhibited by associating with particular VHH, comprising the following steps:

(a) obtaining a single-domain antibody having target antigen binding activity;

(b) associating the single-domain antibody obtained in the step (a) with a particular VHH; and (c) confirming that the binding activity of the single-domain antibody associated with the particular VHH in the step (b) against the antigen is weakened or lost.

In the present invention, the phrase "binding activity is weakened" means that the binding activity against the target antigen is decreased as compared with that before the association, and the degree of this decrease is not limited.

Examples of the method for associating the single-domain antibody with the particular VL, VH or VHH include a method of designing a molecule having the sequence of the single-domain antibody as a substitute for the sequence of one of VH and VL in an antibody or an antibody fragment comprising both VH and VL, such as a complete antibody, Fab, Fab', or (Fab)$_2$, and expressing a polypeptide having the sequence.

The present invention also relates to a method for producing a single-domain antibody whose antigen binding activity is inhibited by promoting the association of the single-domain antibody with particular VL, VH or VHH, promoting the association of the single-domain antibody with particular VL, promoting the association of the single-domain antibody with particular VH, or promoting the association of the single-domain antibody with particular VHH, in addition to screening for a single-domain antibody whose antigen binding activity is inhibited by associating with particular VL, associating with particular VH, or associating with particular VHH.

In one embodiment, the present invention provides a method for producing a single-domain antibody whose antigen binding activity is inhibited by associating with particular VL, comprising the following step:

(a) substituting an amino acid residue in a single-domain antibody that involves in association with antibody VL, to prepare an single-domain antibody variant retaining the binding activity of the single-domain antibody against the target antigen.

In a particular embodiment, the present invention provides the method for producing a single-domain antibody whose antigen binding activity is inhibited by associating with particular VL, further comprising the following steps:

(b) associating the single-domain antibody variant prepared in the step (a) with the particular VL; and (c) confirming that the antigen binding activity of the single-domain antibody variant associated with the VL is weakened or lost.

In the present invention, the phrase "binding activity is weakened" means that the binding activity against the target antigen is decreased as compared with that before the association, and the degree of this decrease is not limited.

In one embodiment, the present invention provides a method for producing a single-domain antibody whose antigen binding activity is inhibited by associating with particular VH, comprising the following step:

(a) substituting an amino acid residue in a single-domain antibody that involves in association with antibody VH, to prepare an single-domain antibody variant retaining the binding activity of the single-domain antibody against the target antigen.

In a particular embodiment, the present invention provides the method for producing a single-domain antibody whose antigen binding activity is inhibited by associating with particular VH, further comprising the following steps:

(b) associating the single-domain antibody variant prepared in the step (a) with the particular VH; and (c) confirming that the antigen binding activity of the single-domain antibody variant associated with the VH is weakened or lost.

In the present invention, the phrase "binding activity is weakened" means that the binding activity against the target antigen is decreased as compared with that before the association, and the degree of this decrease is not limited.

In one embodiment, the present invention provides a method for producing a single-domain antibody whose antigen binding activity is inhibited by associating with particular VHH, comprising the following step:

(a) substituting an amino acid residue in a single-domain antibody that involves in association with VHH, to prepare an single-domain antibody variant retaining the binding activity of the single-domain antibody against the target antigen.

In a particular embodiment, the present invention provides the method for producing a single-domain antibody whose antigen binding activity is inhibited by associating with particular VHH, further comprising the following steps:

(b) associating the single-domain antibody variant prepared in the step (a) with the particular VHH; and (c) confirming that the antigen binding activity of the single-domain antibody variant associated with the VHH is weakened or lost.

In the present invention, the phrase "binding activity is weakened" means that the binding activity against the target antigen is decreased as compared with that before the association, and the degree of this decrease is not limited.

The step of associating the single-domain antibody with the particular VL, VH or VHH is performed by a method of designing a molecule having the sequence of the single-domain antibody as a substitute for the sequence of one of VH and VL in an antibody or an antibody fragment comprising both VH and VL, such as a complete antibody, Fab, Fab', or (Fab)$_2$, and expressing a polypeptide having the sequence.

According to a certain embodiment of the present invention, the single-domain antibody of the present invention whose antigen binding activity is inhibited or lost by associating with particular VL, VH or VHH can be obtained from a library comprising a plurality of fusion polypeptides of single-domain antibodies each linked to a first association sustaining domain.

In the present specification, an embodiment of the "library" can provide a library that permits efficient obtainment of a single-domain antibody whose antigen binding activity is inhibited or lost by associating with particular VL, VH or VHH.

In the present specification, the "library" refers to a set of a plurality of fusion polypeptides having different sequences, or nucleic acids or polynucleotides encoding these fusion polypeptides. A plurality of fusion polypeptides contained in the library are fusion polypeptides differing in sequence from each other, not having a single sequence.

In the present specification, the term "differing in sequence from each other" in a plurality of fusion polypeptides differing in sequence from each other means that the individual fusion polypeptides in the library have distinct sequences. More preferably, the term means that the single-domain antibody moieties of the individual fusion polypeptides in the library have distinct sequences. Specifically, the number of the distinct sequences in the library reflects the number of independent clones differing in sequences in the library and is also referred to as a "library size". The library size of a usual phage display library is $10^6$ to $10^{12}$ and may be expanded to $10^{14}$ by the application of a technique known in the art such as a ribosome display method. However, the actual number of phage particles for use in panning selection for the phage library is usually 10 to 10,000 times larger than the library size. This excessive multiple, also called the "number of equivalents of the library", represents that 10 to 10,000 individual clones may have the same amino acid sequence. Accordingly, the term "differing in sequence from each other" according to the present invention means that the individual polypeptides in the library excluding the number of equivalents of the library have distinct sequences and more specifically means that the library has $10^6$ to $10^{14}$ molecules, preferably $10^7$ to $10^{12}$ molecules, of polypeptides differing in sequence from each other.

The term "plurality of" in the library consisting essentially of a plurality of fusion polypeptides according to the present invention usually refers to a set of two or more types of substances as to, for example, the polypeptide, polynucleotide molecule, vector, or virus of the present invention. Provided that, for example, two or more substances differ in particular trait from each other, this means that the substances are of two or more types. Examples thereof can include a mutant amino acid observed at a particular amino acid position in an amino acid sequence. For example, two or more polypeptides of the present invention having substantially the same, preferably identical sequences, except for particular mutant amino acids at surface-exposed, highly diverse amino acid positions are regarded as a plurality of polypeptides of the present invention. In another example, two or more polynucleotide molecules of the present invention having substantially the same, preferably identical sequences except for bases encoding particular mutant amino acids at surface-exposed, highly diverse amino acid positions are regarded as a plurality of polynucleotide molecules of the present invention.

A panning method that utilizes phage vectors is also preferably used as a method for screening the fusion polypeptides with binding activity as an index. A gene encoding each single-domain antibody and a gene encoding an IgG antibody CH1 domain or a light chain constant region can be linked in an appropriate form to form a fusion polypeptide. Genes encoding the fusion polypeptides thus formed can be inserted into phage vectors to obtain phages expressing the fusion polypeptides on the surface. After contact of the phages with the desired antigen, phages bound with the antigen can be recovered to recover DNAs encoding fusion polypeptides having the binding activity of interest. This operation can be repeated, if necessary, to enrich fusion polypeptides having the desired binding activity.

In addition to the phage display method, a technique using a cell-free translation system, a technique of presenting fusion polypeptides on cell or virus surface, a technique of using an emulsion, and the like are known as techniques of obtaining fusion polypeptides by panning using a library. For example, a ribosome display method of forming a complex of mRNA and a translated protein via ribosome by the removal of a stop codon, etc., a cDNA or mRNA display method of covalently binding a gene sequence to a translated protein using a compound such as puromycin, or a CIS display method of forming a complex of a gene and a translated protein using a nucleic acid binding protein can be used as the technique using a cell-free translation system. For example, the phage display method as well as an *E. coli* display method, a gram-positive bacterium display method, a yeast display method, a mammalian cell display method, or a virus display method can be used as the technique of presenting fusion polypeptides on cell or virus surface. For example, an in vitro virus display method using an emulsion containing a gene and a translation-related molecule can be used as the technique using an emulsion. These methods are already known in the art (Nat Biotechnol. 2000 December; 18(12): 1287-92, Nucleic Acids Res. 2006; 34(19): e127, Proc Natl Acad Sci USA. 2004 Mar. 2; 101(9): 2806-10, Proc Natl Acad Sci USA. 2004 Jun. 22; 101(25): 9193-8, Protein Eng Des Sel. 2008 April; 21(4): 247-55, Proc Natl Acad Sci USA. 2000 Sep. 26; 97(20): 10701-5, MAbs. 2010 September-October; 2(5): 508-18, Methods Mol Biol. 2012; 911: 183-98).

An association partner of an inhibiting domain linked to a second association sustaining domain can be used in a method for obtaining the single-domain antibody of interest from the library comprising a plurality of fusion polypeptides of single-domain antibodies each linked to a first association sustaining domain.

In the present specification, the "first association sustaining domain" and the "second association sustaining domain" refer to domains that can interact with each other through a bond such as a hydrophobic bond, a hydrogen bond, or an ionic bond to form an associate. Preferred examples of the first association sustaining domain and the second association sustaining domain include, but are not limited to, an antibody light chain constant region (CL) and a CH1 domain of a heavy chain constant region.

The first association sustaining domain and the second association sustaining domain can interact with each other and form the association of the fusion polypeptide with the association partner, regardless of the degree of associativity between the single-domain antibody and the inhibiting domain In an alternative embodiment, the present invention provides a library comprising a plurality of fusion polypeptides of single-domain antibodies linked to an IgG antibody light chain constant region, wherein the single-domain antibodies include a single-domain antibody whose antigen binding activity is inhibited or lost by associating with particular VL, VH or VHH, and a method for screening the library for a single-domain antibody whose antigen binding activity can be inhibited or could lost by associating with particular VL, VH or VHH.

Figure 9A:
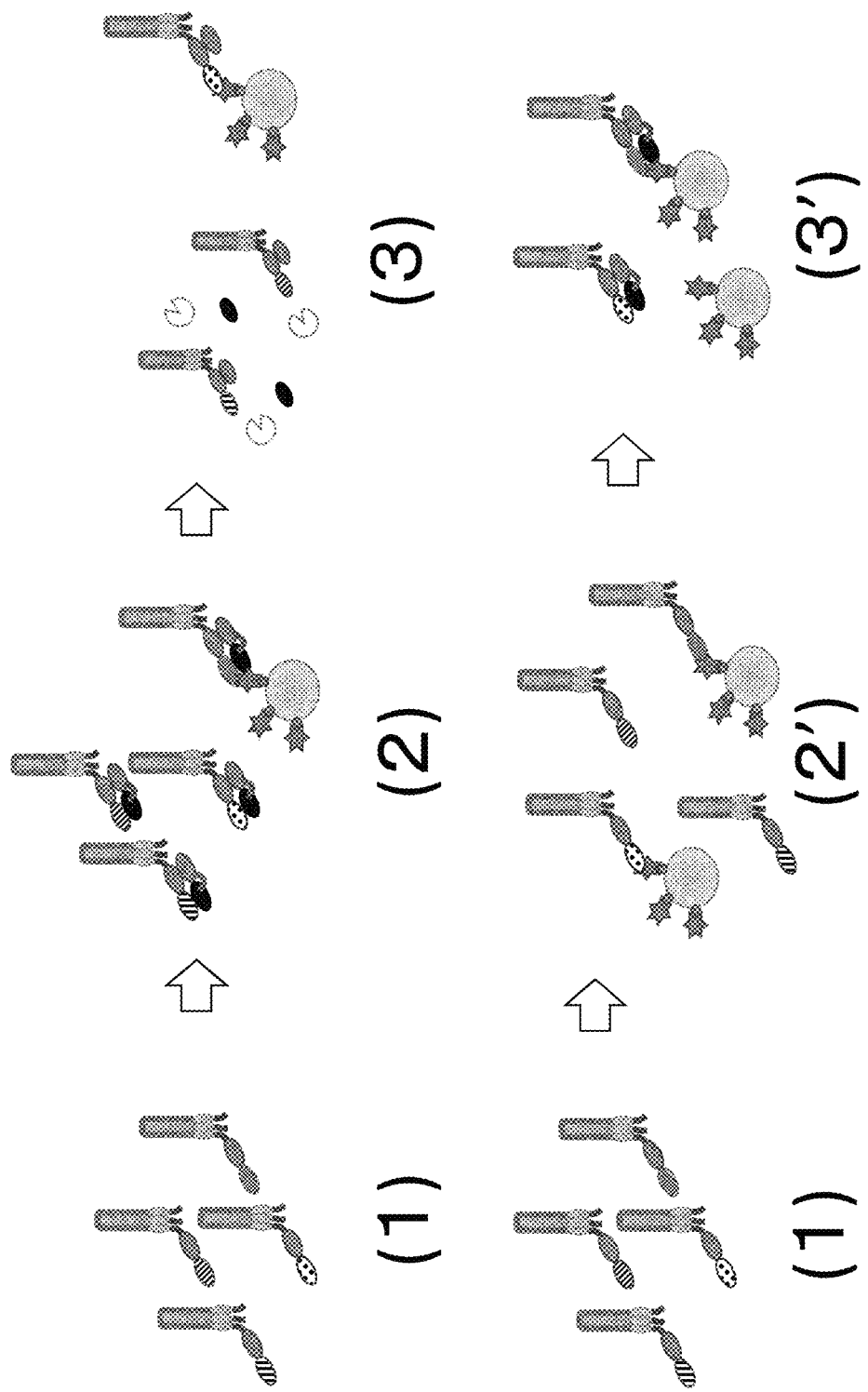
FIG. 9A is a diagram showing one example of a method for screening for a fusion polypeptide comprising a single-domain antibody whose antigen binding activity can be inhibited or could lost by associating with a particular inhibiting domain, from a library comprising a plurality of fusion polypeptides of single-domain antibodies each linked to a first association sustaining domain.

In a specific embodiment, as shown in FIGS. 9A(1), 9A(2), 9A(3), 9B, and 9C, (1) fusion polypeptides of single-domain antibodies each linked to a first association sustaining domain are displayed on the surface of phages or the like by a display method such as phage display.

(2) An association partner of an inhibiting domain linked to a second association sustaining domain is provided, and the fusion polypeptides are associated with the association partner. A fusion polypeptide that does not bind to the target antigen or has antigen binding activity of a predetermined value or lower in this state of the fusion polypeptide associated with the association partner is selected.

(3) The association of the single-domain antibody in the fusion polypeptide selected in (2) with the inhibiting domain in the association partner is canceled. A fusion polypeptide that binds to the target antigen or has antigen binding activity of a predetermined value or higher in a state where the single-domain antibody does not associate with the inhibiting domain is selected.

Figure 9B:
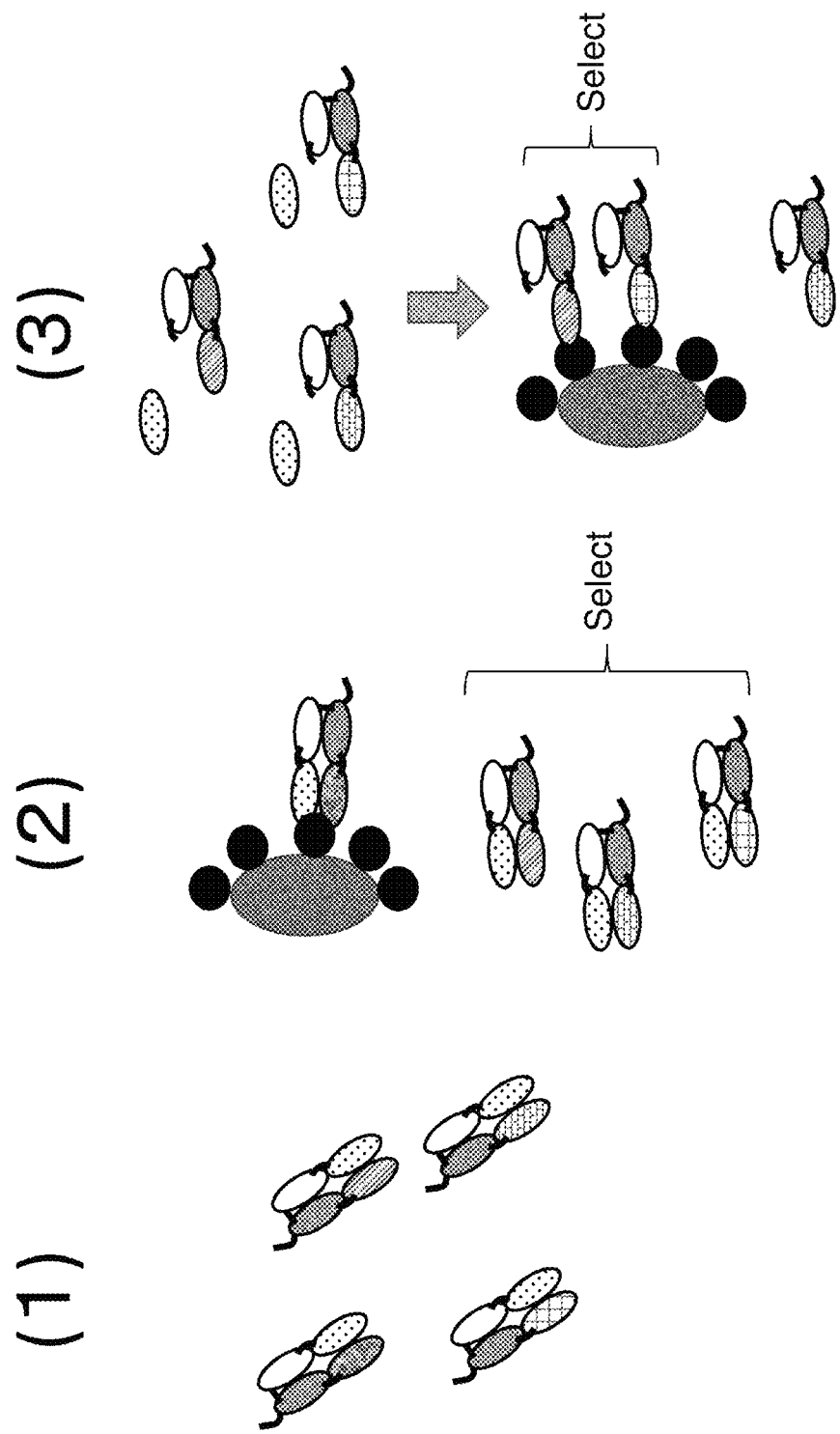
FIG. 9B is a diagram showing one more specific example of the method for screening for a fusion polypeptide comprising a single-domain antibody whose antigen binding activity can be inhibited or could lost by associating with a particular inhibiting domain, from a library comprising a plurality of fusion polypeptides of single-domain antibodies each linked to a first association sustaining domain. (1) The fusion polypeptides each comprising a single-domain antibody and a first association sustaining domain and an association partner harboring a protease cleavage sequence between an inhibiting domain and a second association sustaining domain are displayed together to form a Fab-like structure; (2) from among the Fab-like structures thus displayed, a structure that does not bind to the antigen or has antigen binding activity of a predetermined value or lower is selected; and (3) the association partner is cleaved by protease, and a fragment comprising a single-domain antibody that binds to the antigen or has antigen binding activity of a predetermined value or higher is selected.
Figure 9C:
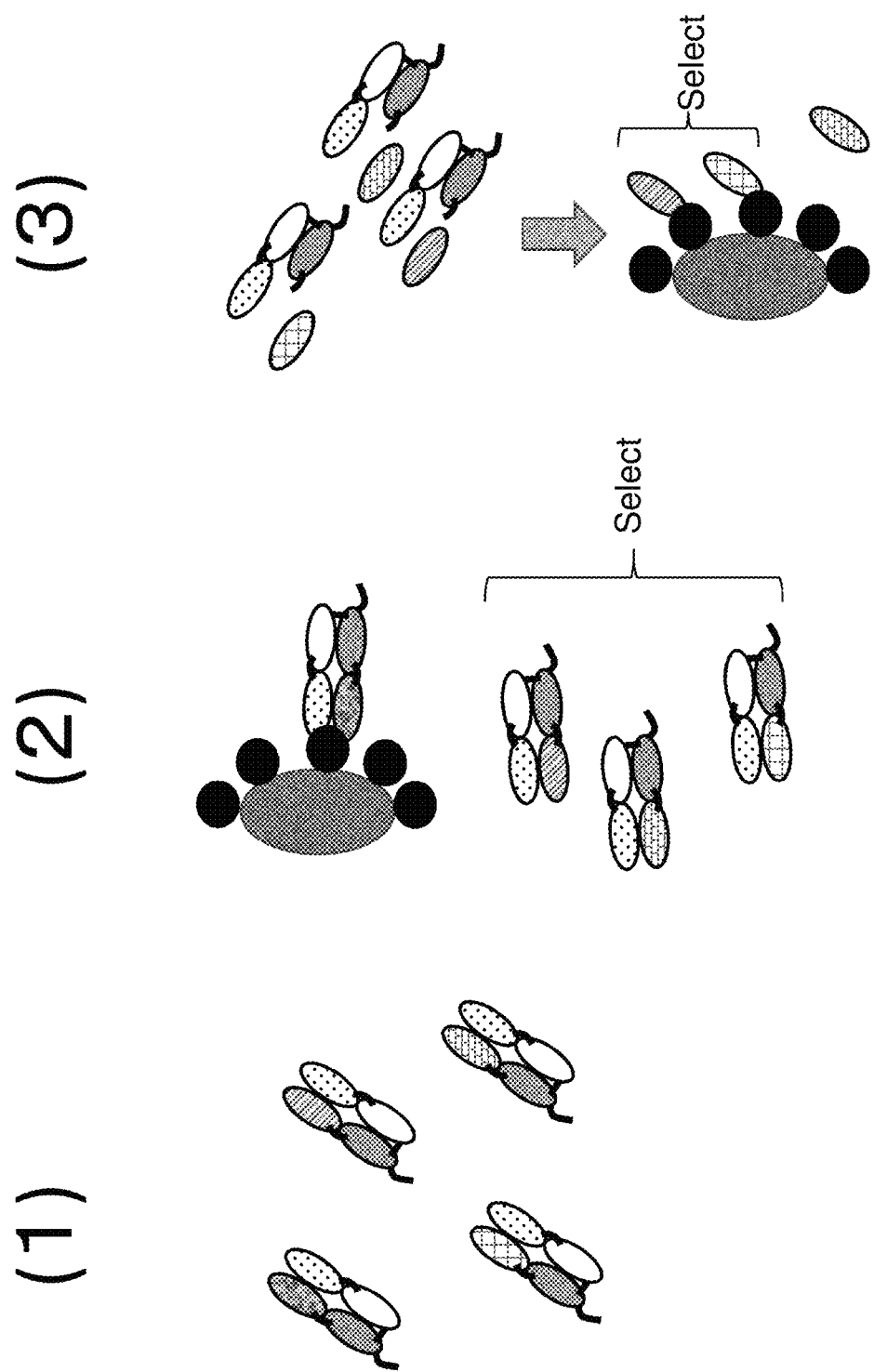
FIG. 9C is a diagram showing another more specific example of the method for screening for a fusion polypeptide comprising a single-domain antibody whose antigen binding activity can be inhibited or could lost by associating with a particular inhibiting domain, from a library comprising a plurality of fusion polypeptides of single-domain antibodies each linked to a first association sustaining domain. (1) The fusion polypeptides each harboring a protease cleavage sequence between a single-domain antibody and a first association sustaining domain and an association partner of an inhibiting domain linked to a second association sustaining domain are displayed together to form a Fab-like structure; (2) from among the Fab-like structures thus selected, a structure that does not bind to the antigen or has antigen binding activity of a predetermined value or lower is selected; and (3) the fusion polypeptide is cleaved by protease, and a fragment comprising a single-domain antibody that binds to the antigen or has antigen binding activity of a predetermined value or higher is selected.

In this context, for example, a method of cleaving the association partner near the boundary between the inhibiting domain and the second association sustaining domain as shown in FIG. 9B, or a method of cleaving the fusion polypeptide near the boundary between the single-domain antibody and the first association sustaining domain as shown in FIG. 9C can be used as a method for canceling the association of the single-domain antibody with the inhibiting domain.

Figure 9D:
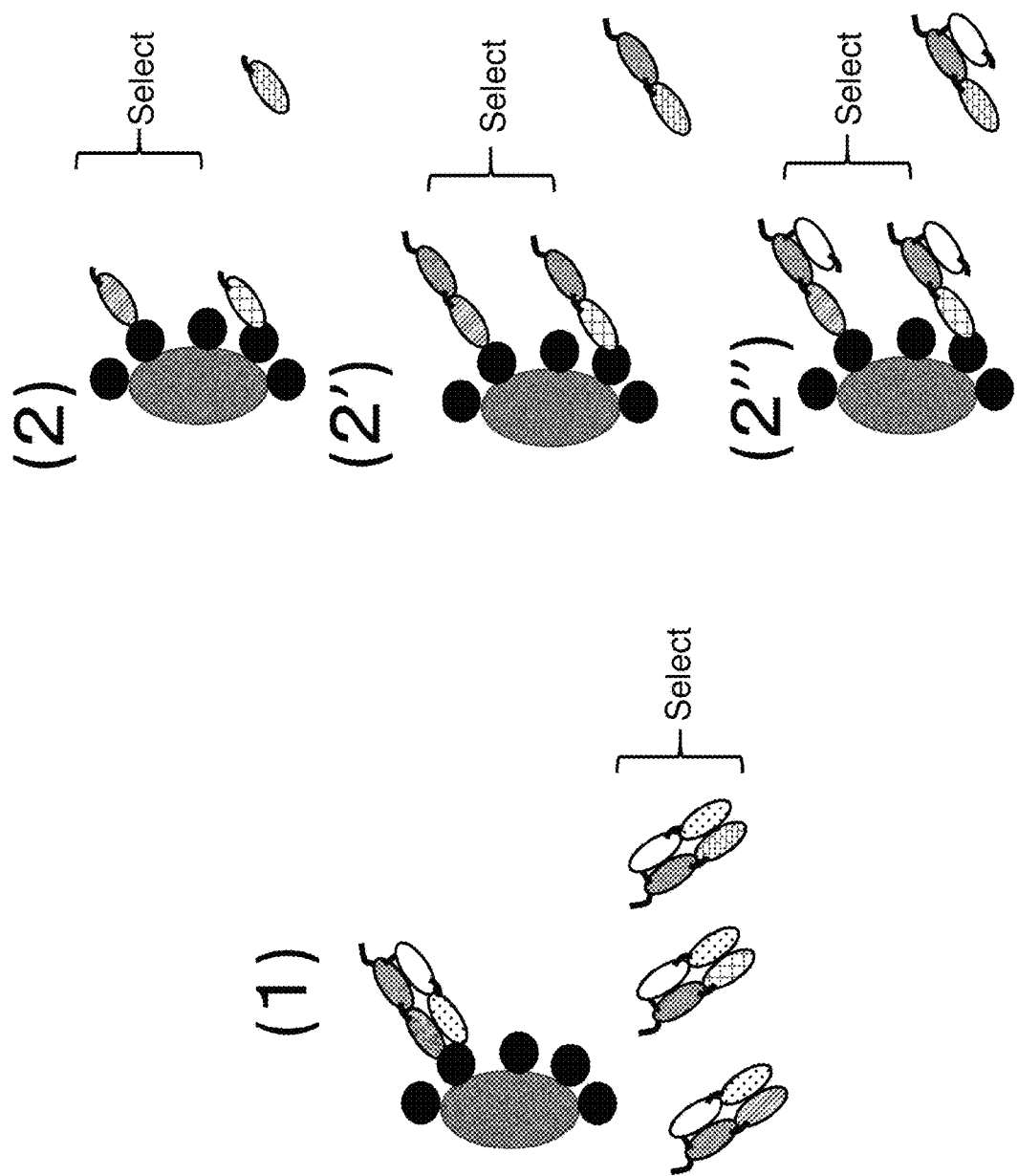
FIG. 9D is a diagram showing an alternative example of the method for screening for a fusion polypeptide comprising a single-domain antibody whose antigen binding activity can be inhibited or could lost by associating with a particular inhibiting domain, from a library comprising a plurality of fusion polypeptides of single-domain antibodies each linked to a first association sustaining domain. (1) The fusion polypeptides each comprising a single-domain antibody and a first association sustaining domain and an association partner of an inhibiting domain linked to a second association sustaining domain are displayed together to form a Fab-like structure, and from among the Fab-like structures thus selected, a structure that does not bind to the antigen or has antigen binding activity of a predetermined value or lower is selected; and (2) moieties comprising the single-domain antibodies in the Fab-like structures thus selected in (1) are displayed again so as not to express the inhibiting domain at the same time therewith, and a fragment that binds to the antigen or has antigen binding activity of a predetermined value or higher is selected. Each of FIGS. 9D(2') and 9D(2") is a diagram showing an alternative embodiment in which the moieties comprising the single-domain antibodies in (2) are displayed again so as not to express the inhibiting domain together therewith. The order of (1) and (2), (2') or (2") may be (2), (2') or (2") preceding (1). Specifically, the moieties comprising the single-domain antibodies are displayed so as not to express the inhibiting domain together therewith, and a fragment having antigen binding activity of a predetermined value or higher is selected. Next, fusion polypeptides each comprising a single-domain antibody comprising the fragment having predetermined or larger binding and a first association sustaining domain, and an association partner of an inhibiting domain linked to a second association sustaining domain are displayed together to form a Fab-like structure, and from among the Fab-like structures thus displayed, a structure that does not bind to the antigen or has antigen binding activity of a predetermined value or lower is selected.

In a further embodiment, the present invention provides a method comprising, as shown in FIG. 9D, comparing the difference in the binding activity of the single-domain antibody between when the single-domain antibody and the inhibiting domain are expressed together and when the single-domain antibody is expressed so as not to express the inhibiting domain together therewith, instead of comparing the difference in the binding activity of the single-domain antibody between the canceled association and non-canceled association of the single-domain antibody with the inhibiting domain as shown in FIGS. 9A to 9C.

As shown in FIG. 9D(1), the single-domain antibody and the inhibiting domain are expressed together to form association. A fusion polypeptide comprising a single-domain antibody that does not bind to the antigen or has antigen binding activity of a predetermined value or lower in this state is selected. As shown in FIGS. 9D(2), 9D(2'), and 9D(2"), the single-domain antibody is expressed so as not to express the inhibiting domain together therewith. A fusion polypeptide comprising a single-domain antibody that binds to the antigen or has antigen binding activity of a predetermined value or higher in this state is selected. As a result, the single-domain antibody whose antigen binding activity is inhibited or lost by associating with a particular inhibiting domain, for example, VH, VL or VHH may be screened for from the library comprising a plurality of fusion polypeptides of single-domain antibodies each linked to a first association sustaining domain. Alternatively, the single-domain antibody is expressed so as not to express the inhibiting domain together therewith. A polypeptide comprising a single-domain antibody that binds to the antigen or has antigen binding activity of a predetermined value or higher in this state is selected. Then, the single-domain antibody and the inhibiting domain are expressed together to form association. A polypeptide comprising a single-domain antibody that does not bind to the antigen or has antigen binding activity of a predetermined value or lower in this state is selected. By this method as well, the single-domain antibody whose antigen binding activity is inhibited or lost by associating with a particular inhibiting domain, for example, VH, VL or VHH may be screened for from the library comprising a plurality of fusion polypeptides of single-domain antibodies each linked to a first association sustaining domain. Alternatively, as shown in FIGS. 9D(2), 9D(2'), and 9D(2"), the single-domain antibody is expressed so as not to express the inhibiting domain together therewith (only the single-domain antibody is expressed; only the fusion polypeptide comprising a single-domain antibody and a first association sustaining domain is expressed; or the fusion polypeptide comprising a single-domain antibody and a first association sustaining domain is associated only with the second association sustaining domain), and a fusion polypeptide comprising a single-domain antibody that binds to the antigen or has antigen binding activity of a predetermined value or higher in this state is selected. Then, as shown in FIG. 9D(1), the single-domain antibody in the selected fusion polypeptide and the inhibiting domain are expressed together to form association. A fusion polypeptide comprising a single-domain antibody that does not bind to the antigen or has antigen binding activity of a predetermined value or lower in this state is selected. As a result, the single-domain antibody whose antigen binding activity is inhibited or lost by associating with a particular inhibiting domain, for example, VH, VL or VHH may also be screened for from the library comprising a plurality of fusion polypeptides of single-domain antibodies each linked to a first association sustaining domain.

The "antigen binding activity of a predetermined value or lower" can refer to, for example, antigen binding activity that falls below a predetermined reference when the antigen binding activity is measured by the method listed in the present specification. Likewise, the "antigen binding activity of a predetermined value or higher" can refer to, for example, antigen binding activity that exceeds a predetermined reference when the antigen binding activity is measured by the method listed in the present specification. A fusion polypeptide having the antigen binding activity of a predetermined value or higher binds more strongly to the antigen than a fusion polypeptide having the antigen binding activity of a predetermined value or lower.

The fusion polypeptide selected in (3) described above comprises a single-domain antibody that has no or weak antigen binding activity in a state of association with the inhibiting domain and has (strong) antigen binding activity in a state of non-association with the inhibiting domain. The sequence of the fusion polypeptide selected by such a method can be analyzed to also elucidate the sequence of the single-domain antibody contained therein. Thus, the single-domain antibody can be produced.

For the method for screening for a fusion polypeptide comprising the single-domain antibody of interest by using fusion polypeptides and an association partner, it is important to compare the antigen binding activity of the single-domain antibody between states of association and non-association with the inhibiting domain. As shown in FIGS. 9A(2') and 9A(3'), the antigen binding activity of the displayed fusion polypeptides is first confirmed, and a fusion polypeptide that binds to the antigen or has antigen binding activity of a predetermined value or higher is selected. Then, the fusion polypeptides thus selected are associated with the association partner. A fusion polypeptide that does not binds to the antigen or has antigen binding activity of a predetermined value or lower in this state of association is selected. By this method as well, the fusion polypeptide comprising the single-domain antibody of interest can be obtained.

Hereinafter, some embodiments using an IgG antibody CH1 domain as the first association sustaining domain and using IgG antibody CL as the second association sustaining domain will be described.

A fusion polypeptide comprising the single-domain antibody of interest can be screened for from a library comprising a plurality of fusion polypeptides of single-domain antibodies each linked to an IgG antibody CH1 domain.

In some embodiments, the present invention provides a library comprising a plurality of fusion polypeptides of single-domain antibodies each linked to an IgG antibody CH1 domain, wherein the single-domain antibodies include a single-domain antibody whose antigen binding activity is inhibited or lost by associating with particular VL, VH or VHH, and a method for screening the library for a fusion polypeptide comprising a single-domain antibody whose antigen binding activity can be inhibited or could lost by associating with particular VL, VH or VHH.

In a particular embodiment, the present invention provides a method for screening for a fusion polypeptide comprising a single-domain antibody whose antigen binding activity can be inhibited or could lost by associating with particular VL, from a library comprising a plurality of fusion polypeptides of single-domain antibodies each linked to an IgG antibody CH1 domain. Specifically, the present invention provides a method for screening for a single-domain antibody, comprising the following steps:

(a) in vitro displaying the fusion polypeptides of the library according to the present invention;

(b) providing an association partner of an IgG antibody light chain constant region fused with the particular VL;

(c) associating the fusion polypeptides displayed in the step (a) with the association partner provided in the step (b) and selecting a fusion polypeptide that does not bind to the antigen or has antigen binding activity of a predetermined value or lower in a state where the single-domain antibody associates with the VL; and (d) selecting, from the fusion polypeptides thus selected in the step (c), a fusion polypeptide that binds to the antigen or has antigen binding activity of a predetermined value or higher in a state where the single-domain antibody contained therein does not associate with the VL.

The association partner provided in the step (b) further comprises a protease cleavage sequence. In this case, in the step (d), the association of the single-domain antibody with the VL is canceled by protease treatment, and the antigen binding activity of the single-domain antibody may be confirmed in a state where the single-domain antibody does not associate with the VL. The protease cleavage sequence in the association partner is not limited by its position as long as the association of the single-domain antibody with the VL is canceled by cleavage. As an example of the position, the protease cleavage sequence may be located, for example, near the boundary between the VL and the IgG antibody light chain constant region in the association partner, preferably at any position between amino acid position 96 (Kabat numbering) of the VL and amino acid position 130 (EU numbering) (Kabat numbering position 130) of the antibody light chain constant region, more preferably at any position between amino acid position 104 (Kabat numbering) of the VL and amino acid position 113 (EU numbering) (Kabat numbering position 113) of the antibody light chain constant region.

Instead of using the association partner comprising a protease cleavage sequence, the protease cleavage sequence may be introduced into the fusion polypeptides in the library, and the fusion polypeptides can be cleaved by protease so that the association of the single-domain antibody with the VL is canceled. The protease cleavage sequence in each fusion polypeptide is not limited by its position as long as the association of the single-domain antibody with the VL is canceled by cleavage and the single-domain antibody retains its antigen binding activity even after the cleavage. As an example of the position, the protease cleavage sequence may be located, for example, near the boundary between the single-domain antibody and the IgG antibody CH1 domain in the fusion polypeptide.

In the step (d), the full lengths of the fusion polypeptides selected in the step (c) or their moieties comprising the single-domain antibodies may be displayed again, and the antigen binding activity of the single-domain antibody can be confirmed in a state where the single-domain antibody does not associate with the VL.

In a particular embodiment, the present invention provides a method for screening for a fusion polypeptide comprising a single-domain antibody whose antigen binding activity can be inhibited or could lost by associating with particular VH, from a library comprising a plurality of fusion polypeptides of single-domain antibodies each linked to an IgG antibody light chain constant region. Specifically, the present invention provides a method for screening for a fusion polypeptide comprising a single-domain antibody, comprising the following steps:

(a) in vitro displaying the fusion polypeptides of the library according to the present invention;

(b) providing an association partner of an IgG antibody CH1 domain fused with the particular VH;

(c) associating the fusion polypeptides displayed in the step (a) with the association partner provided in the step (b) and selecting a fusion polypeptide that does not bind to the antigen or has antigen binding activity of a predetermined value or lower in a state where the single-domain antibody associates with the VH; and (d) selecting, from the fusion polypeptides thus selected in the step (c), a fusion polypeptide that binds to the antigen or has antigen binding activity of a predetermined value or higher in a state where the single-domain antibody contained therein does not associate with the VH.

The association partner provided in the step (b) further comprises a protease cleavage sequence. In this case, in the step (d), the association of the single-domain antibody with the VH is canceled by protease treatment, and the antigen binding activity of the single-domain antibody may be confirmed in a state where the single-domain antibody does not associate with the VH. The protease cleavage sequence in the association partner is not limited by its position as long as the association of the single-domain antibody with the VH is canceled by cleavage. As an example of the position, the protease cleavage sequence may be located, for example, near the boundary between the VH and the IgG antibody CH1 domain in the association partner, preferably at any position between amino acid position 101 (Kabat numbering) of the VH and amino acid position 140 (EU numbering) of the antibody heavy chain constant region, more preferably at any position between amino acid position 109 (Kabat numbering) of the VH and amino acid position 122 (EU numbering) of the antibody heavy chain constant region.

Instead of using the association partner comprising a protease cleavage sequence, the protease cleavage sequence may be introduced into the fusion polypeptides in the library, and the fusion polypeptides can be cleaved by protease so that the association of the single-domain antibody with the VH is canceled. The protease cleavage sequence in each fusion polypeptide is not limited by its position as long as the association of the single-domain antibody with the VH is canceled by cleavage and the single-domain antibody retains its antigen binding activity even after the cleavage. As an example of the position, the protease cleavage sequence may be located, for example, near the boundary between the single-domain antibody and the IgG antibody light chain constant region in the fusion polypeptide.

In the step (d), the full lengths of the fusion polypeptides selected in the step (c) or their moieties comprising the single-domain antibodies may be displayed again, and the antigen binding activity of the single-domain antibody can be confirmed in a state where the single-domain antibody does not associate with the VH.

An amino acid contained in each amino acid sequence described in the present invention may be posttranslationally modified (e.g., the modification of N-terminal glutamine to pyroglutamic acid by pyroglutamylation is a modification well known to those skilled in the art). Such an amino acid sequence containing the posttranslationally modified amino acid is also included in the amino acid sequence described in the present invention, as a matter of course.

It should be understood by those skilled in the art that arbitrary combinations of one or more embodiments described in the present specification are also included in the present invention unless there is technical contradiction on the basis of the technical common sense of those skilled in the art.

EXAMPLES

Hereinafter, Examples of the method and the composition of the present invention will be described. It shall be

Example 1

Problem of Existing Protease-Activated Antibody

A method for preparing an antibody that exerts antigen binding activity only through cleavage by protease expressed at a lesion site such as a cancer tissue or an inflammatory tissue has been reported. This antibody, called Probody, is an antibody molecule, as shown in FIG. 1, whose antigen binding activity is inhibited by connecting an antibody to a peptide masking the antigen binding site of the antibody via a linker that is cleaved by protease expressed at a lesion site (Non Patent Literature 18). The masking peptide is dissociated from the Probody by the cleavage of the constituent linker by the protease expressed at the target pathological site so that the resulting antibody molecule restores its antigen binding activity and becomes capable of binding to the antigen in the target pathological tissue.

Figure 2:
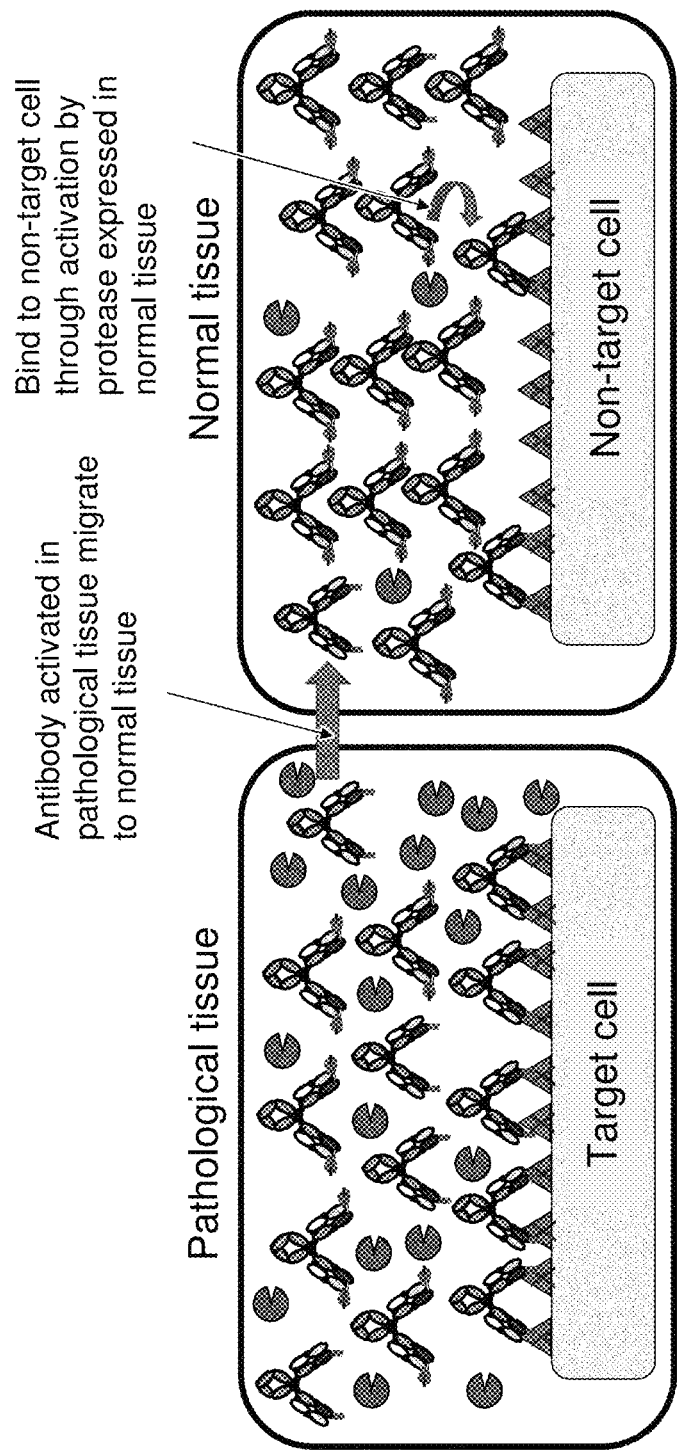
FIG. 2 is a diagram showing a cause of adverse reactions that might be exhibited by Probody. Activated Probody accumulated in blood might exhibit adverse reactions by binding to an antigen expressed in a normal tissue.

It is believed that the Probody can bind to the antigen selectively at the target pathological site under the mechanism as mentioned above and thereby expand the therapeutic window. However, because the cleavage of the antibody by protease is irreversible in the case of Probody, there may be the possibility that the antibody cleaved at the pathological site is capable of being brought back into blood from the pathological site and binds to the antigen expressed in normal tissue as a result of distributing the antibody to the normal tissues through blood flow., The Probody activated by protease retains a Fc region same as in the Probody before the activation and therefore possesses a long circulation time in blood. Therefore, the antibody activated by protease expressed at a pathological site might circulate long in blood. Even protease expressed at an elevated level at a pathological site is also expressed at a low level in normal tissues, and free protease produced at a pathological site may be leaked into blood (The Chinese-German Journal of Clinical Oncology June 2004, Vol. 3, No. 2 P78-P80). Therefore, the Probody may be activated by such free protease. Hence, there may be a possibility that the Probody is activated at a site other than a pathological site. The Probody thus activated also circulates long in blood. Thus, there is a possibility that the Probody is continuously activated at a pathological site, in normal tissues, and in blood, and the activated Probody, if having a long circulation time in blood, accumulates in blood. The activated Probody accumulated in blood might exhibit adverse reactions by binding to the antigen expressed in normal tissues (FIG. 2).

Figure 3:
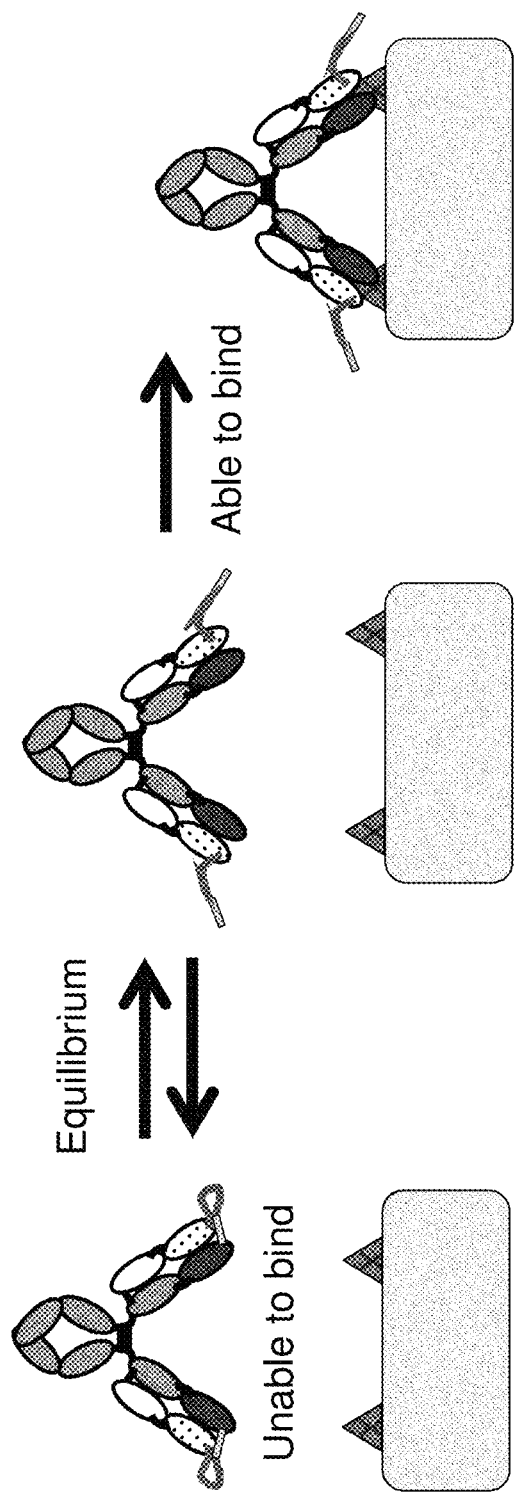
FIG. 3 is a diagram showing a cause of adverse reactions that might be exhibited by Probody. The Probody is in equilibrium between a state where the masking peptide linked via the linker is bound with the antigen binding site and a state where the masking peptide is dissociated. A molecule in the dissociated state can bind to the antigen.

The antigen binding activity of the Probody is inhibited by a masking peptide linked to an antibody via a linker, but the antigen binding activity is not completely inhibited. The Probody is in equilibrium between a state where the masking peptide linked via the linker is bound with the antigen binding site and a state where the masking peptide is dissociated. A molecule in the dissociated state can bind to the antigen (FIG. 3). In actuality, anti-EGFR Probody described in Non Patent Literature 17 has binding activity against EGFR even before protease cleavage of the linker. Although the antigen binding activity increases 30 to 100 fold by the protease cleavage of the linker, the Probody present at a high concentration before activation might exhibit adverse reactions by binding to the antigen expressed in normal tissues, because the Probody before activation has 1/30 to 1/100 of the binding activity of the activated Probody.

The Probody employs an artificial peptide for masking the antigen binding site of the antibody. The artificial peptide has a sequence absent in natural human proteins and might therefore has immunogenicity in humans. Such immunogenicity is known to decrease the effects of antibody drugs by inducing anti-drug antibodies (Blood. 2016 Mar. 31; 127 (13): 1633-41).

Figure 4:
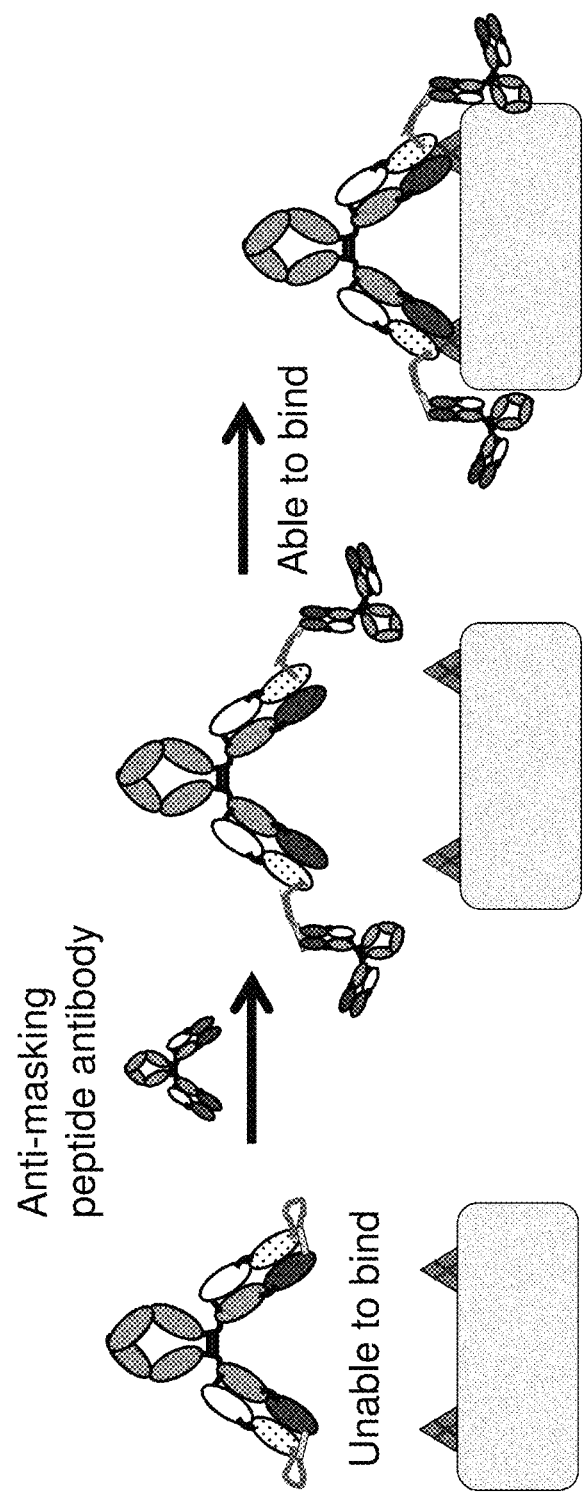
FIG. 4 is a diagram showing a cause of adverse reactions that might be exhibited by Probody. An anti-drug antibody against the masking peptide (anti-masking peptide antibody) might bind to the masking peptide of Probody before activation and thereby activate the Probody without protease cleavage.

Possible anti-drug antibodies against Probody are an anti-drug antibody against a complex of the antibody and the masking peptide (Probody before activation), an anti-drug antibody against the antibody dissociated from the masking peptide (activated Probody), an anti-drug antibody against the masking peptide (masking peptide dissociated from the activated Probody), and the like. Among them, the anti-drug antibody against the masking peptide (anti-masking peptide antibody) might bind to the masking peptide of Probody before activation and thereby activate the Probody without protease cleavage (FIG. 4). The Probody activated by the anti-masking peptide antibody might exhibit adverse reactions by binding to the antigen expressed in normal tissues.

Example 2

Concept of Protease-Activated Polypeptide Comprising Single-Domain Antibody

As shown in Example 1, the Probody technology presents the following problems:
1. Probody activated by protease cleavage has a long circulation time in blood.
2. Even Probody before protease cleavage has binding activity against the antigen.
3. The masking peptide is an artificial non-human sequence and may induce an anti-masking peptide antibody.

The present inventors thought that a useful way for solving these problems and providing an antibody drug exerting activity at a pathological site is to satisfy the following conditions:
1. An antigen binding domain activated by protease cleavage has a short half-life in blood.
2. The antigen binding activity of a molecule before protease cleavage is minimized
3. The masking peptide having an artificial non-human sequence is not used.

Figure 5:
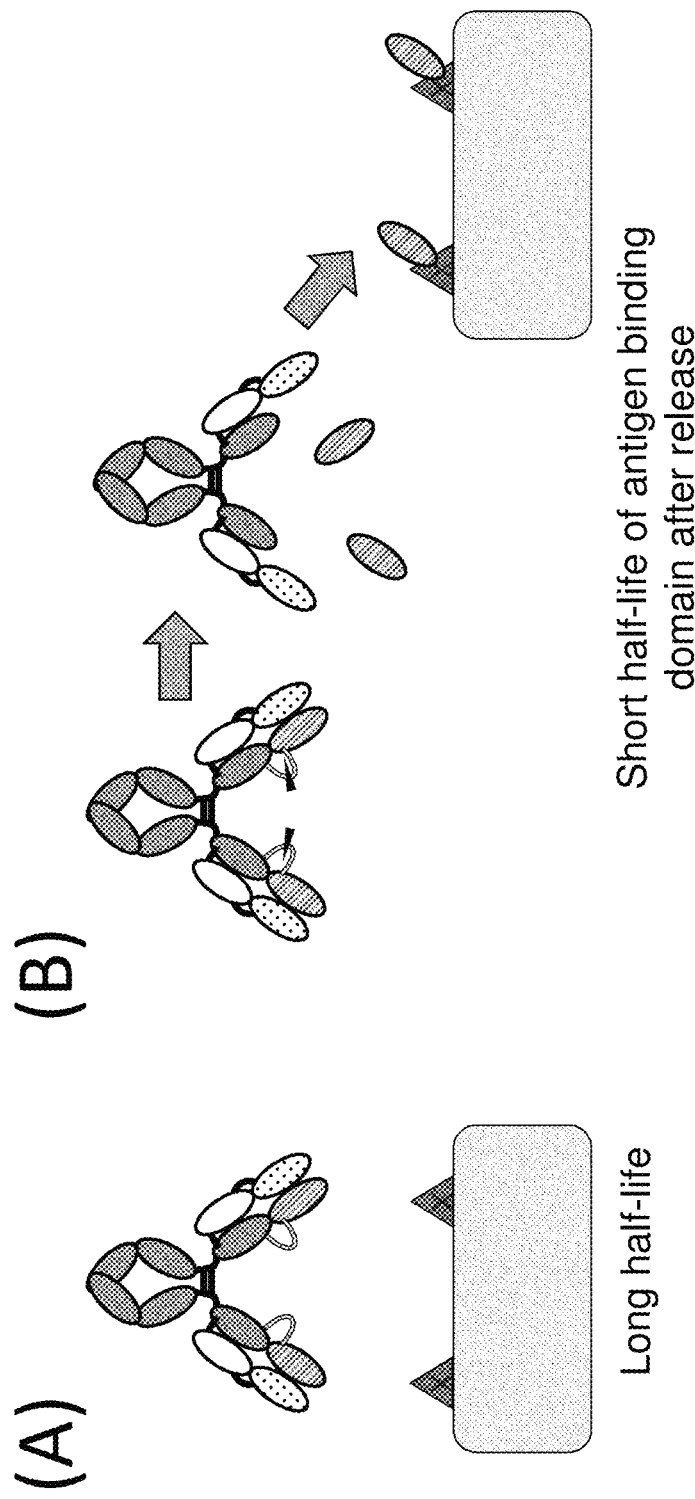
FIG. 5 is a diagram showing the concept of a polypeptide comprising an antigen binding domain and a carrying moiety. (A) The polypeptide with the antigen binding domain linked to the carrying moiety has a long half-life and does not bind to the antigen. (B) The antigen binding domain is released by, for example, cleavage at a cleavage site to bind to the antigen, and the antigen binding domain thus released has a short half-life.

The present inventors devised a molecule shown in FIG. 5 as one example of a polypeptide that satisfied the conditions described above. The polypeptide with an antigen binding domain linked to a carrying moiety has a long half-life and does not bind to the antigen because the antigen binding activity of the antigen binding domain is inhibited (A). The antigen binding domain is released, and the antigen binding domain thus released restores its antigen binding activity and also has a short half-life (B).

Figure 6:
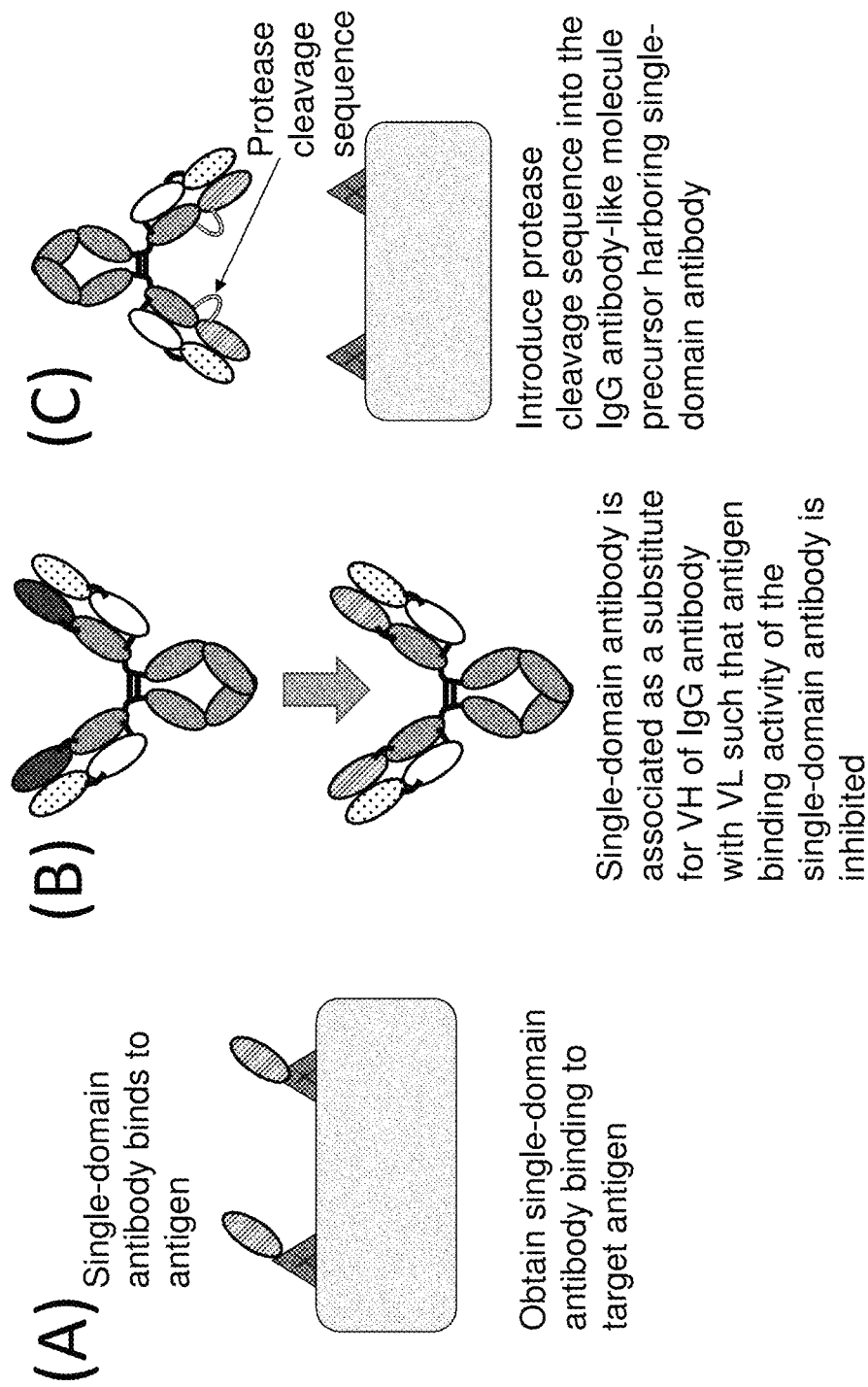
FIG. 6 is a diagram showing one embodiment of a method for producing the polypeptide of the present invention. In the present embodiment, the polypeptide of interest is an IgG antibody-like molecule. (A) A single-domain antibody binding to the target antigen is obtained. (B) The single-domain antibody is associated as a substitute for VH of an IgG antibody with VL such that the antigen binding activity of the single-domain antibody is inhibited. (C) A protease cleavage sequence is introduced into an IgG antibody-like molecule precursor harboring the single-domain antibody.

The polypeptide shown in FIG. 5 has various variations. In the case of using an IgG antibody-like molecule, the polypeptide may be produced by a production method as illustrated in FIG. 6. First, a single-domain antibody (e.g., VH or VHH) binding to the target antigen is obtained (A). The obtained single-domain antibody is associated, as a substitute for one of VH and VL of an IgG antibody having a germline sequence, with the other one (VL or VH) to form an IgG antibody-like molecule (B). A protease cleavage sequence is introduced into the IgG antibody-like molecule (C). Examples of the introduction position include a position near the boundary between the harbored single-domain antibody (VH or VHH) and the constant region (CH1 or CL).

The single-domain antibody has antigen binding activity when existing alone, but loses its antigen binding activity upon formation of a variable region with VL, VH, VHH, or the like. VL or VH is a natural human antibody sequence having a germline sequence and therefore has a low risk of immunogenicity and is unlikely to induce an anti-drug antibody recognizing this VL or VH. In the case of forming a variable region of the single-domain antibody with VHH, the humanization of the VHH reduces the risk of immunogenicity and reduces the likelihood of inducing an anti-drug antibody recognizing this humanized VHH. The protease cleavage sequence inserted into the IgG antibody-like molecule is cleaved by protease so that the single-domain antibody is released. The released single-domain antibody has antigen binding activity. The IgG antibody-like molecule before protease cleavage is structurally similar to general IgG molecules and therefore has a long circulation time in blood, whereas the single-domain antibody released by protease cleavage has a molecular weight of approximately 13 kDa without retaining a Fc region and therefore disappears rapidly by renal excretion. In actuality, the half-life of full-length IgG is on the order of 2 to 3 weeks (Blood. 2016 Mar. 31; 127 (13): 1633-41), whereas the half-life of the single-domain antibody is approximately 2 hours (Antibodies 2015, 4 (3), 141-156). Hence, the antigen binding molecule activated by protease has a short half-life in blood and becomes unlikely to bind to the antigen in normal tissues.

When the single-domain antibody is VL, the same concept as above may be achieved, for example, by introducing the protease cleavage sequence to near the boundary between VL and CL.

Example 3

Preparation of Protease-Activated Polypeptide Using VHH Binding to IL6R 3-1 Preparation of Polypeptide with Incorporated VHH Binding to IL6R An expression vector encoding IL6R90-G1m (SEQ ID NO: 2) containing IL6R90 (SEQ ID NO: 1), VHH having binding and neutralizing activities against human IL6R as described in International Publication No. WO2010/115998, fused with a human IgG1 constant region (CH1-hinge-CH2-CH3) was prepared by a method known to those skilled in the art.

Expression vectors encoding VK1-39-k0MT (SEQ ID NO: 3), VK2-28-k0MT (SEQ ID NO: 4), VK3-20-k0MT (SEQ ID NO: 5), VL1-40-lamL (SEQ ID NO: 6), VL1-44-lamL (SEQ ID NO: 7), VL2-14-lamL (SEQ ID NO: 8), VL3-21-lamL (SEQ ID NO: 9), k0 (SEQ ID NO: 10), and lamL (SEQ ID NO: 11) as light chains (variable region-constant region) of various subclasses having a human germline sequence were prepared by a method known to those skilled in the art.

IgG antibody-like molecules IL6R90-G1m/VK1-39-k0MT (heavy chain: SEQ ID NO: 2, light chain: SEQ ID NO: 3), IL6R90-G1m/VK2-28-k0MT (heavy chain: SEQ ID NO: 2, light chain: SEQ ID NO: 4), IL6R90-G1m/VK3-20-k0MT (heavy chain: SEQ ID NO: 2, light chain: SEQ ID NO: 5), IL6R90-G1m/VL1-40-lamL (heavy chain: SEQ ID NO: 2, light chain: SEQ ID NO: 6), IL6R90-G1m/VL1-44-lamL (heavy chain: SEQ ID NO: 2, light chain: SEQ ID NO: 7), IL6R90-G1m/VL2-14-lamL (heavy chain: SEQ ID NO: 2, light chain: SEQ ID NO: 8), IL6R90-G1m/VL3-21-lamL (heavy chain: SEQ ID NO: 2, light chain: SEQ ID NO: 9), IL6R90-G1m/k0 (heavy chain: SEQ ID NO: 2, light chain: SEQ ID NO: 10), and IL6R90-G1m/lamL (heavy chain: SEQ ID NO: 2, light chain: SEQ ID NO: 11) were expressed by transient expression using FreeStyle 293 cells (Invitrogen Corp.) by a method known to those skilled in the art, and purified by a method known to those skilled in the art using protein A.

3-2 IL6R Binding Evaluation of Polypeptide with Incorporated VHH Binding to Human IL6R IL6R90-G1m/VK1-39-k0MT, IL6R90-G1m/VK2-28-k0MT, IL6R90-G1m/VK3-20-k0MT, IL6R90-G1m/VL1-40-lamL, IL6R90-G1m/VL1-44-lamL, IL6R90-G1m/VL2-14-lamL, IL6R90-G1m/VL3-21-lamL, IL6R90-G1m/k0, and IL6R90-G1m/lamL were evaluated for their binding activity against human IL6R by the following method.

Recombinant human IL6R used as an antigen was prepared as follows: a CHO line stably expressing soluble human IL-6R (hereinafter, also referred to as hsIL-6R, IL6R or IL-6R) consisting of an amino acid sequence from positions 1 to 357 counted from the N terminus as reported in J. Immunol. 152, 4958-4968 (1994) was constructed by a method known to those skilled in the art, cultured, and caused to express hsIL-6R. From the obtained culture supernatant, hsIL-6R was purified by 2 steps of Blue Sepharose 6 FF column chromatography and gel filtration column chromatography. A fraction eluted as a main peak in the final step was used as a final purified product.

Figure 10:
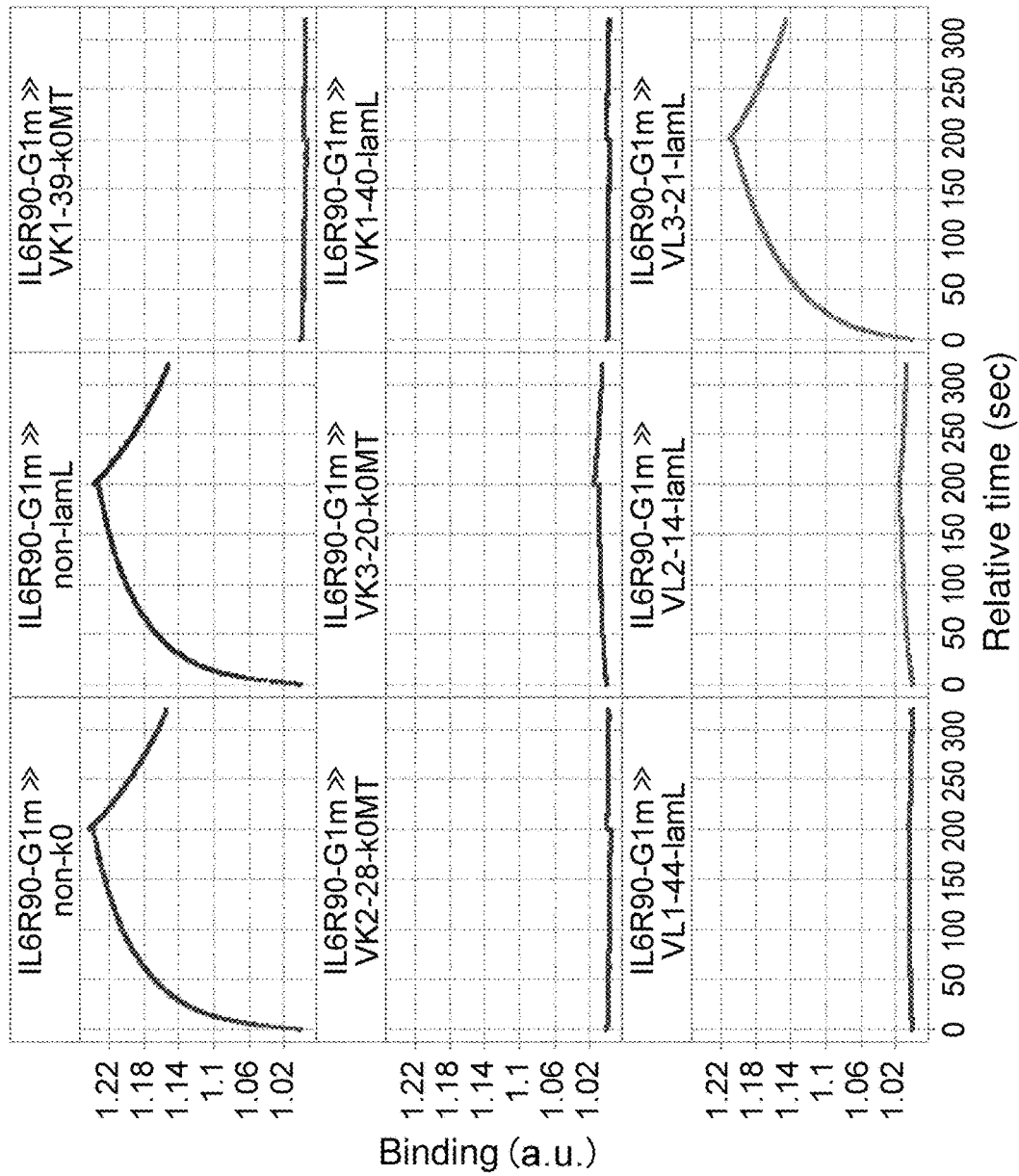
FIG. 10 is a diagram showing results of evaluating the human IL6R binding of antibody-like molecules prepared by associating various light chains with IL6R90-G1m containing anti-human IL6R VHH (IL6R90) fused with a human IgG1 constant region (CH1-hinge-CH2-CH3). The time of onset of the action of the antibody-like molecules on antigen-immobilized sensors is a starting point on the abscissa.

The hsIL-6R binding evaluation of each molecule was conducted using Octet HTX (Pall ForteBio Corp.). Specifically, each molecule was bound to Biosensor/Protein A (ProA) (Pall ForteBio Corp., 18-5013), and hsIL-6R was allowed to act thereon, followed by binding evaluation at 30° C. Sensorgrams showing real time binding responses measured using Octet HTX are shown in FIG. 10. IL6R90-G1m/k0 and IL6R90-G1m/lamL lacking VL bound to hsIL-6R, whereas IL6R90-G1m/VK1-39-k0MT, IL6R90-G1m/VK2-28-k0MT, IL6R90-G1m/VK3-20-k0MT, IL6R90-G1m/VL1-40-lamL, IL6R90-G1m/VL1-44-lamL, and IL6R90-G1m/VL2-14-lamL containing a variable region formed with VL were shown to be unable to bind to hsIL-6R. From this, it was found that VHH having binding activity against human IL6R can lose its IL6R binding activity by forming a variable region through association with VL.

3-3 Introduction of Protease Cleavage Sequence to Polypeptide with Incorporated VHH Binding to IL6R Study was conducted to insert a protease cleavage sequence near the boundary between the anti-human IL6R VHH IL6R90 and CH1. Six types of heavy chains shown in FIG. 11 were designed such that peptide sequence A (SEQ ID NO: 12), a reported sequence cleavable by cancer-specifically expressed urokinase (uPA) and MT-SP1, was inserted at 3 sites near the boundary between IL6R90 and CH1 with or without a glycine-serine linker. Expression vectors encoding IL6R90H1001 (SEQ ID NO: 13), IL6R90H1002 (SEQ ID NO: 14), IL6R90H1003 (SEQ ID NO: 15), IL6R90H1004 (SEQ ID NO: 16), IL6R90H1005 (SEQ ID NO: 17), and IL6R90H1006 (SEQ ID NO: 18) were prepared by a method known to those skilled in the art.

IgG antibody-like molecules IL6R90H1001/VK1-39-k0MT (heavy chain: SEQ ID NO: 13, light chain: SEQ ID NO: 3), IL6R90H1002/VK1-39-k0MT (heavy chain: SEQ ID NO: 14, light chain: SEQ ID NO: 3), IL6R90H1003/VK1-39-k0MT (heavy chain: SEQ ID NO: 15, light chain: SEQ ID NO: 3), IL6R90H1004/VK1-39-k0MT (heavy chain: SEQ ID NO: 16, light chain: SEQ ID NO: 3), IL6R90H1005/VK1-39-k0MT (heavy chain: SEQ ID NO: 17, light chain: SEQ ID NO: 3), and IL6R90H1006/VK1-39-k0MT (heavy chain: SEQ ID NO: 18, light chain: SEQ ID NO: 3) were expressed by transient expression using these heavy chains and VK1-39-k0MT (SEQ ID NO: 3) as light chain and using FreeStyle 293 cells (Invitrogen Corp.) by a method known to those skilled in the art, and purified by a method known to those skilled in the art using protein A.

3-4 Activation of Polypeptide Harboring Protease Cleavage Sequence by Protease Cleavage Whether IL6R90H1001/VK1-39-k0MT, IL6R90H1002/VK1-39-k0MT, IL6R90H1003/VK1-39-k0MT, IL6R90H1004/VK1-39-k0MT, IL6R90H1005/VK1-39-k0MT, and IL6R90H1006/VK1-39-k0MT would release VHH having binding activity against IL6R by protease cleavage was verified.

Soluble human IL6R was prepared by a method known to those skilled in the art. The prepared soluble human IL6R was biotinylated by a method known to those skilled in the art.

For the purpose of attaching biotin to the C terminus of soluble human IL-6R (also referred to as hsIL-6R or soluble human IL6R; SEQ ID NO: 35), a gene fragment encoding a specific sequence (AviTag sequence; SEQ ID NO: 36) to be biotinylated by biotin ligase was linked via a gene fragment encoding a linker to downstream of a gene fragment encoding hsIL-6R. A gene fragment encoding a protein containing hsIL-6R linked to the AviTag sequence (hsIL-6R-Avitag; SEQ ID NO: 37) was integrated to a vector for expression in animal cells. The constructed plasmid vector was transfected into FreeStyle 293 cells (Invitrogen Corp.) using 293Fectin (Invitrogen Corp.). In this operation, the cells were cotransfected with a gene for EBNA1 (SEQ ID NO: 57) expression and a gene for biotin ligase (BirA; SEQ ID NO: 58) expression, and biotin was further added thereto for the purpose of biotin-labeling hsIL-6R-Avitag. The cells transfected according to the procedures mentioned above were cultured at 37° C. under 8% $CO_2$ and the protein of interest (hsIL-6R-BAP1) was secreted into the culture supernatant. This cell culture solution was filtered through a 0.22 μm bottle-top filter to obtain a culture supernatant.

An anti-human IL-6R antibody was immobilized on HiTrap NHS-activated HP (GE Healthcare Japan Corp.) according to the protocol of the manufacturer to prepare a column (anti-human IL-6R antibody column) The culture supernatant was applied to the anti-human IL-6R antibody column equilibrated with TBS, followed by the elution of the bound hsIL-6R with 2 M arginine (pH 4.0). Next, the eluate from the anti-human IL-6R antibody column was diluted with TBS and then applied to SoftLink Avidin column (Promega Corp.) equilibrated with TBS, followed by the elution of hsIL-6R-BAP1 with 5 mM biotin, 50 mM Tris-HCl (pH 8.0) and 2 M arginine (pH 4.0). From this eluate, aggregates of hsIL-6R-BAP1 were removed by gel filtration chromatography using Superdex 200 (GE Healthcare Japan Corp.) to obtain purified hsIL-6R-BAP1 with the buffer replaced with D-PBS and 0.05% CHAPS.

Figures 1, 12:
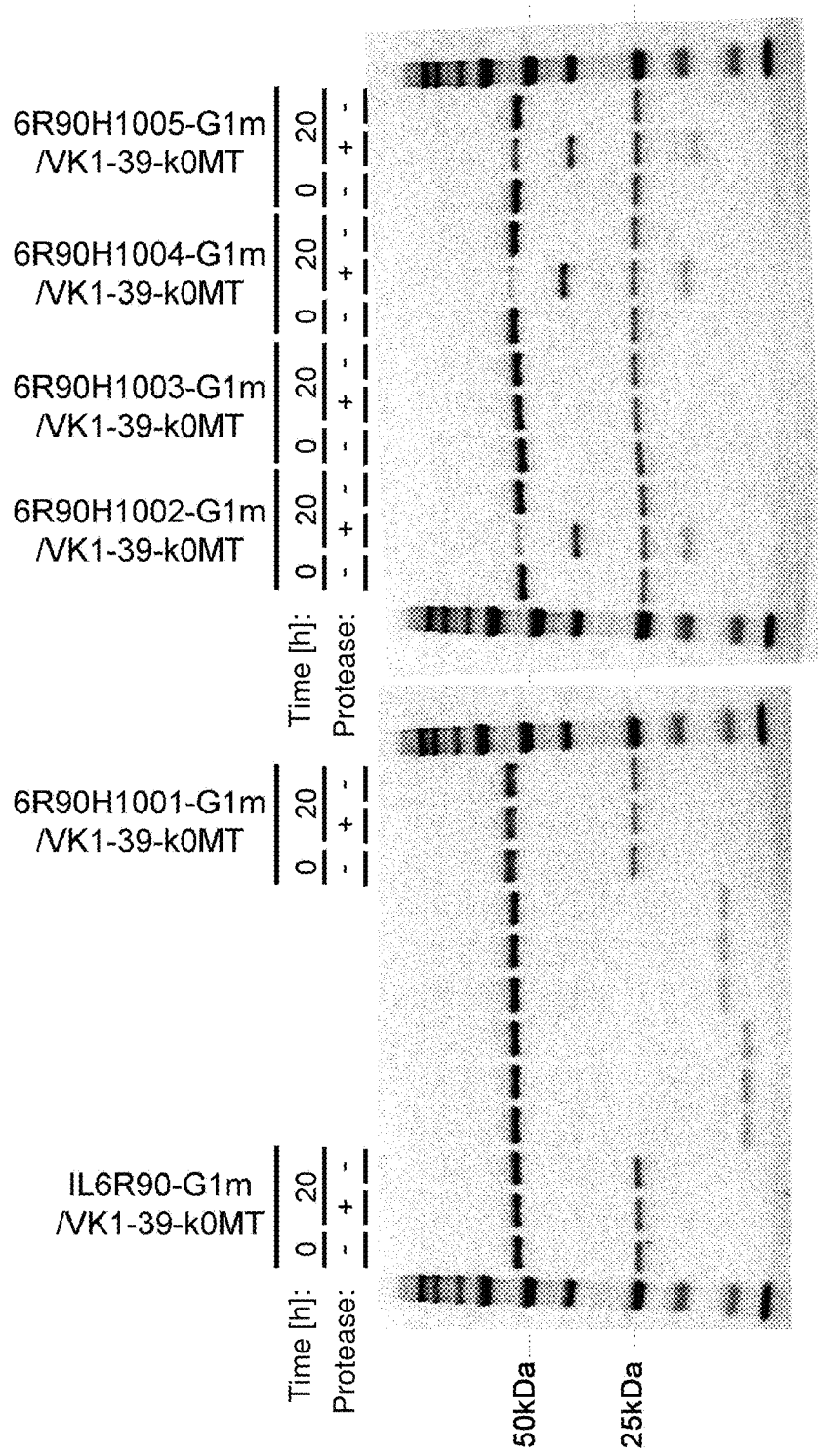
Figures 2, 12:
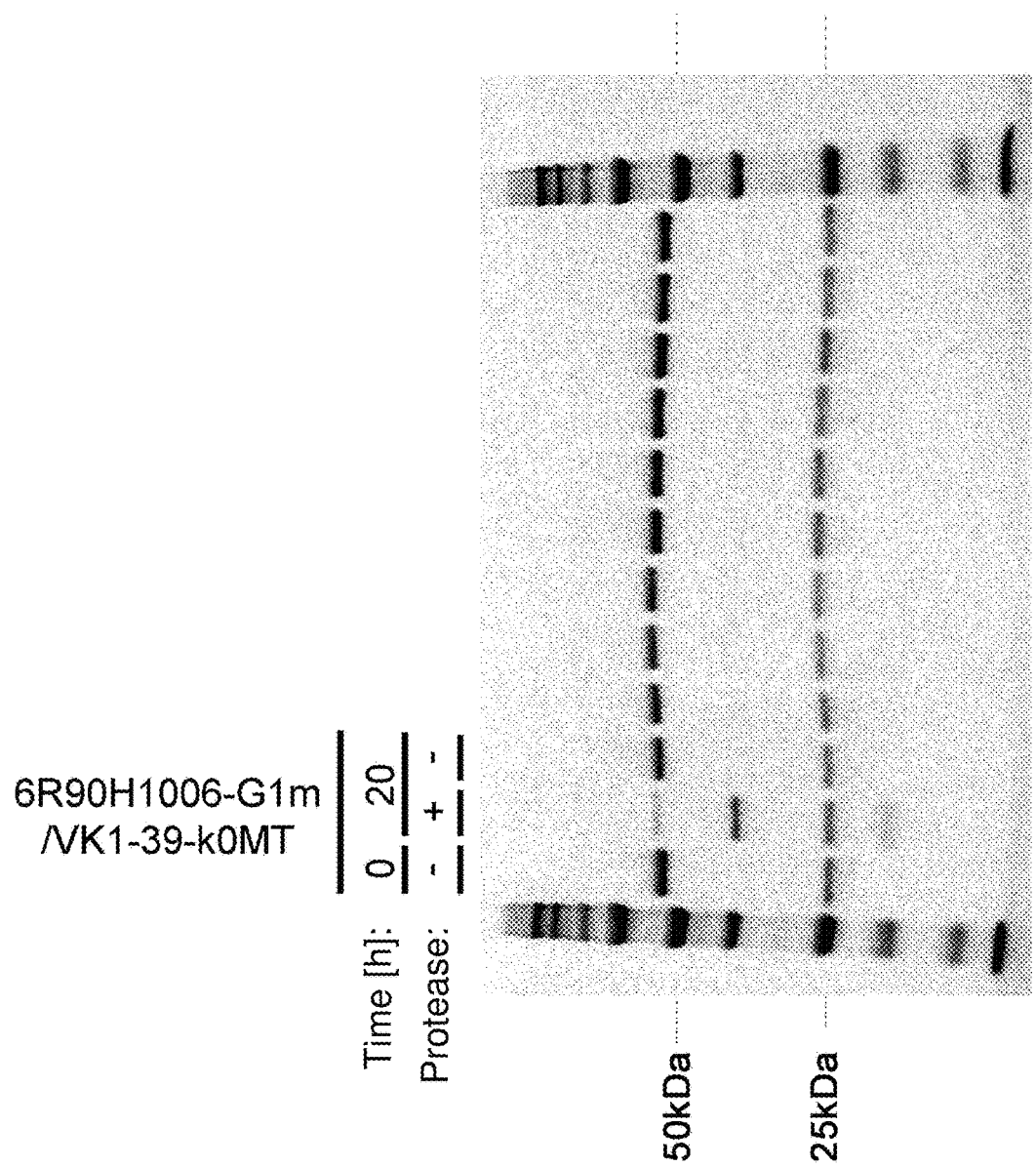

Recombinant Human Matriptase/ST14 Catalytic Domain (R&D Systems, Inc., 3946-SE-010) was used as the protease. 12.5 nM protease and 100 μg/mL of each IgG antibody-like molecule were incubated in PBS under a condition of 37° C. for 20 hours. Then, cleavage by the protease was evaluated by reducing SDS-PAGE. The results are shown in FIG. 12. As a result, the protease cleavage of the protease cleavage sequence near the boundary between the VHH and the heavy chain constant region was confirmed in IL6R90H1002/VK1-39-k0MT, IL6R90H1004/VK1-39-k0MT, IL6R90H1005/VK1-39-k0MT, and IL6R90H1006/VK1-39-k0MT.

Figure 13:
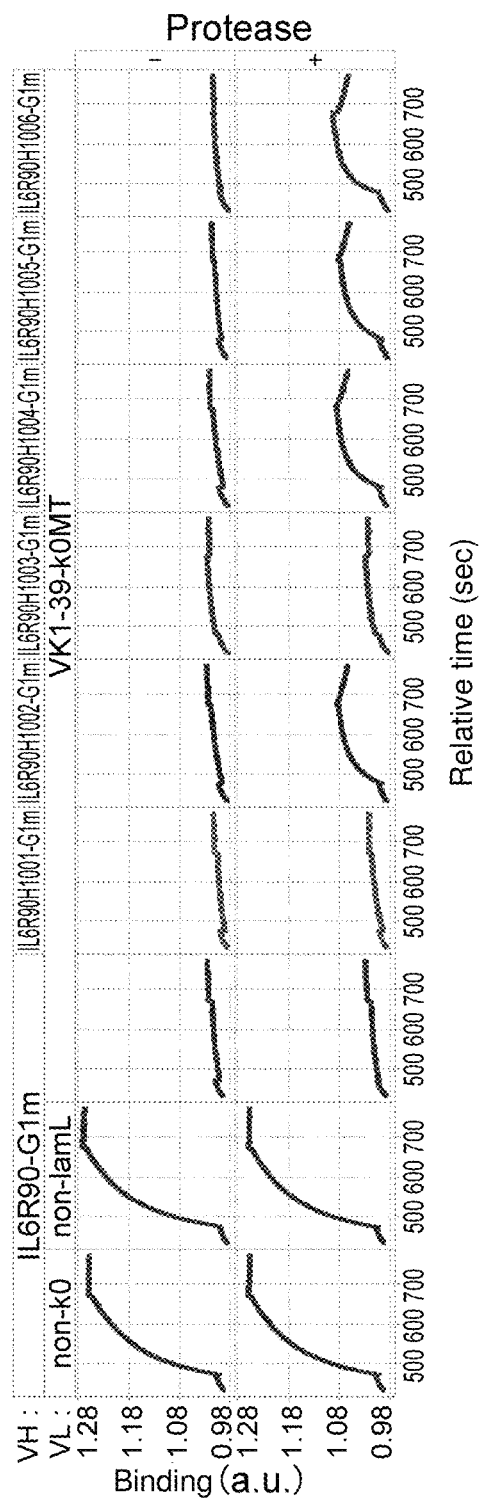
FIG. 13 is a diagram showing results of evaluating the human IL6R binding of IL6R90-G1m or antibody-like molecules prepared by inserting a protease cleavage sequence near the boundary between VHH and the constant region in IL6R90-G1m, or these samples after protease (MT-SP1) treatment. Protease—depicts sensorgrams of evaluating the binding of the protease-untreated antibody-like molecules to the antigen, and Protease+ depicts sensorgrams of evaluating the binding of the protease-treated antibody-like molecules to the antigen. 30 seconds before onset of the action of the antibody-like molecules on antigen-immobilized sensors are a starting point on the abscissa.

Next, the IL6R binding evaluation of VHH released by protease treatment was conducted using Octet HTX (Pall ForteBio Corp.). Specifically, hsIL-6R-BAP1 was bound to a streptavidin sensor (Pall ForteBio Corp., 18-5021), and each cleaved IgG antibody-like molecule was allowed to act thereon, followed by binding evaluation at 30° C. Sensorgrams showing real time binding responses measured using Octet HTX are shown in FIG. 13. As a result, the binding was confirmed in IL6R90H1002/VK1-39-k0MT, IL6R90H1004/VK1-39-k0MT, IL6R90H1005/VK1-39-k0MT, and IL6R90H1006/VK1-39-k0MT. IL6R90-G1m/k0 and IL6R90-G1m/lamL divalently bound with avidity, whereas the released VHH bound with affinity. Therefore, the protease-treated IL6R90H1002/VK1-39-k0MT, IL6R90H1004/VK1-39-k0MT, IL6R90H1005/VK1-39-k0MT, and IL6R90H1006/VK1-39-k0MT exhibited a faster dissociation rate from IL6R than that of IL6R90-G1m/k0 and IL6R90-G1m/lamL Also, the VHH had a smaller molecular weight than that of IL6R90-G1m/k0 and IL6R90-G1m/lamL. Therefore, its response, binding amount, was lower.

These results demonstrated that IL6R90H1002/VK1-39-k0MT, IL6R90H1004/VK1-39-k0MT, IL6R90H1005/VK1-39-k0MT, or IL6R90H1006/VK1-39-k0MT does not exhibit binding activity against IL6R as is, whereas the peptide sequence A inserted near the boundary between the VHH and the heavy chain constant region is cleaved by protease treatment so that the VHH domain is released, and the released VHH can bind to IL6R. From this, it was concluded that the molecule conforming to the concept described in Example 2 was actually able to be prepared.

Example 4

Preparation of Protease-Activated Polypeptide by Alteration Using VHH Binding to IL6R 4-1 IL6R Binding Evaluation of Polypeptide with Incorporated VHH Binding to IL6R An expression vector encoding 20A11-G1m (SEQ ID NO: 38) containing 20A11 (SEQ ID NO: 19), VHH having binding and neutralizing activities against IL6R as described in International Publication No. WO2010/115998, fused with a human IgG1 constant region (CH1-hinge-CH2-CH3) in the same way as in Example 3 was prepared by a method known to those skilled in the art.

Polypeptides 20A11-G1m/VK1-39-k0MT, 20A11-G1m/VK2-28-k0MT, 20A11-G1m/VK3-20-k0MT, 20A11-G1m/VL1-40-lamL, 20A11-G1m/VL1-44-lamL, 20A11-G1m/VL2-14-lamL, and 20A11-G1m/VL3-21-lamL were expressed and purified in the same way as in Example 3 using this heavy chain and VK1-39-k0MT (SEQ ID NO: 3), VK2-28-k0MT (SEQ ID NO: 4), VK3-20-k0MT (SEQ ID NO: 5), VL1-40-lamL (SEQ ID NO: 6), VL1-44-lamL (SEQ ID NO: 7), VL2-14-lamL (SEQ ID NO: 8), and VL3-21-lamL (SEQ ID NO: 9) as light chains.

Figure 14:
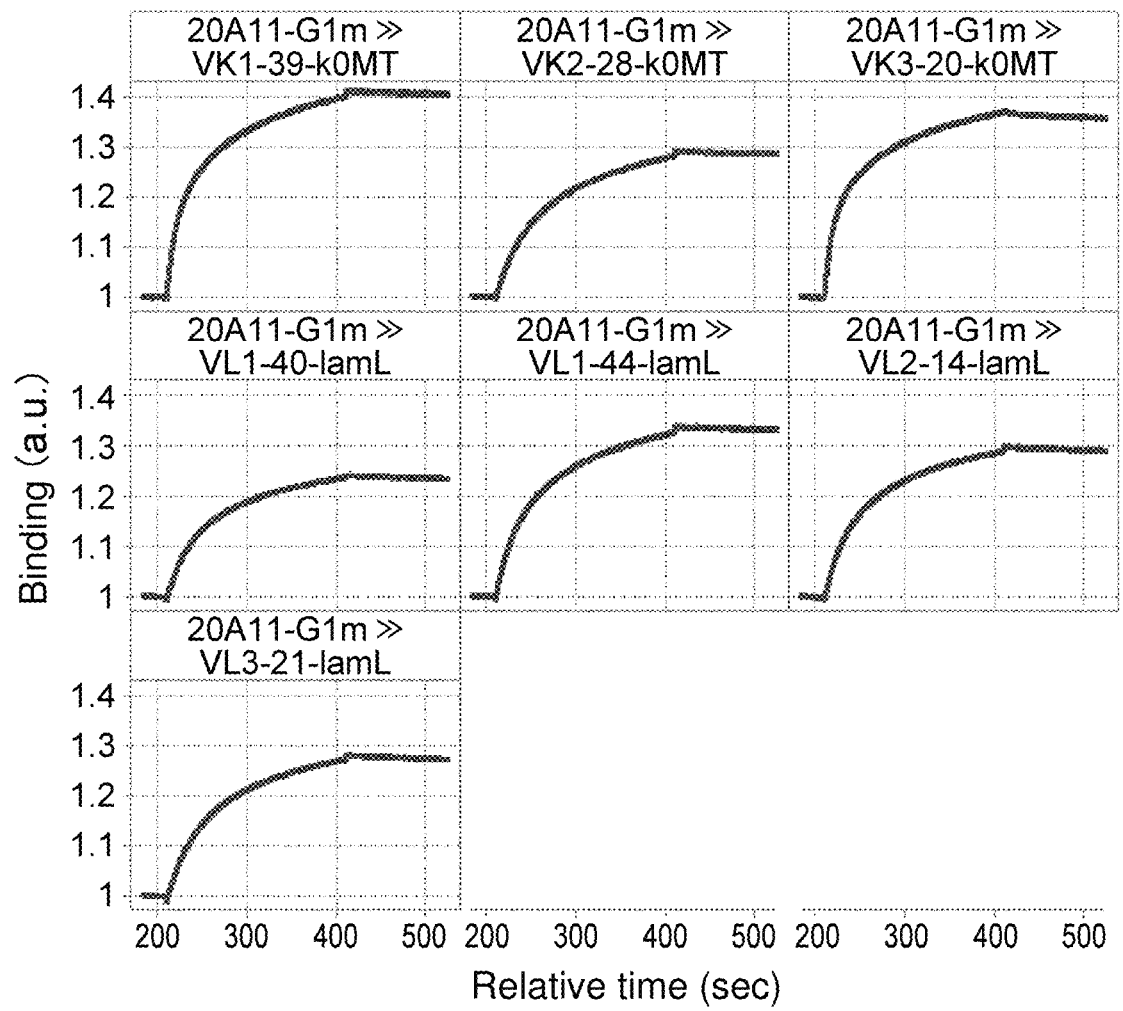
FIG. 14 is a diagram showing results of evaluating the human IL6R binding of antibody-like molecules prepared by associating various light chains with 20A11-G1m containing anti-human IL6R VHH (20A11) fused with a human IgG1 constant region (CH1-hinge-CH2-CH3). 30 seconds before the time of onset of the action of the antibody-like molecules on antigen-immobilized sensors are a starting point on the abscissa.

The obtained 20A11-G1m/VK1-39-k0MT (heavy chain: SEQ ID NO: 38, light chain: SEQ ID NO: 3), 20A11-G1m/VK2-28-k0MT (heavy chain: SEQ ID NO: 38, light chain: SEQ ID NO: 4), 20A11-G1m/VK3-20-k0MT (heavy chain: SEQ ID NO: 38, light chain: SEQ ID NO: 5), 20A11-G1m/VL1-40-lamL (heavy chain: SEQ ID NO: 38, light chain: SEQ ID NO: 6), 20A11-G1m/VL1-44-lamL (heavy chain: SEQ ID NO: 38, light chain: SEQ ID NO: 7), 20A11-G1m/VL2-14-lamL (heavy chain: SEQ ID NO: 38, light chain: SEQ ID NO: 8), and 20A11-G1m/VL3-21-lamL (heavy chain: SEQ ID NO: 38, light chain: SEQ ID NO: 9) were evaluated for their binding to IL6R in the same way as in Example 3. The results are shown in FIG. 14. As a result, none of the light chains used in this Example inhibited the IL6R binding activity of 20A11 by associating with the heavy chain containing the 20A11 fused with the human germline IgG1 constant region (CH1-hinge-CH2-CH3).

This is probably because 20A11 did not form a stable variable region with VL used in this Example.

4-2 Introduction of Amino Acid Alteration to Interface Site Between VHH and VL in Polypeptide with Incorporated VHH not Losing Antigen Binding In order to form a stable variable region between 20A11 and VL, mutations were introduced to amino acids present at the interface between the 20A11 and the VL. An expression vector encoding 20A11hu-G1m (SEQ ID NO: 39) containing 20A11hu (derived from 20A11 by the introduction of mutations to substitute F at position 37 by V (F37V), R at position 45 by L, and G at position 47 by W (all according to the Kabat numbering)) (SEQ ID NO: 20) fused with a human IgG1 constant region (CH1-hinge-CH2-CH3) in the same way as in
Example 3 was prepared by a method known to those skilled in the art.

Polypeptides 20A11hu-G1m/VK1-39-k0MT (heavy chain: SEQ ID NO: 39, light chain: SEQ ID NO: 3), 20A11hu-G1m/VK2-28-k0MT (heavy chain: SEQ ID NO: 39, light chain: SEQ ID NO: 4), 20A11hu-G1m/VK3-20-k0MT (heavy chain: SEQ ID NO: 39, light chain: SEQ ID NO: 5), 20A11hu-G1m/VL1-40-lamL (heavy chain: SEQ ID NO: 39, light chain: SEQ ID NO: 6), 20A11hu-G1m/VL1-44-lamL (heavy chain: SEQ ID NO: 39, light chain: SEQ ID NO: 7), 20A11hu-G1m/VL2-14-lamL (heavy chain: SEQ ID NO: 39, light chain: SEQ ID NO: 8), and 20A11hu-G1m/VL3-21-lamL (heavy chain: SEQ ID NO: 39, light chain: SEQ ID NO: 9) were expressed and purified in the same way as in Example 3 using this heavy chain and VK1-39-k0MT (SEQ ID NO: 3), VK2-28-k0MT (SEQ ID NO: 4), VK3-20-k0MT (SEQ ID NO: 5), VL1-40-lamL (SEQ ID NO: 6), VL1-44-lamL (SEQ ID NO: 7), VL2-14-lamL (SEQ ID NO: 8), and VL3-21-lamL (SEQ ID NO: 9) as light chains.

Figure 15:
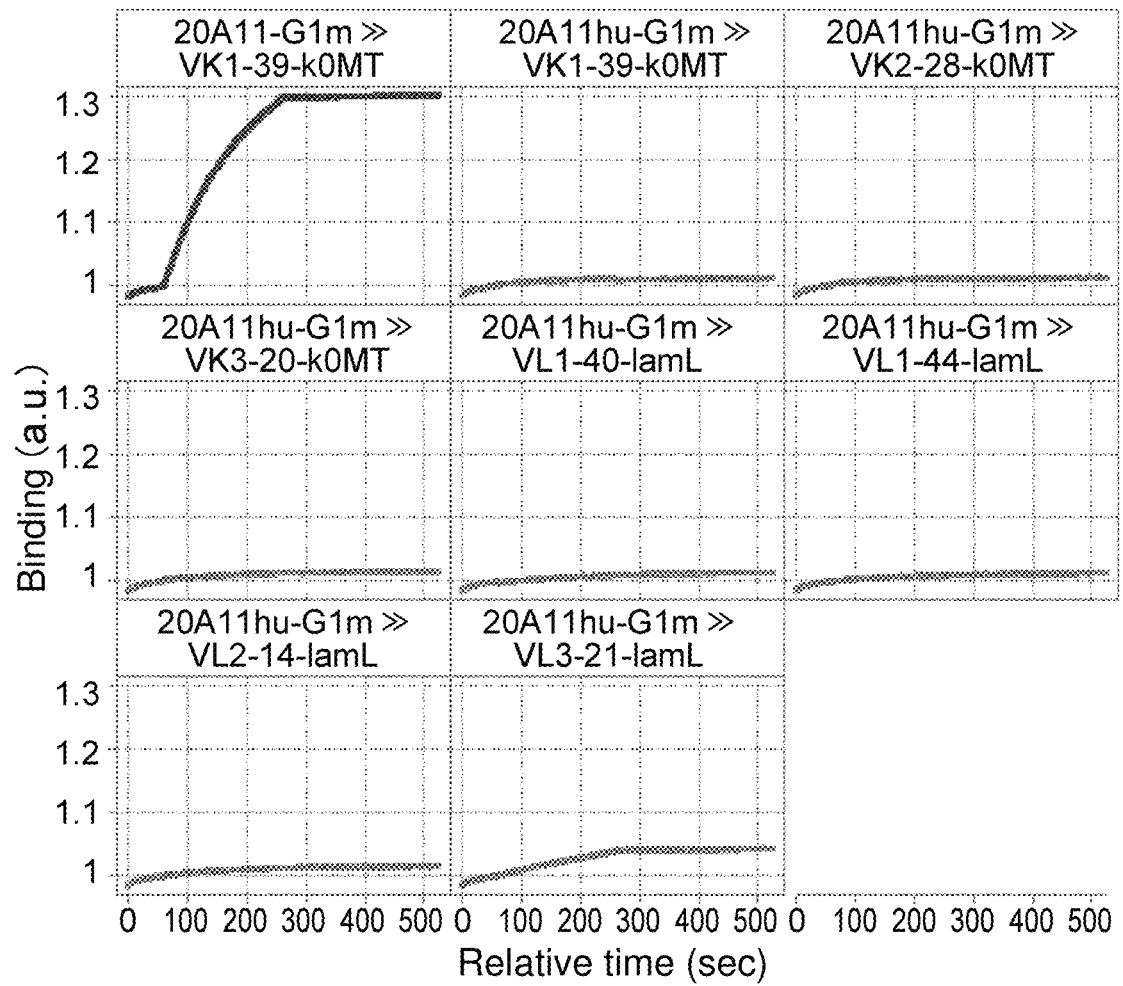
FIG. 15 is a diagram showing results of evaluating the human IL6R binding of 20A11-G1m or antibody-like molecules prepared by introducing mutations to amino acids present at the interface between 20A11 and VL and associating various light chains with 20A11hu-G1m containing the thus-prepared 20A11hu fused with a human IgG1 constant region (CH1-hinge-CH2-CH3). 60 seconds before the time of onset of the action of the antibody-like molecules on antigen-immobilized sensors are a starting point on the abscissa.

4-3 IL6R Binding Evaluation of Polypeptide with Incorporated VHH Containing Amino Acid Alteration at Interface Site Between the VHH and VL The obtained 20A11hu-G1m/VK1-39-k0MT, 20A11hu-G1m/VK2-28-k0MT, 20A11hu-G1m/VK3-20-k0MT, 20A11hu-G1m/VL1-40-lamL, 20A11hu-G1m/VL1-44-lamL, 20A11hu-G1m/VL2-14-lamL, and 20A11hu-G1m/VL3-21-lamL were evaluated for their binding to IL6R at 30° C. or 25° C. in the same way as in Example 3. The results are shown in FIG. 15.

As a result, 20A11hu-G1m/VK1-39-k0MT, 20A11hu-G1m/VK2-28-k0MT, 20A11hu-G1m/VK3-20-k0MT, 20A11hu-G1m/VL1-40-lamL, 20A11hu-G1m/VL1-44-lamL, and 20A11hu-G1m/VL2-14-lamL were shown to be unable to bind to IL6R.

These results demonstrated that the VHH 20A11, which did not lose its IL6R binding activity by associating with VL, used in Example 3, can form a stable variable region with VL and can lose its IL6R binding activity, by converting amino acids present at the interface site between the VHH and the VL to 37V, 45L, and 47W (Kabat numbering) and thereby altering the 20A11 to 20A11hu.

4-4 Introduction of Protease Cleavage Sequence to Polypeptide with Incorporated VHH Containing Amino Acid Alteration at Interface Site Between the VHH and VL Heavy chains 20A11huH1001 (SEQ ID NO: 40), 20A11huH1002 (SEQ ID NO: 41), 20A11huH1004 (SEQ ID NO: 42), and 20A11huH1006 (SEQ ID NO: 43) were prepared in the same way as in Example 3 such that a protease cleavage sequence (SEQ ID NO: 12) or a protease cleavage sequence linked to a flexible linker (SEQ ID NO: 44) was inserted near the boundary between 20A11hu and CH1.

Polypeptides 20A11huH1001/VK1-39-k0MT (heavy chain: SEQ ID NO: 40, light chain: SEQ ID NO: 3), 20A11huH1002/VK1-39-k0MT (heavy chain: SEQ ID NO: 41, light chain: SEQ ID NO: 3), 20A11huH1004/VK1-39-k0MT (heavy chain: SEQ ID NO: 42, light chain: SEQ ID NO: 3), and 20A11huH1006/VK1-39-k0MT (heavy chain: SEQ ID NO: 43, light chain: SEQ ID NO: 3) were expressed and purified in the same way as in Example 3 using these heavy chains and VK1-39-k0MT (SEQ ID NO: 3) as a light chain.

Figure 16:
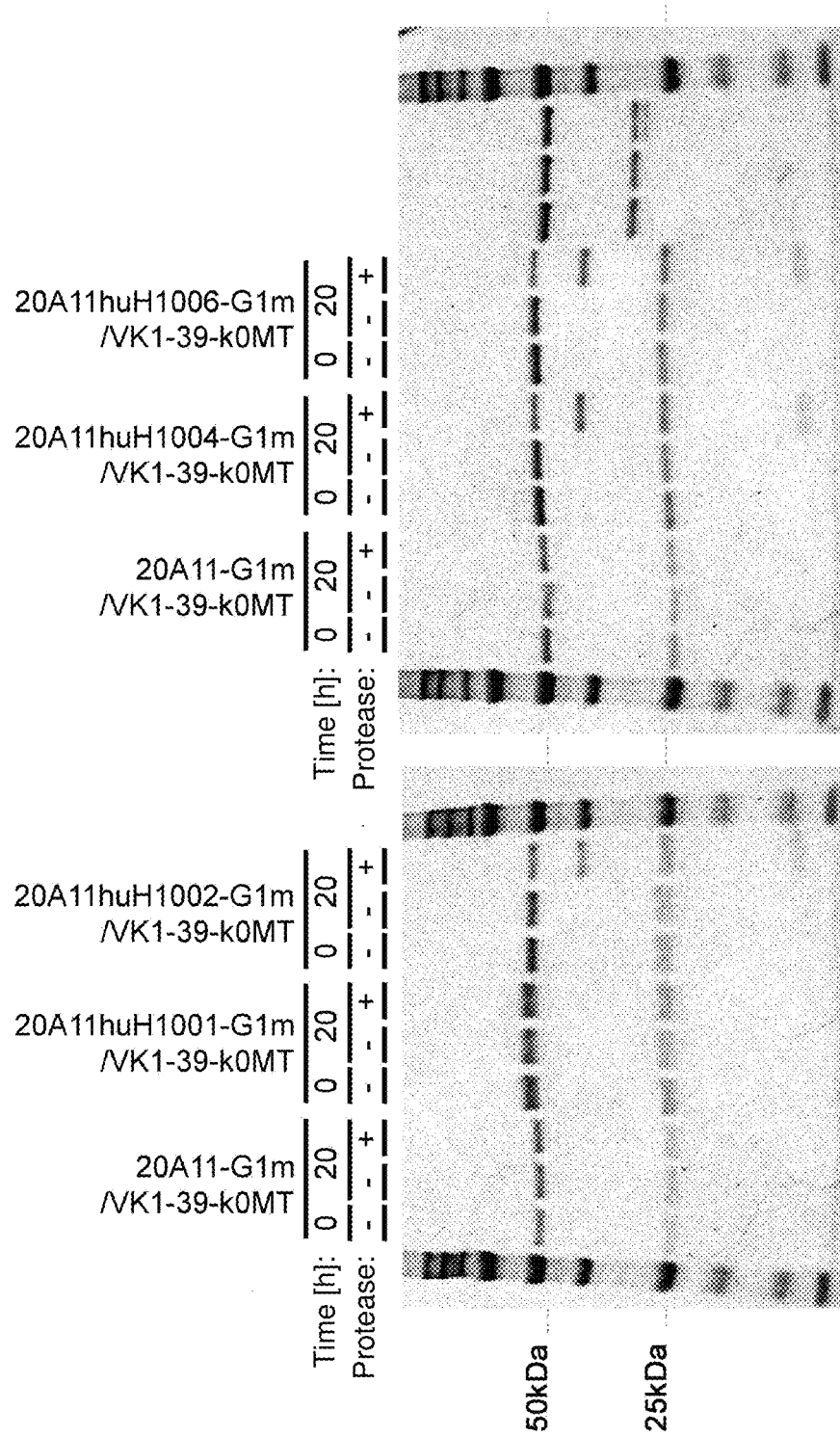
FIG. 16 is a diagram showing results of evaluating the degree of cleavage by reducing SDS-PAGE after protease (MT-SP1) treatment of 20A11-G1m or 4 types of antibody-like molecules prepared by inserting a protease cleavage sequence near the boundary between 20A11hu and the constant region in 20A11hu-G1m. Of two new bands resulting from the protease treatment, the band appearing at 25 kDa or smaller is a band derived from the VHH, and the band appearing at a position of 25 to 50 kDa is a band derived from the constant region.

4-5 Activation of Polypeptide Harboring Protease Cleavage Sequence by Protease Cleavage 20A11huH1001/VK1-39-k0MT, 20A11huH1002/VK1-39-k0MT, 20A11huH1004/VK1-39-k0MT, and 20A11huH1006/VK1-39-k0MT were cleaved by protease in the same way as in Example 3, and the degree of the cleavage was evaluated by reducing SDS-PAGE. The results are shown in FIG. 16.

As a result, 20A11huH1002/VK1-39-k0MT, 20A11huH1004/VK1-39-k0MT, and 20A11huH1006/VK1-39-k0MT were confirmed to undergo protease cleavage near the boundary between VHH and CH1.

Figure 17:
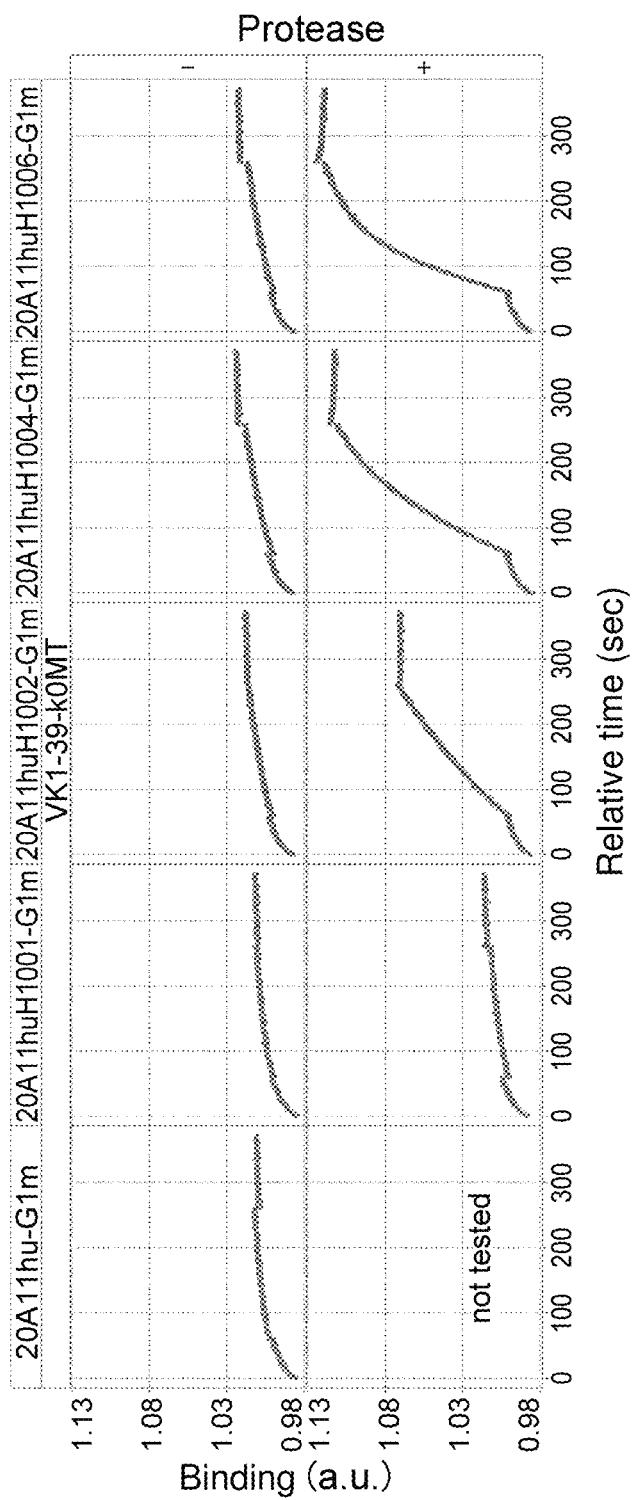
FIG. 17 is a diagram showing results of evaluating the human IL6R binding of 20A11-G1m or antibody-like molecules prepared by inserting a protease cleavage sequence near the boundary between VHH and the constant region in 20A11hu-G1m, or these samples after protease (MT-SP1) treatment. Protease—depicts sensorgrams of evaluating the binding of the protease-untreated antibody-like molecules to the antigen, and Protease+ depicts sensorgrams of evaluating the binding of the protease-treated antibody-like molecules to the antigen. 60 seconds before onset of the action of the antibodies on antigen-immobilized sensors are a starting point on the abscissa. The sample with the term "not tested" represents that the sample was not assayed.

Next, the IL6R binding evaluation of VHH released by protease treatment was conducted at 30° C. or 25° C. in the same way as in Example 3. Octet sensorgrams are shown in FIG. 17.

As a result, the IL6R binding was confirmed in 20A11huH1002/VK1-39-k0MT, 20A11huH1004/VK1-39-k0MT, and 20A11huH1006/VK1-39-k0MT confirmed to undergo cleavage near the boundary between VHH and CH1 by protease treatment.

These results demonstrated that even if VHH incorporated in a polypeptide does not lose its antigen binding activity immediately after association with particular VL, the antigen binding activity can be lost by introducing an association promoting mutation to an amino acid present at the interface between the VHH and the VL.

From these results, it was concluded that the molecule conforming to the concept described in Example 2 can also be prepared by a method of combining a light chain with VHH containing a substituted amino acid involved in association with the light chain, in addition to the method of combining a light chain with VHH obtained in advance as in Example 3.

Example 5

Preparation of Protease-Activated Polypeptide Using VHH Derived from Immunized Alpaca 5-1 Obtainment of VHH Derived from Immunized Alpaca Alpacas were immunized with IL6R, CD3 or plexin A1 by a method known to those skilled in the art. 4 and 8 weeks later, PBMC was collected. From the collected PBMC, VHH gene was amplified with reference to a method described in J. Immunol. Methods (2007) 324, 13. The amplified VHH gene fragment was connected with gene 3 gene and inserted into a phagemid vector. The phagemid vector having the insert of the VHH fragment was transfected into *E. coli* by the electroporation method, and phages presenting VHH were obtained by a method already known to those skilled in the art. The obtained phages were evaluated for their binding to IL6R, CD3 or plexin A1 by ELISA. The sequence of a bound clone was analyzed by a method known to those skilled in the art to identify VHH binding to the antigen.

5-2 Enrichment of VHH Binding to CD3

VHH binding to human CD3 was identified from the VHH library constructed in Example 5-1. VHH clones having binding capacity against human CD3 were enriched using a biotin-labeled protein containing human CD3E and human CD3δ linked to a human antibody constant region (human CD3ed-Fc) as an antigen. The human CD3ed-Fc was prepared as follows: an expression vector for animal cells having a gene encoding the amino acid sequence represented by SEQ ID NO: 59, a gene encoding the amino acid sequence represented by SEQ ID NO: 60 and a gene encoding BirA (SEQ ID NO: 58) was transfected into FreeStyle 293 cells (Invitrogen Corp.). After the transfection, L-biotin was added thereto, and biotinylation was carried out in a culture solution. Cell culture was performed by shake culture at 37° C. according to the protocol. 4 to 5 days later, the supernatant was collected. From the supernatant, a protein fused with the antibody constant region was obtained using a protein A column (Eshmuno A (Merck KGaA)). For the purpose of further obtaining only a CD3εδ heterodimer, a fraction of the CD3εδ heterodimer fused with the antibody constant region (referred to as human CD3ed-Fc) was separated using Anti-FLAG M2 column. Subsequently, gel filtration chromatography (Superdex 200, GE Healthcare Japan Corp.) was carried out to obtain the fraction of the CD3εδ heterodimer of interest (referred to as human CD3ed-Fc).

Phage production was performed from E. coli retaining the constructed phagemids for phage display. A phage population was precipitated by the addition of 2.5 M NaCl/10% PEG to the culture solution of the E. coli after the phage production, and then diluted with TB S to obtain a phage library solution. Next, BSA was added to the phage library solution so as to attain a final BSA concentration of 4%. Panning was performed with reference to a general panning method using an antigen immobilized on magnetic beads (J. Immunol. Methods. (2008) 332 (1-2), 2-9; J. Immunol. Methods. (2001) 247 (1-2), 191-203; Biotechnol. Frog. (2002) 18 (2) 212-20; and Mol. Cell Proteomics (2003) 2 (2), 61-9). The magnetic beads used were NeutrAvidin coated beads (FG beads NeutrAvidin) or Streptavidin coated beads (Dynabeads MyOne Streptavidin T1).

Specifically, 100 pmol of the biotin-labeled antigen was added to the prepared phage library solution, and the phage library solution was contacted with the antigen at room temperature for 60 minutes. The magnetic beads blocked with BSA were added thereto, and the complexes of the antigen and the phages were bound to the magnetic beads at room temperature for 15 minutes. The beads were washed twice with 0.5 mL of TBST (TBS containing 0.1% Tween 20; TBS was manufactured by Takara Bio Inc.) and then further washed once with 0.5 mL of TBS. Then, 0.5 mL of 1 mg/mL trypsin was added thereto, and the beads were suspended at room temperature for 15 minutes and immediately thereafter, separated using a magnetic stand to recover a phage solution. The recovered phage solution was added to 20 mL of an E. coli line ER2738 in an exponential stage of growth (OD600: 0.4-0.5). The E. coli was cultured with mild stirring at 37° C. for 1 hour and thereby infected by the phages. The infected E. coli was inoculated to a 225 mm×225 mm plate. Next, the phages were recovered from the culture solution of the inoculated E. coli to prepare a phage library solution. This cycle, called panning, was repeated twice. In the second cycle of panning, the beads were washed three times with TBST and subsequently twice with TBS. Also, 4 nmol of human Fc was added in the case of the panning against the human CD3ed-Fc.

5-3 Preparation of Protease-Activated IgG Antibody-Like Molecule with Incorporated VHH Binding to CD3

A nucleotide sequence encoding the VHH sequence (Table 1) of each binding clone for human CD3 obtained in Example 5-1 or 5-2 was connected to a nucleotide sequence encoding a protease cleavage site and a constant region by the method described in Example 3 and inserted into an expression vector for animal cells. The resultant was used as the heavy chain of an IgG antibody-like molecule.

TABLE 1

| VHH binding to human CD3 | |
| --- | --- |
| VHH | SEQ ID NO |
| bC3edL 1R1N160H01 | 61 |
| bC3edL 1R1N161H01 | 62 |
| bC3edL 1R1N164H01 | 63 |

Protease-activated IgG antibody-like molecules shown in Table 2 below were expressed by transient expression using FreeStyle 293 cells (Invitrogen Corp.) by a method known to those skilled in the art, and purified by a method known to those skilled in the art using protein A.

TABLE 2

| Protease-activated IgG antibody-like molecules with incorporated VHH binding to CD3 | | |
| --- | --- | --- |
| IgG antibody-like molecule | SEQ ID NO of heavy chain | SEQ ID NO of light chain |
| bC3edL 1R1N160H01-G1mISHI01/VK1-39-k0MT | 64 | 3 |
| bC3edL 1R1N161H01-G1mISHI01/VK1-39-k0MT | 65 | |
| bC3edL 1R1N164H01-G1mISHI01/VK1-39-k0MT | 66 | |

Figure 18:
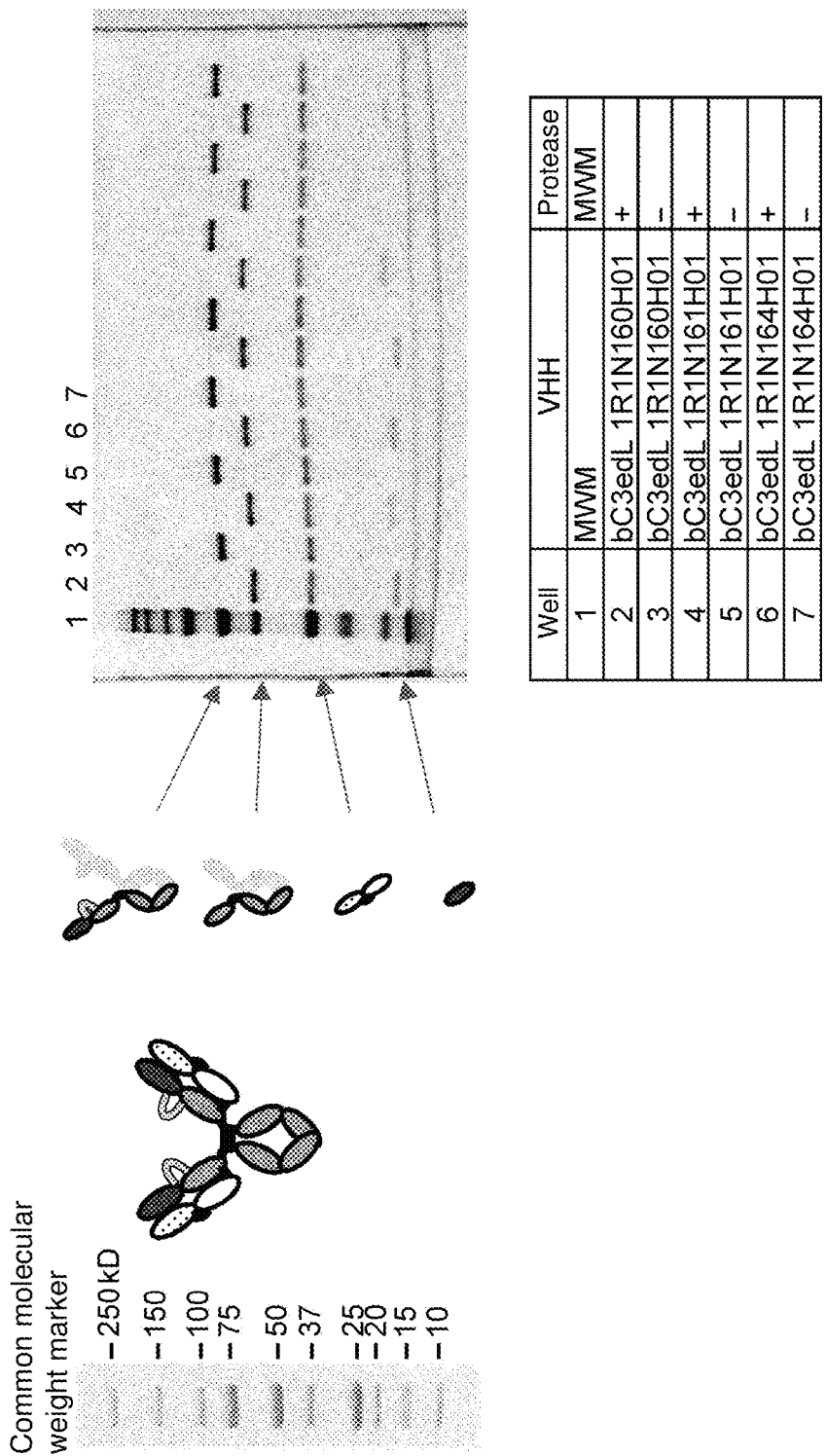
FIG. 18 is a diagram showing results of evaluating the degree of cleavage by migration in reducing SDS-PAGE and detection with CBB after protease (MT-SP1) treatment of antibody-like molecules that had anti-human CD3 VHH in their heavy chain variable regions and were prepared by inserting a protease cleavage sequence near the boundary between the VHH and the heavy chain constant region. Of two new bands resulting from the protease treatment, the band appearing around 10 to 15 kDa is a band derived from the VHH, and the band appearing around 37 kDa is a band derived from the heavy chain constant region.

5-4 Activation of Protease-Activated IgG Antibody-Like Molecule by Protease Cleavage The IgG antibody-like molecules prepared in Example 5-3 were cleaved by protease in the same way as in Example 3, and the degree of the cleavage was evaluated by reducing SDS-PAGE. The results are shown in FIG. 18. The protease concentration was set to 25 nM, and Octet RED (Pall ForteBio Corp.) was used in the assay.

As a result, the IgG antibody-like molecules were confirmed to undergo protease cleavage at the protease cleavage sequence.

Figure 19:
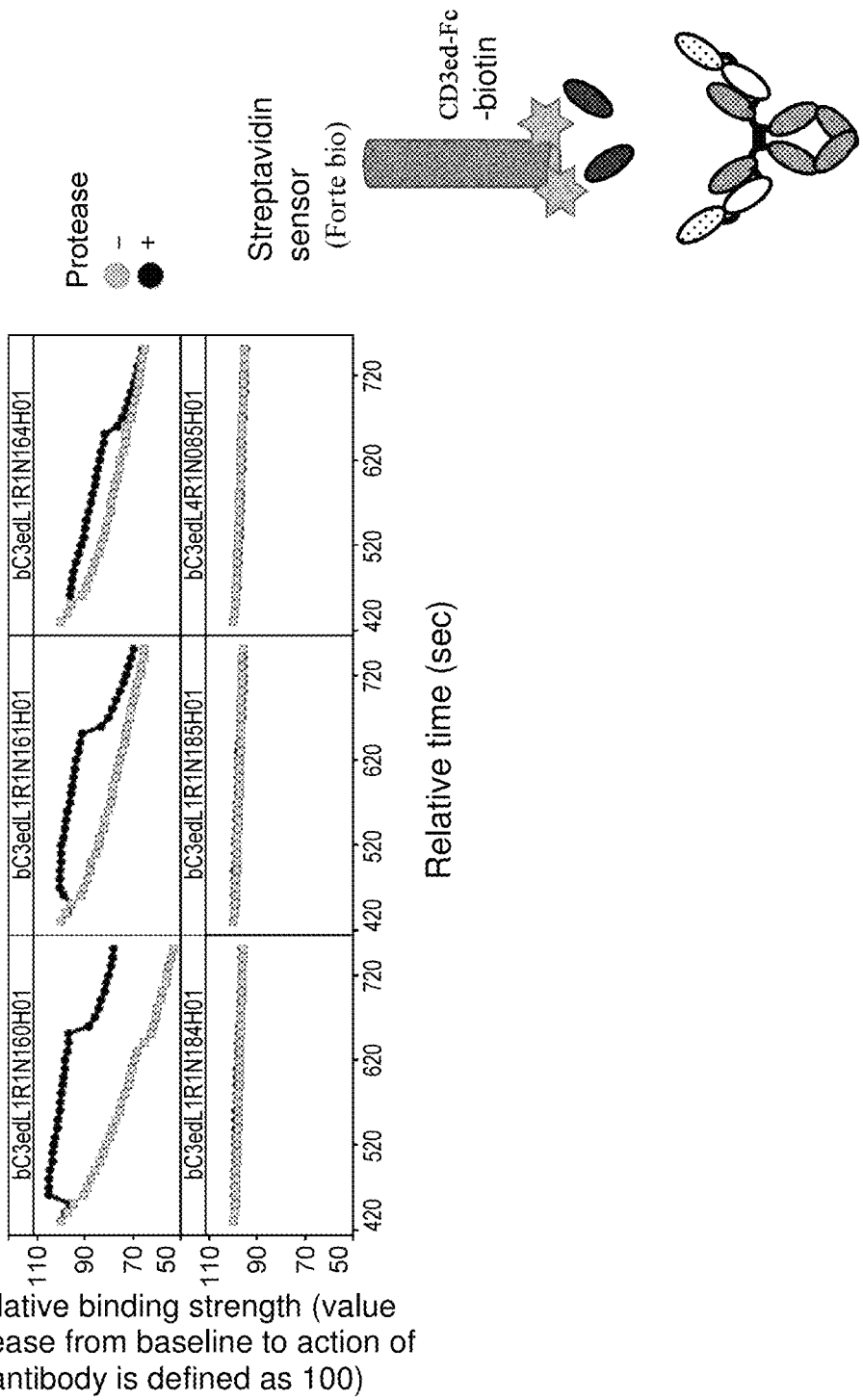
FIG. 19 is a diagram showing results of evaluating the human CD3ed-Fc binding of samples after protease (MT-SP1) treatment of antibody-like molecules that had anti-human CD3 VHH in their heavy chain variable regions and were prepared by inserting a protease cleavage sequence near the boundary between the VHH and the heavy chain constant region. Protease-depicts sensorgrams of evaluating the binding of the protease-untreated antibody-like molecules to the antigen, and Protease+ depicts sensorgrams of evaluating the binding of the protease-treated antibody-like molecules to the antigen. 30 seconds before onset of the action of the antibody-like molecules on antigen-immobilized sensors are a starting point on the abscissa. The binding is shown when a response before antigen binding was defined as 0 and a response before action of the antibodies was defined as 100. The time starting at 30 seconds before action of the antibodies is shown.

Next, the CD3 binding evaluation of VHH released by protease treatment was conducted in the same way as in Example 3. Octet sensorgrams are shown in FIG. 19.

As a result, the IgG antibody-like molecules bC3edL1R1N160H01-G1mISHI01/VK1-39-k0MT, bC3edL1R1N161H01-G1mISHI01/VK1-39-k0MT, and bC3edL1R1N164H01-G1mISHI01/VK1-39-k0MT did not exhibit antigen binding before the protease treatment, whereas the antigen binding was confirmed after the protease treatment. Plurality of VHH binding to CD3 molecules, obtained in the same way as in the VHH described in Table 1, was also used to prepare an IgG-like molecule containing the same protease cleavage site as in the IgG antibody-like molecules described in Table 2. As a result, the antigen binding was confirmed by protease treatment. These results demonstrated that in addition to the polypeptides shown in Examples 3 and 4, an IgG antibody-like molecule harboring a protease cleavage sequence can undergo cleavage at the protease cleavage sequence by protease treatment and thereby release the antigen binding domain, and the released antigen binding domain can bind to the antigen.

Example 6

Polypeptide Harboring Protease Cleavage Sequence in its Light Chain

Light chains VK1-39P-2-Pk0MT (SEQ ID NO: 67), VK1-39P-1-Pk0MT (SEQ ID NO: 68), VK1-39P-Pk0MT (SEQ ID NO: 69), VK1-39P+2-Pk0MT (SEQ ID NO: 70), VK1-39P+3-Pk0MT (SEQ ID NO: 71), VK1-39P+4-Pk0MT (SEQ ID NO: 72), and VK1-39P+5-Pk0MT (SEQ ID NO: 73) harboring a protease cleavage sequence at each position were prepared in the same way as in Example 3.

IgG antibody-like molecules were expressed and purified in the same way as in Example 3 using these light chains and IL6R90-G1m (SEQ ID NO: 2) as a heavy chain. The protease concentration was set to 25 nM. IL6R90-G1m/VK1-39-k0MT (heavy chain: SEQ ID NO: 2, light chain: SEQ ID NO: 3) was used as an IgG antibody-like molecule harboring no cleavage sequence.

Figure 20:
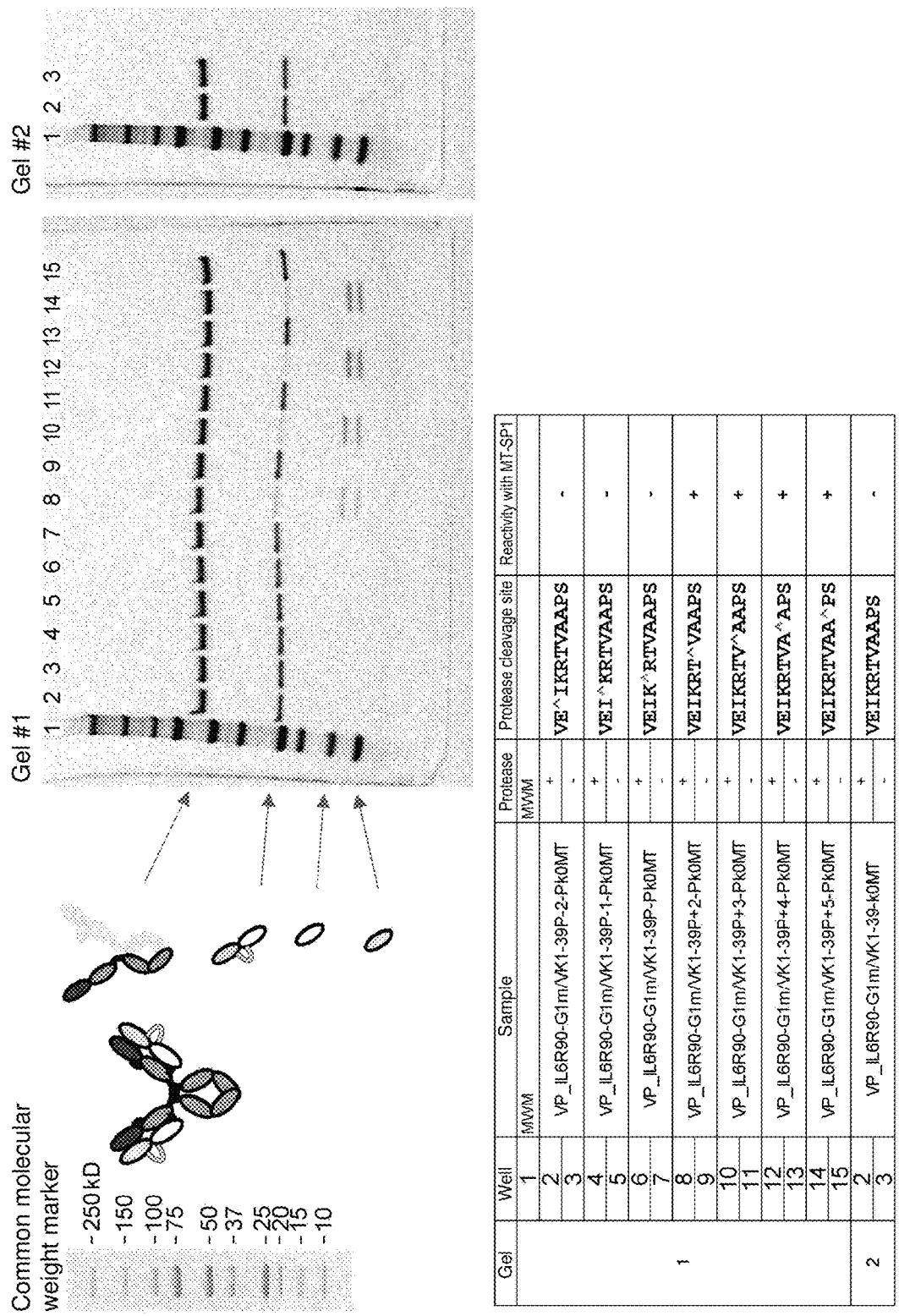
FIG. 20 is a diagram showing results of evaluating the degree of cleavage by migration in reducing SDS-PAGE and detection with CBB after protease (MT-SP1) treatment of a molecule having IL6R90-G1m as a heavy chain and Vk1-39-k0MT as a light chain, or antibody-like molecules prepared by inserting a protease cleavage sequence near the boundary between the light chain variable region and the light chain constant region of the molecule having IL6R90-G1m as a heavy chain and Vk1-39-k0MT as a light chain. Two bands derived from the light chain resulted from the protease treatment, and the light chain was cleaved by protease.
Figure 21:
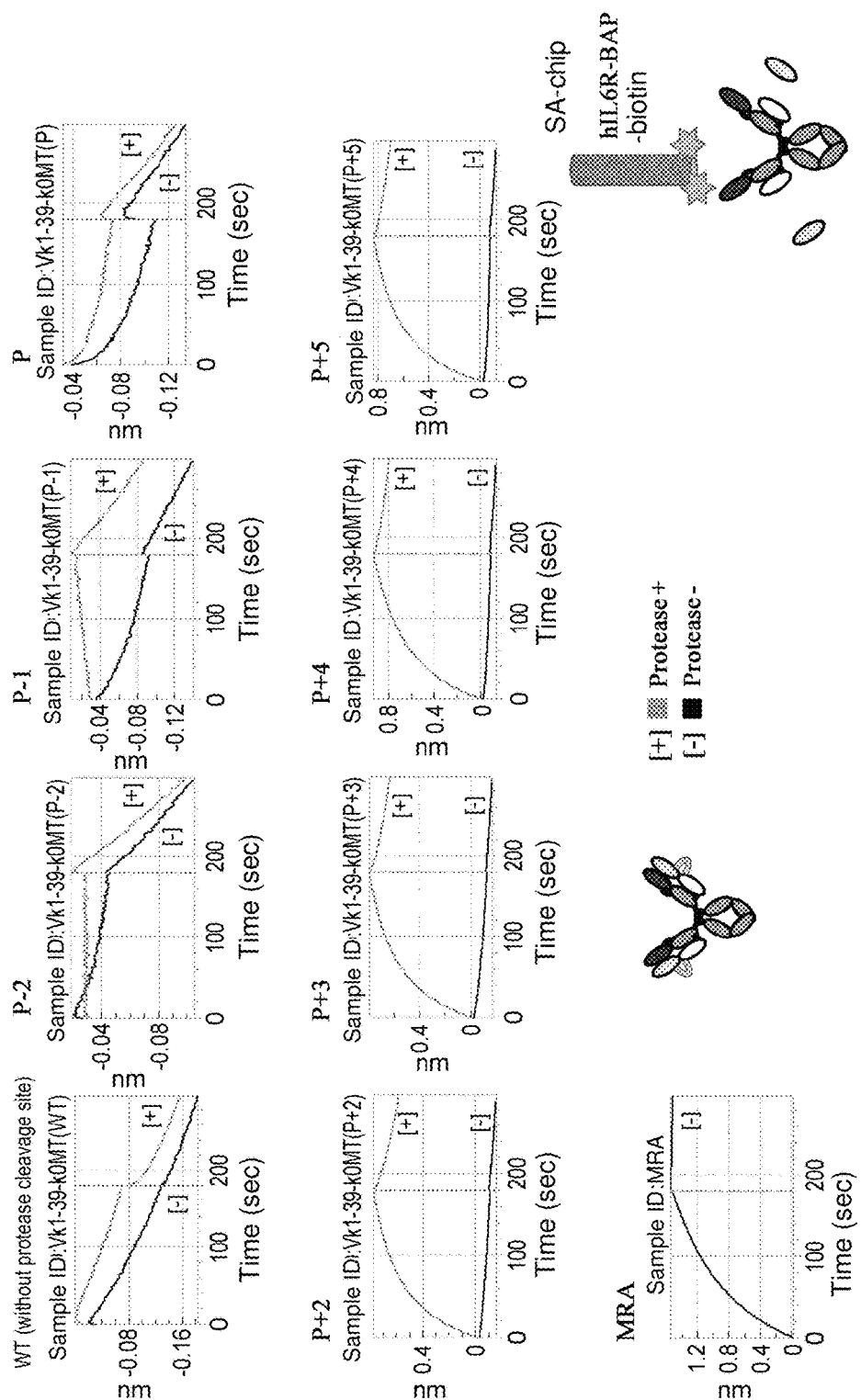
FIG. 21 is a diagram showing results of evaluating the human IL6R binding of samples after protease (MT-SP1) treatment of a molecule having IL6R90-G1m as a heavy chain and Vk1-39-k0MT as a light chain, or antibody-like molecules prepared by inserting a protease cleavage sequence near the boundary between the light chain variable region and the light chain constant region of the molecule having IL6R90-G1m as a heavy chain and Vk1-39-k0MT as a light chain. Protease—depicts sensorgrams of evaluating the binding of the protease-untreated antibody-like molecules to the antigen, and Protease+ depicts sensorgrams of evaluating the binding of the protease-treated antibody-like molecules to the antigen. An antibody (MRA) confirmed to bind to IL6R was used as a positive control. The time of onset of the action of the antibody-like molecules on antigen-immobilized sensors is a starting point on the abscissa.

Subsequently, the prepared IgG antibody-like molecules were cleaved by protease in the same way as in Example 3, and the degree of the cleavage was evaluated by reducing SDS-PAGE. The results are shown in FIG. 20. As a result, VK1-39P+2-Pk0MT (SEQ ID NO: 70), VK1-39P+3-Pk0MT (SEQ ID NO: 71), VK1-39P+4-Pk0MT (SEQ ID NO: 72), and VK1-39P+5-Pk0MT (SEQ ID NO: 73) were confirmed to undergo protease cleavage at the protease cleavage sequence. The IL6R binding evaluation of VHH exposed by protease treatment was further conducted in the same way as in Example 3. Octet sensorgrams are shown in FIG. 21. As a result, the binding was also confirmed by the protease treatment of the cleavage sequence introduced into the light chain, demonstrating that a protease-activated polypeptide harboring a protease cleavage sequence in its light chain can be obtained such that the antigen binding domain is exposed to exhibit antigen binding capacity by the protease cleavage of the light chain.

Example 7

Library Containing Heavy Chain Having Antigen Binding Domain and Light Chain Harboring Protease Cleavage Sequence, and Obtainment of Protease-Activated Polypeptide by Phage Display Method from the Library As confirmed in Example 6, even when a protease cleavage sequence is introduced into the light chain of a protease-activated polypeptide, the antigen binding domain is exposed after cleavage of the light chain to bind to the antigen.

Accordingly, a heavy chain containing an antigen binding domain such as a single-domain antibody and a light chain harboring a protease cleavage sequence are incorporated in a phagemid and presented by a phage. A plurality of phagemids for phage display containing different types of antigen binding domains are constructed, followed by phage production from E. coli retaining these phagemids. A phage population is precipitated by the addition of 2.5 M NaCl/10% PEG to the culture solution of the E. coli after the phage production, and then diluted with TBS to obtain a phage library solution. BSA is added to the phage library solution so as to attain a final BSA concentration of 4%.

The protease-activated polypeptide is obtained by panning from the phage library thus prepared. The panning is performed with reference to a general panning method using an antigen immobilized on magnetic beads (J. Immunol. Methods. (2008) 332 (1-2), 2-9; J. Immunol. Methods. (2001) 247 (1-2), 191-203; Biotechnol. Prog. (2002) 18 (2) 212-20; and Mol. Cell Proteomics (2003) 2 (2), 61-9). Phages unbound with the antigen-immobilized magnetic beads are recovered before addition of protease, and phages bound with the antigen-immobilized magnetic beads are recovered after addition of protease. The magnetic beads used are NeutrAvidin coated beads (Sera-Mag SpeedBeads NeutrAvidin-coated, FG beads NeutrAvidin) or Streptavidin coated beads (Dynabeads M-280 Streptavidin). An antigen binding clone may be selected from the recovered phages by phage ELISA described in the preceding section, or the antibody gene is subcloned into a vector for expression in animals and expressed using animal cells, and the binding activity is compared between before and after protease treatment to select a binding clone.

Example 8

Library Containing Heavy Chain Having Antigen Binding Domain and Light Chain, and Obtainment of Heavy Chain Whose Antigen Binding Capacity is Controlled by Light Chain by Phage Display Method from the Library As confirmed in Example 3, the antigen binding capacity of a heavy chain containing an antigen binding domain is controlled by the association of a light chain. Accordingly, a heavy chain that loses its antigen binding capacity when associated with a light chain and exhibits antigen binding capacity when presented alone or in combination with a light chain constant region is obtained by the phage display method.

A heavy chain containing an antigen binding domain such as a single-domain antibody is incorporated in a phagemid and presented by a phage. A plurality of phagemids for phage display containing different types of antigen binding domains are constructed, followed by phage production from E. coli retaining these phagemids. A phage population is precipitated by the addition of 2.5 M NaCl/10% PEG to the culture solution of the E. coli after the phage production, and then diluted with TBS to obtain a phage library solution. BSA is added to the phage library solution so as to attain a final BSA concentration of 4%.

The heavy chain that exhibits antigen binding capacity when presented alone or in combination with a light chain constant region and loses its antigen binding capacity when associated with the light chain variable region is obtained by panning from the phage library thus prepared. The panning is performed with reference to the panning method using an antigen immobilized on magnetic beads described in Example 5. Phages bound with the antigen-immobilized magnetic beads are recovered from the phage library presenting heavy chains or heavy chains with light chain constant regions. The recovered phages are allowed to infect E. coli, and phages presenting heavy and light chains are produced using a helper phage expressing a light chain.

Phages presenting a heavy chain containing an antigen binding domain and a light chain are obtained by the method mentioned above from the culture solution of the E. coli after the phage production. Phages unbound with the antigen-immobilized magnetic beads are recovered from the population of phages presenting heavy and light chains.

As shown in FIG. 9D, the panning may be carried out by changing the order of the recovery of a phage population presenting a heavy chain, either alone or in combination with a light chain constant region, binding to antigen-immobilized magnetic beads, and the recovery of a phage population presenting heavy and light chains without binding to antigen-immobilized magnetic beads. In addition to the method of expressing a light chain using a helper phage, a region encoding a light chain and a region encoding a heavy chain may be incorporated to the same phagemid as usual, and a gene encoding only a light chain constant region or a full-length light chain may be incorporated in each cycle of panning and used.

An antigen binding clone may be selected from the recovered phages by phage ELISA described in the preceding section, or the antibody gene is subcloned into a vector for expression in animals and expressed using animal cells, and the binding activity is compared between before and after protease treatment to select a binding clone.

Example 9

Obtainment of VHH Whose Antigen Binding Capacity is Controlled by Light Chain by Use of Phage Display Method, and Preparation of IgG Antibody-Like Molecule Containing the VHH In Example 3, it was confirmed that the antigen binding capacity of VHH contained as a substitute for VH in a heavy chain is controlled by association with a light chain. Accordingly, VHH that lost its antigen binding capacity when associated with a particular light chain and exhibited antigen binding capacity when the heavy chain was presented alone or in combination with a light chain constant region, i.e., when not associated with a light chain variable region, was obtained from a phage library presenting CH1 linked to VHH derived from immunized alpaca PBMC. An IgG antibody-like molecule containing the VHH was prepared.

9-1 Construction of Light Chain-Expressing Helper Phage with Integrated Light Chain Expression Unit On the basis of a method described in International Publication No. WO2015/046554, a promoter, a signal sequence, antibody light chain variable region and light chain constant region genes or a light chain constant region gene, etc. were integrated into the genome of a helper phage to construct a light chain-expressing helper phage. E. coli infected with this helper phage is capable of expressing the antibody light chain variable region and the light chain constant region, or only the light chain constant region.

Specifically, the genome was extracted from a helper phage M13KO7TC constructed by the method described in International Publication No. WO2015/046554, and a light chain expression unit was introduced to the genome. A gene encoding a light chain variable region and a light chain constant region (VK1-39-k0MTdC; SEQ ID NO: 152), or a gene encoding a light chain constant region (k0MTdC; SEQ ID NO: 153) was used as the light chain gene to be introduced. lac promoter-pelB signal sequence-light chain gene was inserted into M13KO7TC/SacI by the method described above and transfected into an E. coli line ER2738 by the electroporation method.

The obtained E. coli was cultured, and 2.5 M NaCl/10% PEG was added to the culture supernatant to purify helper phages by the PEG precipitation method. The titers of the obtained helper phages M13KO7TC-Vk1-39-k0MTdC and M13KO7TC-k0MTdC were confirmed by the general plaque formation method.

9-2 Preparation of Library Containing a Plurality of VHH-CH1 Molecules

Alpacas were immunized by a method known to those skilled in the art using 4 types of immunogens: a human IL6R extracellular domain, a human CD3εγ heterodimer, a monkey CD3εγ heterodimer and a cell domain of human plexin A1. 4 weeks later, PBMC was collected. The CD3εγ heterodimers were prepared with reference to Journal of Molecular Biology (2000) 302: 899-916. From the collected PBMC, VHH gene was amplified with reference to a method described in J. Immunol. Methods (2007) 324, 13. The amplified VHH gene fragment was connected with CH1-gene 3 gene and inserted into phagemid vectors to prepare a library containing a plurality of VHH-CH1 molecules containing VHH linked to CH1.

9-3 Method for preparing phage population presenting VHH-CH1/full-length light chain or VHH-CH1/light chain constant region A phagemid vector having an insert of a gene encoding VHH-CH1 is transfected into E. coli by the electroporation method. The obtained E. coli can be cultured and infected by the helper phage M13KO7TC-Vk1-39-k0MTdC prepared in Example 9-1 so that VHH-CH1 expressed from the phagemid vector and the full-length light chain expressed from the helper phage form a Fab structure to prepare a phage population presenting VHH-CH1/full-length light chain (VHH-CH1/Vk1-39-k0MTdC) on the surface of phagemids containing the gene encoding VHH-CH1. Also, the E. coli harboring the phagemid vector having an insert of a gene encoding VHH-CH1 can be cultured and infected by the helper phage M13KO7TC-k0MTdC prepared in Example 9-1 so that VHH-CH1 expressed from the phagemid vector and the light chain constant region expressed from the helper phage form a structure of VHH-CH1 and CL associated to prepare a phage population presenting VHH-CH1/light chain constant region (VHH-CH1/k0MTdC). 2.5 M NaCl/10% PEG can be added to the culture supernatant to purify phages by the PEG precipitation method. The titers of the obtained phages can be confirmed by the general plaque formation method.

9-4 Obtainment of VHH-CH1 Containing Plexin A1 VHH Whose Antigen Binding is Inhibited by Association with Light Chain Variable Region and that Exhibits Antigen Binding Capacity in Absence of Light Chain Variable Region, from VHH-CH1 Phage Library VHH-CH1 containing VHH whose antigen binding was inhibited by association with a light chain variable region and that exhibited antigen binding capacity in absence of the light chain variable region was obtained by panning from the VHH-CH1 library prepared in Example 9-2.

The antigen used was biotin-labeled human plexin A1 prepared in Reference Example.

The panning method was performed according to the following steps:

(1) A phage population presenting VHH-CH1/light chain constant region (VHH-CH1/k0MTdC) is produced by the method of Example 9-3 from the VHH-CH1 phage library prepared in Example 9-2, and phages bound with antigen-immobilized magnetic beads are recovered from the population.

(2) A phage population presenting VHH-CH1/full-length light chain (VHH-CH1/Vk1-39-k0MTdC) is produced by the method of Example 9-3 from the recovered phages, and phages unbound with the antigen-immobilized magnetic beads are recovered from the population.

(3) The recovered phages are repetitively subjected to the steps (1) and (2) to recover the desired phage.

As a result of the panning, a plurality of VHH-CH1 molecules were able to be selected whose plexin A1 binding was inhibited by association with the light chain Vk1-39-k0MTdC and that exhibited binding capacity against plexin A1 in the absence of the light chain variable region.

Another panning method was performed according to the following steps:

(1) A phage population presenting VHH-CH1/light chain constant region (VHH-CH1/k0MTdC) is produced by the method of Example 9-3 from the VHH-CH1 phage library prepared in Example 9-2, and phages bound with antigen-immobilized magnetic beads are recovered from the population.

(2) A phage population presenting VHH-CH1/full-length light chain (VHH-CH1/Vk1-39-k0MTdC) is produced by the method of Example 9-3 from the recovered phages, and phages unbound with the antigen-immobilized magnetic beads are recovered from the population. Phages binding to anti-light chain antibody (EY Laboratories, Inc., Cat. BAT-2107-2)-immobilized magnetic beads are further recovered from the recovered phages.

(3) The recovered phages are repetitively subjected to the steps (1) and (2) to recover the desired phage.

As a result of the panning, a plurality of VHH-CH1 molecules were able to be selected whose plexin A1 binding was inhibited by association with the light chain Vk1-39-k0MTdC and that exhibited binding capacity against plexin A1 in the absence of the light chain variable region.

The VHH in the VHH-CH1 thus selected by panning can be used in the preparation of IgG antibody-like molecules.

9-5 Preparation of Protease-Activated IgG Antibody-Like Molecule with Incorporated VHH Binding to Plexin A1

A nucleotide sequence encoding the VHH contained in each VHH-CH1 molecule selected in Example 9-4 was connected to a nucleotide sequence encoding a protease cleavage site and a heavy chain constant region by the method described in Example 3. The resultant was used as the heavy chain of an IgG antibody-like molecule and combined with a full-length light chain VK1-39-k0MT (SEQ ID NO: 3). IgG antibody-like molecules were expressed by transient expression using FreeStyle 293 cells (Invitrogen Corp.) by a method known to those skilled in the art, and purified by a method known to those skilled in the art using protein A.

The prepared IgG antibody-like molecules are shown in Table 3.

Table 3

Figure 22:
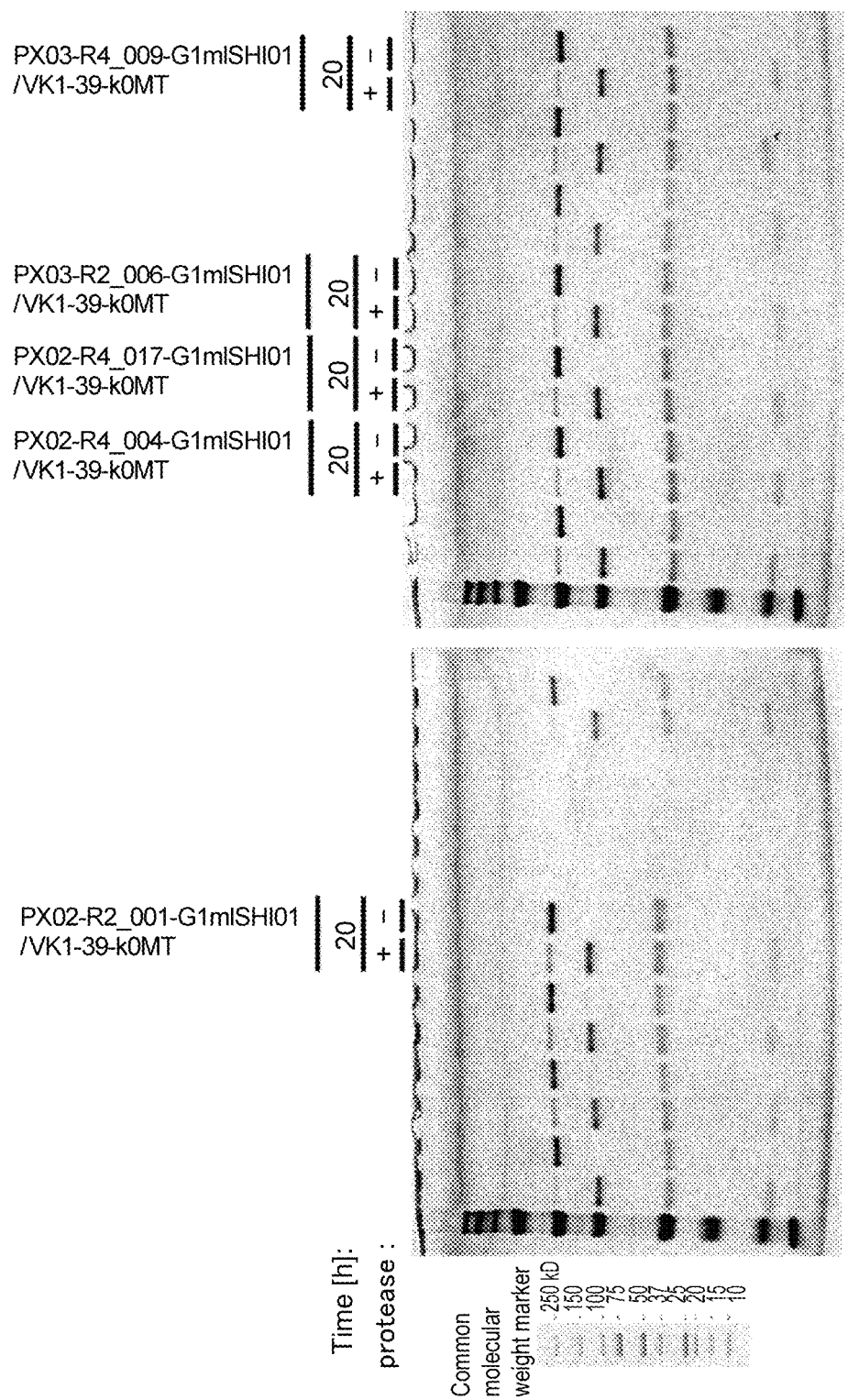
FIG. 22 is a diagram showing SDS-PAGE results of evaluating the protease cleavage of IgG antibody-like molecules with incorporated VHH binding to human plexin A1. Protease(+) lane depicts samples treated by protease cleavage, and protease(−) lane depicts negative control samples without the protease cleavage treatment.

9-6 Activation of Protease-Activated IgG Antibody-Like Molecule by Protease Cleavage The IgG antibody-like molecules prepared in Example 9-4 were cleaved by protease in the same way as in Example 3, and the degree of the cleavage was evaluated by reducing SDS-PAGE. The results are shown in FIG. 22. The protease concentration was set to 25 nM.

As a result, the prepared IgG antibody-like molecules were each confirmed to undergo protease cleavage at the protease cleavage sequence.

Figure 23:
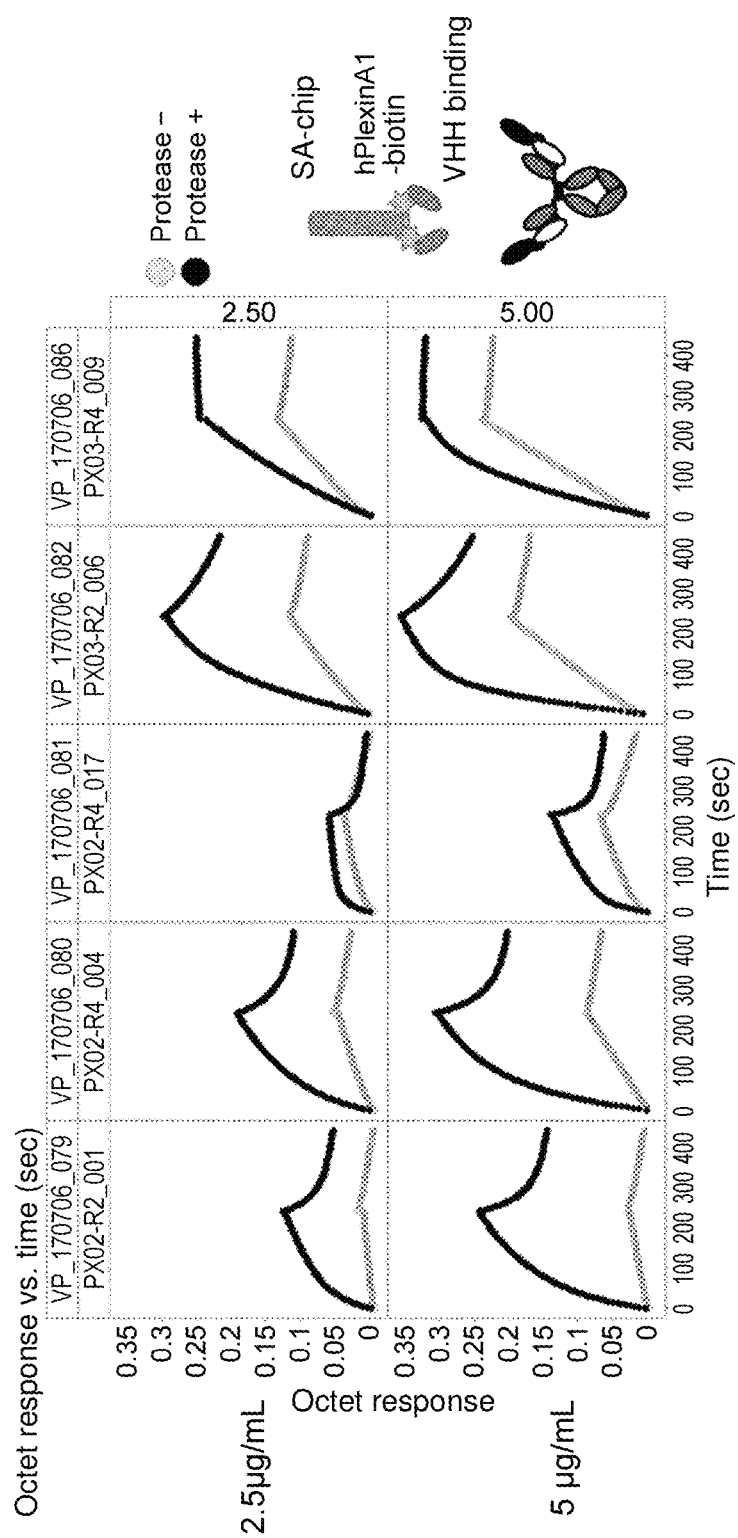
FIG. 23 is a diagram showing Octet sensorgrams of evaluating the human plexin A1 binding of VHH released by protease cleavage from IgG antibody-like molecules with incorporated VHH binding to human plexin A1. Protease+ depicts samples treated by protease cleavage, and protease—depicts samples without the protease cleavage treatment. The concentrations of the IgG antibody-like molecules used are described on the left side of the diagram.

Next, the human plexin A1 binding evaluation of VHH released by protease treatment was conducted in the same way as in Example 3. Octet sensorgrams are shown in FIG. 23.

As a result, each of the prepared IgG antibody-like molecule did not exhibit antigen binding before the protease treatment, whereas the antigen binding of the released VHH was confirmed after the protease treatment.

Example 10

Polypeptide Containing Bispecific VHH-VHH 10-1 Bispecific VHH-VHH Binding to Cancer Antigen and CD3, and Preparation of Polypeptide Containing the Bispecific VHH-VHH As shown in FIG. 8, a protease-activated antigen binding domain may form a bispecific antigen binding molecule with a second antigen binding domain.

VHH HN3 (SEQ ID NO: 159) recognizing human glypican 3 and VHH G03 (SEQ ID NO: 160) recognizing CD3 were connected via a linker constituted by glycine and serine to prepare bispecific VHH-VHH HN3G03. An antibody heavy chain constant region shown in SEQ ID NO: 161 was further connected thereto via a protease cleavage sequence, and the resulting heavy chain HN3G03-cF760mnHIF (SEQ ID NO: 162) containing the bispecific VHH-VHH was inserted into a vector for expression in animals.

VHH HerF07 (SEQ ID NO: 163) recognizing Her2 and VHH G03 (SEQ ID NO: 160) recognizing CD3 were connected via a linker constituted by glycine and serine to prepare bispecific VHH-VHH HerF07G03. An antibody heavy chain constant region shown in SEQ ID NO: 161 was further connected thereto via a protease cleavage sequence, and the resulting heavy chain HerF07G03-cF760mnHIF (SEQ ID NO: 164) containing the bispecific VHH-VHH was inserted into a vector for expression in animals.

Expi293 cells (Life Technologies Corp.) were cotransfected with each heavy chain containing the bispecific

TABLE 3

IgG antibody-like molecules containing VHH binding to human plexin A1

| IgG antibody-like molecule | Heavy chain | | Light chain | |
|---|---|---|---|---|
| | Name | SEQ ID NO | Name | SEQ ID NO |
| PX02-R2_001-G1mISHI01/ VK1-39-k0MT | PX02-R2_001-G1mISHI01 | 154 | VK1-39-k0MT | 3 |
| PX02-R4_004-G1mISHI01/ VK1-39-k0MT | PX02-R4_004-G1mISHI01 | 155 | | |
| PX02-R4_017-G1mISHI01/ VK1-39-k0MT | PX02-R4_017-G1mISHI01 | 156 | | |
| PX03-R2_006-G1mISHI01/ VK1-39-k0MT | PX03-R2_006-G1mISHI01 | 157 | | |
| PX03-R4_009-G1mISHI01/ VK1-39-k0MT | PX03-R4_009-G1mISHI01 | 158 | | |

VHH-VHH and vectors for expression in animals respectively having inserts of a light chain VK1.39-k0MT (SEQ ID NO: 3) and a human constant region sequence VHn-Kn010dGK (SEQ ID NO: 166) from the hinge region to the C terminus, to express a polypeptide containing the bispecific VHH-VHH. Then, the polypeptide containing the bispecific VHH-VHH was purified by a method known to those skilled in the art using a MonoSpin ProA 96-well plate type (GL Sciences Inc., Cat No.: 7510-11312). The polypeptide containing the bispecific VHH-VHH HN3G03 is HN3G03-cF760mnHIF/VHn-Kn010dGK/VK1.39-k0MT, and the polypeptide containing the bispecific VHH-VHH HerF07G03 is HerF07G03-cF760mnHIF/VHn-Kn010dGK/VK1.39-k0MT.

Figure 24:
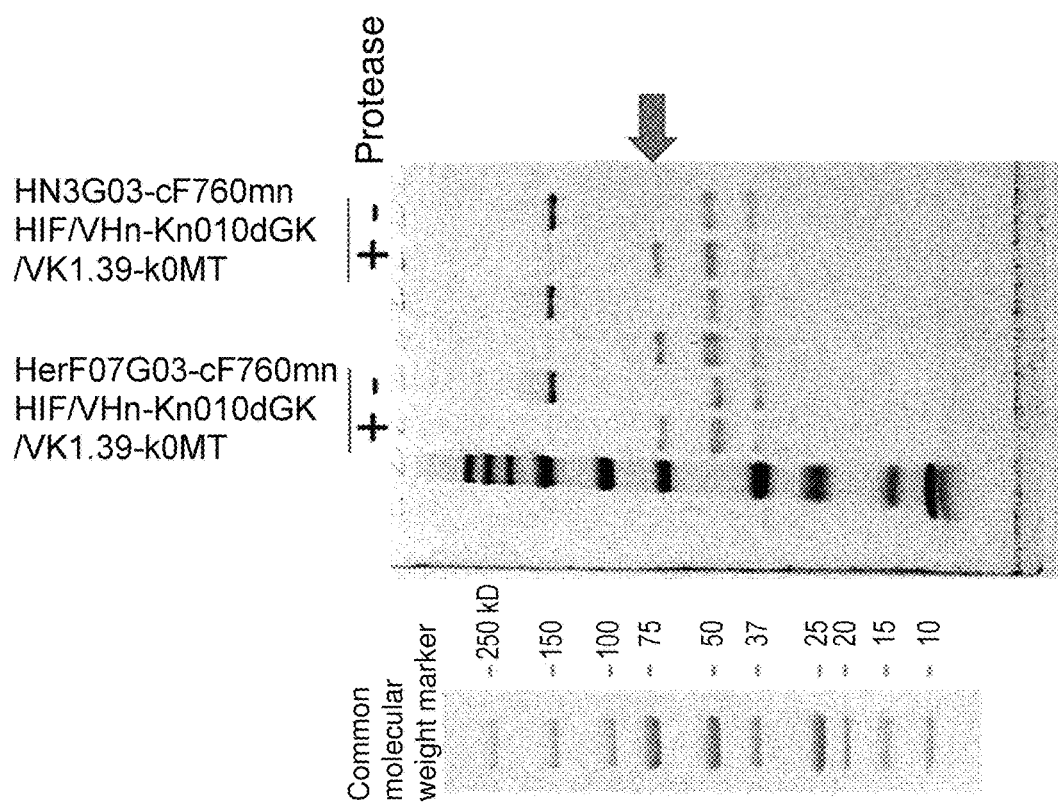
FIG. 24 is a diagram showing SDS-PAGE results of evaluating the protease cleavage of polypeptides containing bispecific VHH-VHH.

For protease treatment, uPA (Recombinant Human u-Plasminogen Activator, R&D Systems, Inc.) (final concentration: 25 nM) was added to 40 µg of each purified polypeptide containing the bispecific VHH-VHH and incubated at 37° C. for 20 hours or longer. Protease-untreated samples were incubated after addition of PBS instead of protease in the same amount as in the protease. Whether the protease-cleaved polypeptide containing the bispecific VHH-VHH underwent the cleavage as intended was confirmed by reducing SDS-PAGE. The results are shown in FIG. 24. As shown in FIG. 24, it was suggested that the bispecific VHH-VHH was separated from the whole molecule by the protease cleavage.

Figure 25:
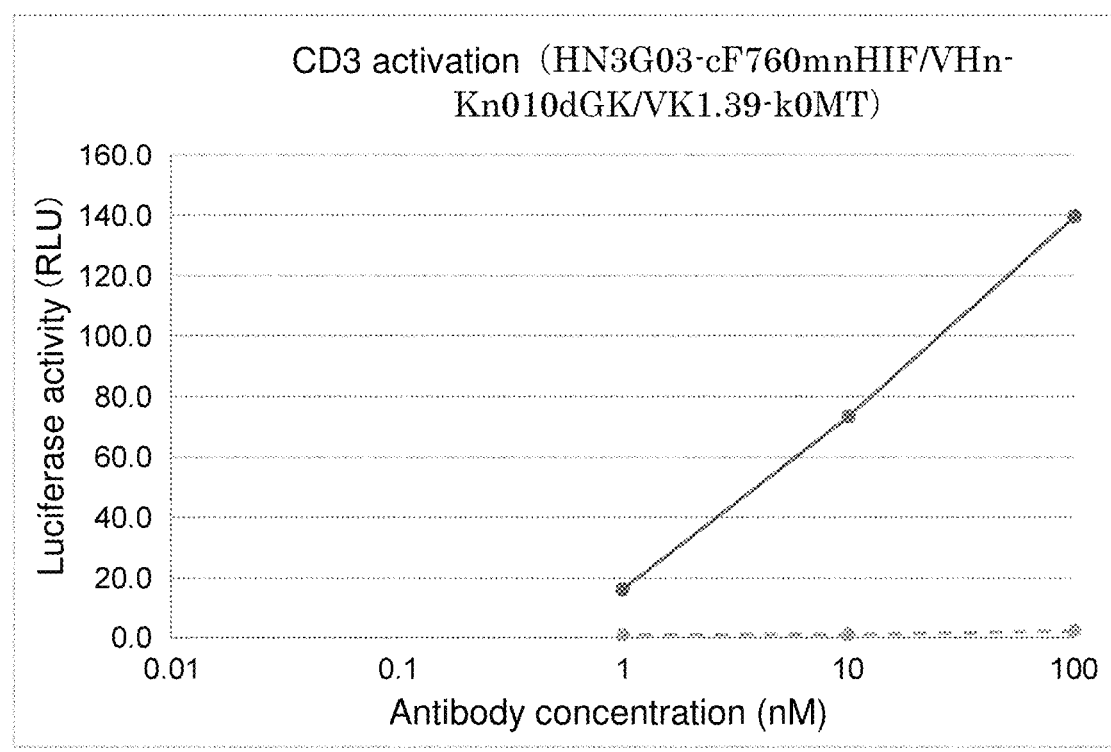
FIG. 25 is a diagram showing luciferase activity before and after protease cleavage. The broken line depicts samples without protease treatment, and the solid line depicts samples with protease treatment.

10-2 CD3 Activation Evaluation of Polypeptide Containing Bispecific VHH-VHH Against GPC3 and CD3 by Protease Cleavage Agonist activity against CD3 was evaluated using Jurkat-NFAT reporter cells (NFAT luc2_jurkat cell). The Jurkat-NFAT reporter cells are a cell line of CD3-expressing human acute T-cell leukemia-derived cells fused with a NFAT response element and luciferase (luc2P) and express luciferase by the activation of a signal downstream of CD3. The target cells used for antibodies based on GPC3 were a SK-pca60 cell line established by forcing a human liver cancer-derived cell line SK-HEP-1 to express human GPC3. The target cells and the effector cells were added at 1.25 E+04 cells/well and 7.50 E+04 cells/well, respectively, to each well of White-bottomed, 96-well assay plate (Costar, 3917). HN3G03-cF760mnHIF/VHn-Kn010dGK/VK1.39-k0MT with or without protease treatment was added at a final concentration of 1, 10, or 100 nM to the well. After 24-hour incubation at 37° C. in the presence of 5% $CO_2$, the luciferase enzyme activity was measured as luminescence intensity using Bio-Glo luciferase assay system (Promega Corp., G7940) according to the attached protocol. 2104 EnVision was used in detection. The results are shown in FIG. 25. No elevation in luciferase activity was seen in the sample without protease treatment, whereas elevation in luciferase activity was shown in HN3G03-cF760mnHIF/VHn-Kn010dGK/VK1.39-k0MT treated with protease. Specifically, HN3G03-cF760mnHIF/VHn-Kn010dGK/VK1.39-k0MT treated with protease was able to be confirmed to have agonist activity against CD3, while the bispecific VHH-VHH against GPC3 and CD3 was released from HN3G03-cF760mnHIF/VHn-Kn010dGK/VK1.39-k0MT by the protease cleavage and exerted the CD3 binding activity inhibited without cleavage.

Figure 26:
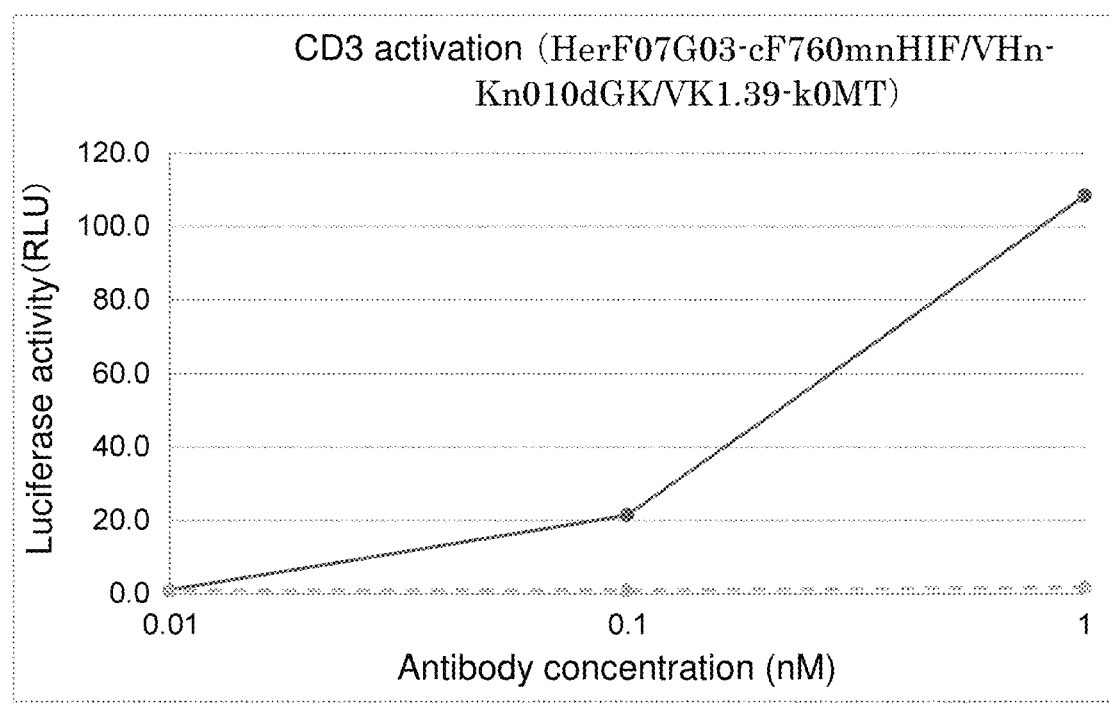
FIG. 26 is a diagram showing luciferase activity before and after protease cleavage. The broken line depicts samples without protease treatment, and the solid line depicts samples with protease treatment.

10-3 CD3 Activation Evaluation of Polypeptide Containing Bispecific VHH-VHH Against Her2 and CD3 by Protease Cleavage Agonist activity against CD3 was evaluated using Jurkat-NFAT reporter cells (NFAT luc2_jurkat cell). The Jurkat-NFAT reporter cells (effector cells) are a cell line of CD3-expressing human acute T-cell leukemia-derived cells fused with a NFAT response element and luciferase (luc2P) and express luciferase by the activation of a signal downstream of CD3. The target cells used were a LS1034 cell line. The target cells and the effector cells were added at 2.50 E+04 cells/well and 7.50 E+04 cells/well, respectively, to each well of White-bottomed, 96-well assay plate (Costar, 3917). HerF07G03-cF760mnHIF/VHn-Kn010dGK/VK1.39-k0MT with or without protease treatment was added at a final concentration of 0.01, 0.1, and 1 nM to the well. After 24-hour incubation at 37° C. in the presence of 5% $CO_2$, the luciferase enzyme activity was measured as luminescence intensity using Bio-Glo luciferase assay system (Promega Corp., G7940) according to the attached protocol. 2104 EnVision was used in detection. The results are shown in FIG. 26. No elevation in luciferase activity was seen in the sample without protease treatment, whereas elevation in luciferase activity was shown in HerF07G03-cF760mnHIF/VHn-Kn010dGK/VK1.39-k0MT treated with protease. Specifically, HerF07G03-cF760mnHIF/VHn-Kn010dGK/VK1.39-k0MT treated with protease was able to be confirmed to have agonist activity against CD3, while the bispecific VHH-VHH against Her2 and CD3 was released from HerF07G03-cF760mnHIF/VHn-Kn010dGK/VK1.39-k0MT by the protease cleavage and exerted the CD3 binding activity inhibited without cleavage.

Example 11

Introduction of Protease Cleavage Site to Polypeptide with Incorporated VHH 11-1 Introduction of Protease Cleavage Sequence to Polypeptide with Incorporated VHH Binding to IL6R An expression vector encoding IL6R90-G1T4 (SEQ ID NO: 167) containing IL6R90 (SEQ ID NO: 1), VHH having binding and neutralizing activities against human IL6R as described in International Publication No. WO2010/115998, fused with a human IgG1 constant region (CH1-hinge-CH2-CH3) was prepared by a method known to those skilled in the art. An IgG antibody-like molecule IL6R90-G1T4/VK1-39-k0MT (heavy chain: SEQ ID NO: 167, light chain: SEQ ID NO: 3) was expressed by transient expression using FreeStyle 293 cells (Invitrogen Corp.) or Expi293 cells (Life Technologies Corp.) by a method known to those skilled in the art, and purified by a method known to those skilled in the art using protein A.

A protease cleavage sequence shown in SEQ ID NO: 178 was inserted near the boundary between VHH and CH1 in the heavy chain of IL6R90-G1T4/VK1-39-k0MT to prepare a VHH-containing heavy chain IL6R90.12aa-G1T4 (SEQ ID NO: 189) harboring the protease cleavage sequence. An IL6R90.12aa-G1T4 expression vector was prepared by a method known to those skilled in the art.

IL6R90.12aa-G1T4 was combined with a light chain shown in SEQ ID NO: 3. An IgG1 antibody-like molecule IL6R90.12aa-G1T4/VK1-39-k0MT harboring the protease cleavage sequence near the boundary between VHH and CH1 was expressed by transient expression using FreeStyle 293 cells (Invitrogen Corp.) or Expi293 cells (Life Technologies Corp.) by a method known to those skilled in the art, and purified by a method known to those skilled in the art using protein A.

11-2 Protease Cleavage Evaluation of IgG Antibody-Like Molecule Containing Anti-Human IL6R VHH and Harboring Protease Cleavage Sequence in its Heavy Chain Region Whether the IgG antibody-like molecule prepared in Example 11-1 would be cleaved by protease was verified.

Figure 27:
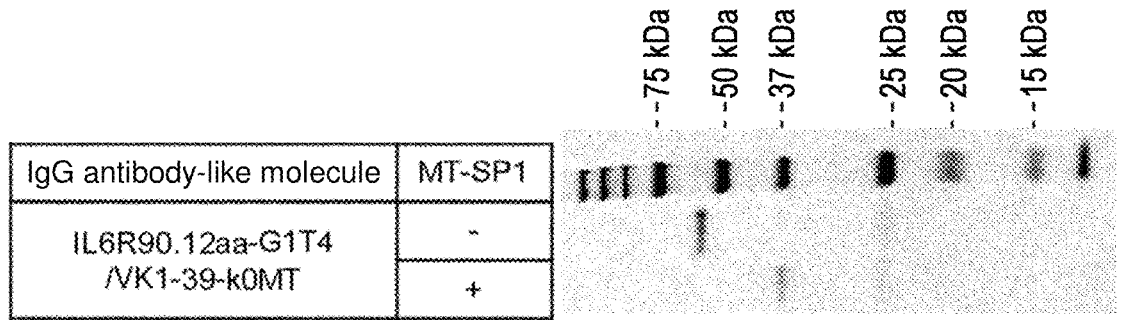
FIG. 27 is a diagram showing the SDS-PAGE evaluation of the protease cleavage of an IgG antibody-like molecule containing anti-human IL6R VHH.

Recombinant Human Matriptase/ST14 Catalytic Domain (MT-SP1) (R&D Systems, Inc., 3946-SE-010) was used as the protease. 10 nM protease and 50 μg/mL of the antibody were reacted in PBS under a condition of 37° C. for 20 hours. Then, cleavage by the protease was evaluated by reducing SDS-PAGE. The results are shown in FIG. 27. As a result, the protease treatment of the IgG antibody-like molecule IL6R90.12aa generated a new band around 37 kDa. Thus, the IgG antibody-like molecule was confirmed to undergo protease cleavage at the protease cleavage sequence (SEQ ID NO: 178) inserted near the boundary between VHH and CH1. Also, a protease cleavage sequence represented by SEQ ID NO: 178 was also confirmed to be cleaved by human uPA and mouse uPA when incorporated in an IgG antibody by a similar method.

Example 12

Evaluation of Degree of Activation by Protease Cleavage of IgG Antibody-Like Molecule Harboring Protease Cleavage Sequence in its Light Chain An expression vector encoding IL6R75-G1m (SEQ ID NO: 191) containing IL6R75 (SEQ ID NO: 190), VHH having binding and neutralizing activities against human IL6R as described in International Publication No. WO2010/115998, fused with a human IgG1 constant region (CH1-hinge-CH2-CH3) was prepared by a method known to those skilled in the art. IL6R75hu-G1m (SEQ ID NO: 192) was prepared by introducing amino acid alterations to the interface site between VHH and VL in the same way as in Example 4-2. IgG antibody-like molecules IL6R90-G1m/VK1-39P+4-Pk0MT (heavy chain: SEQ ID NO: 2, light chain: SEQ ID NO: 72), 20A11hu-G1m/K1-39P+4-Pk0MT (heavy chain: SEQ ID NO: 39, light chain: SEQ ID NO: 72), and IL6R75hu-G1m/VK1-39P+4-Pk0MT (heavy chain: SEQ ID NO: 192, light chain: SEQ ID NO: 72) were expressed and purified in the same way as in Example 3 using the protease cleavage sequence-incorporated light chain VK1-39P+4-Pk0MT (SEQ ID NO: 72) and IL6R90-G1m (SEQ ID NO: 2), 20A11hu-G1m (SEQ ID NO: 39), and IL6R75hu-G1m (SEQ ID NO: 192) as heavy chains.

Figure 28:
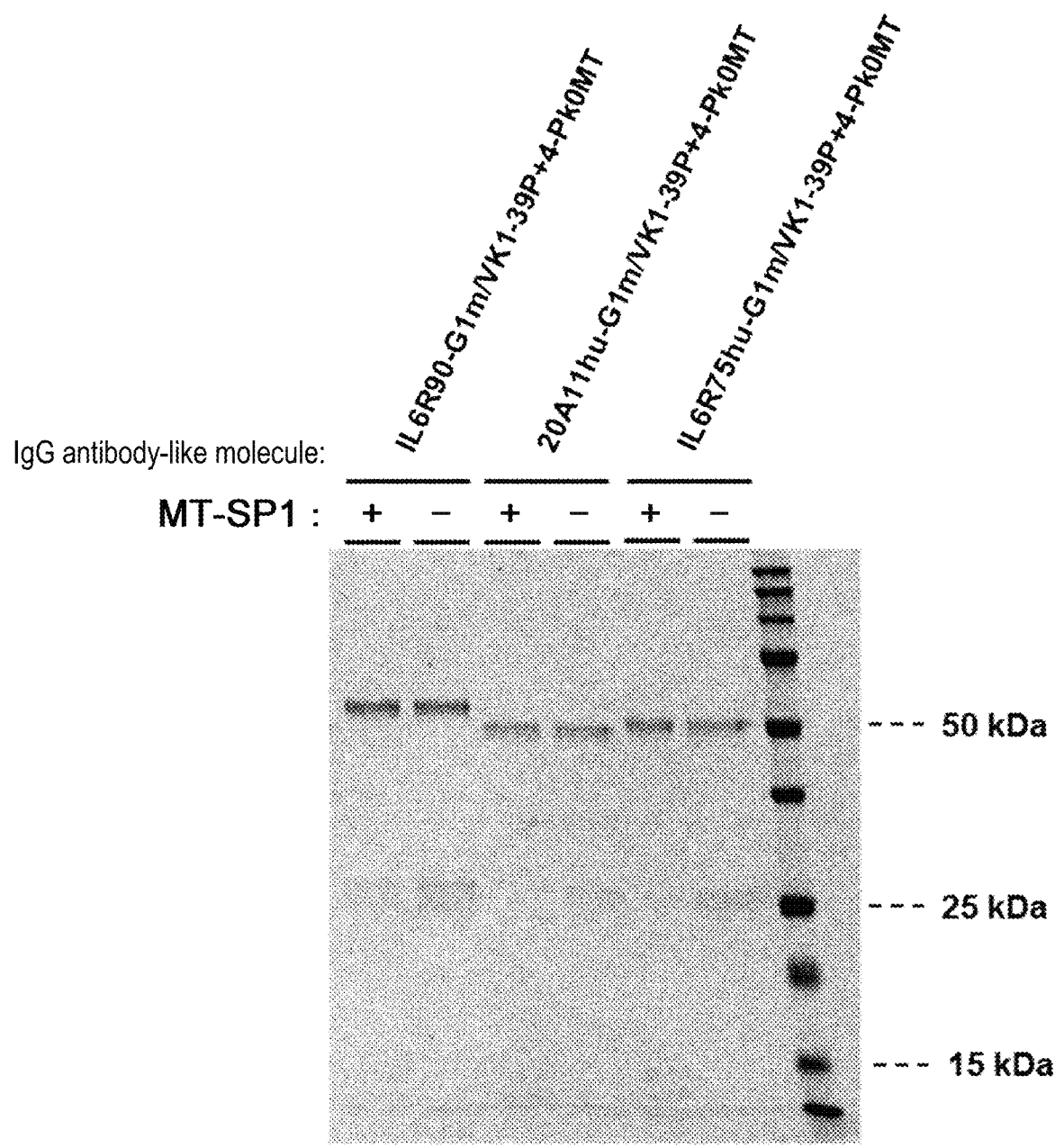
FIG. 28 is a diagram showing the evaluation of the protease cleavage of IgG antibody-like molecules harboring a protease cleavage sequence in their light chains.

IL6R90-G1m/VK1-39P+4-Pk0MT, 20A11hu-G1m/VK1-39P+4-Pk0MT, and IL6R75hu-G1m/VK1-39P+4-Pk0MT were cleaved by protease in the same way as in Example 3, and the degree of the cleavage was evaluated. The results are shown in FIG. 28. Specifically, recombinant Human Matriptase/ST14 Catalytic Domain (R&D Systems, Inc., 3946-SE-010) was used as the protease. 50 nM protease and 50 μg/mL of each IgG antibody-like molecule were reacted in PBS under a condition of 37° C. for 20 hours. Then, cleavage by the protease was evaluated by reducing SDS-PAGE. As a result, IL6R90-G1m/VK1-39P+4-Pk0MT, 20A11hu-G1m/VK1-39P+4-Pk0MT, and IL6R75hu-G1m/VK1-39P+4-Pk0MT were confirmed to undergo protease cleavage near the boundary between VL and CL.

Figure 29:
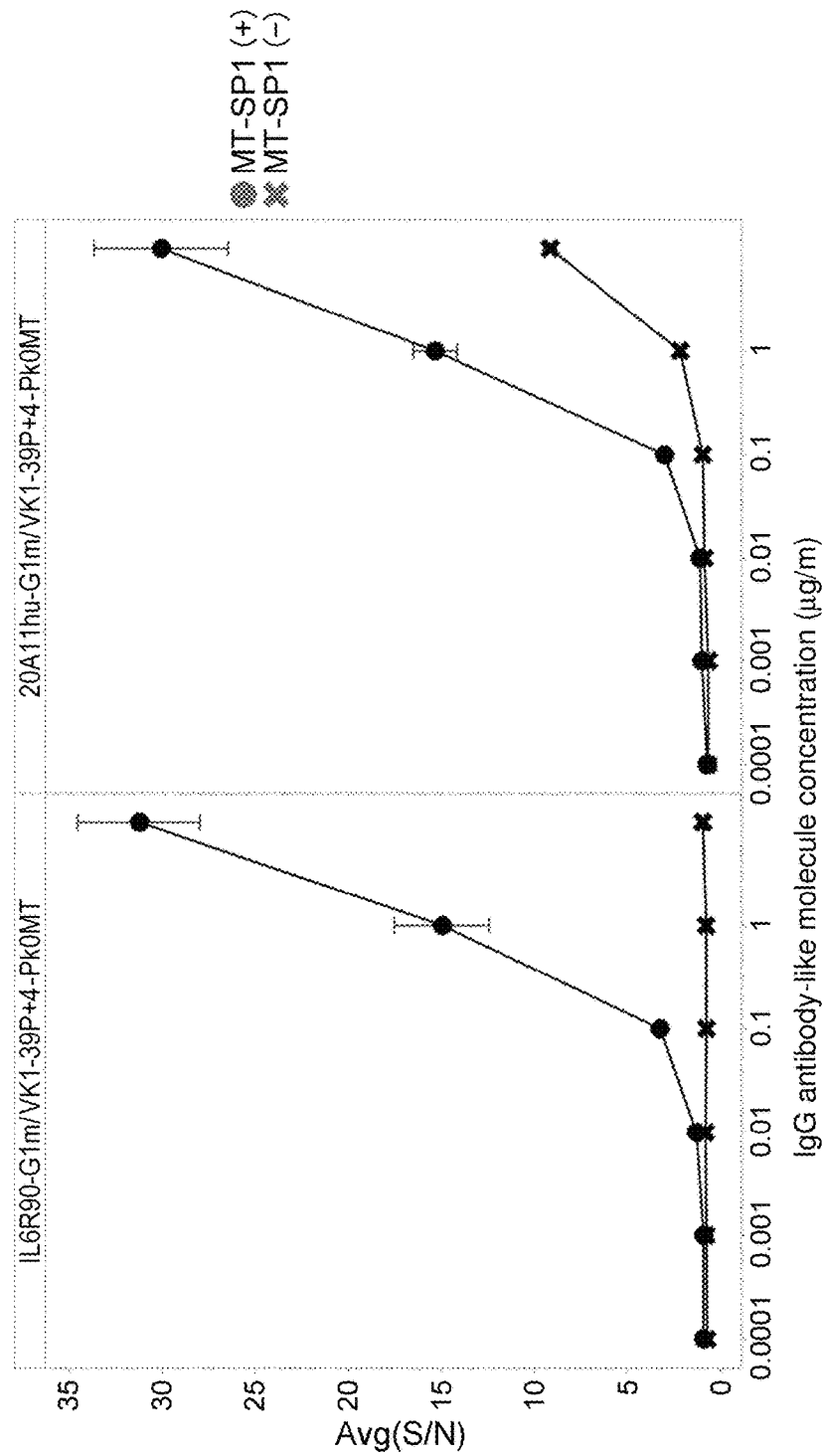
FIG. 29 is a diagram showing the evaluation of the degree of activation based on the presence or absence of the protease treatment of IgG-like antibody molecules harboring a protease cleavage sequence in their light chains.

Next, the IL6R binding of VHH exposed by protease treatment was evaluated by ELISA. Specifically, the hsIL-6R-BAP1 used in Example 3 was immobilized onto a streptavidin-coated 384-well plate (Greiner Bio-One GmbH, 781990), and each cleaved IgG antibody-like molecule was bound thereto at room temperature. After reaction for 30 minutes, a HRP-labeled anti-human IgG antibody (Sigma-Aldrich Co. LLC, SAB3701362-2MG) was allowed to act thereon at room temperature for 10 minutes, and TMB Chromogen Solution (Life Technologies Corp., 002023) was reacted therewith. After reaction at room temperature for 30 minutes, the reaction was terminated with sulfuric acid, followed by the measurement of absorbance at 450 nm using Synergy HTX multi-mode reader (BioTek Instruments, Inc.). The absorbance ratio of the antigen-immobilized wells to immobilized wells was calculated and used as a S/N ratio. The S/N ratio (mean) of ELISA was plotted on the ordinate against the concentration of each IgG antibody-like molecule on the abscissa. The results are shown in FIG. 29. These results showed that the protease-treated IgG antibody-like molecule 20A11hu-G1m/VK1-39P+4-Pk0MT harboring the cleavage sequence in its light chain had 10 or more times the IL6R binding activity of the protease-untreated IgG antibody-like molecule, and the protease-treated IgG antibody-like molecule IL6R90-G1m/VK1-39P+4-Pk0MT had 1,000 or more times the IL6R binding activity of the protease-untreated one.

Example 13

Preparation and Evaluation of IgG Antibody-Like Molecules Harboring Diverse Protease Cleavage Sequences 13-1 Preparation of Polypeptides Harboring Diverse Protease Cleavage Sequences IgG antibody-like molecules were prepared in the same way as in Example 3 using recognition sequences for proteases other than urokinase or matriptase. Various peptide sequences known to be cleaved by MMP-2, MMP-7, MMP-9, or MMP-13 were each inserted near the boundary between the variable and constant regions of IL6R90-G1m, and a peptide sequence containing a flexible linker consisting of a glycine-serine polymer was inserted in the vicinity of these cleavage sequences. The inserted sequences are shown in Table 4.

TABLE 4

| Various inserted sequences | | |
| --- | --- | --- |
| Protease | Inserted sequence | SEQ ID NO |
| MMP-2<br>MMP-9 | PLGLAG | 34 |
| MMP-2 | GAGIPVSLRSGAG | 70 |
| MMP-2 | GPLGIAGQ | 71 |
| MMP-2 | GGPLGMLSQS | 72 |
| MMP-2 | PLGLWA | 73 |
| MMP-7 | VPLSLTMG | 35 |
| MMP-7 | GAGVPLSLTMGAG | 75 |
| MMP-9 | GAGVPLSLYSGAG | 76 |
| MMP-13 | GAGPQGLAGQRGIVAG | 91 |
| MMP-2<br>MMP-9 | GGGGSPLGLAGGGGGS | 193 |
| MMP-2 | GGGGSGPLGIAGQGGGGS | 194 |
| MMP-9 | GGGGSGAGVPLSLYSGAGGGGGS | 195 |

Heavy chains were designed such that these sequences were inserted near the boundary between the variable and constant regions of IL6R90-G1m. Expression vectors encoding the heavy chain variants 6R90EIVHEMP2.1-6R90EICHEMP2.1G1m (SEQ ID NO: 165), 6R90EIVHEMP2.2-6R90EICHEMP2.2G1m (SEQ ID NO: 202), 6R90EIVHEMP2.3-6R90EICHEMP2.3G1m (SEQ ID NO: 203), 6R90EIVHEMP2.4-6R90EICHEMP2.4G1m (SEQ ID NO: 204), 6R90EIVHEMP7.1-6R90EICHEMP7.1G1m (SEQ ID NO: 205), 6R90EIVHEMP7.2-6R90EICHEMP7.2G1m (SEQ ID NO: 206), 6R90EIVHEMP13-6R90EICHEMP13G1m (SEQ ID NO: 207), 6R90EIVHEG4SMP2MP9G4S-6R90EICHEG4SMP2MP9G4SG1m (SEQ ID NO: 196), 6R90EIVHEG4SMP2.2G4S-6R90EIVHEG4SMP2.2G4SG1m (SEQ ID NO: 197), and 6R90EIVHEG4SMP9G4S-6R90EIVHEG4SMP9G4SG1m (SEQ ID NO: 198) were prepared by a method known to those skilled in the art.

Table 5 shows the IgG antibody-like molecules combining these heavy chain variants with a light chain and harboring the protease cleavage sequence near the boundary between the variable and constant regions of the heavy chain. These IgG antibody-like molecules were expressed by transient expression using FreeStyle 293 cells (Invitrogen Corp.) or Expi293 cells (Life Technologies Corp.) by a method known to those skilled in the art, and purified by a method known to those skilled in the art using protein A.

buffer (MMP Activity Assay Kit (Fluorometric-Green) (ab112146), Component C: Assay Buffer).

As a result, 6R90EIVHEMP2.1-6R90EICHEMP2.1G1m/VK1-39-k0MT, 6R90EIVHEMP2.2-6R90EICHEMP2.2G1m/VK1-39-k0MT, 6R90EIVHEMP2.3-6R90EICHEMP2.3G1m/VK1-39-k0MT, 6R90EIVHEMP2.4-6R90EICHEMP2.4G1m/VK1-39-k0MT, 6R90EIVHEG4SMP2MP9G4S-6R90EICHEG4SMP2MP9G4SG1m/VK1-39-k0MT, and 6R90EIVHEG4SMP2.2G4S-6R90EICHEG4SMP2.2G4SG1m/VK1-39-k0MT were confirmed to be cleaved by MMP-2. 6R90EIVHEMP7.1-6R90EICHEMP7.1G1m/VK1-39-k0MT and 6R90EIVHEMP7.2-6R90EICHEMP7.2G1m/VK1-39-k0MT were confirmed to be cleaved by MMP-7. 6R90EIVHEG4SMP2MP9G4S-6R90EICHEG4SMP2MP9G4SG1m/VK1-39-k0MT and 6R90EIVHEG4SMP9G4S-6R90EICHEG4SMP9G4S G1m/VK1-39-k0MT were confirmed to be cleaved by MMP-9. 6R90EIVHEMP13-6R90EICHEMP13G1m/VK1-39-k0MT was confirmed to be cleaved by MMP-13.

TABLE 5

IgG antibody-like molecules

| Protease | IgG antibody-like molecule | SEQ ID NO of heavy chain | SEQ ID NO of light chain |
|---|---|---|---|
| MMP-2 | 6R90EIVHEMP2.1-6R90EICHEMP2.1G1m/VK1-39-k0MT | 165 | 3 |
| MMP-2 | 6R90EIVHEMP2.2-6R90EICHEMP2.2G1m/VK1-39-k0MT, | 202 | 3 |
| MMP-2 | 6R90EIVHEMP2.3-6R90EICHEMP2.3G1m/VK1-39-k0MT, | 203 | 3 |
| MMP-2 | 6R90EIVHEMP2.4-6R90EICHEMP2.4G1m/VK1-39-k0MT, | 204 | 3 |
| MMP-7 | 6R90EIVHEMP7.1-6R90EICHEMP7.1G1m/VK1-39-k0MT, | 205 | 3 |
| MMP-7 | 6R90EIVHEMP7.2-6R90EICHEMP7.2G1m/VK1-39-k0MT | 206 | 3 |
| MMP-13 | 6R90EIVHEMP13-6R90EICHEMP13G1m/VK1-39-k0MT | 207 | 3 |
| MMP-2 MMP-9 | 6R90EIVHEG4SMP2MP9G4S-6R90EICHEG4SMP2MP9G4SG1m/VK1-39-k0MT | 196 | 3 |
| MMP-2 | 6R90EIVHEG4SMP2.2G4S-6R90EICHEG4SMP2.2G4SG1m/VK1-39-k0MT | 197 | 3 |
| MMP-9 | 6R90EIVHEG4SMP9G4S-6R90EICHEG4SMP9G4SG1m/VK1-39-k0MT | 198 | 3 |

Figure 30B:
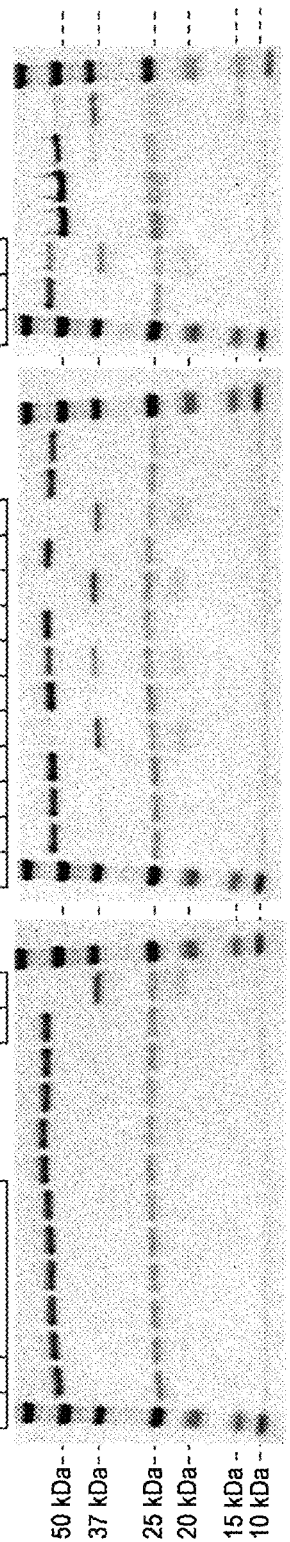
FIG. 30B is a diagram showing the evaluation of the protease cleavage of IgG antibody-like molecules harboring a protease cleavage sequence in their heavy chains. The cleavage by protease was carried out using an assay buffer (MMP Activity Assay Kit (Fluorometric-Green) (ab112146), Component C: Assay Buffer).

13-2 Protease Cleavage Evaluation of IgG Antibody-Like Molecules Harboring Diverse Protease Cleavage Sequences Whether the IgG antibody-like molecules prepared in Example 13-1 would be cleaved by protease was verified. Recombinant human MMP-2 (R&D Systems, Inc., 902-MP-010), recombinant human MMP-7 (R&D Systems, Inc., 907-MP-010), recombinant human MMP-9 (R&D Systems, Inc., 911-MP-010), or recombinant human MMP-13 (R&D Systems, Inc., 511-MM-010) was used as the protease. MMP-2, MMP-7, MMP-9, and MMP-13 were used after being each mixed with 1 MMP-aminophenylmercuric acetate (APMA; Abcam PLC, ab112146) and activated at 37° C. for 1 or 24 hours. 50 nM, 100 nM, or 500 nM protease and 50 µg/mL or 100 µg/mL of each IgG-antibody like molecule were reacted in PBS or 20 mM Tris-HCl, 150 mM NaCl, and 5 mM CaCl$_2$) (pH 7.2) (hereinafter, referred to as Tris) under a condition of 37° C. for 20 hours. Then, cleavage by the protease was evaluated by reducing SDS-PAGE. The results are shown in FIGS. 30A and 30B. In FIG. 30B, the protease cleavage was carried out using an assay Reference Example 1 Preparation of Biotinylated Plexin A1

Biotinylated plexin A1 (also referred to as biotin-labeled human plexin A1) was prepared by a method known to those skilled in the art. Specifically, a gene fragment encoding a specific sequence (AviTag sequence; SEQ ID NO: 36) to be biotinylated by biotin ligase and a gene fragment encoding a FLAG tag sequence (SEQ ID NO: 199; DYKDDDDK) were linked via a gene fragment encoding a linker constituted by glycine and serine to downstream of a gene fragment encoding the extracellular region of plexin A1. A gene fragment encoding a protein containing plexin A1 linked to the AviTag sequence and the FLAG tag sequence (SEQ ID NO: 200) was integrated to a vector for expression in animal cells. The constructed plasmid vector was transfected into FreeStyle 293 cells (Invitrogen Corp.) using 293Fectin (Invitrogen Corp.). In this operation, the cells were cotransfected with a gene for EBNA1 (SEQ ID NO: 57) expression and a gene for biotin ligase (BirA; SEQ ID NO: 58)

expression, and biotin was further added thereto for the purpose of biotin-labeling plexin A1. The cells transfected according to the procedures mentioned above were cultured at 37° C. under 8% $CO_2$ and caused to secrete the protein of interest (biotinylated plexin A1) into the culture supernatant. This cell culture solution was filtered through a 0.22 µm bottle-top filter to obtain a culture supernatant.

A column was packed with Anti FLAG M2 agarose (Sigma-Aldrich Co. LLC, #A2220) to prepare a FLAG column. The FLAG column was equilibrated in advance with D-PBS(−). The culture supernatant was applied thereto to bind the biotinylated plexin A1 to the column. Subsequently, the biotinylated plexin A1 was eluted using FLAG peptide dissolved in D-PBS(−). Aggregates were removed from this eluate by gel filtration chromatography using HiLoad 26/600 Superdex 200 pg, 320 mL (GE Healthcare Japan Corp., 28-9893-36) to obtain purified biotinylated plexin A1.

The embodiments of the invention mentioned above are described in detail with reference to actual examples and illustrated examples with the aim of helping clear understanding. However, the description and illustration in the present specification should not be interpreted as limiting the scope of the present invention. The disclosure of all patent literatures and scientific literatures cited herein is explicitly incorporated herein by reference in its entirety.

INDUSTRIAL APPLICABILITY

The polypeptide of the present invention comprising an antigen binding domain and a carrying moiety having a longer half-life in blood than that of the antigen binding domain and having an inhibiting domain that inhibits the binding activity of the antigen binding domain, and a pharmaceutical composition comprising the polypeptide can transport the antigen binding domain in blood while inhibited the antigen binding activity of the antigen binding domain. Also, use of the polypeptide of the present invention can allow the antigen binding domain to exert its antigen binding activity specifically at a disease site. Furthermore, since the antigen binding domain has a shorter half-life at the time of exerting its antigen binding activity than at the time of transport, the risk of acting systemically is decreased. Thus, the polypeptide and the pharmaceutical composition of the present invention are very useful in the treatment of a disease.

A single-domain antibody whose antigen binding activity is inhibited by associating with particular VL, VH or VHH can be screened for or produced as one example of the antigen binding domain to thereby efficiently produce the polypeptide of the present invention. Furthermore, a necessary antigen binding domain can be efficiently obtained when the polypeptide of the present invention is prepared by use of a library including the single-domain antibody whose antigen binding activity is inhibited by associating with particular VL, VH or VHH, as one example of the antigen binding domain that can be used in the polypeptide of the present invention.

The invention claimed is:

1. A polypeptide comprising an antigen binding domain, a cleavage site and a carrying moiety, the carrying moiety having an inhibiting domain that inhibits the antigen binding activity of the antigen binding domain, and the antigen binding domain having a shorter half-life in blood than that of the carrying moiety,
wherein the carrying moiety is the moiety other than the antigen binding domain in the polypeptide,
wherein the antigen binding domain comprises a single-domain antibody or is a single-domain antibody, and the inhibiting domain of the carrying moiety is an antibody VL,
wherein the inhibiting domain of the carrying moiety associates with the antigen binding domain and thereby inhibits the antigen binding activity of the antigen binding domain, wherein the molecular weight of the antigen binding domain is 60 kDa or smaller, and the molecular weight of the antigen binding domain is smaller than that of the carrying moiety, or wherein the carrying moiety has FcRn binding activity, and the antigen binding domain has no FcRn binding activity or has weaker FcRn binding activity than that of the carrying moiety,
wherein the cleavage site comprises a protease cleavage sequence,
and wherein the cleavage site is in a position in the polypeptide such that if the cleavage site is cleaved, then the inhibiting domain of the carrying moiety and the antigen binding domain are no longer associated.

2. The polypeptide according to claim 1, wherein the antigen binding domain released from the polypeptide has higher antigen binding activity than that before the release.

3. The polypeptide according to claim 1, wherein the carrying moiety comprises an antibody constant region.

4. The polypeptide according to claim 1, wherein the protease cleavage sequence is located near the boundary between the antigen binding domain and the antibody constant region.

5. A pharmaceutical composition comprising the polypeptide of claim 1.

6. The polypeptide of claim 1, wherein the protease cleavage sequence is a target tissue specific protease cleavage sequence.

7. The polypeptide of claim 3, wherein the antibody constant region is an IgG antibody constant region.

8. The polypeptide according to claim 1, wherein the antigen binding domain is an antigen binding domain directed to plexin A1, IL6R or CD3 as a target antigen.

* * * * *